(12) United States Patent
Walker et al.

(10) Patent No.: US 7,109,186 B2
(45) Date of Patent: Sep. 19, 2006

(54) HIV INTEGRASE INHIBITORS

(75) Inventors: Michael A. Walker, Durham, CT (US); Zhuping Ma, Chandler, AZ (US); B. Narasimhulu Naidu, Durham, CT (US); Margaret E. Sorenson, Meriden, CT (US); Annapurna Pendri, Glastonbury, CT (US); Jacques Banville, St-Hubert (CA); Serge Plamondon, Ste-Catherine (CA); Roger Remillard, Napierville (CA)

(73) Assignee: Bristol-Myers Squibb Company, Princeton, NJ (US)

( * ) Notice: Subject to any disclaimer, the term of this patent is extended or adjusted under 35 U.S.C. 154(b) by 602 days.

(21) Appl. No.: 10/616,031

(22) Filed: Jul. 9, 2003

(65) Prior Publication Data

US 2004/0110804 A1    Jun. 10, 2004

Related U.S. Application Data

(60) Provisional application No. 60/399,248, filed on Jul. 29, 2002, provisional application No. 60/394,548, filed on Jul. 9, 2002.

(51) Int. Cl.
| | |
|---|---|
| *A61K 31/675* | (2006.01) |
| *A61K 31/496* | (2006.01) |
| *A61K 31/4015* | (2006.01) |
| *A61K 31/541* | (2006.01) |
| *C07D 403/06* | (2006.01) |
| *C07D 413/06* | (2006.01) |
| *C07D 417/06* | (2006.01) |
| *C07D 207/36* | (2006.01) |

(52) U.S. Cl. .................. 514/91; 514/227.8; 514/232.2; 514/235.5; 514/254.01; 514/326; 514/343; 514/397; 514/422; 514/423; 544/58.5; 544/60; 544/82; 544/141; 544/372; 546/208; 546/278.7; 548/112; 548/314.7; 548/427; 548/517; 548/537

(58) Field of Classification Search .............. 544/58.5, 544/60, 82, 141, 372; 546/208, 278.7; 548/427, 548/517, 537, 112, 314.7; 514/227.8, 232.2, 514/235.5, 254.01, 326, 343, 422, 423, 91, 514/397

See application file for complete search history.

(56) References Cited

U.S. PATENT DOCUMENTS 6,727,275 B1    4/2004   Zou et al.

FOREIGN PATENT DOCUMENTS

| WO | WO 02/070491 | 9/2002 |
|---|---|---|
| WO | WO 03/016266 | 2/2003 |
| WO | WO 03/016275 | 2/2003 |
| WO | WO 03/035076 | 5/2003 |
| WO | WO 03/035077 | 5/2003 |

*Primary Examiner*—Emily Bernhardt
(74) *Attorney, Agent, or Firm*—James Epperson

(57) ABSTRACT

The present invention describes novel compounds of Formula I which inhibit HIV integrase. The invention also describes compositions and treatments of AIDS or ARC by using these compounds

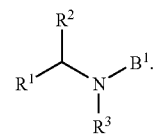

11 Claims, No Drawings

HIV INTEGRASE INHIBITORS

This application claims the benefit of U.S. Provisional Application No. 60/399,248, filed Jul. 29, 2002 and U.S. Provisional Application No. 60/394,548, filed Jul. 9, 2002.

BACKGROUND OF THE INVENTION

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics (UNAIDS: Report on the Global HIV/AIDS Epidemic, December 1998), indicate that as many as 33 million people worldwide are infected with the virus. In addition to the large number of individuals already infected, the virus continues to spread. Estimates from 1998 point to close to 6 million new infections in that year alone. In the same year there were approximately 2.5 million deaths associated with HIV and AIDS.

There are currently a number of antiviral drugs available to combat the infection. These drugs can be divided into three classes based on the viral protein they target and their mode of action. In particular, saquinavir, indinavir, ritonavir, nelfinavir and amprenavir are competitive inhibitors of the aspartyl protease expressed by HIV. Zidovudine, didanosine, stavudine, lamivudine, zalcitabine and abacavir are nucleoside reverse transcriptase inhibitors that behave as substrate mimics to halt viral cDNA synthesis. The non-nucleoside reverse transcriptase inhibitors, nevaripine, delavaridine and efavirenz inhibit the synthesis of viral cDNA via a non-competitive (or uncompetitive) mechanism. Used alone these drugs are effective in reducing viral replication. The effect is only temporary as the virus readily develops resistance to all known agents. However, combination therapy has proven very effective at both reducing virus and suppressing the emergence of resistance in a number of patients. In the US, where combination therapy is widely available, the number of HIV-related deaths has declined (Palella, F. J.; Delany, K. M.; Moorman, A. C.; Loveless, M. O.; Further, J.; Satten, G. A.; Aschman, D. J.; Holmberg, S. D. *N. Engl. J. Med.* 1998, 338, 853).

Unfortunately, not all patients are responsive and a large number fail this therapy. In fact, approximately 30–50% of patients ultimately fail combination therapy. Treatment failure in most cases is caused by the emergence of viral resistance. Viral resistance in turn is caused by the rapid turnover of HIV-1 during the course of infection combined with a high viral mutation rate. Under these circumstances incomplete viral suppression caused by insufficient drug potency, poor compliance to the complicated drug regiment as well as intrinsic pharmacological barriers to exposure provides fertile ground for resistance to emerge. More disturbing are recent findings which suggest that low-level replication continues even when viral plasma levels have dropped below detectable levels (<50 copies/ml) (Carpenter, C. C. J.; Cooper, D. A.; Fischl, M. A.; Gatell, J. M.; Gazzard, B. G.; Hammer, S. M.; Hirsch, M. S.; Jacobsen, D. M.; Katzenstein, D. A.; Montaner, J. S. G.; Richman, D. D.; Saag, M. S.; Schecter, M.; Schoolery, R. T.; Thompson, M. A.; Vella, S.; Yeni, P. G.; Volberding, P. A. *JAMA* 2000, 283, 381). Clearly there is a need for new antiviral agents, preferably targeting other viral enzymes to reduce the rate of resistance and suppress viral replication even further.

HIV expresses three enzymes, reverse transcriptase, an aspartyl protease and integrase, all of which are potential antiviral targets for the development of drugs for the treatment of AIDS. However, integrase stands out as being the only viral enzyme not targeted by current therapy. The integrase enzyme is responsible for insertion of the viral cDNA into the host cell genome, which is a critical step in the viral life cycle. There are a number of discrete steps involved in this process including processing of the viral cDNA by removal of two bases from each 3'-terminus and joining of the recessed ends to the host DNA. Studies have shown that in the absence of a functional integrase enzyme HIV is not infectious. Therefore, an inhibitor of integrase would be useful as a therapy for AIDS and HIV infection.

A number of inhibitors of the enzyme have been reported. These include, nucleotide-based inhibitors, known DNA binders, catechols and hydrazide containing derivatives (Neamati, N. *Expert Opin. Ther. Patents* 2002, 12, 709–724). Diketoamide HIV integrase inhibitors have been disclosed (WO 0316266, WO 0335076, WO 0335077, WO 02070486). However, no clinically approved compound has resulted from these leads. Thus, clinically effective inhibitors of HIV integrase would fulfill a therapeutic need.

SUMMARY OF INVENTION

The present invention relates to compounds of Formula I, or pharmaceutically acceptable salts and solvates thereof

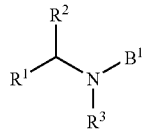

Formula I

Formula I wherein $R^1$, $R^2$, $R^3$, and $B^1$ are described as below. The invention includes compositions and methods of treatment using these compounds.

DETAILED DESCRIPTION OF THE INVENTION

The present invention describes compounds of Formula I, or pharmaceutically acceptable salts or solvates thereof

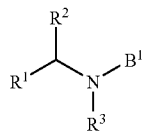

I wherein:

$R^1$ is
  -phenyl substituted with 1–3 $R^4$,
  -naphthyl, furanyl, thienyl, pyridyl, or imidazolyl unsubtituted or substituted with 1–3 $R^4$,
  —$C_1$–$C_6$ alkyl-aryl unsubtituted or substituted with 1–3 $R^4$, or
  —$C_1$–$C_5$ alkyl-O-aryl unsubtituted or substituted with 1–3 $R^4$;

R² is
- —H,
- —C₁–C₆ alkyl,
- -aryl unsubstituted or substituted with 1–3 R⁴, or
- —C₁–C₆ alkyl aryl unsubstituted or substituted with 1–3 R⁴;

R³ is
- —H,
- —C₁–C₆ alkyl,
- —C₁–C₆ alkyl-aryl unsubstituted or substituted with 1–3 R, or
- —OR⁹;

R⁴ is independently selected from
- -halo,
- -CN,
- —C₁–C₆ alkyl,
- —C₃–C₆ cycloalkyl,
- —C₁–C₆ haloalkyl,
- —OR⁵,
- —CO₂R⁶,
- —N(R⁷)(R⁸),
- —CON(R⁷)(R⁸),
- —SR⁵,
- —SOC₁–C₆alkyl, and
- —SO₂C₁–C₆alkyl;

R⁵ and R⁶ are independently selected from —H and —C₁–C₆ alkyl;

R⁷ and R⁸ are independently selected from —H and —C₁–C₆ alkyl, or NR⁷R⁸ is a heterocycle selected from pyrrolidine, piperidine, 4-hydroxypiperidine, morpholine, thiomorpholine, piperazine, and 4-methylpiperazine;

R⁹ is
- —H,
- —C₁–C₁₀ alkyl,
- —C₁–C₆ alkyl-aryl,
- —C₂–C₁₀ alkyl-OR⁵,
- —C₁–C₁₀ alkyl-CO₂R⁶,
- —C₁–C₁₀ alkyl-N(R⁷)(R⁸),
- —C₁–C₁₀ alkyl-CON(R⁷)(R⁸), or
- —C₁–C₆ alkyl-heterocycle where the heterocycle is selected from pyrrolidine, piperidine, 4-hydroxypiperidine, morpholine, thiomorpholine, piperazine, 4-methylpiperazine, and thiazinanedioxide;

B¹ is selected from the group consisting of

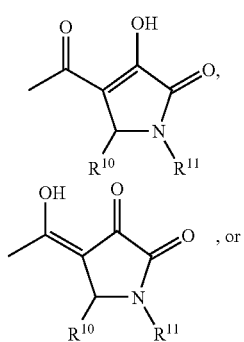

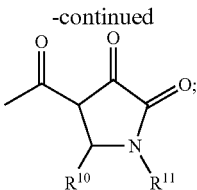

R¹⁰ is
- —H,
- —C₁–C₆ alkyl,
- -cycloalkyl,
- —C₁–C₆ alkyl-aryl,
- -phenyl unsubstituted or substituted with 1–3 R¹²,
- -benzofuran, dihydrobenzofuran, benzodioxane, or
- -heteroaryl selected from furan, thiophene, pyrrole, imidazole, oxazole, thiazole, and pyridine;

R¹¹ is
- —C₁–C₆ alkyl,
- -cycloalkyl,
- -aryl unsubstituted or substituted with 1–2 R⁴,
- —C₁–C₆ alkyl-aryl unsubstituted or substituted with 1–2 R⁴,
- —C₁–C₆ alkyl-heteroaryl where the heteroaryl is selected from furan, thiophene, pyrrole, imidazole, oxazole, thiazole, and pyridine,
- —C₁–C₆ alkyl-NR⁷R⁸,
- —C₁–C₆ alkyl-OR⁵,
- —C₁–C₆ alkyl-P(O)(OR⁶)₂,
- —C₁–C₆ alkyl-CO₂R⁶, or
- —C₁–C₆ alkyl-C(O)N(R⁷)(R⁸);

R¹² is
- halogen,
- —C₁–C₆ alkyl,
- —C₁–C₂ haloalkyl,
- —C₁–C₃ thioalkyl,
- —OR¹³,
- tetrahydrofuran,
- dihydropyran,
- —NR⁷R⁸,
- —CO₂R⁶,
- —CONR⁷R⁸, or
- —CONHCH₂Ph where Ph is unsubstituted or substituted with 1–2 R⁴;

R¹³ is
- —H,
- —C₁–C₆ alkyl,
- —C₁–C₆ fluoroalkyl,
- allyl,
- propargyl,
- phenyl,
- benzyl,
- —COC₁–C₆alkyl,
- —CH₂CO₂R⁶, or
- —CH₂CONR⁷R⁸.

In the present invention, unless otherwise specified the following definitions apply.

The numbers in the subscript after the symbol "C" define the number of carbon atoms a particular group can contain. For example, "C₁–C₆" means a substituent containing from one to six carbon atoms.

As used herein, the term "alkyl" means a saturated, straight chain or branched monovalent hydrocarbon radical having the stated number of carbon atoms. Examples of such alkyl radicals include methyl, ethyl, n-propyl, isopropyl, n-butyl, isobutyl, sec-butyl, t-butyl and, where indicated, higher homologues and isomers such as n-pentyl, n-hexyl, 2-methylpentyl and the like. Haloalkyl refers to an alkyl radical that is substituted with one or more halo radicals, such as trifluoromethyl.

As used herein, the term "cycloalkyl" means a non-aromatic 3–6 membered ring. Examples include, cyclopropyl, cyclobutyl, cyclopentyl and cyclohexyl.

Halo means chloro, bromo, iodo or fluoro.

"Aryl" means an aromatic hydrocarbon having from six to ten carbon atoms; examples include phenyl and napthyl, indenyl, azulenyl, fluorenyl and anthracenyl.

The term "heterocycle" refers to a monocyclic saturated heterocyclic nuclei having 3–6 atoms containing 1–3 heteroatoms selected from nitrogen, oxygen or sulfur. Heterocycles include, for example, piperidinyl, piperazinyl, pyrrolidinyl and morpholinyl.

"Heteroaryl" means a five- or six-membered aromatic ring containing at least one and up to four non-carbon atoms selected from oxygen, sulfur and nitrogen. Examples of heteroaryl include 2-furyl, 3-furyl, 2-pyridyl, 3-pyridyl, 4-pyridyl, pyrazinyl, 2-thienyl, 3-thienyl, pyrrolyl, oxazolyl, thiazolyl, imidazolyl, pyrazolyl, isoxazolyl, isothiazolyl, 1,2,3-oxadiazolyl, 1,2,3-triazolyl, 1,3,4-thiadiazolyl, pyridazinyl, pyrimidinyl, 1,3,5-triazinyl and 1,3,5-trithianyl.

By virtue of its acidic moiety, where applicable, a compound of Formula I forms salts by the addition of a pharmaceutically acceptable base. Such base addition salts include those derived from inorganic bases which include, for example, alkali metal salts (e.g. sodium and potassium), alkaline earth metal salts (e.g. calcium and magnesium), aluminum salts and ammonium salts. In addition, suitable base addition salts include salts of physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl) amine, procaine, dibenzylpiperidine, N-benzylphenethylamine, dehydroabietylamine, N,N'-bishydroabietylamine, glucamine, N-methylglucamine, collidine, quinine, quinoline, ethylenediamine, ornithine, choline, N,N'-benzylphenethylamine, chloroprocaine, diethanolamine, diethylamine, piperazine, tris(hydroxymethyl)aminomethane and tetramethylammonium hydroxide and basic amino aids such as lysine, arginine and N-methylglutamine. These salts may be prepared by methods known to those skilled in the art.

Salts of an amine group may also comprise quaternary ammonium salts in which the amino nitrogen carries a suitable organic group such as an alkyl, alkenyl, alkynyl or aryl moiety.

Compounds of Formula I which are substituted with a basic group may exist as salts formed through acid addition. The acid addition salts are formed from a compound of Formula I and a pharmaceutically acceptable inorganic acid, including but not limited to hydrochloric, hydrobromic, hydroiodic, sulfuric, phosphoric, or an organic acid such as p-toluenesulfonic, methanesulfonic, acetic, benzoic, citric, malonic, fumaric, maleic, oxalic, succinic, sulfamic, or tartaric. Thus, examples of such pharmaceutically acceptable salts include chloride, bromide, iodide, sulfate, phosphate, methanesulfonate, citrate, acetate, malonate, fumarate, sulfamate, and tartrate.

Certain compounds of Formula I, and their salts, may also exist in the form of solvates with water, for example hydrates, or with organic solvents such as methanol, ethanol or acetonitrile to form, respectively, a methanolate, ethanolate or acetonitrilate. The present invention includes each solvate and mixtures thereof.

In addition, a compound of Formula I, or its salt or solvate, may exhibit polymorphism. The present invention also encompasses any such polymorphic form.

Certain compounds of Formula I may contain one or more chiral centers and exist in different optically active forms. When compounds of Formula I contain one chiral center, the compounds exist in two enantiomeric forms. The present invention includes both enantiomers and mixtures of enantiomers such as racemic mixtures. The enantiomers may be resolved by methods known to those skilled in the art, for example, by formation of diastereoisomeric salts which may be separated by crystallization, gas-liquid or liquid chromatography, selective reaction of one enantiomer with an enantiomer-specific reagent. It will be appreciated that where the desired enantiomer is converted into another chemical entity by a separation technique, then an additional step is required to form the desired enantiomeric form. Alternatively, specific enantiomers may be synthesized by asymmetric synthesis using optically active reagents, substrates, catalysts or solvents, or by converting one enantiomer into the other by asymmetric transformation.

Certain compounds of Formula I may also exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Formula I and mixtures thereof.

Certain compounds of Formula I may exist in zwitterionic form and the present invention includes each zwitterionic form of compounds of Formula I and mixtures thereof.

The compounds of this invention can also exist as tautomers; therefore the present invention also includes all tautomeric forms.

The compounds of Formula I are useful in the inhibition of HIV integrase, the prevention or treatment of infection by the human immunodeficiency virus and the treatment of consequent pathological conditions such as AIDS or ARC. The treatment involves administering to a patient, in need of such treatment, a compound of Formula I, or a pharmaceutically acceptable salt, solvate or prodrug thereof, or a pharmaceutical composition comprising a pharmaceutical carrier and a therapeutically effective amount of a compound of the present invention, or a pharmaceutically acceptable salt, solvate or prodrug therefor.

Treatment extends to prophylaxis as well as established infections or symptoms. This includes initiating treatment pre- and post-exposure to the virus. In addition, the present invention can be administered in conjunction with other anti-HIV agents (HIV protease inhibitors, nucleoside reverse transcriptase inhibitors, non-nucleoside reverse transcriptase inhibitors, and HIV-entry inhibitors), immunomodulators, antiinfectives and/or vaccines.

The compounds of the present invention are also useful in the preparation and execution of screening assays for antiviral compounds. Further, the compounds of the present invention are useful in establishing or determining the binding site of other antiviral compounds to HIV integrase, for example, by competitive inhibition.

The compounds of the present invention may be administered orally, parenterally (including subcutaneous injections, intravenous, intramuscular, intrasternal injection or infusion techniques), by inhalation spray or rectally, in dosage unit formulations containing conventional non-toxic pharmaceutically acceptable carriers, adjuvants and vehicles.

This invention also provides a pharmaceutical composition for use in the above described therapeutic method. A pharmaceutical composition of the present invention comprises an effective amount of a compound of Formula I in association with a pharmaceutically acceptable carrier, excipient or diluent.

The active ingredient in such formulations comprises from 0.1 percent to 99.9 percent by weight of the formulation. By "pharmaceutically acceptable" it is meant that the carrier, diluent or excipient must be compatible with the other ingredients of the formulation and not deleterious to the recipient thereof.

The present pharmaceutical compositions are prepared by known procedures using well known and readily available ingredients. The compositions of this invention may be formulated so as to provide quick, sustained or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, beadlets, lozenges, sachets, elixirs, suspensions, emulsions, solutions, syrups, aerosols, (as a solid or in a liquid medium), soft and hard gelatin capsules, suppositories, sterile injectable solutions, sterile packaged powders and the like.

The compounds can be administered by a variety of routes including oral, rectal, transdermal, subcutaneous, intravenous, intramuscular and intranasal.

When administered orally, these compositions are prepared according to techniques well-known in the art of pharmaceutical formulation. For oral administration, the compound is typically formulated with excipients such as binders, fillers, lubricants, extenders, diluents, disintegration agents and the like as are known in the art.

For parenteral administration, the compound is formulated in pharmaceutically acceptable non-toxic, parenterally-acceptable diluents or solvents, such as mannitol, 1,3-butanediol, water, 5 percent dextrose, Ringer's solution or isotonic sodium chloride solution, or suitable dispersing or wetting and suspending agents, such as sterile, bland, fixed oils, including synthetic mono- or diglycerides, and fatty acids, including oleic acid.

A compound of the present invention, or a salt or solvate thereof, can be formulated in unit dosage formulations comprising a dose between about 0.1 mg and about 1000 mg, or more, according to the particular treatment involved. An example of a unit dosage formulation comprises 5 mg of a compound of the present invention in a 10 mL sterile glass ampoule. Another example of a unit dosage formulation comprises about 10 mg of a compound of the present invention as a pharmaceutically acceptable salt in 20 mL of isotonic saline contained in a sterile ampoule.

The compounds of the present invention can also be administered to humans in a dosage range of 1 to 100 mg/kg body weight in divided doses. One preferred dosage range is 1 to 20 mg/kg body weight orally in divided doses. It will be understood, however, that the specific dose level and frequency of dosage for any particular patient may be varied and will depend upon a variety of factors including the activity of the specific compound employed, the metabolic stability and length of action of that compound, the route of administration, the age, body weight, general health, sex, diet, mode and time of administration, rate of excretion, drug combination, the severity of the particular condition, and the host undergoing therapy.

General methods useful for the synthesis of compounds embodied in this invention are shown below. The preparations shown below are disclosed for the purpose of illustration and are not meant to be interpreted as limiting the processes to make the compounds by any other methods. It will be appreciated by those skilled in the art that a number of methods are available for the preparation of the compounds of the present invention as provided by Formula I.

Formula I compounds can be prepared by processes which include processes known in the chemical art for the production of structurally analogous compounds or by a novel process described herein. A process for the preparation of a compound of Formula I (or a pharmaceutically acceptable salt thereof) and novel intermediates for the manufacture of a compound of Formula I, as defined above, provide further features of the invention and are illustrated by the following procedures in which the meanings of the generic radicals are as defined above, unless otherwise specified. It will be recognized that it may be preferred or necessary to prepare a compound of Formula I in which a functional group is protected using a conventional protecting group, and then to remove the protecting group to provide the compound of Formula I.

Thus, there is provided a process for preparing a compound of Formula I (or a pharmaceutically acceptable salt thereof) as provided in any of the above descriptions which is selected from any of those described in the examples, including the following.

The compounds of the present invention can be synthesized according to the following schemes. Schemes I-III represent general methods for the synthesis of the compounds. In Scheme I, an appropriately substituted amine, I-1, can be acylated under standard amide bond forming conditions to yield I-3. Methods for this type of transformation are described, in Jerry March, Advanced Organic Chemistry, 3$^{rd}$ edition, John Wiley & Sons, 1985. The acetylamide I-3 can be condensed with dimethyl oxalate in the presence of a base such as NaOMe or LiHMDS. In the final step of the sequence, I-5 can be treated with and aldehyde, I-6, and an amine, I-7, to deliver the desired product I-8.

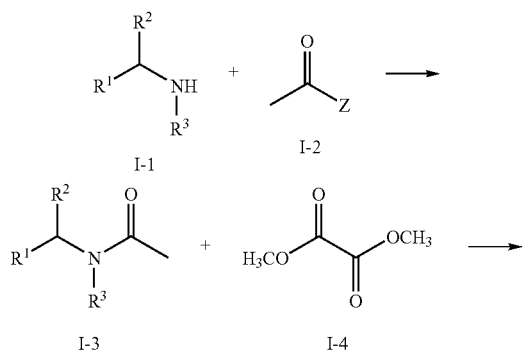

Scheme I

Scheme II illustrates an alternative synthesis. In this route, amine I-1 can be coupled to II-1 using standard amide bond forming methods. The product of this reaction is II-2 which can be converted into I-5 by methanolysis of the dioxalane ring system and the resulting product carried on to the final product in a manner similar to that in Scheme I. In scheme III, compound II-2 can be synthesized as before, but instead of forming intermediate I-5 it can be converted directly to I-8 according to the equation.

In Scheme IV, a substituted benzoic acid derivative can be coupled with amine IV-2 using standard amide bond forming methods to yield IV-3. This intermediate can be reduced to the corresponding benzylic amine, IV-4, which can be coupled to I-2. Intermediate IV-5 can then be condensed with dimethyl oxalate under basic conditions resulting in ketoacid IV-6. The final product can be delivered by treating IV-6 with paraformaldehyde and amine I-7 in acetic acid at elevated temperature.

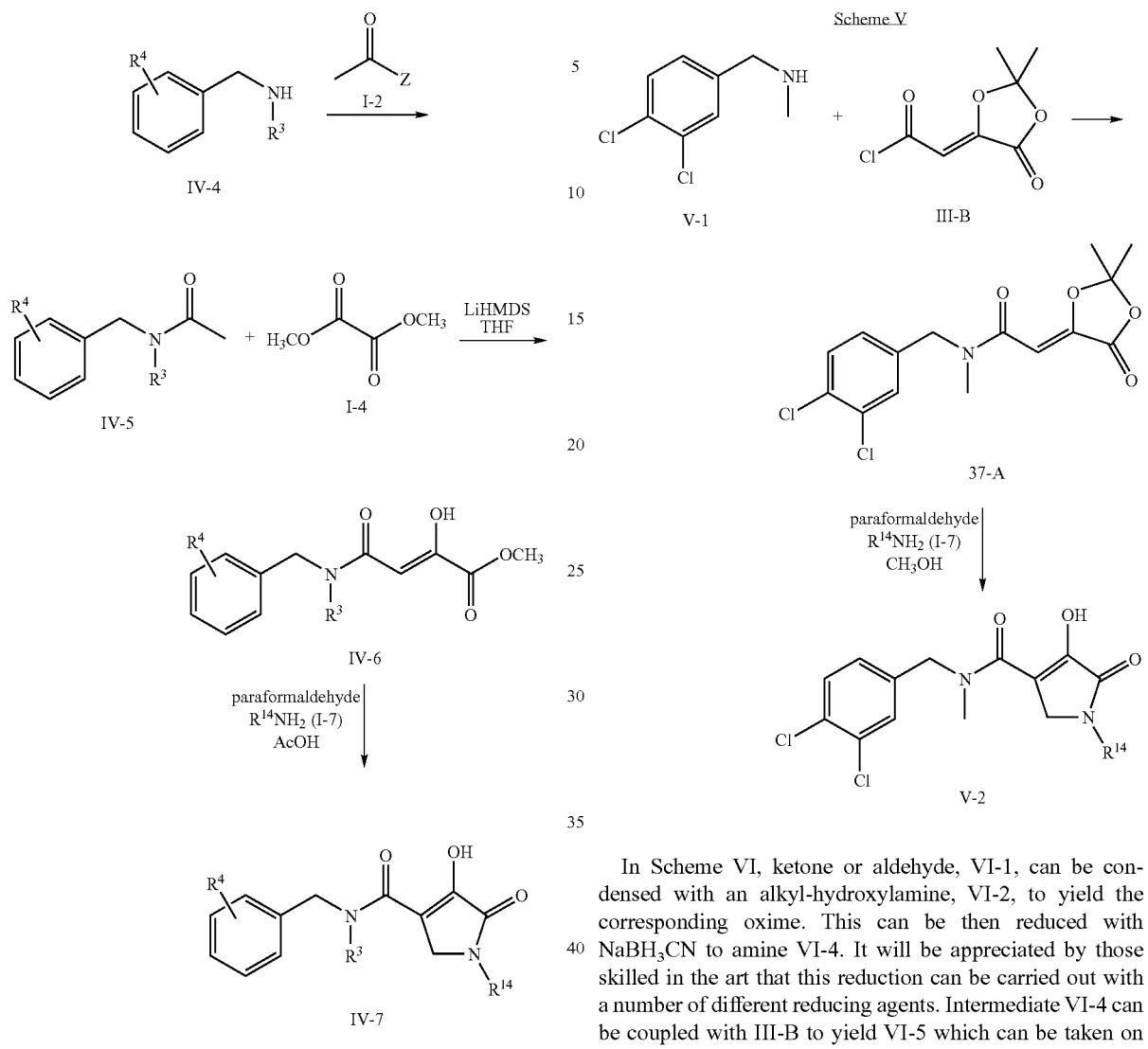

In Scheme V, (3,4-dichloro-benzyl)-methylamine, V-1, can be coupled to III-B to yield Compound 37-A. This compound can then be treated with paraformaldehyde and amine I-7 resulting in V-2.

In Scheme VI, ketone or aldehyde, VI-1, can be condensed with an alkyl-hydroxylamine, VI-2, to yield the corresponding oxime. This can be then reduced with $NaBH_3CN$ to amine VI-4. It will be appreciated by those skilled in the art that this reduction can be carried out with a number of different reducing agents. Intermediate VI-4 can be coupled with III-B to yield VI-5 which can be taken on to VI-7 by two alternative routes. In one, VI-5 can be first treated with methanol to yield the corresponding methyl ester, VI-6, which can be converted to VI-7 as described previously. In the alternative procedure VI-5 can be treated with paraformaldehyde and I-7 as described in Scheme III.

Scheme VI

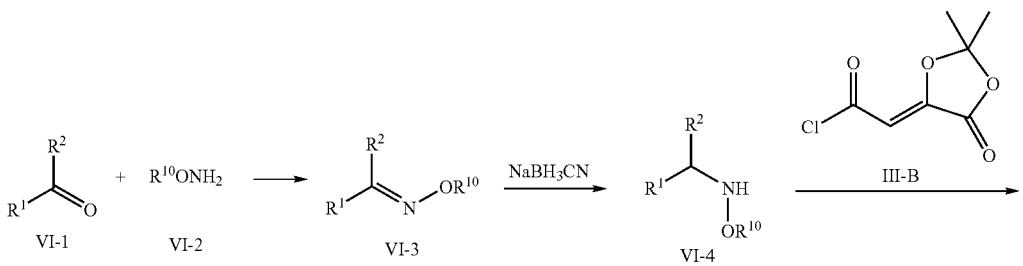

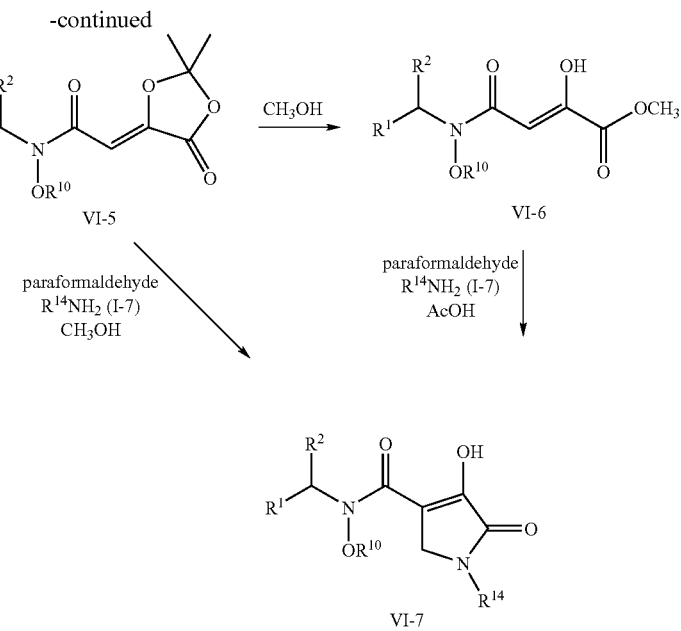

In Scheme VII, amine VII-2 can be attached to an aldehyde-functionalized polystyrene resin (4-formyl-3-methoxy-phenoxymethyl functionalized polystyrene), VII-1, via reductive amination using methodology well known in the art. This intermediate can be coupled to acid, III-A using standard amide bond forming reaction conditions. Intermediate VII-4 can be treated with I-6 and I-7 to yield VII-5. The final product can be cleaved from the resin under acidic conditions to yield product VII-6.

Scheme VII

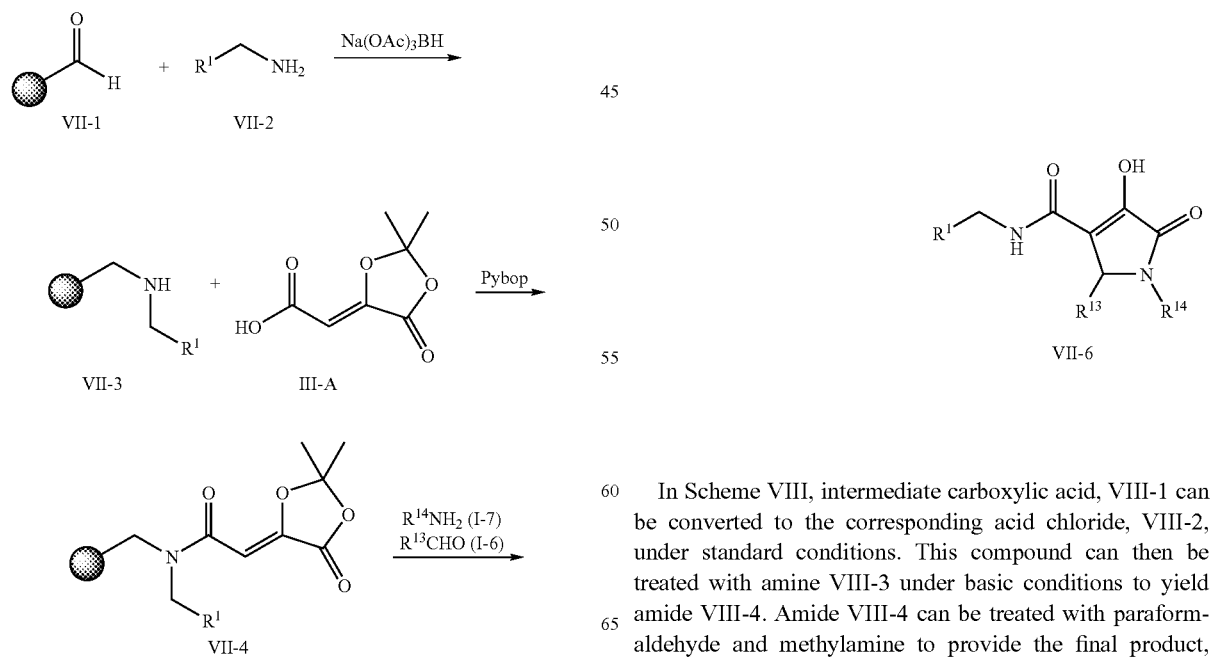

In Scheme VIII, intermediate carboxylic acid, VIII-1 can be converted to the corresponding acid chloride, VIII-2, under standard conditions. This compound can then be treated with amine VIII-3 under basic conditions to yield amide VIII-4. Amide VIII-4 can be treated with paraformaldehyde and methylamine to provide the final product, VIII-5.

Scheme VIII

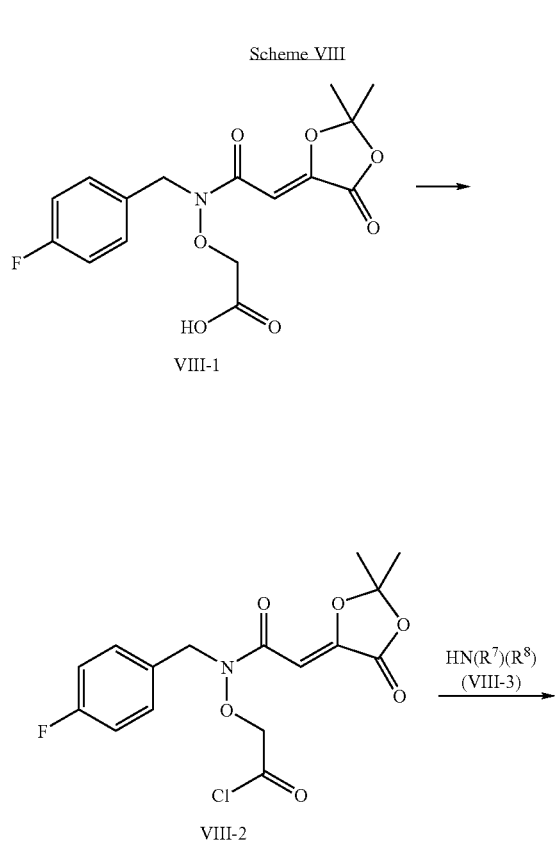

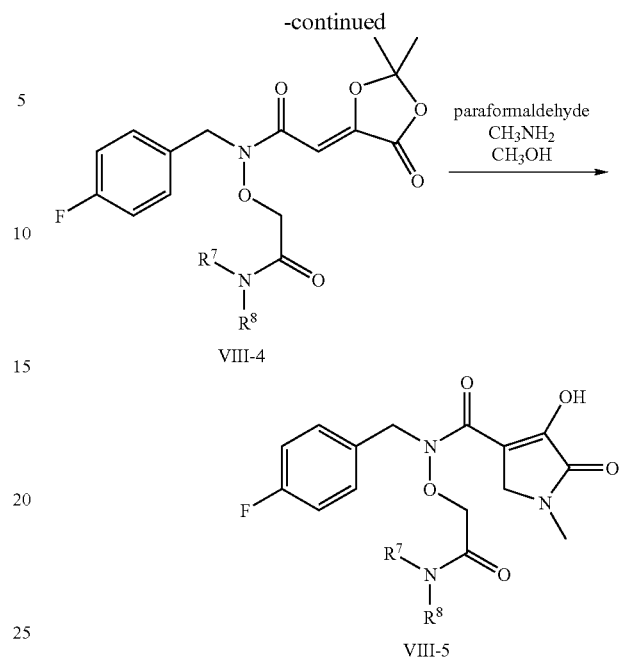

In Scheme IX, compound IX-1 can be synthesized according to the procedure of Heynes R. et al. Bull. Soc. Chim. Fr. (1977) 906–910 and reacted with $CH_3I$ or $Ac_2O$ to yield intermediates IX-2 and IX-5 respectively. Saponification or hydrogenolysis of the benzyl ester can provide carboxylic acids IX-3 and IX-6 which can be coupled with I-1 under amide bond forming reaction conditions. In the final step of the synthesis the methyl enol of XI-4 and the acetyl enol of IX-7 can be removed to deliver the final product IX-8.

Scheme IX

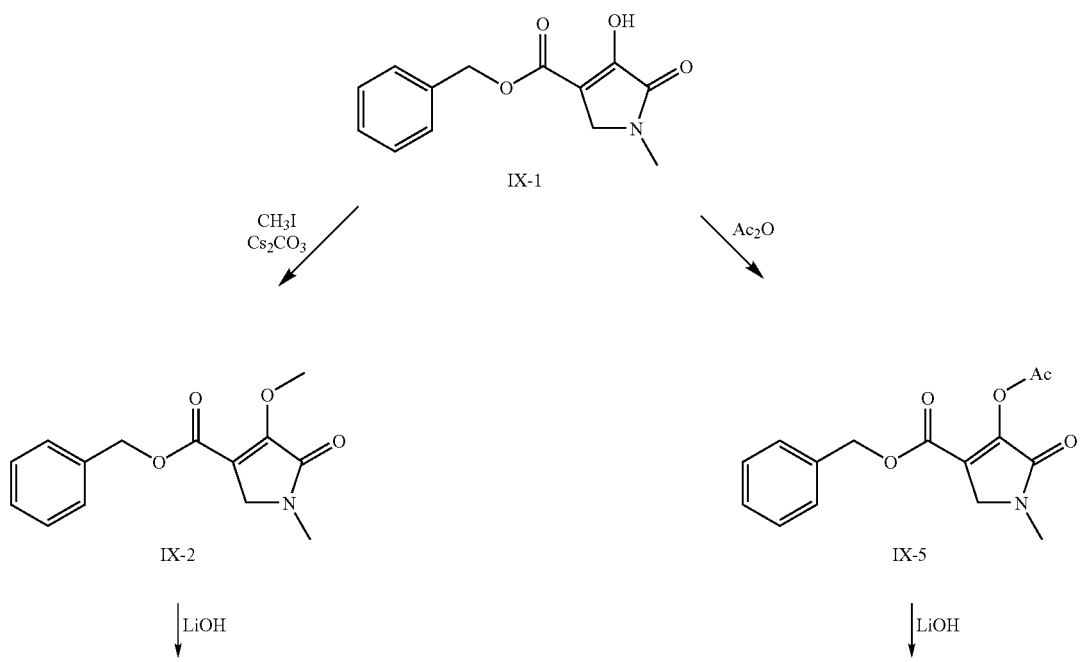

-continued

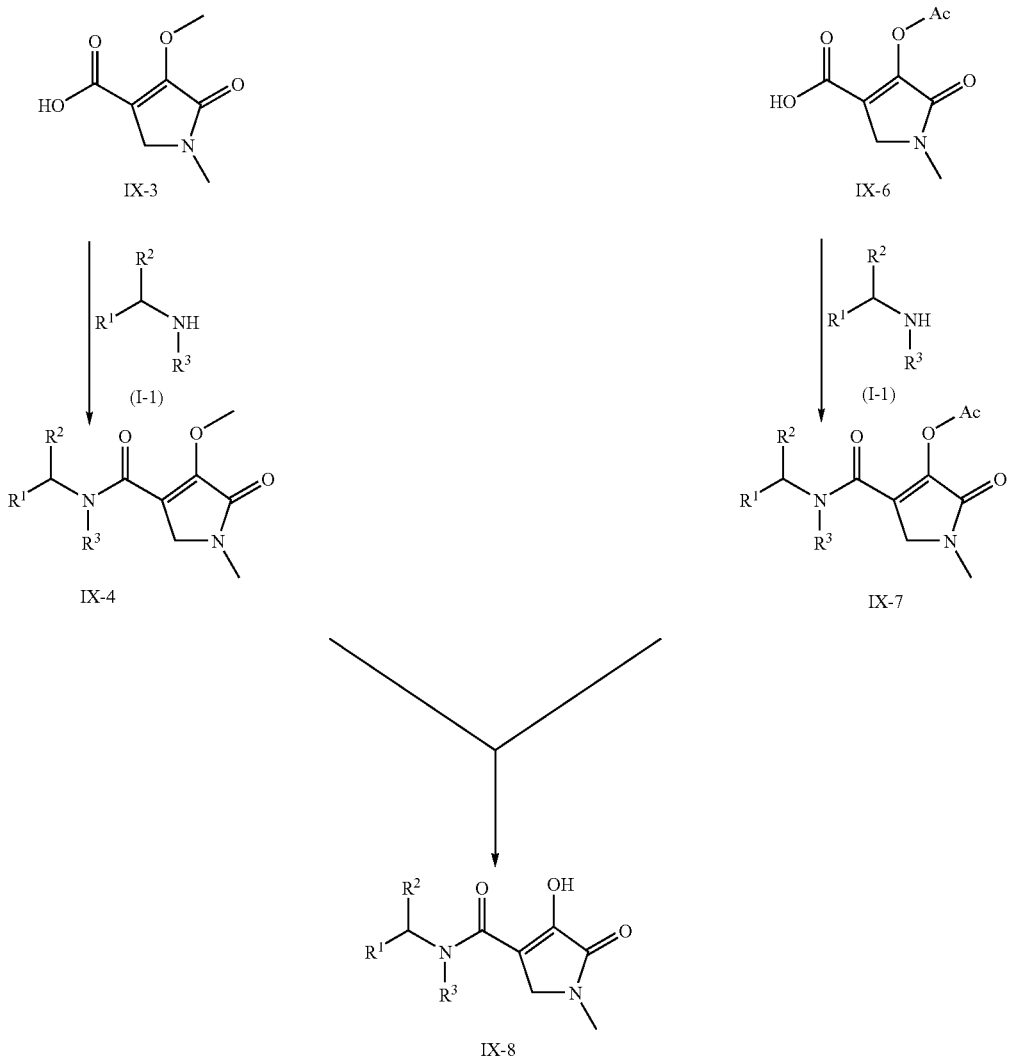

In scheme X, Compound 82-A can be treated with trifluoroacetic acid to effect hydrolysis of the dimethyl-acetal. This then can be reacted with an heterocycle X-1 and a reducing agent such as sodium cyanoborohydride (NaBH₃CN) to yield X-2. It will be understood by those skilled in the art that alternative reducing agents exist which can be used to carry out the same transformation.

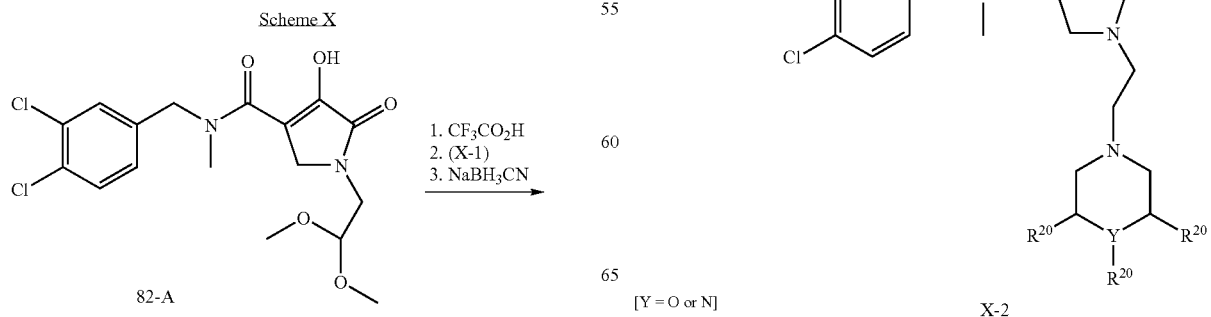

In scheme XI Compound 24 can be reacted with amines, XI-1 and XI-3, using standard amide bond forming reagents to form compounds XI-2 and XI-4 respectively.

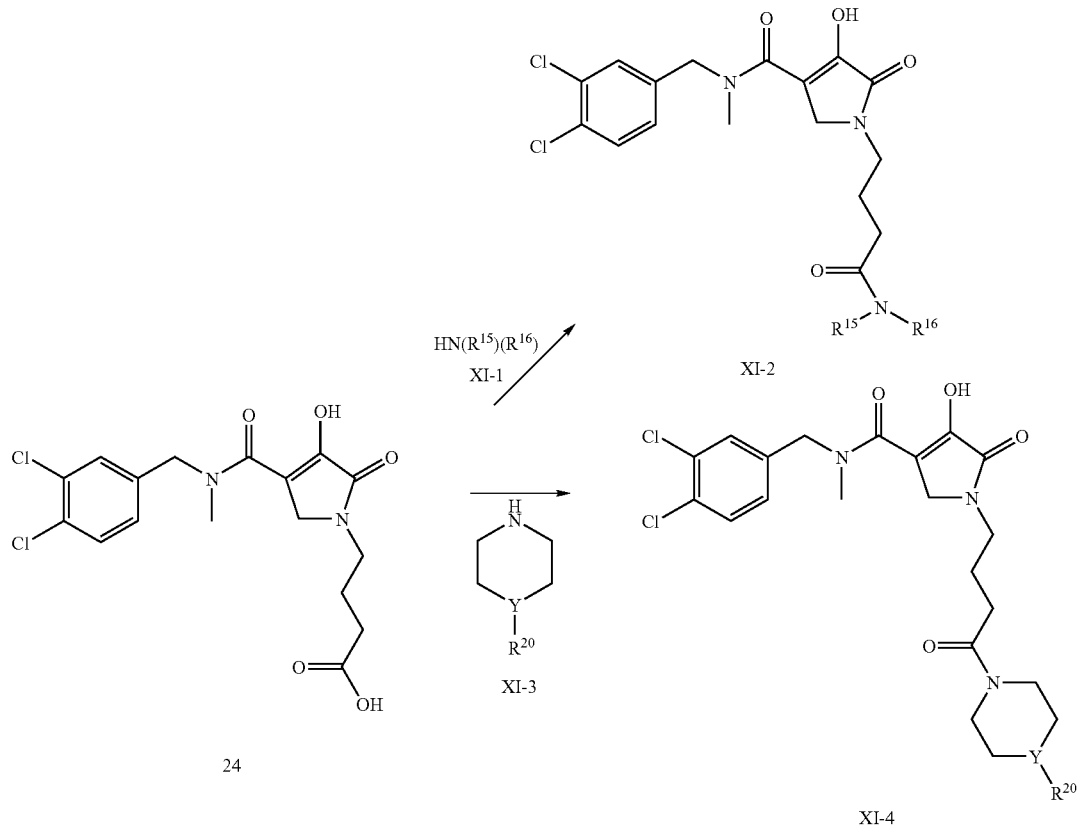

Scheme XI

Another method for the synthesis of compounds of the current invention is illustrated in scheme XII. In this scheme Compound 84-A can be reacted with the corresponding acid chloride XII-1, sulfamoyl chloride XII-3 or sulfonyl chloride XII-5 under basic conditions to deliver compounds XII-2, XII-4 and XII-6 respectively.

Scheme XII

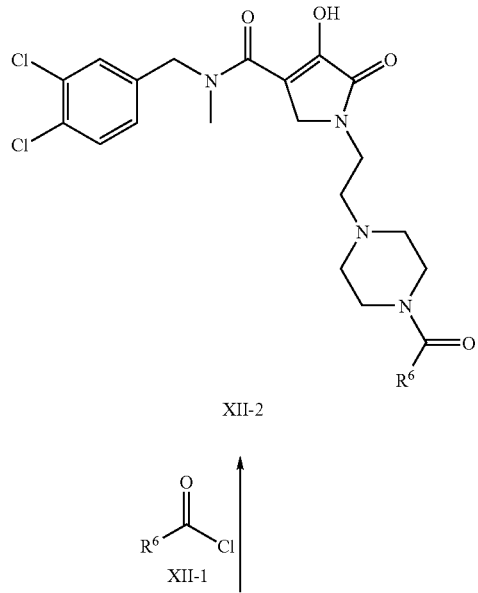

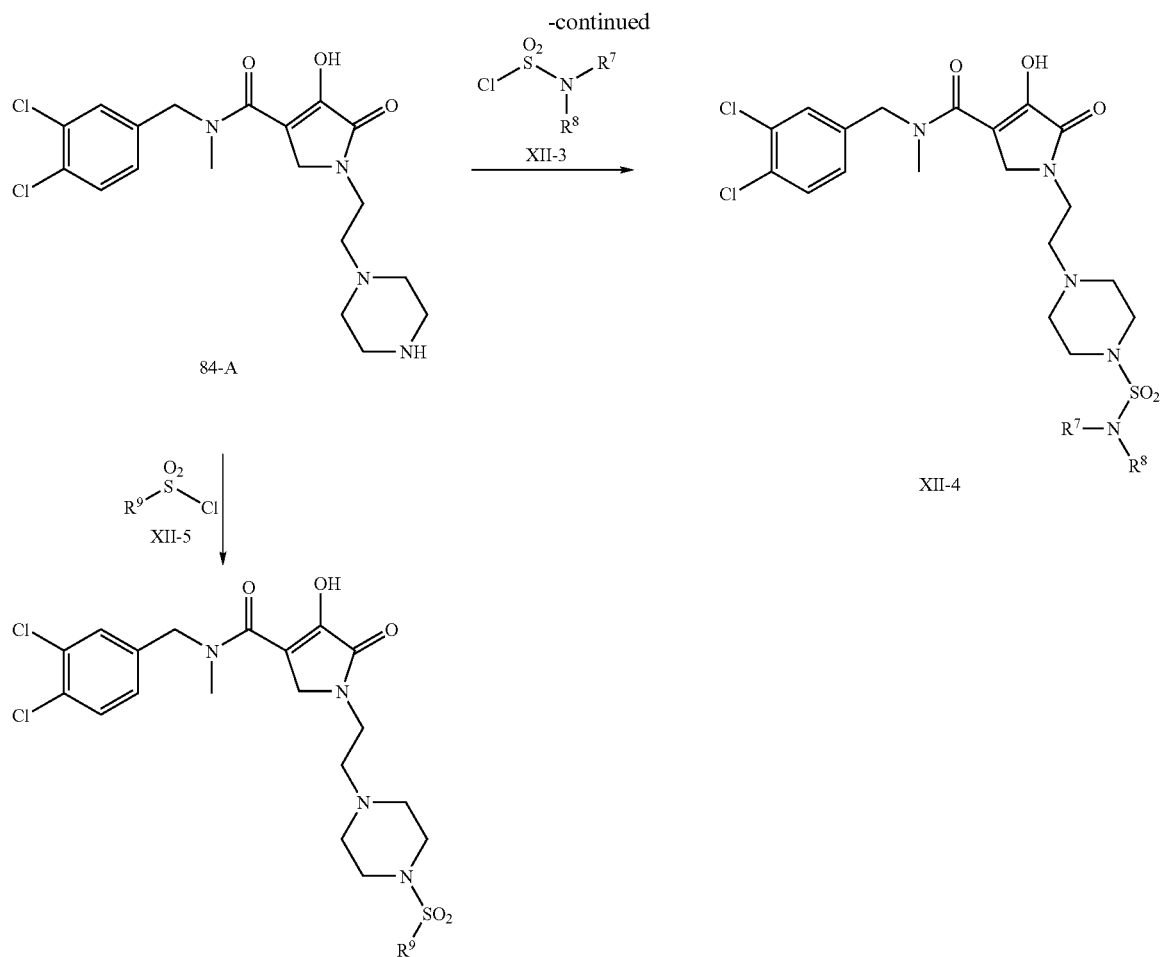
In still another method to synthesize compounds of formula V-2, amine I-7 and paraformaldehyde can be reacted in methanol at elevated temperature to form intermediate XIII-1 as shown in scheme XIII. This intermediate is not isolated but added to a methanolic solution of Compound 37-A to yield compounds of formula V-2.
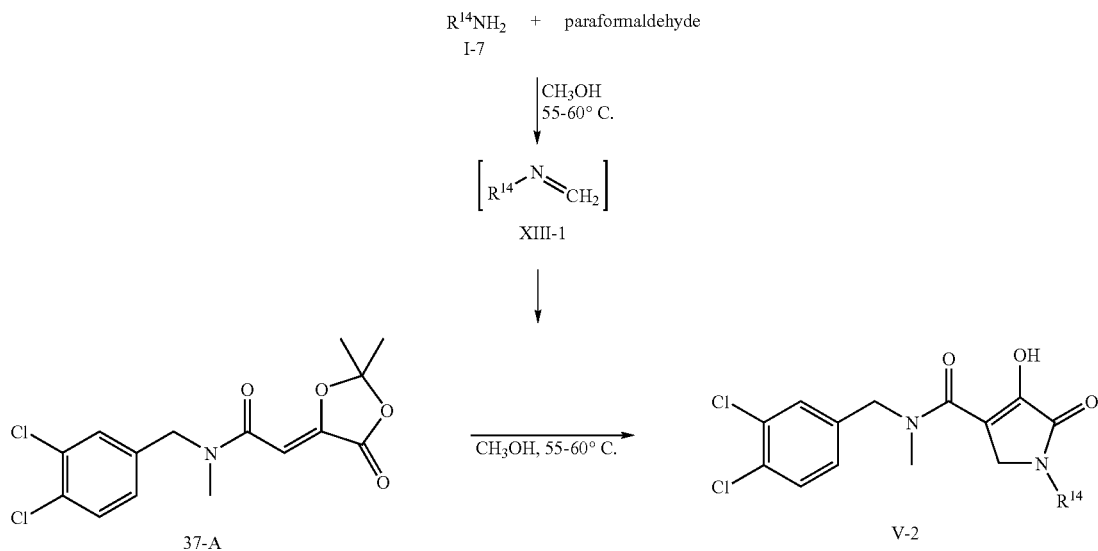

The synthesis of compounds of formula XVI-1 is illustrated in Scheme XIV. In this scheme Compound 93-A can be converted to the corresponding methyl ester, 93-B, as described in the schemes above. Amine I-7 and paraformaldehyde can be condensed to form intermediate XIII-1 which is reacted with 93-B as before to yield XIV-1.

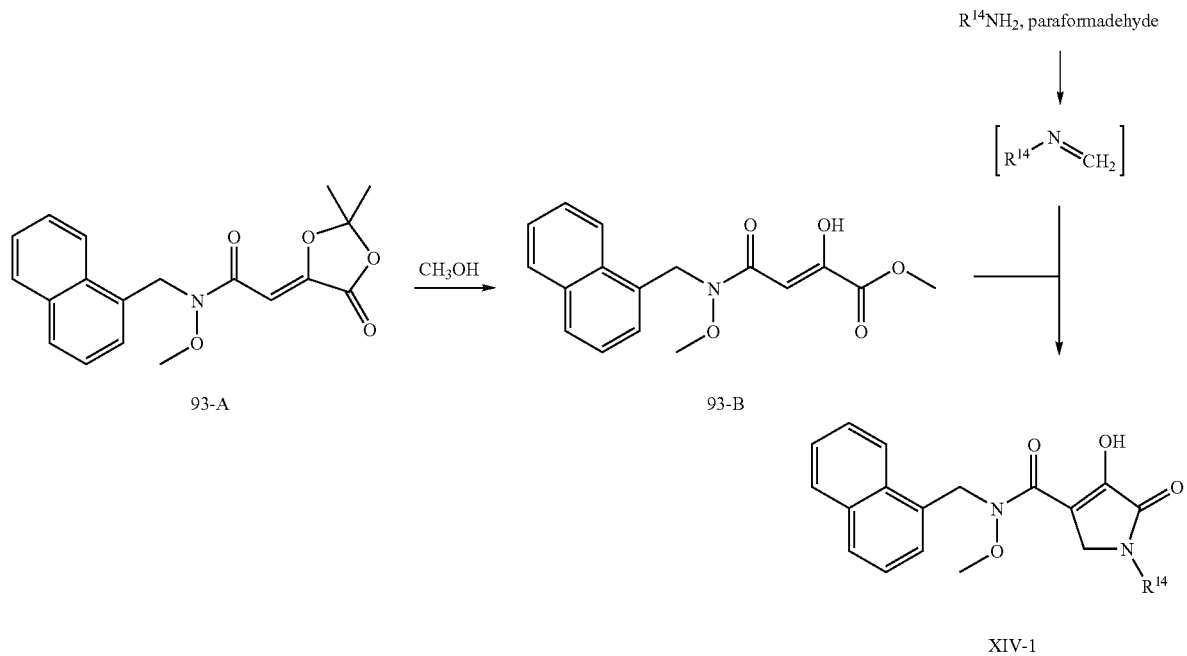

Compounds of this invention can also be synthesized according to the method illustrated in Scheme XV. In this method 2,4-difluorobenzaldehyde can be treated with thiomethoxide to generate 2-methylthio-4-fluorobenzaldehyde which can be converted to compound XV-1 via reductive amination with amine $R^3NH_2$ (IV-2). This intermediate in turn can be acylated with III-B to yield XV-2. Oxidation of the sulfide to the corresponding sulfoxide and sulfone can be carried out under conditions familiar to those skilled in the art. Conversion of XV-3 and XV-4 to the corresponding compounds of formulas XV-5 and XV-6 can be achieved by reaction with amine I-7 and paraformaldehyde as described in previous methods.

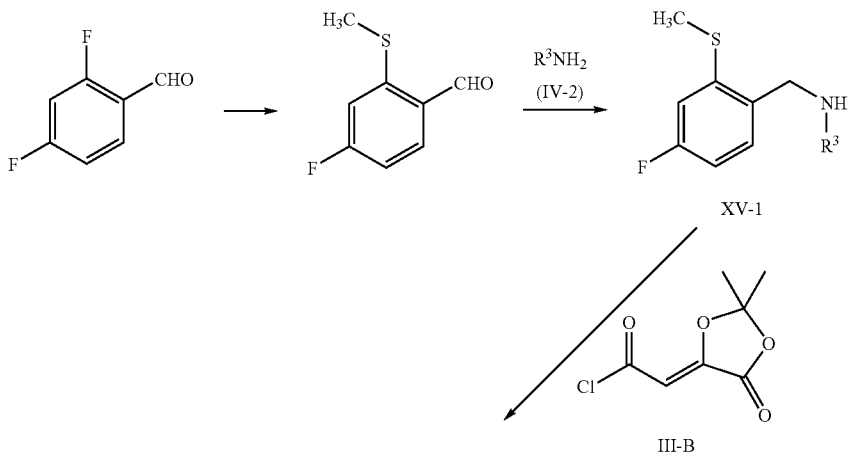

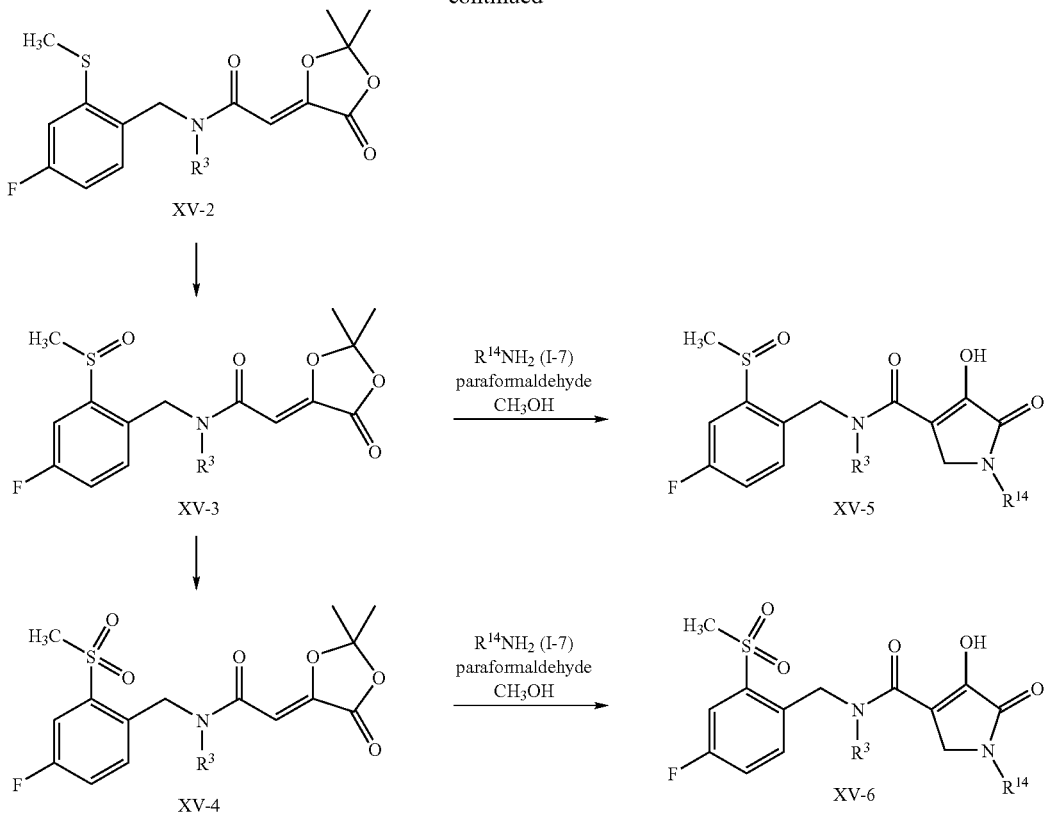

In another method Compound 120-B can be treated with I-7 and paraformaldehyde to yield compounds of formula XVI-1, as illustrated in Scheme XVI.

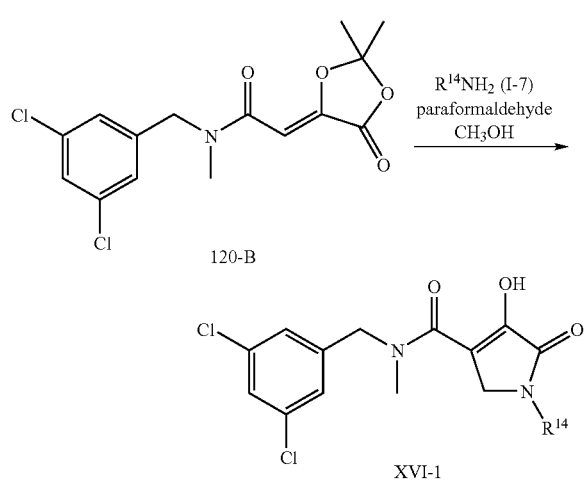

DESCRIPTION OF SPECIFIC EMBODIMENTS

The specific examples that follow illustrate the syntheses of the compounds of the instant invention, and are not to be construed as limiting the invention in sphere or scope. The methods may be adapted to variations in order to produce compounds embraced by this invention but not specifically disclosed. Further, variations of the methods to produce the same compounds in somewhat different manner will also be evident to one skilled in the art.

In the following experimental procedures, all temperatures are understood to be in Centigrade (C) when not specified. The nuclear magnetic resonance (NMR) spectral characteristics refer to chemical shifts ($\delta$) expressed in parts per million (ppm) versus tetramethylsilane (TMS) as reference standard. The relative area reported for the various shifts in the proton NMR spectral data corresponds to the number of hydrogen atoms of a particular functional type in the molecule. In certain cases where the product is isolated as an inseparable mixture of isomers the integration of protons is given in decimal fractions corresponding to the proportion of that particular isomer's protons in the mixture. The nature of the shifts as to multiplicity is reported as broad singlet (bs or br s), broad doublet (bd or br d), broad triplet (bt or br t), broad quartet (bq or br q), singlet (s), multiplet (m), doublet (d), quartet (q), triplet (t), doublet of doublet (dd), doublet of triplet (dt), and doublet of quartet (dq). The solvents employed for taking NMR spectra are acetone-$d_6$ (deuterated acetone), DMSO-$d_6$ (perdeuterodimethylsulfoxide), $D_2O$ (deuterated water), $CDCl_3$ (deuterochloroform) and other conventional deuterated solvents.

The abbreviations used herein are conventional abbreviations widely employed in the art. Some of which are: calcd (calculated); DMSO (dimethylsulfoxide); EDC (1-(3-dimethylaminopropyl)-3-ethylcarbodiimide hydrochloride); EtOAc (ethyl acetate); HOBt (1-hydroxybenzotriazole); HPLC (high-pressure liquid chromatography); LC/MS (liquid chromatography, mass spectroscopy); LDA (lithium diisopropyl amide); LiHMDS (lithium bis(trimethylsilyl) amide); MCPBA (3-chloroperoxybenzoic acid) SiO₂ (silica gel); THF (tetrahydrofuran), TFA (trifluoroacetic acid), Me (methyl), Et (ethyl), Ph (phenyl), tBuOK (potassium tert-butoxide), NaOMe (sodium methoxide), NaOEt (sodium ethoxide), Boc (tert-butoxycarbonyl), and DEAD (diethylazo dicarboxylate).

Method A

Compound A-1: (S)-(+)-2,2-Dimethyl-5-oxo-1,3-dioxolane-4-acetic acid, tert-butyldiphenylsilyl ester

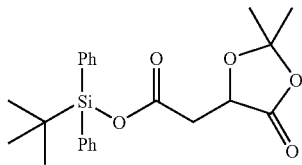

A solution of (S)-(+)-2,2-dimethyl-5-oxo-1,3-dioxolane-4-acetic acid (2.08 g, 11.9 mmol) in dry dichloromethane (20 ml) was treated with triethylamine (1.83 ml, 13.1 mmol) followed by a solution of t-butylchlorodiphenylsilane (3.44 g, 12.5 mmol) in dichloromethane (5 ml) added dropwise over 5 minutes. After 3 hours at 22° C., the reaction mixture was diluted with toluene (250 ml) washed with water, saturated sodium bicarbonate, brine and dried over magnesium sulfate. Evaporation of the solvent under reduced pressure and chromatography of the residue on silica gel (4×12 cm) using a mixture of toluene and ethyl acetate (0–2%) as eluent gave 4.90 g (99% yield) of the title material as a clear oil. ¹H NMR (400 MHz, CDCl₃) δ: 1.13 (s, 9), 1.58 (s, 3), 3.05 (m, 2), 4.79 (dd, 1, J=4, 7), 7.4–7.8 (m, 10).

Compound A-2: 4-Bromo-2,2-dimethyl-5-oxo-1,3-dioxolane-4-acetic acid, tert-butyldiphenylsilyl ester

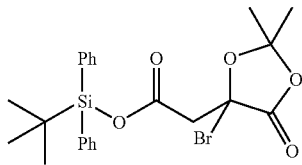

A solution of (S)-(+)-2,2-dimethyl-5-oxo-1,3-dioxolane-4-acetic acid, tert-butyldiphenylsilyl ester (21.65 g, 52.4 mmol) in carbon tetrachloride (160 ml) was treated with N-bromosuccinimide (9.35 g, 52.4 mmol) and 2,2'-azobisisobutyronitrile (200 mg) and the resulting mixture was heated under reflux (bath temperature 85° C.) while irradiating with a 500 watt lamp. After 10 minutes, the reaction mixture was cooled and the succinimide was filtered. The solvent was evaporated under vacuum to give the title bromide as a light yellow oil (~26 g) which was used immediately for the next step. ¹H NMR (400 MHz, CDCl₃) δ: 1.12 (s, 9), 1.41 (s, 3), 1.80 (s, 3), 3.80 (m, 2), 7.3–7.7 (m, 10).

Compound A-3: (Z)-2,2-Dimethyl-5-(tert-butyl-diphenylsilyloxycarbonyl-methylene)-1,3-dioxolan-4-one

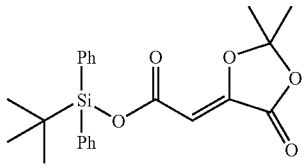

A solution of 4-bromo-2,2-dimethyl-5-oxo-1,3-dioxolane-4-acetic acid, tert-butyldiphenylsilyl ester (~26 g, 52.4 mmol) in dry tetrahydrofuran (160 ml) was cooled to 0° C. and treated dropwise over 5 minutes with 1,8-diazabicyclo[5,4,0]undec-7-ene (12.7 g, 78.8 mmol) and the resulting mixture was stirred at 5° C. for 1.5 hour. The solid formed was filtered and washed with a small amount of tetrahydrofuran. The filtrate was used as such for the next step.

Alternatively, the reaction mixture can be diluted with toluene, washed with water, saturated sodium bicarbonate, brine and dried (magnesium sulfate). Evaporation of the solvent gave an oil which was chromatographed on silica gel using a mixture of toluene and ethyl acetate (0–2%) as eluent. The title ester was obtained as an oil in 30–50% yield. ¹HNMR (400 MHz, CDCl₃) δ: 1.16 (s, 9), 1.76 (s, 6), 5.97 (s, 1), 7.4–7.8 (m, 10).

Compound III-A: (2,2-Dimethyl-5-oxo-[1,3]dioxolan-4-ylidene)-acetic acid

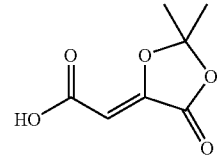

A solution of pure (Z)-2,2 dimethyl-5-(t-butyldiphenylsilyloxy-carbonylmethylene)-1,3-dioxolan-4-one (2.80 g, 6.82 mmol) in tetrahydrofuran (40 ml) was treated at 22° C. with acetic acid (2 ml) followed by 6.8 ml of a 1 M solution of tetrabutylammonium fluoride in tetrahydrofuran. After 15 minutes at 22° C., the reaction mixture was diluted with ethyl acetate, washed with water, brine and dried (magnesium sulfate). The solvent was concentrated under reduced pressure and the residue was triturated with toluene to give 1.00 g (85% yield) of the title compound as a white crystalline material: mp 203–204° C. (dec.). IR (KBr) v max (cm⁻¹): 1805, 1707 and 1662. ¹H NMR (400 MHz, CDCl₃) δ: 1.78 (s, 6), 5.89 (s, 1). Anal. calcd for C₇H₈O₅: C, 48.84; H, 4.68. Found: C, 48.84; H, 4.65.

Preparation of (2,2-Dimethyl-5-oxo-[1,3]dioxolan-4-ylidene)-acetic acid from crude A-3

A solution of the crude (Z)-2,2-dimethyl-5-(tert-butyl-diphenylsilyloxycarbonyl methylene)-1,3-dioxolan-4-one (52.4 mmol) in tetrahydrofuran (200 ml) was treated with acetic acid (13 ml) followed with 50 ml of a 1 M solution of tetrabutylammonium fluoride in tetrahydrofuran. After 15 minutes at 22° C., the reaction mixture was filtered and the filtrate was concentrated in vacuo. Trituration of the residue with toluene gave 6.3 g (70% yield for three steps) of the title material as a white solid (>95% pure by $^1$HNMR).

Method B

Compound B-1: (+)-2,2-Dimethyl-5-oxo-1,3-dioxolane-4-acetic acid, tert-butyldimethylsilyl ester

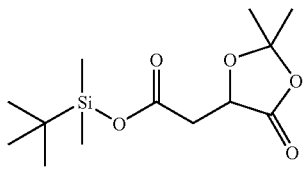

A solution of (S)-(+)-2,2-dimethyl-5-oxo-1,3-dioxolane-4-acetic acid (13.20 g, 75.8 mmol) in N,N-dimethylformamide (25 ml) was treated at 22° C. with imidazole (10.56 g, 0.155 mmol) followed by tert-butyldimethylsilyl chloride (12.0 g, 79.6 mmol) and the resulting mixture was stirred at 22° C. for 18 hours. The reaction mixture was then diluted with toluene (500 ml), washed with water (x3), saturated sodium bicarbonate and brine. After drying (magnesium sulfate), the solvent was evaporated under reduced pressure to give an oil. Distillation under vacuum gave 20.9 g (96% yield) of the title material as a clear oil: Bp 80–90° C./0.1 torr (bulb to bulb distillation, air bath temperature). $^1$H NMR (400 MHz, CDCl$_3$) δ: 0.33 (s, 3), 0.36 (s, 3), 1.00 (s, 9), 1.11 (s, 3), 1.37 (s, 3), 2.72 (m, 2), 4.35 (dd, 1, J=4, 6).

Compound B-2: 4-Bromo-2,2-dimethyl-5-oxo-1,3-dioxolane-4-acetic acid, tertbutyldimethylsilyl ester

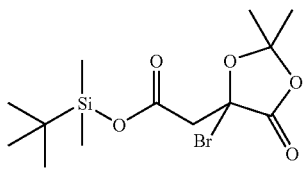

A solution of (S)-(+)-2,2-dimethyl-5-oxo-1,3-dioxolane-4-acetic acid, t-butyldimethylsilyl ester (20.9 g, 72.4 mmol) in carbon tetrachloride (200 ml) was treated with N-bromosuccinimide (14.18 g, 79.6 mmol) and 2,2'-azobisisobutyronitrile (0.30 g) and the resulting mixture was heated under reflux while irradiating with a 500 W lamp. After approximately 5 minutes, a mild exothermic reaction was observed and the mixture was heated for an additional 5 minutes. The reaction mixture was then cooled in an ice bath and the floating succinimide was filtered and washed with a small amount of carbon tetrachloride. The filtrate was used immediately as such for the next step. $^1$H NMR (400 MHz, CDCl$_3$) δ: 0.27 (s, 3), 0.28 (s, 3), 0.94 (s, 9), 1.66 (s, 3), 1.84 (s, 3), 3.62 (m, 2).

Compound B-3: (Z)-2,2-Dimethyl-5-(tert-butyldimethylsilyloxycarbonyl-methylene)-1,3-dioxolane

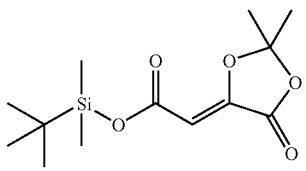

The solution of crude 4-bromo-2,2-dimethyl-5-oxo-1,3-dioxolane-4-acetic acid, tert-butyldimethylsilyl ester (72.4 mmol) in carbon tetrachloride (approximately 220 ml) was cooled to 0–5° C. and treated dropwise over 10 minutes and under vigorous stirring with a solution of 1,8-diazabicyclo[5,4,0]undec-7-ene (12.1 g, 79.6 mmol) in dry tetrahydrofuran (125 ml). A heavy precipitate was formed which gradually became a granular solid. After 1 h, the solid obtained was filtered and washed with a small amount of tetrahydrofuran. The filtrate was concentrated under reduced pressure to give a light orange oil which was used as such for the next step.

Compound III-A: (2,2-Dimethyl-5-oxo-[1,3]dioxolan-4-ylidene)-acetic acid

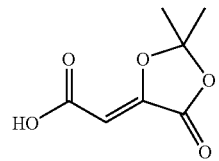

The crude (Z)-2,2-dimethyl-5-(tert-butyldimethylsilyloxycarbonyl-methylene)-1,3-dioxolan-4-one (72.4 mmol) in tetrahydrofuran (50 ml) was treated at 22° C. with acetic acid (13 ml, 0.227 mmol) followed by 73 ml (73.0 mmol) of a 1M solution of tetrabutylammonium fluoride in tetrahydrofuran. After 1 h at 22° C., the reaction mixture was diluted with ethyl acetate (500 ml), washed with water, brine and dried (anhydrous magnesium sulfate). Evaporation of the solvent under reduced pressure and trituration of the residual solid with toluene (50 ml) gave 7.70 g (62% yield for 3 steps) of the title Z-isomer as a white crystalline solid. Concentration of the mother liquors yielded another 0.2 g of a 75:25 mixture of Z and E isomers. Z-Isomer; $^1$H NMR (400 MHz, CDCl$_3$) δ: 1.78 (s, 3), 5.89 (s, 1). E-Isomer: $^1$H NMR (400 MHz, CDCl$_3$) δ: 1.80 (s, 3), 6.03 (s, 1).

Method C

Compound III-B (2,2-Dimethyl-5-oxo-[1,3]dioxolan-4-ylidene)-acetyl chloride

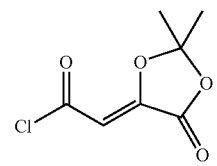

A mixture of (2,2-dimethyl-5-oxo-[1,3]dioxolan-4-ylidene)-acetic acid (0.50 g, 2.9 mmol) in dry dichloromethane (10 ml) was treated at 22° C. with oxalyl chloride (0.5 ml, 5.8 mmol) followed by a trace (capillary) of N,N-dimethylformamide. After 1 h at 22° C., the clear solution was concentrated in vacuo to give 0.55 g (quantitative) of the title acid chloride as a white crystalline solid.

EXAMPLE 1

Compound 1-A: 4-Fluoro-N-methyl-benzamide

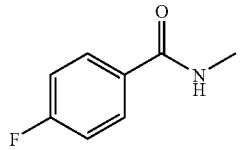

To a solution of 30 mL MeNH$_2$ (40% wt in H$_2$O) was added 139 mL of 1N NaOH. To this was added 130 mL of CH$_2$Cl$_2$ followed by 4-fluorobenzoyl chloride (22 grams, 139 mmol) while the mixture was rapidly stirred. After 1 hour the organic layer was separated, washed with H$_2$O, dried over Na$_2$SO$_4$ and solvent removed under vacuum to yield 20 grams (94% yield) solid. $^1$H NMR (500 MHz, DMSO) δ: 2.78 (d, 3, J=5), 7.28 (t, 2, J=9), 7.91 (m, 2), 8.46 (br s, 1). $^{13}$C NMR (125 MHz, DMSO) δ: 26.13, 114.95, 115.13, 129.49, 129.56, 130.87, 130.90, 162.67, 164.64, 165.46.

Compound 1-B: (4-Fluoro-benzyl)-methyl-amine; hydrochloride

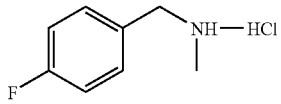

4-Fluoro-N-methyl-benzamide (18.8 grams, 123 mmol) was dissolved in 180 mL of THF. To this was added BF$_3$.Et$_2$O (5.51 mL, 43 mmol) and the resulting mixture heated to reflux for 15 min. The solution was then cooled to −20° C. and BH$_3$.S(CH$_3$)$_2$ (16.5 mL, 174 mmol) added over 10 min. After this the reaction mixture was heated and the solvent removed by distillation for 20 min. The distillation apparatus was replaced with a reflux condenser and the reaction heated to 110° C. for 2 h. After cooling to room temperature 75 mL of 6N HCl was slowly added. After gas evolution had ceased the mixture was heated at reflux for 1 h then allowed to regain room temperature. To this was added 200 mL of 6N NaOH. The mixture was extracted with Et$_2$O. The organic layer was washed with saturated NaCl, dried over Na$_2$SO$_4$, filtered and the solvent removed to yield an oil. The oil was dissolved in Et$_2$O and 30 mL of 4N HCl (dioxane) added resulting in a white ppt. which was filtered to yield 18.9 grams solid (88% yield). $^1$H NMR (500 MHz, DMSO) δ: 2.48 (s, 3), 4.08 (s, 2), 7.26 (m, 2), 7.63 (m, 2), 9.60 (br s, 2). $^{13}$C NMR (125 MHz, DMSO) δ: 31.57, 50.04, 115.24, 115.41, 128.29, 128.32, 132.29, 132.36, 161.24, 163.19.

Compound 1-C: N-(4-Fluoro-benzyl)-N-methyl-acetamide

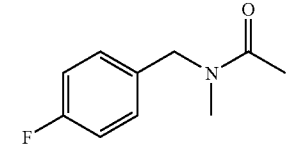

4-Fluoro-benzyl)-methyl-amine; hydrochloride (8.75 grams, 50 mmol) was added to a rapidly stirring mixture of 100 mL CH$_2$Cl$_2$ and 150 mL of 1N NaOH. To this was added acetyl chloride (3.55 mL, 50 mmol) and the resulting mixture stirred overnight. The organic layer was then separated, washed with 1N HCl, dried over Na$_2$SO$_4$, filtered and the solvent removed to yield 2 grams oil (22% yield). HRMS (M+H) calcd for C$_{10}$H$_{14}$FNO: 182.0891; found: 182.0979. $^1$H NMR (500 MHz, DMSO) δ: 2.04 (s), 2.05 (s), 2.77 (s), 2.90 (s), 4.46 (s), 4.53 (s), 7.13–7.28 (m, 4). $^{13}$C NMR (125 MHz, DMSO) δ: 21.16, 21.47, 32.85, 35.24, 48.81, 52.40, 114.97, 115.14, 115.30, 115.47, 128.52, 128.59, 129.38, 128.44, 133.58, 133.60, 134.01, 134.03, 160.23, 160.33, 162.16, 162.26, 169.70, 169.84.

Compound 1-D: 3-[(4-Fluoro-benzyl)-methyl-carbamoyl]-2-hydroxy-acrylic acid methyl ester N-(4-Fluoro-benzyl)-N-methyl-acetamide (3.6 grams, 20 mmol) was dissolved in 20 mL of THF and cooled to −78° C. To this was added 40 mL of 1M LiHMDS (in THF) and the resulting solution stirred for 30 min. Next dimethyl oxalate (3.5 grams, 30 mmol) dissolved in 8 mL of THF is added and the reaction stirred for 2 h at −78° C., then warmed to 0° C. and stirred an additional 30 min. To this was added 1N HCl and the mixture then extracted with EtOAc. The organic layer was washed with saturated NaCl, dried over Na$_2$SO$_4$, filtered and the solvent removed. The crude product was purified by column chromatography (4×4 cm SiO$_2$, 80:20 Hex/EtOAc) to yield 4.3 grams solid (80% yield). HRMS (M+H) calcd for C$_{13}$H$_{15}$NO$_4$F: 268.0985; found: 268.0983. Anal calcd for C$_{13}$H$_{14}$NO$_4$F: C, 58.42; H, 5.28; N, 5.24. found: C, 58.48; H, 5.21; N, 5.26. $^1$H NMR and $^{13}$C NMR show a mixture of rotamers at room temperature. $^1$H NMR (500 MHz, CDCl$_3$) δ: 3.00 (s), 3.86 (s), 3.89 (s), 4.55 (s), 6.29 (s), 6.31 (s), 7.00–7.24 (overlapping m, 4). $^{13}$C NMR δ; 33.43, 34.79, 49.97, 52.63, 52.97, 93.27, 93.55, 115.63, 115.80, 115.95, 116.13, 128.36, 128.42, 129.71, 129.78, 131.32, 132.03, 159.70, 161.40, 163.25, 163.35, 170.93, 171.16.

33

Compound 1: 4-Hydroxy-1-methyl-5-oxo-2,5-dihydro-1H-pyrrole-3-carboxylic acid (4-fluoro-benzyl)-methyl amide

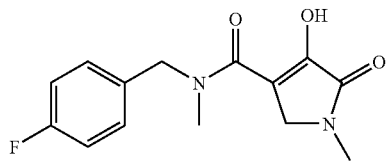

To 1.6 mL of ethanol at 60° C. was added paraformaldehyde (46.6 mg, 1.6 mmol. eq. of formaldehyde) and 0.78 mL of 2 M (THF) $CH_3NH_2$ and the resulting mixture stirred for 5 min. Compound 1-D (41.5 mg, 1.6 mmol) was added and the reaction stirred for 1 hr. The reaction mixture was then diluted with $H_2O$ and extracted with EtOAc. The organic layer was separated, washed with satd NaCl, dried over $Na_2SO_4$, filtered and the solvent removed to yield crude product, which was purified by preparative TLC ($SiO_2$, 20% EtOH/$CH_2Cl_2$). HRMS [M+H] calcd for $C_{14}H_{16}FN_2O_3$: 279.1145. Found: 279.1148. $^1H$ NMR ($CDCl_3$, 500 MHz) δ: 2.99 (s, 3), 3.03 (s, 3), 4.13 (s, 2), 4.60 (s, 2), 6.98–7.23 (overlapping m, 4).

EXAMPLE 2

Compound 2: 1-[2-(4-Chloro-phenyl)ethyl]-4-hydroxy-5-oxo-2,5-dihydro-1H-pyrrole-3-carboxylic acid (4-fluoro-benzyl)-methyl amide

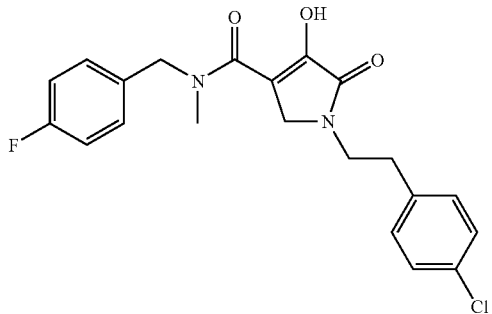

3-[(4-Fluoro-benzyl)-methyl-carbamoyl]-2-hydroxy-acrylic acid methyl ester (Compound 1-D) was treated with paraformaldehyde and 2-(4-chlorophenyl)-ethylamine as described in the preparation of Compound 1. HRMS (M–H) calcd for $C_{21}H_{19}ClFN_2O_3$; 401.1068. found: 401.1080. $^1H$ NMR (500 MHz, $CDCl_3$)δ: 2.90 (t, 2, j=7), 2.95 (s, 3), 3.72 (t, 2, J=7), 3.95 (s, 2), 4.57 (s, 2), 7.03–7.26 (overlapping m, 8). $^{13}C$ NMR (125 MHz, $CDCl_3$) δ: 33.92, 34.45, 44.42, 49.37, 51.46, 108.49, 118.91, 128.87, 129.22, 129.98, 131.99, 132.67, 136.60, 154.21, 161.42, 163.37, 164.51, 166.31.

34

EXAMPLE 3

Compound 3: 1-[2-(Chloro-phenyl)-ethyl]-4-hydroxy-5-oxo-2,5-dihydro-1H-pyrrole-3-carboxylic acid (4-fluoro-benzyl)-methyl amide

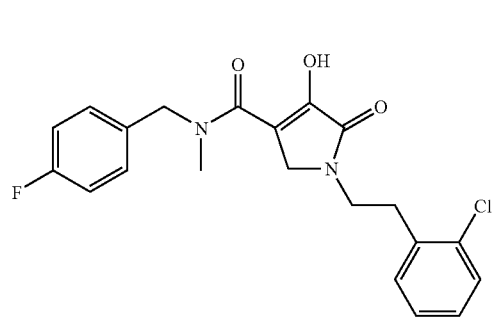

3-[(4-Fluoro-benzyl)-methyl-carbamoyl]-2-hydroxy-acrylic acid methyl ester (Compound 1-D) was treated with paraformaldehyde and 2-(2-chlorophenyl)-ethylamine as described in the preparation of Compound 1. HRMS (M+H) calcd for $C_{21}H_{21}ClFN_2O_3$: 403.1225. found: 403.1237. $^1H$ NMR (500 MHz, $CDCl_3$) δ: 2.96 (s, 3), 3.05 (t, 2, J=7), 3.75 (t, 2, J=7), 3.99 (s, 2), 4.58 (s, 2), 7.01–7.34 (overlapping m, 8). $^{13}C$ NMR (125 MHz, $CDCl_3$) δ: 32.37, 34.52, 42.90, 49.36, 51.47, 109.38, 115.66, 115.83, 127.18, 128.37, 129.26, 129.32, 129.67, 130.92, 132.13, 132.15, 134.01, 135.79, 152.71, 161.37, 163.33, 164.91, 166.11.

EXAMPLE 4

Compound 4: 4-Hydroxy-5-oxo-1-(2-thiophen-2-yl-ethyl)-2,5-dihydro-1H-pyrrole-3-carboxylic acid (4-fluoro-benzyl)-methyl-amide

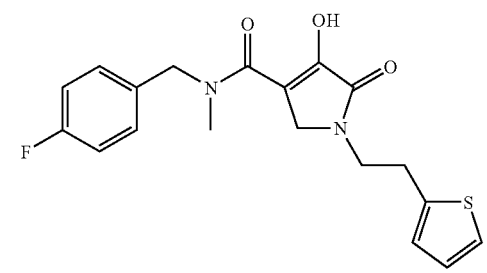

3-[(4-Fluoro-benzyl)-methyl-carbamoyl]-2-hydroxy-acrylic acid methyl ester (Compound 1-D) was treated with paraformaldehyde and 2-thiophen-2-yl-ethylamine as described in the preparation of Compound 1. HRMS (M–H) calcd for $C_{19}H_{18}FN_2O_3S$: 373.1022. found: 373.1029. $^1H$ NMR (500 MHz, $CDCl_3$) δ: 2.95 (s, 3), 3.14 (t, 2, J=7), 3.76 (t, 2, J=7), 3.97 (s, 2), 4.57 (s, 2), 6.81–7.21 (overlapping m, 7). $^{13}C$ NMR (125 MHz, $CDCl_3$) δ: 28.76, 34.49, 44.93, 49.46, 51.47, 109.48, 115.65, 115.82, 124.20, 125.59, 127.15, 129.28, 129.34, 132.12, 132.14, 140.34, 152.72, 161.37, 163.33, 164.94, 166.11.

EXAMPLE 5

Compound 5: 1-[2-(2-Fluoro-phenyl)-ethyl]-4-hydroxy-5-oxo-2,5-dihydro-1H-pyrrole-3-carboxylic acid (4-fluoro-benzyl)-methyl-amide

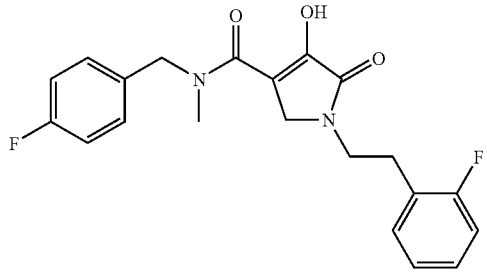

3-[(4-Fluoro-benzyl)-methyl-carbamoyl]-2-hydroxy-acrylic acid methyl ester (Compound 1-D) was treated with paraformaldehyde and 2-(2-fluoro-phenyl)-ethylamine as described in the preparation of Compound 1. HRMS (M+H) calcd for $C_{21}H_{21}N_2F_2O_3$: 387.1520. found: 387.1525. $^1$H NMR (500 MHz, CDCl$_3$) δ: 2.96 (overlapping m, 5), 3.75 (t, 2, J=7), 4.02 (s, 2), 4.58 (s, 2), 6.98–7.22 (overlapping m, 8). $^{13}$C NMR (125 MHz, CDCl$_3$) δ: 28.13, 28.14, 34.55, 43.38, 49.34, 51.52, 109.53, 115.31, 115.48, 115.68, 115.85, 124.38, 124.41, 124.87, 124.99, 128.68, 128.75, 129.29, 129.35, 130.96, 130.99, 131.98, 132.01, 152.46, 160.26, 161.40, 162.21, 163.36, 165.04, 166.09.

EXAMPLE 6

Compound 6: 1-[2-(2,4-Dichloro-phenyl)-ethyl]-4-hydroxy-5-oxo-2,5-dihydro-1H-pyrrole-3-carboxylic acid (4-fluoro-benzyl)-methyl-amide

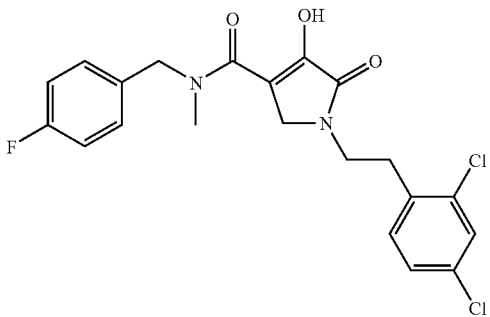

3-[(4-Fluoro-benzyl)-methyl-carbamoyl]-2-hydroxy-acrylic acid methyl ester (Compound 1-D) was treated with paraformaldehyde and 2-(2,4-dichloro-phenyl)-ethylamine as described in the preparation of Compound 1. $^1$H NMR (500 MHz, CDCl$_3$) δ: 2.99 (s, 3), 3.03 (t, 2, J=7), 3.74 (t, J=7), 4.06 (s, 2), 4.60 (s, 2), 7.03–7.37 (overlapping m, 7). $^{13}$C NMR (125 MHz, CDCl$_3$) δ: 31.76, 34.67, 42.95, 49.48, 51.61, 109.74, 115.76, 115.93, 127.53, 129.27, 129.32, 129.53, 131.63, 131.78, 131.80, 133.57, 134.14, 134.65, 152.19, 161.44, 163.40, 165.24, 165.98.

EXAMPLE 7

Compound 7: 4-Hydroxy-5-oxo-1-(2-pyridin-4-yl-ethyl)-2,5-dihydro-1H-pyrrole-3-carboxylic acid (4-fluoro-benzyl)-methyl-amide

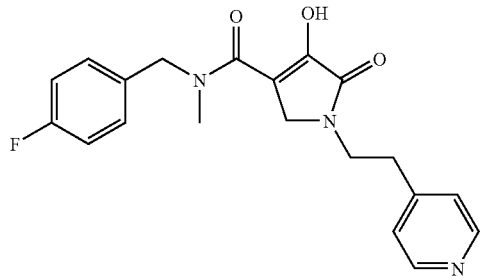

3-[(4-Fluoro-benzyl)-methyl-carbamoyl]-2-hydroxy-acrylic acid methyl ester (Compound 1-D) was treated with paraformaldehyde and 2-pyridin-4-yl-ethylamine as described in the preparation of Compound 1. HRMS (M+H) calcd for $C_{20}H_{21}FN_3O_3$: 370.1567. found: 370.1568. $^1$H NMR (500 MHz, CDCl$_3$) δ: 3.00 (s, 3), 3.23 (t, 2, J=7), 3.90 (t, 2, J=7), 4.20 (s, 2), 4.60 (s, 2), 7.03 (m, 2), 7.21 (m, 2), 7.80 (d, 2, J=6), 8.73 (d, 2, J=6). $^{13}$C NMR (125 MHz, CDCl$_3$) δ: 34.55, 34.63, 42.47, 49.04, 51.55, 109.53, 114.58, 115.74, 115.91, 127.10, 129.30, 129.50, 131.76, 141.92, 153.22, 158.36, 160.92, 161.23, 161.43, 163.40, 165.33, 166.13.

EXAMPLE 8

Compound 8: 4-Hydroxy-5-oxo-1-phenethyl-2,5-dihydro-1H-pyrrole-3-carboxylic acid (4-fluoro-benzyl)-methyl-amide

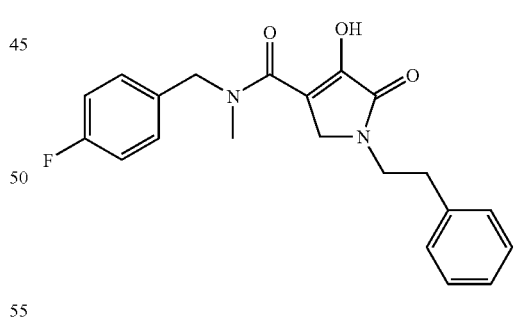

3-[(4-Fluoro-benzyl)-methyl-carbamoyl]-2-hydroxy-acrylic acid methyl ester (Compound 1-D) was treated with paraformaldehyde and 2-phenyl-ethylamine as described in the preparation of Compound 1. HRMS (M+H) calcd for $C_{21}H_{22}FN_2O_3$: 369.1615. found: 369.1625. $^1$H NMR (500 MHz, CDCl$_3$) δ: 2.92 (overlapping m, 5), 3.74 (t, 2, J=7), 3.92 (s, 2), 4.56 (s, 2), 7.01–7.29 (overlapping m, 9). $^{13}$C NMR (125 MHz, CDCl$_3$) δ: 34.45, 34.60, 44.70, 49.42, 51.46, 109.12, 115.66, 115.83, 126.75, 128.63, 128.72, 129.26, 129.33, 132.09, 132.11, 138.18, 153.11, 161.38, 163.34, 164.79, 166.18.

EXAMPLE 9

Compound 9: 1-[2-(4-Fluoro-phenyl)-ethyl]-4-hydroxy-5-oxo-2,5-dihydro-1H-pyrrole-3-carboxylic acid (4-fluoro-benzyl)-methyl amide

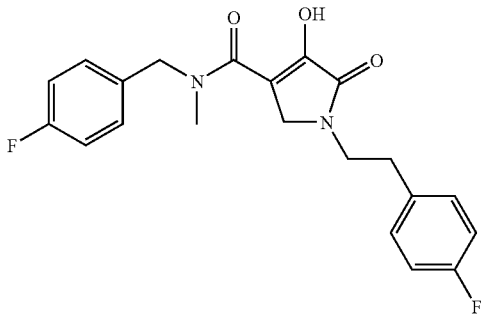

3-[(4-Fluoro-benzyl)-methyl-carbamoyl]-2-hydroxyacrylic acid methyl ester (Compound 1-D) was treated with paraformaldehyde and 2-(4-fluoro-phenyl)-ethylamine as described in the preparation of Compound 1. (HRMS (M−H) calcd for $C_{21}H_{19}F_2N_2O_3$: 385.1364. found: 385.1377. $^1$H NMR (500 MHz, CDCl$_3$) δ: 2.90 (t, 2, J=7), 2.95 (s, 3), 3.71 (t, 2, J=7), 3.95 (s, 2), 4.57 (s, 2), 6.95–7.26 (overlapping m, 8). $^{13}$C NMR (125 MHz, CDCl$_3$) δ: 33.74, 34.48, 44.70, 49.41, 51.47, 108.82, 115.49, 115.66, 115.71, 115.77, 115.89, 129.22, 129.27, 130.04, 130.10, 131.97, 133.72, 153.60, 160.81, 161.42, 162.76, 163.38, 164.71, 166.21.

EXAMPLE 10

Compound 10: 4-Hydroxy-5-oxo-1-(3-phenyl-propyl)-2,5-dihydro-1H-pyrrole-3-carboxylic acid (4-fluoro-benzyl)-methyl-amide

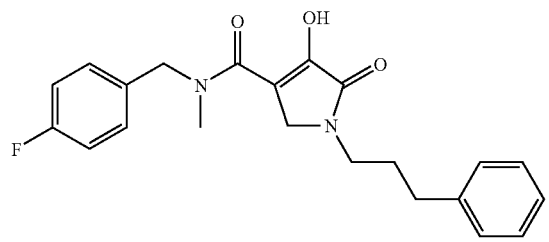

3-[(4-Fluoro-benzyl)-methyl-carbamoyl]-2-hydroxyacrylic acid methyl ester (Compound 1-D) was treated with paraformaldehyde and 3-phenyl-propylamine as described in the preparation of Compound 1. $^1$H NMR (500 MHz, CDCl$_3$) δ: 1.93 (p, 2, J=7), 2.64 (t, 2, J=7), 2.99 (s, 3), 3.53 (t, 2, J=2), 4.10 (s, 2), 4.60 (s, 2), 7.02–7.28 (overlapping m, 9). $^{13}$C (125 MHz, CDCl$_3$) δ: 29.77, 33.05, 34.56, 42.81, 48.79, 51.47, 109.05, 115.66, 115.83, 126.14, 128.30, 128.49, 129.34, 129.40, 132.16, 132.79, 140.88, 152.46, 161.39, 163.34, 165.02, 166.08.

EXAMPLE 11

Compound 11: 4-Hydroxy-1-isopropyl-5-oxo-2,5-dihydro-1H-pyrrole-3-carboxylic acid (4-fluoro-benzyl)-methyl-amide

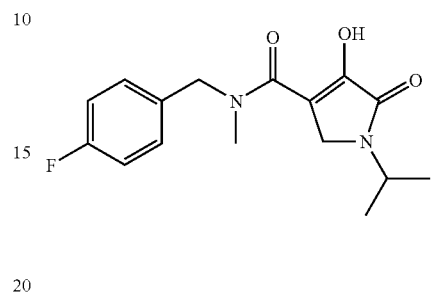

3-[(4-Fluoro-benzyl)-methyl-carbamoyl]-2-hydroxyacrylic acid methyl ester (compound 1-D) was treated with paraformaldehyde and isopropylamine as described in the preparation of Compound 1. $^1$H NMR (500 MHz, CDCl$_3$) δ: 1.23 (d, 6, J=7), 3.02 (s, 3), 4.10 (s, 2), 4.45 (heptet, 1, J=7), 4.62 (s, 2), 7.03 (m, 2), 7.24 (m, 2). $^{13}$C NMR (125 MHz, CDCl$_3$) δ: 20.61, 34.72, 44.09, 44.34, 110.21, 115.57, 115.75, 129.43, 129.50, 132.28, 132.30, 149.92, 161.35, 163.31, 164.76, 165.80.

EXAMPLE 12

Compound 12-A:
N-(3,4-Dichloro-benzyl)-N-methyl-acetamide

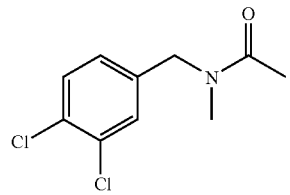

A solution of (3,4-dichlorobenzyl)-methylamine (0.50 g, 2.63 mmol) (Shapiro et al. J. Amer. Chem. Soc., (1959) 81, 3725) in a mixture of tetrahydrofuran (20 ml) and 40% aqueous sodium acetate (10 ml) was cooled to 0–5° C. (ice bath) and treated with a solution of acetyl chloride (0.3 g in tetrahydrofuran) added dropwise over 5 min. After 1 h at 0–5° C., the reaction mixture was diluted with ethyl acetate, washed successively with 1 N hydrochloric acid, saturated sodium bicarbonate, brine and dried (magnesium sulfate). Evaporation of the solvent and distillation of the residue in vacuo gave 0.51 g (83% yield) of the title amide as a clear oil: bp 110–120° C./0.2 torr, (bulb to bulb distillation, air bath temperature). $^1$HNMR 400 MHz (CDCl$_3$) δ (ppm), mixture of rotamers: 2.36 and 2.39 (3H, 2 s, COCH$_3$), 3.16 (3H, s, NCH$_3$), 4.70 and 4.75 (2H, 2 s, NCH$_2$), 7.2–7.7 (3H, m, aromatics). Anal. calcd for $C_{10}H_{11}Cl_2NO$: C, 51.74; H, 4.78; N, 6.03. Found: C, 51.70; H, 4.77; N, 6.04.

Compound 12-B: 3-[(3,4-Dichloro-benzyl-methyl-carbamoyl]-2-hydroxy-acrylic acid methyl ester

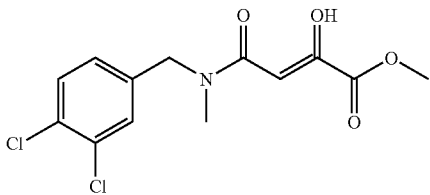

A solution of N-(3,4-dichlorobenzyl)-N-methyl-acetamide (0.83 g, 3.57 mmol) in tetrahydrofuran (15 ml) was cooled to −78° C. and treated dropwise with 7.1 ml (7.1 mmol) of 1M lithium bis(trimethylsilyl)amide in tetrahydrofuran. After 20 min, the mixture was treated dropwise with a solution of dimethyl oxalate (0.63 g, 5.35 mmol) in tetrahydrofuran (3 ml), stirred at −78° C. for 1 h and then at 5° C. for another 45 min. The reaction mixture was then quenched by the addition of 1 N hydrochloric acid and ethyl acetate. The organic phase was washed successively with water, saturated sodium bicarbonate and brine and dried over anhydrous sodium sulfate. Evaporation of the solvent under reduced pressure and chromatography of the residue on silica gel (elution toluene-ethyl acetate, 85:15) gave 0.70 g (61% yield) of the title ester as clear oil. $^1$HNMR 400 MHz ($C_6D_6$) δ (ppm); mixture of rotamers: 2.01 and 2.49 (3H, 2 s, $NCH_3$), 3.43 and 3.5 (3H, 2 s, $OCH_3$), 4.0 and 4.4 (2H, 2 s, $NCH_2$), 6.26 and 6.33 (1H, 2 s, CH), 6.62–7.2 (3H, m, aromatics). Anal. calcd for $C_{13}H_{13}Cl_2NO_4$: C, 49.08; H, 4.12; N, 4.40. Found: C, 49.38; H, 4.23; N, 4.30.

Compound 12: 4-Hydroxy-1-methyl-5-oxo-2,5-dihydro-1H-pyrrole-3-carboxylic acid (3,4-dichloro-benzyl)-methyl amide

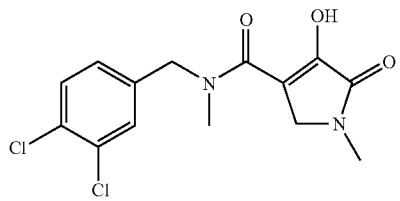

A solution of 2 M methylamine in tetrahydrofuran (0.5 ml, 1.0 mmol) was added to a mixture of paraformaldehyde (0.3 g, 1.0 mmol, equivalent of formaldehyde) in anhydrous ethanol (1 ml) and the resulting mixture was heated at 60° C. for 5 min. Then a solution of 3-[(3,4-dichlorobenzyl)-methyl-carbamoyl]-2-hydroxy-acrylic acid methyl ester (0.318 g, 1.0 mmol) in ethanol (3 ml) was added all at once and the resulting mixture was maintained at 60° C. for another 20 min. The reaction mixture was then quenched by the addition of ethyl acetate and pH 2 phosphate buffer. The organic phase was washed with brine, dried (anhydrous magnesium sulfate) and concentrated under reduced pressure. Recrystallization of the solid residue from a mixture of ethyl acetate and hexane gave 0.180 g (54% yield) of the title material as a white solid: mp 148–150° C.

EXAMPLE 13

Compound 13; 4-Hydroxy-1-(2-morpholin-4-yl-ethyl)-5-oxo-2,5-dihydro-1H-pyrrole-3-carboxylic acid (3,4-dichloro-benzyl)-methyl-amide

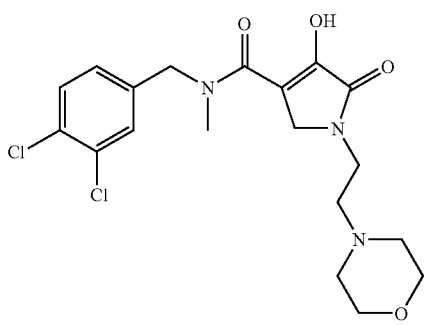

To 0.5 mL of AcOH at 60° C. was added N-(2-aminoethyl)morpholine (0.066 mL, 0.5 mmol) and paraformaldehyde (15 mg, 0.5 mmol). After stirring for 5 min, 3-[(3,4-dichloro-benzyl)-methyl-carbamoyl]-2-hydroxy-acrylic acid methyl ester (159 mg, 0.5 mmol) was added and the resulting mixture stirred at 60° C. for 2 h. The reaction mixture was cooled to room temperature and extracted with EtOAc. The remaining aqueous layer was extracted with $CH_2Cl_2$, and dried over $Na_2SO_4$. Concentration yielded 51.1 mg (24% yield) of the title compound as a white solid. $^1$H NMR (300 MHz, $CDCl_3$) δ: 10.52 (bs, 1H), 7.40 (d, 1H, J=10.61), 7.39 (s, 1H), 7.11 (dd, 1H, J=10.24, J=1.83), 4.60 (s, 2H), 4.23 (s, 2H), 3.64 (m, 6H), 3.01 (s, 3H), 2.63 (t, 2H, J=6.22), 2.54, (m, 4H), 2.05 (s, 3H). MS (M+H) calcd for $C_{19}H_{23}N_3O_4Cl_2$: 427.1; found: 428.11.

EXAMPLE 14

Compound 14: 1-Cyclopropyl-4-hydroxy-5-oxo-2,5-dihydro-1H-pyrrole-3-carboxylic acid (3,4-dichloro-benzyl)-methyl-amide

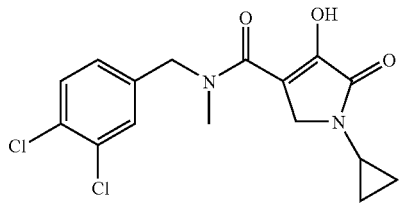

3-[(3,4-Dichloro-benzyl-methyl-carbamoyl]-2-hydroxy-acrylic acid methyl ester (Compound 12-B) was treated with paraformaldehyde and cyclopropylamine as described in the preparation of Compound 12. The title compound was extracted with EtOAc and the organic layer was washed with $H_2O$, and dried over $Na_2SO_4$. After concentration, the resulting residue was triturated with EtOAc/Hexane (1:1) to give a white solid (52.7 mg, 30% yield). Mp=163–164° C. $^1$H NMR (300 MHz, $CDCl_3$) δ: 9.97 (bs, 1H), 7.42, (d, 1H, J=8.42), 7.35 (s, 1H), 7.10 (dd, 1H, J=8.42, J=1.47), 4.60 (s, 2H), 4.09 (s, 2H), 3.02 (s, 3H), 2.81 (m, 1H), 0.86 (m, 4H). HRMS (M+H) calcd for $C_{16}H_{17}N_2Cl_2O_3$: 355.0616. found: 355.0618.

EXAMPLE 15

Compound 15: 4-Hydroxy-1-(2-methylamino-ethyl)-5-oxo-2,5-dihydro-1H-pyrrole-3-carboxylic acid (3,4-dichloro-benzyl)-methyl-amide

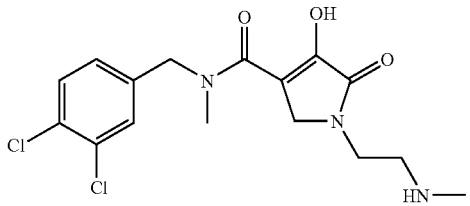

3-[(3,4-Dichloro-benzyl-methyl-carbamoyl]-2-hydroxy-acrylic acid methyl ester (Compound 12-B) was treated with paraformaldehyde and methyl-ethane-1,2-diamine as described in the preparation of Compound 12. The title compound was triturated with EtOAc to give a white solid (7.8 mg, 4% yield). $^1$H NMR (300 MHz, CDCl$_3$) δ: 9.14, (bs, 1H), 7.40, (d, 1H, J=8.05), 7.34 (s, 1H), 7.11 (dd, 1H, J=8.05, J=1.10), 4.58, (s, 2H), 4.34, (s, 2H), 3.94 (m, 2H), 3.25 (m, 2H), 3.03 (s, 3H), 2.78 (s, 3H). HRMS (M+H) calcd for $C_{16}H_{19}N_3Cl_2O_3$: 372.0881. found: 372.0886.

EXAMPLE 16

Compound 16: 1-(2,2-Dimethyl-propyl)-4-hydroxy-5-oxo-2,5-dihydro-1H-pyrrole-3-carboxylic acid (3,4-dichloro-benzyl)-methyl-amide

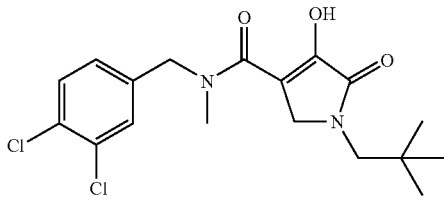

3-[(3,4-Dichloro-benzyl-methyl-carbamoyl]-2-hydroxy-acrylic acid methyl ester (Compound 12-B) was treated with paraformaldehyde and 2,2-dimethyl-propylamine as described in the preparation of Compound 12. The resulting residue was purified by chromatography (YMC Combiprep ODS-A, 30 mm×50 mm, MeOH/H2O/0.1% TFA) to yield the title compound as a white powder (7.9 mg, 4% yield). $^1$H NMR (500 MHz, DMSO) δ: 7.42 (d, 1H, J=8.24), 7.36 (s, 1H), 7.12 (d, 1H, J=8.24), 4.61 (s, 2H), 4.26 (s, 2H), 3.27 (s, 2H), 3.04 (s, 3H), 0.93 (s, 9H). HRMS (M+H) calcd for $C_{18}H_{23}N_2Cl_2O_3$: 385.1085; found: 385.1079.

EXAMPLE 17

Compound 17: 4-Hydroxy-5-oxo-1-[2-(4-sulfamoyl-phenyl)-ethyl]-2,5-dihydro-1H-pyrrole-3-carboxylic acid (3,4-dichloro-benzyl)-methyl-amide

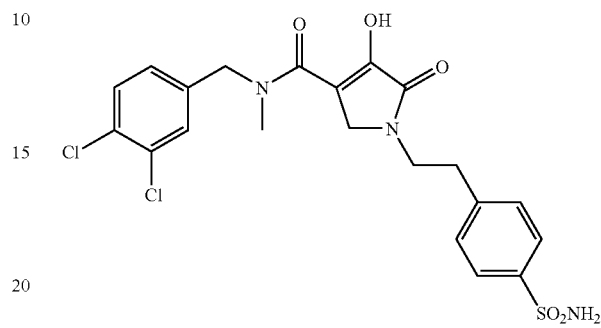

3-[(3,4-Dichloro-benzyl-methyl-carbamoyl]-2-hydroxy-acrylic acid methyl ester (Compound 12-B) was treated with paraformaldehyde and 4-(2-amino-ethyl)benzenesulfona-mide as described in the preparation of Compound 12. The resulting residue was purified by chromatography (YMC Combiprep ODS-A, 30 mm×50 mm, MeOH/H2O/0.1% TFA) to yield the title compound as a white powder (47.9 mg, 19% yield). Decomposition point=110–113° C. $^1$H NMR (500 MHz, DMSO) δ: 10.97 (s, 1H), 7.72, (m, 2H), 7.61 (d, 1H, J=8.54), 7.51 (s, 1H), 7.42 (m, 2H), 7.29 (m, 2H), 7.25, (m, 1H), 4.56, (s, 2H), 4.04, (s, 2H), 3.67 (m, 2H), 3.34 (m, 2H), 2.95 (d, 3H, J=6.41). HRMS (M−H) calcd for $C_{21}H_{20}SN_3Cl_2O_5$: 496.0500. found: 496.0503.

EXAMPLE 18

Compound 18: 3-[4-[(3,4-dichloro-benzyl)-methyl-carbamoyl]-3-hydroxy-2-oxo-2,5-dihydro-pyrrol-1-yl]-propionic acid

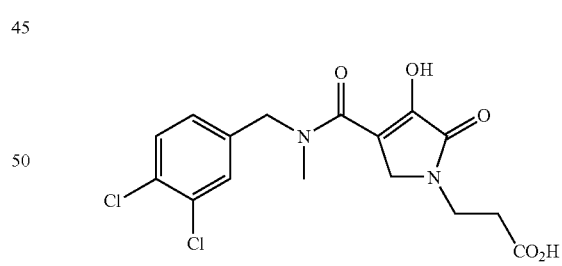

3-[(3,4-Dichloro-benzyl-methyl-carbamoyl]-2-hydroxy-acrylic acid methyl ester (Compound 12-B) was treated with paraformaldehyde and β-alanine as described in the preparation of Compound 12. The resulting residue was purified by chromatography (YMC Combiprep ODS-A, 30 mm×50 mm, MeOH/H2O/0.1% TFA) to yield the title compound as an amber solid (48.5 mg, 25% yield). Mp=183–184° C. $^1$H NMR (500 MHz, DMSO) δ: 12.34 (s, 2H), 10.79 (s, 1H), 7.61 (d, 1H, J=8.54), 7.51 (s, 1H), 7.24 (bs, 1H), 4.57 (s, 2H), 4.06 (s, 2H), 3.58 (t, 2H, J=6.40), 2.96 (bs, 3H), 2.54 (t, 2H, J=7.02). HRMS (M−H) calcd for $C_{16}H_{15}N_2Cl_2O_5$: 385.0358. found: 385.0364.

EXAMPLE 19

Compound 19: 1-(3,4-Dichloro-benzyl)-4-hydroxy-5-oxo-2,5-dihydro-1H-pyrrole-3-carboxylic acid (3,4-dichloro-benzyl)-methyl-amide

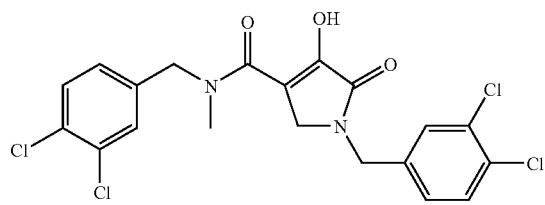

3-[(3,4-Dichloro-benzyl-methyl-carbamoyl]-2-hydroxy-acrylic acid methyl ester (Compound 12-B) was treated with paraformaldehyde and 3,4 dichloro-benzylamine as described in the preparation of Compound 12. The title compound was isolated as a white foam (155 mg, 66% yield). $^1$H NMR (500 MHz, CDCl$_3$) δ: 10.70 (bs, 1H), 7.42 (d, 1H, J=3.05), 7.40 (d, 1H, J=3.05), 7.34 (d, 2H, J=1.83), 7.09 (dd, 2H, J=8.24, J=1.83), 4.62 (s, 2H), 4.57 (s, 2H), 4.06 (s, 2H), 3.00 (s, 3H). HRMS (M−H) calcd for C$_{20}$H$_{15}$N$_2$Cl$_4$O$_3$: 470.9836. found: 470.9832.

EXAMPLE 20

Compound 20: {4-[(3,4-Dichloro-benzyl)-methyl-carbamoyl]-3-hydroxy-2-oxo-2,5-dihydro-pyrrol-1-yl}-acetic acid

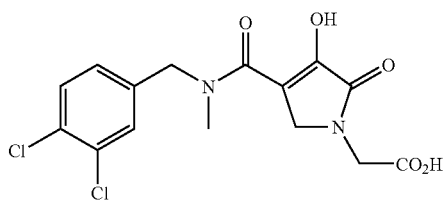

3-[(3,4-Dichloro-benzyl-methyl-carbamoyl]-2-hydroxy-acrylic acid methyl ester (Compound 12-B) was treated with paraformaldehyde and glycine as described in the preparation of Compound 12. The title compound was isolated as a white solid (80 mg, 43% yield). Mp=178–180° C. $^1$H NMR (300 MHz, DMSO) δ: 12.97 (bs, 1H), 11.07 (s, 1H), 7.62 (d, 1H, J=8.41), 7.53 (s, 1H), 7.25 (d, 1H, J=6.95), 4.59 (s, 2H), 4.15 (s, 2H), 4.10 (s, 2H), 2.98 (s, 3H). HRMS (M−H) calcd for C$_{15}$H$_{13}$N$_2$Cl$_2$O$_5$: 371.0201. found: 371.0216.

EXAMPLE 21

Compound 21: 4-Hydroxy-5-oxo-1-pyridin-4-yl methyl-2,5-dihydro-1H-pyrrole-3-carboxylic acid (3,4-dichloro-benzyl)-methyl-amide

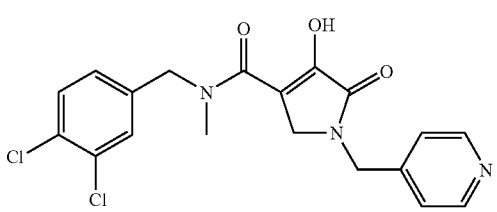

3-[(3,4-Dichloro-benzyl-methyl-carbamoyl]-2-hydroxy-acrylic acid methyl ester (Compound 12-B) was treated with paraformaldehyde and 4-(amino-methyl)pyridine as described in the preparation of Compound 12. The resulting residue was purified by chromatography (YMC Combiprep ODS-A, 30 mm×50 mm, MeOH/H2O/0.1% TFA) to yield the title compound as a sticky orange solid (10.5 mg, 5% yield). $^1$H NMR (300 MHz, DMSO) δ: 8.75 (d, 2H, J=6.22), 7.63–7.52 (m, 4H), 7.25 (d, 2H, J=7.31), 4.80 (s, 2H), 4.59 (s, 2H), 4.1 (s, 2H), 2.99 (bs, 3H). HRMS (M−H) calcd for C$_{19}$H$_{16}$N$_3$Cl$_2$O$_3$: 404.0568. found: 404.0554.

EXAMPLE 22

Compound 22: 1-(1-Ethyl-pyrrolidin-2-yl methyl)-4-hydroxy-5-oxo-2,5-dihydro-3-carboxylic acid (3,4-dichloro-benzyl)-methyl-amide

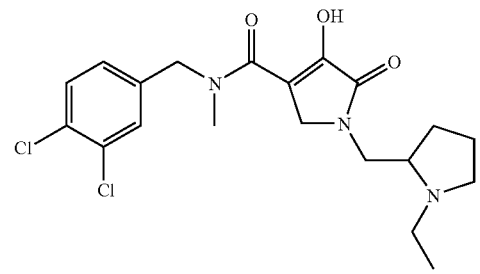

3-[(3,4-Dichloro-benzyl-methyl-carbamoyl]-2-hydroxy-acrylic acid methyl ester (Compound 12-B) was treated with paraformaldehyde and 2-(aminomethyl)-1-ethylpyrrolidine as described in the preparation of Compound 12. The title compound was isolated as an orange solid (18.8 mg, 9% yield). $^1$H NMR (300 MHz, CDCl$_3$) δ: 12.26 (bs, 1H), 7.43 (d, 1H, J=8.42), 7.36 (s, 1H), 7.13 (dd, 1H, J=8.05, J=1.46), 4.61 (s, 2H), 4.12 (s, 2H), 3.93 (m, 2H), 3.22 (t, 1H, J=8.78), 3.09 (s, 3H), 2.93 (m, 2H), 2.21–1.72 (m, 6H), 1.42 (t, 3H, J=6.95). HRMS (M−H) calcd for C$_{20}$H$_{24}$N$_3$Cl$_2$O$_3$: 424.11948. found: 424.1200.

EXAMPLE 23

Compound 23-A: (2-[4-[(3,4-Dichloro-benzyl)-methyl-carbamoyl]-3-hydroxy-2-oxo-2,5-dihydro-pyrrol-1-yl]-ethyl)-phosphonic acid diethyl ester

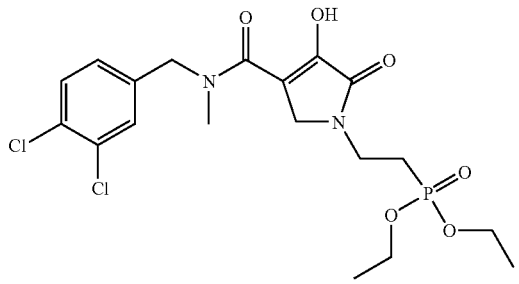

3-[(3,4-Dichloro-benzyl-methyl-carbamoyl]-2-hydroxy-acrylic acid methyl ester (Compound 12-B) was treated with paraformaldehyde and (2-aminoethyl)phosphonic acid diethylester as described in the preparation of Compound 12. Trituration with $CH_2Cl_2$/hexane gave the title compound (106 mg, 44% yield). $^1$H NMR (300 MHz, $CDCl_3$) δ: 7.41 (d, 1H, J=8.05), 7.35 (s, 1H), 7.10 (dd, 1H, J=8.05, J=1.47), 4.60 (s, 2H), 4.25 (s, 2H), 4.11 (m, 4H), 3.77 (m, 2H), 3.02 (s, 3H), 2.17 (m, 2H), 1.31 (t, 6H, J=7.32). HRMS (M–H) calcd for $C_{19}H_{24}PN_2Cl_2O_6$: 477.0749. found: 477.0749.

Compound 23: (2-{4-[(3,4-Dichloro-benzyl)-methyl-carbamoyl]-3-hydroxy-2-oxo-2,5-dihydro-pyrrol-1-yl}-ethyl)-phosphonic acid

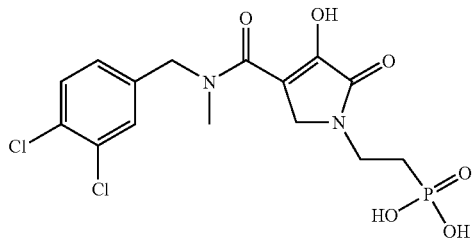

Compound 23-A (77 mg, 0.16 mmol) was stirred in acetic acid (4 mL) and concentrated HCl (1 mL) at 120° C. 18 hours. Mixture was cooled to room temp and concentrated. Residue was purified by chromatography (YMC Combiprep ODS-A, 30 mm×50 mm, MeOH/H2O/0.1% TFA) to give the title compound as a white powder (4.4 mg, 6.5% yield). $^1$H NMR (300 MHz, DMSO) δ: 7.61 (d, 1H, J=8.05), 7.52 (s, 1H), 7.24 (d, 1H, J=8.05), 4.58 (s, 2H), 4.09 (s, 2H), 3.55 (m, 2H), 2.96 (bs, 3H), 1.84 (m, 2H). HRMS (M–H) calcd for $C_{15}H_{16}PN_2Cl_2O_6$: 421.0123. found: 421.0139.

EXAMPLE 24

Compound 24: 4-{4-[(3,4-Dichloro-benzyl)-methyl-carbamoyl]-3-hydroxy-2-oxo-2,5-dihydro-pyrrol-1-yl}-butyric acid

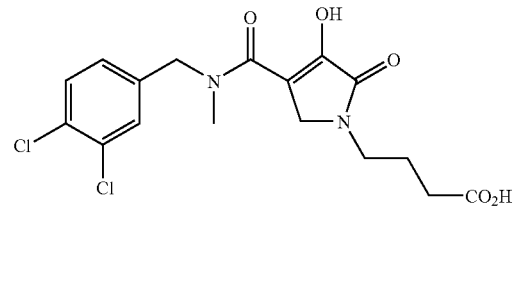

3-[(3,4-Dichloro-benzyl-methyl-carbamoyl]-2-hydroxy-acrylic acid methyl ester (Compound 12-B) was treated with paraformaldehyde and -aminobutyric acid as described in the preparation of Compound 12. The resulting residue was purified by chromatography (YMC Combiprep ODS-A, 30 mm×50 mm, MeOH/H2O/0.1% TFA) to yield the title compound as a white powder (42.1 mg, 21% yield). $^1$H NMR (300 MHz, $CDCl_3$) δ: 7.42 (d, 1H, J=8.05), 7.36 (s, 1H), 7.11 (dd, 1H, J=8.05, J=1.10), 4.60 (s, 2H), 4.21 (s, 2H), 3.58 (t, 2H, J=6.22), 3.03 (s, 3H), 2.40 (t, 2H, J=6.95), 1.96 (t, 2H, J=6.59). HRMS (M–H) calcd for $C_{17}H_{17}N_2Cl_2O_5$: 399.0514. found: 399.0509.

EXAMPLE 25

Compound 25: 2-{4-[(3,4-Dichloro-benzyl)-methyl-carbamoyl]-3-hydroxy-2-oxo-2,5-dihydro-pyrrol-1-yl}-succinamic acid

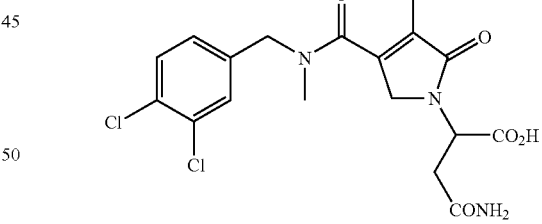

3-[(3,4-Dichloro-benzyl-methyl-carbamoyl]-2-hydroxy-acrylic acid methyl ester (Compound 12-B) was treated with paraformaldehyde and asparagine as described in the preparation of Compound 12. The resulting residue was purified by chromatography (YMC Combiprep ODS-A, 30 mm×50 mm, MeOH/H2O/0.1% TFA) to yield the title compound as a white powder (12 mg, 6% yield). $^1$H NMR (300 MHz, DMSO) δ: 13.1 (bs, 1H), 11.05 (bs, 1H), 7.62 (d, 1H, J=8.42), 7.53 (s, 1H), 7.51 (s, 1H), 7.25 (bs, 1H), 6.97 (s, 1H), 4.90 (m, 1H), 4.58 (s, 2H), 4.07 (s, 2H), 2.96 (s, 3H), 2.73 (m, 2H). HRMS (M–H) calcd for $C_{17}H_{16}N_3Cl_2O_6$: 428.0416. found: 428.0415.

EXAMPLE 26

Compound 26: 4-Hydroxy-5-oxo-1-(2-piperidin-1-yl-ethyl)-2,5-dihydro-1H-pyrrole-3-carboxylic acid (3,4-dichloro-benzyl)-methyl-amide

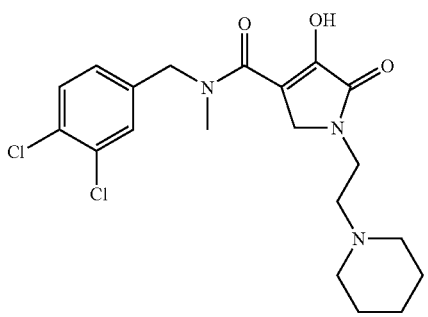

3-[(3,4-Dichloro-benzyl-methyl-carbamoyl]-2-hydroxy-acrylic acid methyl ester (Compound 12-B) was treated with paraformaldehyde and 1-(2-aminoethyl)piperidine as described in the preparation of Compound 12. The resulting residue was purified by trituration with $CH_2Cl_2$ to yield the title compound as a white solid (81.2 mg, 38% yield). Decomposition point=178–182° C. $^1$H NMR (300 MHz, DMSO) δ: 10.99 (s, 1H), 7.62 (d, 1H, J=8.25), 7.52 (d, 1H, J=1.46), 7.26 (d, 1H, J=7.68), 4.60 (s, 2H), 4.13 (s, 2H), 3.81 (t, 2H, J=5.85), 3.48 (d, 2H, J=11.34), 3.27 (d, 2H. J=4.76), 3.00 (s, 2H), 2.86 (m, 3H), 1.77 (m, 6H). HRMS (M+H) calcd for $C_{20}H_{26}N_3Cl_2O_3$: 426.1351. found: 426.1346.

EXAMPLE 27

Compound 27: 1-(2-Acetylamino-ethyl)-4-hydroxy-5-oxo-2,5-dihydro-1H-pyrrole-5-carboxylic acid (3,4-dichloro-benzyl)-methyl-amide

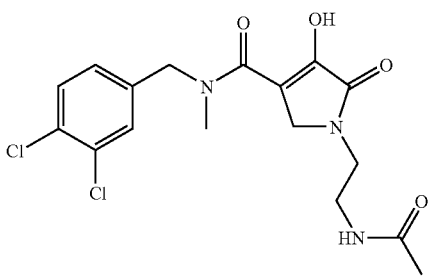

3-[(3,4-Dichloro-benzyl-methyl-carbamoyl]-2-hydroxy-acrylic acid methyl ester (Compound 12-B) was treated with paraformaldehyde and N-acetylethylene diamine as described in the preparation of Compound 12. The resulting residue was purified by chromatography (YMC Combiprep ODS-A, 30 mm×50 mm, MeOH/H2O/0.1% TFA) to yield the title compound as a white powder (60.8 mg, 30% yield). $^1$H NMR (500 MHz, CDCl$_3$) δ: 7.44 (d, 1H, J=8.24), 7.36 (s, 1H), 7.11 (dd, 1H, J=9.76, J=7.93), 6.77 (s, 1H), 4.60 (s, 2H), 4.29 (s, 2H), 3.68 (t, 2H, J=5.18), 3.55 (q, 2H, J=5.80), 3.05 (s, 3H), 2.02 (s, 3H). HRMS (M–H) calcd for $C_{17}H_{18}N_3Cl_2O_4$: 398.0674. found: 398.0682.

EXAMPLE 28

Compound 28: 7-{4-[(3,4-dichloro-benzyl)-methyl-carbamoyl]-3-hydroxy-2-oxo-2,5-dihydro-pyrrol-1-yl}-heptanoic acid

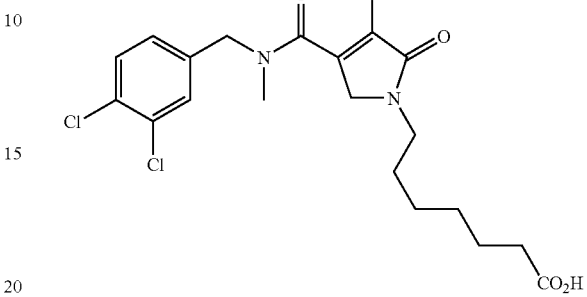

3-[(3,4-Dichloro-benzyl-methyl-carbamoyl]-2-hydroxy-acrylic acid methyl ester (Compound 12-B) was treated with paraformaldehyde and 7-amino-heptanoic acid as described in the preparation of Compound 12. The resulting residue was purified by chromatography (YMC Combiprep ODS-A, 30 mm×50 mm, MeOH/H2O/0.1% TFA) to yield the title compound as a white powder (11.2 mg, 5% yield). $^1$H NMR (500 MHz, CDCl$_3$) δ: 11.95 (bs, 1H), 11.00 (s, 1H), 7.61 d, 1H, J=8.24), 7.52 (s, 1H), 7.25 (s, 1H), 4.58 (s, 2H), 4.04 (s, 2H), 3.36 (m, 2H), 2.98 (s, 3H), 2.18 (t, 2H, J=7.33), 1.48 (m, 4H), 1.26 (m, 4H). HRMS (M+H) calcd for $C_{20}H_{25}N_2Cl_2O_5$: 443.1140. found: 443.1153.

EXAMPLE 29

Compound 29: 2-(3-{4-[(3,4-Dichloro-benzyl)-methyl-carbamoyl]-3-hydroxy-2-oxo-2,5-dihydro-pyrrol-1-yl}-propionylamino-3-(3-methyl-3H-imidazol-4-yl)-propionic acid

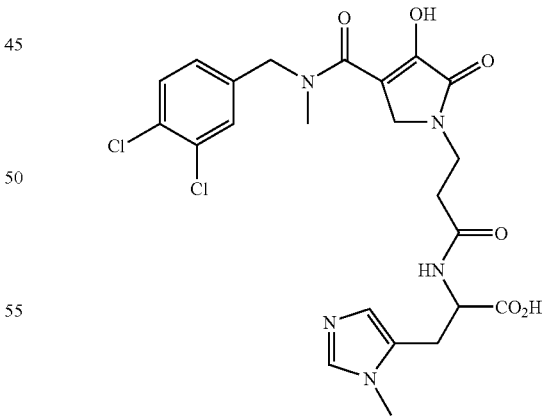

3-[(3,4-Dichloro-benzyl-methyl-carbamoyl]-2-hydroxy-acrylic acid methyl ester (Compound 12-B) was treated with paraformaldehyde and L-anserine nitrate as described in the preparation of Compound 12. The resulting residue was purified by chromatography (YMC Combiprep ODS-A, 30 mm×50 mm, MeOH/H2O/0.1% TFA) to yield the compound as a white solid (3.3 mg, 1% yield). $^1$H NMR (500 MHz, CDCl$_3$) δ: 8.56 (s, 1H), 7.36 (d, 1H, J=8.24) 7.29 (m, 1H), 7.20 (s, 1H), 7.04 (m, 1H), 4.69 (m, 1H), 4.52 (s, 2H), 4.05 (s, 2H), 3.76 (s, 3H), 3.65 (t, 2H, J=5.80), 3.14 (m, 2H), 2.94 (s, 2H), 2.51 (m, 2H). HRMS (M+H) calcd for C$_{23}$H$_{26}$N$_5$Cl$_2$O$_6$: 538.1260. found: 538.1280.

EXAMPLE 30

Compound 30: 4-Hydroxy-1-(3-imidazol-1-yl-propyl)-5-oxo-2,5-dihydro-1H-pyrrole-3-carboxylic acid (3,4-dichloro-benzyl)-methyl-amide

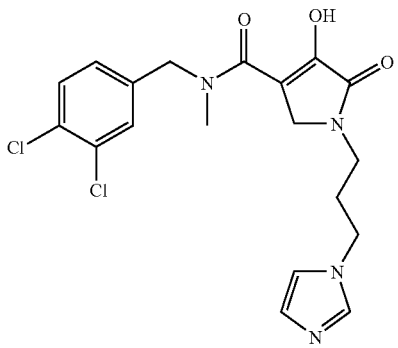

3-[(3,4-Dichloro-benzyl-methyl-carbamoyl]-2-hydroxy-acrylic acid methyl ester (Compound 12-B) was treated with paraformaldehyde and N-propylamino imidazole as described in the preparation of Compound 12. The resulting residue was purified by chromatography (YMC Combiprep ODS-A, 30 mm×50 mm, MeOH/H2O/0.1% TFA) to yield the title compound as an amber foam (59.1 mg, 28% yield). $^1$H NMR (300 MHz, DMSO) δ: 14.47 (bs, 1H), 11.05 (bs, 1H), 9.10 (s, 1H), 7.82 (s, 1H), 7.70 (s, 1H), 7.62 (d, 1H, J=8.05), 7.52 (s, 1H), 7.25 (d, 1H, J=7.32), 4.59 (s, 2H), 4.19 (t, 1H, J=6.95), 4.09 (s, 2H), 3.41 (t, 2H, J=6.59), 2.98 (s, 3H), 2.13 (t, 2H, J=6.59). HRMS (M+H) calcd for C$_{19}$H$_{21}$N$_4$Cl$_2$O$_3$: 423.0990. found: 423.0982.

EXAMPLE 31

Compound 31: 4-Hydroxy-5-oxo-1-thiophen-2-yl methyl-2,5-dihydro-1H-pyrrole-3-carboxylic acid (3,4-dichloro-benzyl)-methyl-amide

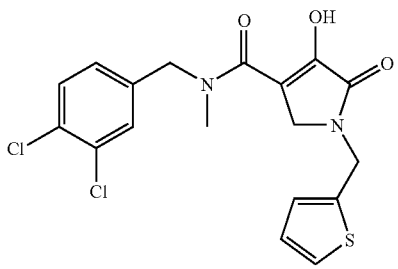

3-[(3,4-Dichloro-benzyl-methyl-carbamoyl]-2-hydroxy-acrylic acid methyl ester (Compound 12-B) was treated with paraformaldehyde and methylamine thiophene as described in the preparation of Compound 12. The resulting residue was purified by chromatography (YMC Combiprep ODS-A, 30 mm×50 mm, MeOH/H2O/0.1% TFA) to yield the title compound as a white powder (58.7 mg, 28% yield). $^1$H NMR (300 MHz, CDCl$_3$) δ: 7.41 (d, 1H, J=8.05), 7.33 (d, 1H, J=1.83), 7.26 (m, 1H), 7.08 (dd, 1H, J=8.05, J=1.83), 6.97 (m, 2H), 4.85 (s, 2H), 4.57 (s, 2H), 4.11 (s, 2H), 3.00 (s, 3H). HRMS (M−H) calcd for C$_{18}$H$_{15}$SN$_2$Cl$_2$O$_3$: 409.0180. found: 409.0190.

EXAMPLE 32

Compound 32-A: (4-Methyl-piperazin-yl)-acetonitrile

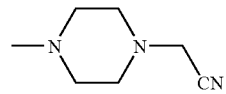

A mixture of 1-methyl piperazine (0.55 mL, 5.0 mmol), potassium carbonate (3.49 g, 25 mmol) and chloroacetonitrile (0.34 mL, 5.6 mmol) in acetonitrile (3 mL) was stirred at room temperature 8 h. The mixture was diluted with diethyl ether and filtered and concentrated to yield the title compound as yellow crystals (536.6 mg, 77% yield). $^1$H NMR (500 MHz, CDCl$_3$) δ: 3.50 (s, 2H), 2.66 (t, 4H, J=4.58), 2.52 (bs, 4H), 2.33 (s, 3H).

Compound 32-B: 2-(4-Methyl-piperazin-1-yl)-ethylamine

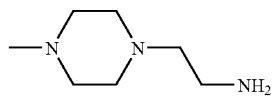

To a suspension of lithium aluminum powder (0.16 g, 4.2 mmol) and diethyl ether (5.0 mL) cooled to 0° C., was added dropwise a solution of the above compound (0.536 g, 3.86 mmol) dissolved in diethyl ether/THF (14 mL, 1:1). The resulting mixture was stirred at room temperature for 5 h. The mixture was cooled to 0° C. and 2N aqueous NaOH added dropwise. The mixture was stirred for 20 min and the precipitate was filtered. The organic solution was concentrated and the resulting oil was dissolved in ethylacetate. A solution of 4N HCl in dioxane (0.97 mL) added and white precipitate filtered to yield the title compound as the HCl salt. $^1$H NMR (500 MHz, DMSO) δ: 9.48 (s, 2H), 4.18 (m, 6H), 3.75 (m, 2H), 3.68 (m, 2H), 3.26 (m, 2H), 2.82 (s, 3H).

Compound 32: 4-Hydroxy-1-[2-(4-methyl-piperazin-1-yl)-ethyl]-5-oxo-2,5-dihydro-1H-pyrrole-3-carboxylic acid (3,4-dichloro-benzyl)-methyl-amide

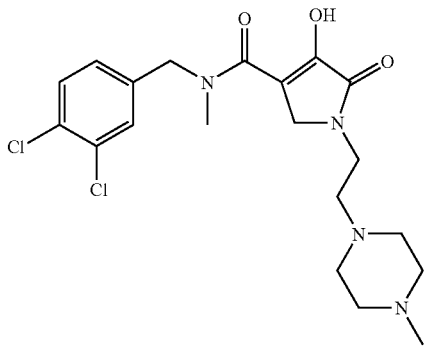

3-[(3,4-Dichloro-benzyl-methyl-carbamoyl]-2-hydroxy-acrylic acid methyl ester (Compound 12-B) was treated with paraformaldehyde and 2-(4-methyl-piperazine-1-yl)-ethyl amine as described in the preparation of Compound 12. The resulting residue was purified by chromatography (YMC Combiprep ODS-A, 30 mm×50 mm, MeOH/H2O/0.1% TFA) to yield the title compound as an amber glass (27 mg, 12% yield). $^1$H NMR (300 MHz, DMSO) δ: 7.63 (d, 1H, J=8.42), 7.52 (s, 1H), 7.25 (d, 1H, J=7.31), 4.59 (s, 2H), 4.24 (m, 10H), 4.11 (s, 2H), 3.58 (s, 2H), 2.98 (s, 3H), 2.78 (s, 3H). HRMS (M−H) calcd for $C_{20}H_{25}N_4Cl_2O_3$: 439.1303. found: 439.1311.

EXAMPLE 33

Compound 33: 4-{4-[(3,4-Dihydro-benzyl)-methyl-carbamoyl]-3-hydroxy-2-oxo-2,5-dihydro-pyrrol-1-yl}-butyric acid methyl ester

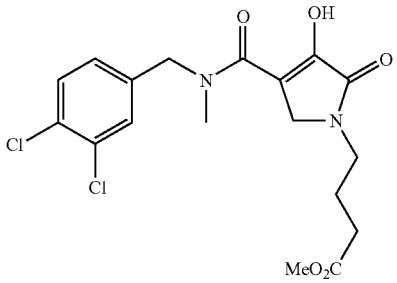

3-[(3,4-Dichloro-benzyl-methyl-carbamoyl]-2-hydroxy-acrylic acid methyl ester (Compound 12-B) was treated with paraformaldehyde and 4-aminobutyrate hydrochloride as described in the preparation of Compound 12. The resulting residue was purified by chromatography (YMC Combiprep ODS-A, 30 mm×50 mm, MeOH/H2O/0.1% TFA) to yield the title compound as an amber oil (18.9 mg, 9% yield). $^1$H NMR (300 MHz, CDCl$_3$) δ: 7.41 (m, 2H), 7.09 (m, 1H), 4.60 (s, 2H), 4.18 (s, 2H), 3.65 (s, 3H), 3.55 (t, 2H, J=7.32), 3.03 (s, 3H), 2.36 (t, 2H, J=7.32), 1.94 (t, 2H, J=6.95). HRMS (M+H) calcd for $C_{18}H_{21}N_2Cl_2O_5$: 415.0827. found: 415.0831.

EXAMPLE 34

Compound 34: 3-{4-[(3,4-Dichloro-benzyl)-methyl-carbamoyl]-3-hydroxy-2-oxo-2,5-dihydro-pyrrol-1-yl}-propionic acid methyl ester

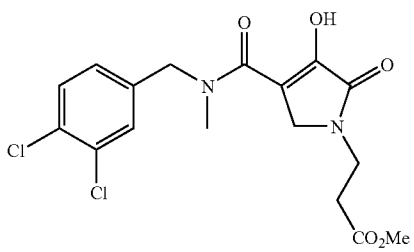

3-[(3,4-Dichloro-benzyl-methyl-carbamoyl]-2-hydroxy-acrylic acid methyl ester (Compound 12-B) was treated with paraformaldehyde and β-alanine methyl ester as described in the preparation of Compound 12. The resulting residue was purified by chromatography (YMC Combiprep ODS-A, 30 mm×50 mm, MeOH/H2O/0.1% TFA) to yield the title compound as an amber oil (34.3 mg, 17% yield). $^1$H NMR (300 MHz, CDCl$_3$) δ: 7.41 (m, 2H), 7.09 (m, 1H), 4.59 (s, 2H), 4.27 (s, 2H), 3.77 (m, 2H), 3.67 (s, 3H), 3.03 (s, 3H), 2.69 (t, 2H, J=6.22). HRMS (M+H) calcd for $C_{17}H_{19}N_2Cl_2O_5$: 401.0671. found: 401.0669.

EXAMPLE 35

Compound 35: {3-[2-(2-{4-[(3,4-Dichloro-benzyl)-methyl-carbamoyl]-3-hydroxy-2-oxo-2,5-dihydro-pyrrol-1-yl}-acetylamino)-acetylamino]-propionylamino}-acetic acid

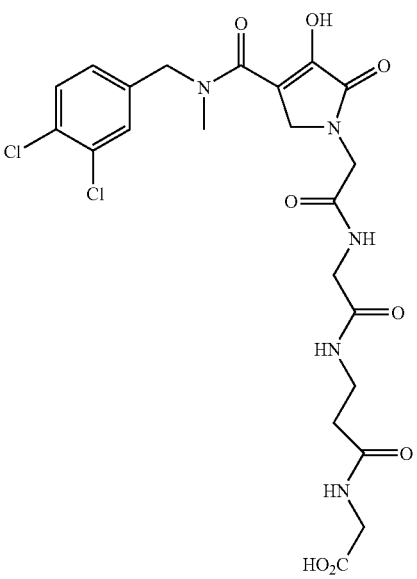

3-[(3,4-Dichloro-benzyl-methyl-carbamoyl]-2-hydroxy-acrylic acid methyl ester (Compound 12-B) was treated with paraformaldehyde and H-gly-gly-β-ala-gly-OH as described in the preparation of Compound 12. The reaction mixture was diluted with water and ethylacetate. The white solids were filtered as the title compound (88.2 mg, 32% yield). $^1$H NMR (300 MHz, DMSO) δ: 8.31 (t, 1H, J=5.49), 8.20 (t, 1H, J=5.49), 7.92 (t, 1H, J=5.49), 7.61 (d, 1H, J=8.42), 7.52 (s, 1H), 7.25 (d, 1H, J=6.59), 4.59 (s, 2H), 4.09 (s, 4H), 3.69 (m, 6H), 2.94 (bs, 3H), 2.30(t, 2H, J=7.31). HRMS (M−H) calcd for $C_{22}H_{24}N_5Cl_2O_8$: 556.1002. found: 556.0994.

EXAMPLE 36

Compound 36: 4-{4-[(3,4-Dichloro-benzyl)-methyl-carbamoyl]-3-hydroxy-2: oxo-2,5-dihydro-pyrrol-1-yl methyl}-benzoic acid

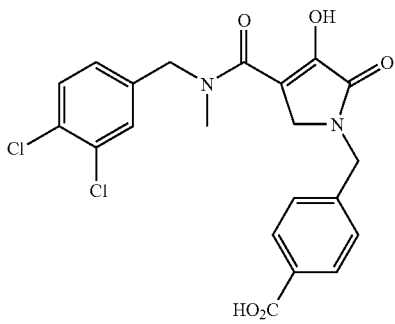

3-[(3,4-Dichloro-benzyl-methyl-carbamoyl]-2-hydroxy-acrylic acid methyl ester (Compound 12-B) was treated with paraformaldehyde and 4-(aminomethyl)benzoic acid as described in the preparation of Compound 12. The resulting residue was triturated with chloroform to give the title compound as a white solid (160 mg, 71% yield). $^1$H NMR (300 MHz, DMSO) δ: 12.94 (s, 1H), 11.14 (s, 1H), 8.32 (s, 1H), 7.93 (d, 2H, J=8.05), 7.60 (d, 1H, J=8.45), 7.50 (s, 1H), 7.35 (d, 2H, J=7.84), 7.23 (ds, 1H, 1=8.05), 4.66 (s, 2H), 4.57 (s, 2H), 3.99 (s, 2H), 2.97 (s, 3H). HRMS (M+H) calcd for $C_{21}H_{17}N_2Cl_2O_5$: 447.0515. found: 447.0530.

EXAMPLE 37

Compound 37-A: N-(3,4-Dichloro-benzyl)-2-(2,2-dimethyl-5-oxo-[1,3]dioxolan-4-ylidene)-N-methyl-acetamide

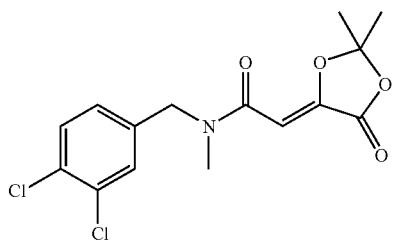

To a suspension of (2,2-Dimethyl-5-oxo-[1,3]dioxolan-4-ylidene)-acetic acid, Compound III-A, (4.5 g, 26.2 mmol) in benzene (30 mL) was added oxalyl chloride (15 mL) and the resulting mixture was heated at reflux for 1 h. The mixture was cooled to room temp. and concentrated. The residue was dissolved in methylene chloride (30 mL) and cooled to 0° C. To this was added a suspension of (3,4-dichloro-benzyl)-methyl-amine hydrochloride salt (5.0 g, 22.1 mmol) in methylene chloride (30 mL) and pyridine (18 mL). The resulting mixture was stirred at room temp for 18 h then diluted with 1N HCl. The aqueous phase was saturated with sodium chloride and extracted with methylene chloride (3 times). The organic layers were combined, dried ($Na_2SO_4$), and concentrated. The brown oil was purified over silica gel eluting with ethyl acetate/hexane (1:1) to give the title compound as a pale yellow oil that solidified to a white solid upon standing (6.2 g, 82% yield). $^1$H NMR (300 MHz, DMSO) δ: 7.44–7.10 (m, 3H), 6.16 (s, 0.66H), 6.08 (s, 0.33H), 4.59 (s, 1.33H), 4.53 (s, 0.67H), 3.02 (s, 2H), 2.97 (s, 1H), 1.74 (s, 4H), 1.69 (s, 2H).

Compound 37: 3-(3-{4-[(3,4-Dichloro-benzyl)-methyl-carbamoyl]-3-hydroxy-2oxo-2,5-dihydro-pyrrol-1-yl}-propionylamino)-propionic acid

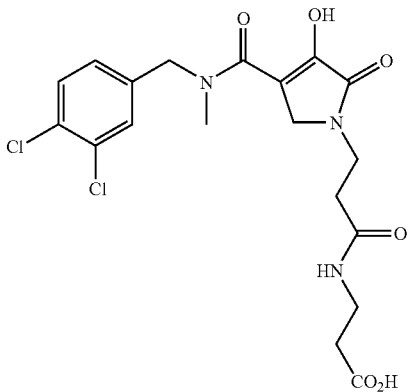

A mixture of paraformaldehyde (0.015 g, 0.5 mmol) and methanol (1.5 mL) was warmed to 55° C. Added to this mixture was H-β-Ala-β-ala-OH (0.08 g, 0.5 mmol) and the solution was stirred 5 min. N-(3,4-Dichloro-benzyl)-2-(2,2-dimethyl-5-oxo[1,3]dioxolane-4-ylidene)-N-methyl-acetamide (0.1715 g, 0.5 mmol) was added and the mixture was stirred at 55° C. for 45 min. The mixture was concentrated and the resulting residue was triturated with ethylacetate and filtered to give the desired product as a white solid (0.0358 g, 16% yield). $^1$H NMR (300 MHz, DMSO) δ: 2.35 (t, J=6.7 Hz, 4H), 2.96 (s, 3H), 3.32 (m, 2H), 3.57 (m, 2H), 4.02 (s, 2H), 4.57 (s, 2H), 7.23 (d, J=6.6 Hz, 1H), 7.51 (s, 1H), 7.61 (d, J=8.4 Hz, 1H), 8.05 (t, J=10.3 Hz, 1H), 10.97 (s, 1H), 12.19 (s, 1H). HRMS (M+H) calcd for $C_{19}H_{21}N_3Cl_2O_6$: 456.07292. found: 456.0738.

EXAMPLE 38

Compound 38: 4-Hydroxy-1-[2-(3-morpholin-4-yl-propionylamino)-ethyl]-5-oxo-2,5-dihydro-1H-pyrrole-3-carboxylic acid (3,4-dichloro-benzyl)-methyl-amide

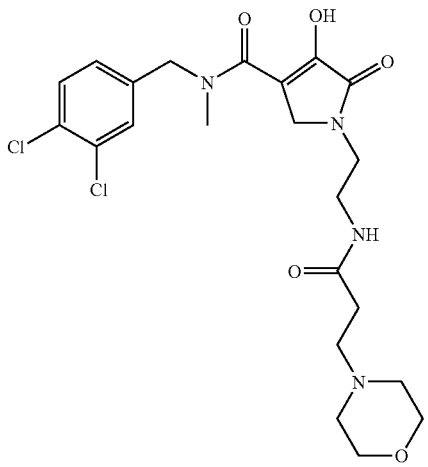

N-(3,4-Dichloro-benzyl)-2-(2,2-dimethyl-5-oxo-[1,3]dioxolan-4-ylidene)-N-methyl-acetamide (Compound 37-A) was treated with paraformaldehyde and N-(2-amino-ethyl)-3-morpholin-4-yl-propionamide as described in the preparation of Compound 37. The desired product was isolated as a white solid (0.0134 g, 5% yield). $^1$H NMR (300 MHz, CDCl$_3$) δ: 2.41 (m, 2H), 2.64 (bs, 2H), 2.72 (bs, 2H), 2.98 (m, 2H), 3.03 (s, 3H), 3.51 (t, J=5.6 Hz, 2H), 3.63 (t, J=5.2 Hz, 2H), 3.78 (m, 4H), 4.35 (s, 2H), 4.59 (s, 2H), 7.11 (d, J=8.1 Hz, 1H), 7.35–7.44 (m, 3H), 8.27 (t, 1H). HRMS (M+H) calcd for C$_{22}$H$_{28}$N$_4$Cl$_2$O$_5$: 497.13585. found: 497.1377.

EXAMPLE 39

Compound 39: (3-{4-[(3,4-Dichloro-benzyl)-methyl-carbamoyl]-3-hydroxy-2-oxo-2,5-dihydro-pyrrol-1-yl}-propionylamino)-acetic acid

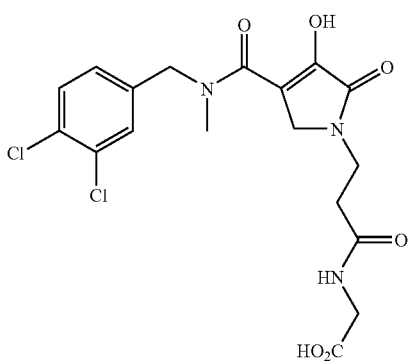

N-(3,4-Dichloro-benzyl)-2-(2,2-dimethyl-5-oxo-[1,3]dioxolan-4-ylidene)-N-methyl-acetamide (Compound 37-A) was treated with paraformaldehyde and H-β-ala-gly-OH as described in the preparation of Compound 37. The title compound was purified by chromatography (YMC Combiprep ODS-A, 30 mm×50 mm, MeOH/H2O/0.1% TFA) to yield the title compound as an amber powder (0.0158 g, 7% yield). $^1$H NMR (300 MHz, DMSO) δ: 2.45 (t, J=6.9 Hz, 2H), 2.98 (m, 3H), 3.60 (m, 2H), 3.73 (d, J=5.7 Hz, 2H), 4.06 (s, 2H), 4.57 (s, 2H), 7.23 (d, J=7.2, 1H), 7.65 (d, J=8.4 Hz, 1H), 8.32 (m, 1H), 10.98 (bs, 1H), 12.50 (bs, 1H). HRMS (M–H) calcd for C$_{18}$H$_{19}$N$_3$Cl$_2$O$_6$: 442.05727. found: 442.0584.

EXAMPLE 40

Compound 40: 1-(2-Carbamoyl-ethyl)-4-hydroxy-5-oxo-2,5-dihydro-1H-pyrrole-3-carboxylic acid (3,4-dichloro-benzyl)-methyl-amide

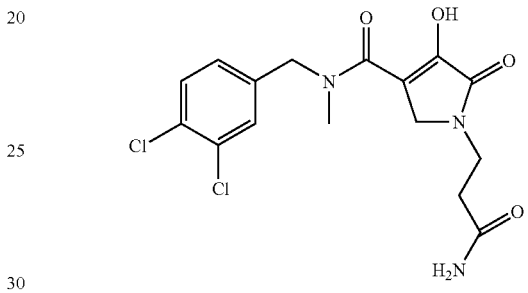

N-(3,4-Dichloro-benzyl)-2-(2,2-dimethyl-5-oxo-[1,3]dioxolan-4-ylidene)-N-methyl-acetamide (Compound 37-A) was treated with paraformaldehyde and β-alaninamide as described in the preparation of Compound 37. The title compound was purified by chromatography (YMC Combiprep ODS-A, 30 mm×50 mm, MeOH/H2O/0.1% TFA) to yield the title compound as an amber powder (0.0158 g, 7% yield). $^1$H NMR (300 MHz, CDCl$_3$) δ: 2.68 (t, J=5.9 Hz, 2H), 3.02 (s, 3H), 3.79 (d, J=5.9 Hz, 2H), 4.29 (s, 2H), 4.58 (s, 2H), 6.23 (s, 1H), 6.59 (s, 1H), 7.09 (dd, J=8.4 Hz, J=10.3 Hz, 1H), 7.34 (d, J=1.8 Hz, 1H), 7.42 (d, J=8.4 Hz, 1H). HRMS (M–H) calcd for C$_{16}$H$_{17}$N$_3$Cl$_2$O$_4$: 384.05179. found: 384.0517.

EXAMPLE 41

Compound 41: 4-{4-[(3,4-Dichloro-benzyl)-methyl-carbamoyl]-3-hydroxy-2-oxo-2,5-dihydro-pyrrol-1-ylmethyl}-benzoic acid methyl ester

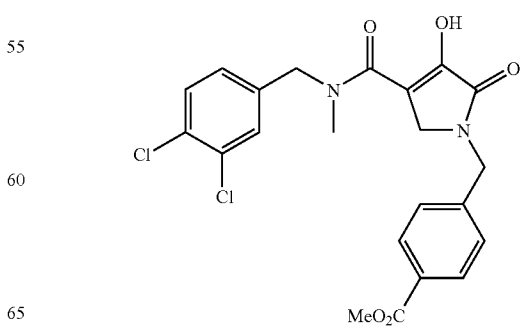

N-(3,4-Dichloro-benzyl)-2-(2,2-dimethyl-5-oxo-[1,3]di-oxolan-4-ylidene)-N-methyl-acetamide (Compound 37-A) was treated with paraformaldehyde and 4-(aminomethyl)-benzoate hydrochloride salt with 1 equivalent of triethyl amine as described in the preparation of Compound 37. The title compound was purified by chromatography (YMC Combiprep ODS-A, 30 mm×50 mm, MeOH/H2O/0.1% TFA) to yield the title compound as a yellow foam (0.060 g, 26% yield). $^1$H NMR (300 MHz, CDCl$_3$) δ: 2.98 (s, 3H), 3.91 (s, 3H), 4.05 (s, 2H), 4.56 (s, 2H), 7.07 (dd, J=1.8 Hz, J=8.1 Hz, 1H), 7.30 (m, 3H), 7.40 (m, 1H), 8.00 (d, J=8.1 Hz, 1H). HRMS (M−H) calcd for $C_{22}H_{20}N_2Cl_2O_5$: 461.0671. found: 461.0690.

EXAMPLE 42

Compound 42: 1-(2-Cyano-ethyl)-4-hydroxy-5-oxo-2,5-dihydro-1H-pyrrole-3carboxylic acid (3,4-dichloro-benzyl)-methyl-amide

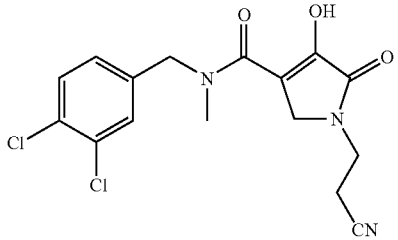

N-(3,4-Dichloro-benzyl)-2-(2,2-dimethyl-5-oxo-[1,3]di-oxolan-4-ylidene)-N-methyl-acetamide (Compound 37-A) was treated with paraformaldehyde and 3-aminopropionitir-ile with 1 equivalent of triethyl amine as described in the preparation of Compound 37. The title compound was purified by chromatography (YMC Combiprep ODS-A, 30 mm×50 mm, MeOH/H2O/0.1% TFA) to yield the title compound as a yellow foam (0.0819 g, 45% yield). $^1$H NMR (300 MHz, CDCl$_3$) δ: 2.73 (t, J=6.3 Hz, 2H), 3.04 (s, 3H), 3.78 (t, J=6.3 Hz, 2H), 4.40 (s, 2H), 4.60 (s, 2H), 7.11 (dd, J=1.8 Hz, J=8.1 Hz, 1H), 7.35 (d, J=1.5 Hz, 1H), 7.43 (d, J=8.4 Hz, 1H). HRMS (M−H) calcd for $C_{16}H_{15}N_3Cl_2O_3$: 366.04122. found: 366.0428.

EXAMPLE 43

Compound 43: 4-Hydroxy-1-(3-morpholin-4-yl-propyl)-5-oxo-2,5-dihydro-1H-pyrrole-3-carboxylic acid (3,4-dichloro-benzyl)-methyl-amide

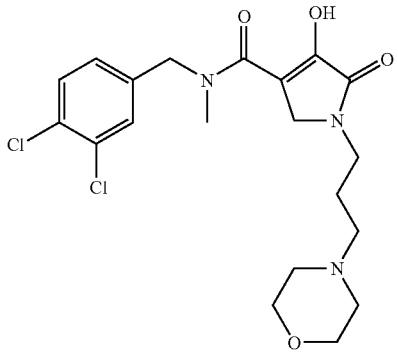

N-(3,4-Dichloro-benzyl)-2-(2,2-dimethyl-5-oxo-[1,3]di-oxolan-4-ylidene)-N-methyl-acetamide (Compound 37-A) was treated with paraformaldehyde and N-(3-aminopropyl) morpholine as described in the preparation of Compound 37. The title compound was isolated as a white solid (0.1345 g, 61% yield). $^1$H NMR (500 MHz, DMSO) δ: 1.69 (t, J=6.4 Hz, 2H), 2.25 (s, 2H), 2.32 (s, 4H), 2.97 (s, 3H), 3.40 (t, J=6.4 Hz, 2H), 3.55 (s, 4H), 4.05 (s, 2H), 4.59 (s, 2H), 7.24 (s, 1H), 7.51 (s, 1H), 7.62 (d, J=8.3 Hz, 1H). HRMS (M−H) calcd for $C_{20}H_{25}N_3Cl_2O_4$: 442.13005. found: 442.1296.

EXAMPLE 44

Compound 44-A: 4-Fluoro-benzaldehyde O-methyl-oxime

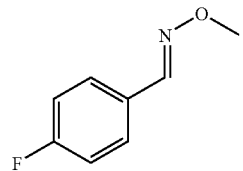

A solution of methoxylamine hydrochloride (13.4 g, 0.16 mol) in a mixture of water (150 ml) and tetrahydrofuran (50 ml) was treated with sodium acetate (11.2 g, 0.136 mol) followed by 4-fluorobenzaldehyde (11.57 g, 93.2 mmol) and the resulting mixture was stirred at 22° C. for 4 hours. The reaction mixture was then diluted with ether, washed with brine and dried over anhydrous magnesium sulfate. Evaporation of the solvent under reduced pressure gave 14.3 g of the crude title material as a clear oil which was used as such for the next step. Distillation of an aliquot in vacuo gave a clear oil; bp 45–50° C./0.5 torr. $^1$HNMR 400 MHz (CDCl$_3$) δ (ppm): 3.99 (3H, s), 7.09 (2H, m), 7.6 (2H, m), 8.06 (1H, s).

Compound 44-B: N-(4-Fluoro-benzyl)-O-methyl-hydroxylamine

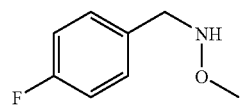

A solution of 4-fluorobenzaldehyde-O-methyloxime (93.2 mmol) in dichloromethane (150 ml) was treated with sodium cyanoborohydride (9.18 g, 0.146 mol) followed by 120 ml of 2 N hydrochloric acid in methanol added dropwise over 30 minutes. After 96 h at 22° C., the solvent was evaporated under reduced pressure and the residue was slurried with water and the pH was adjusted to 9 with 2 N aqueous sodium hydroxide. The aqueous phase was extracted twice with dichloromethane and the combined organic extracts were washed with brine, dried (magnesium sulfate) and concentrated under reduced pressure. The residual oil was chromatographed on silica gel (elution toluene-ethyl acetate 0–10% yield) and gave 5.92 g (41% yield) of the title amine as a clear oil. $^1$HNMR 400 MHz (CDCl$_3$) δ (ppm): 3.49 (3H, s), 4.01 (2H, s), 5.69 (1H, broad s), 7.01 (2H, m), 7.31 (2H, m). The hydrochloride salt was obtained as a white solid: mp 170–171° C. Anal. calcd for $C_8H_{10}FNO$—HCl: C, 50.14; H, 5.78; N, 7.31. Found: C, 50.31; H, 5.80; N, 7.26.

In an alternative procedure a solution of 4-fluorobenzaldehyde O-methyloxime (0.82 g, 5.35 mmol) in acetic acid (8 ml) was treated at 10° C. with sodium cyanoborohydride (0.67 g, 10.7 mmol) added in small portions over 10 min and the resulting solution was stirred at 25° C. for 18 h. The solvent was evaporated under reduce pressure (co-evaporation with toluene twice) and the residue was slurried with water and the pH was adjusted to 9 with 2 N aqueous sodium hydroxide. The aqueous phase was extracted twice with ether and the combined organic extracts were washed with brine, dried (magnesium sulfate) and concentrated under reduced pressure. The residual oil was chromatographed on silica gel (elution hexane-ethyl acetate, 8:2) and distilled in vacuo to give 0.62 g (75% yield) of the title amine as a clear oil.

Compound 44-C: 2-(2,2-Dimethyl-5-oxo-[1,3]dioxolan-4-ylidene)-N-(4-fluoro-benzyl)-N-methoxy-acetamide

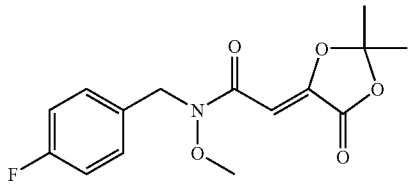

A solution of (2,2-dimethyl-5-oxo-[1,3]dioxolan-4-ylidene)-acetyl chloride (2.45 g, 12.9 mmol) in dichloromethane (15 ml) was added dropwise over 10 minutes to a cold (0–5° C.) mixture of N-4-fluorobenzyl-O-methyl-hydroxylamine (2.0 g, 12.9 mmol) and pyridine (2.1 ml, 25.7 mmol) in dichloromethane (50 ml). The cooling bath was then removed and the solution was stirred at 22° C. for 30 minutes. The reaction mixture was then quenched by the addition of water and ethyl acetate. The organic phase was washed successively with 0.1 N hydrochloric acid, saturated sodium bicarbonate, brine and dried (magnesium sulfate). Evaporation of the solvent and chromatography of the residue on silica gel (toluene-ethyl acetate, 8:2) gave 3.72 g (93% yield) of the title amide as white crystals: mp 111° C. (ethyl acetate-hexane). $^1$HNMR 400 MHz (CDCl$_3$) δ (ppm): 1.75 (6H, s), 3.68 (3H, s), 4.79 (2H, s), 6.38 (1H, s), 7.0 (2H, m), 7.34 (2H, m). Anal. calcd for C$_{15}$H$_{16}$FNO$_5$: C, 58.25; H, 5.21; N, 4.52. Found: C, 58.33; H, 5.38; N, 4.51.

Compound 44-D: 3-[(4-Fluoro-benzyl)-methoxy-carbamoyl]-2-hydroxy-acrylic acid methyl ester

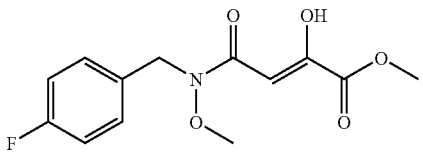

A solution of 2-(2,2-dimethyl-5-oxo-[1,3]dioxolan-4-ylidene)-N-(4-fluorobenzyl)-N-methoxy-acetamide (0.64 g, 2.07 mmol) in methanol (50 ml), was treated at 22° C. with 0.025 ml of a 4.6 M solution of sodium methoxide in methanol and the resulting mixture was stirred for 2 h at the same temperature. The reaction mixture was then quenched by the addition of 1 ml of 1 N hydrochloric acid and the solvent was concentrated under reduced pressure. The residue was diluted with ethyl acetate, washed with water and brine and then dried over anhydrous magnesium sulfate. Evaporation of the solvent and crystallization of the residue from a mixture of ethyl acetate and hexane gave 0.559 g (95% yield) of the title ester as white prisms; mp 71° C. $^1$HNMR 400 MHz (CDCl$_3$) δ (ppm), mixture of rotamers, major: 3.69 (3H, s, OCH$_3$), 3.89 (3H, s, OCH$_3$), 4.80 (2H, s, NCH$_2$), 6.45 (1H, s, CH), 7.03 (2H, m, aromatics), 7.30 (2H, m, aromatics). Anal. calcd for C$_{13}$H$_{14}$FNO$_5$: C, 55.12; H, 4.98; N, 4.94. Found: C, 54.95; H, 4.73; N, 4.67.

Compound 44: 4-Hydroxy-1-methyl-5-oxo-2,5-dihydro-1H-pyrrole-3-carboxylic acid (4-fluoro-benzyl)-methoxy-amide

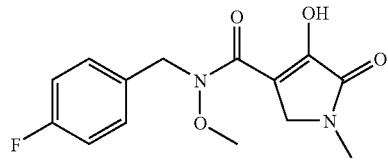

Method 44A: 3-[(4-Fluorobenzyl)-methoxy-carbamoyl]-2-hydroxy-acrylic acid methyl ester was treated with paraformaldehyde and methylamine as described in the preparation of Compound 12 to give the title compound as a white solid (48% yield); mp 125° C., dec. $^1$HNMR 400 MHz (CDCl$_3$) δ (ppm): 3.1 (3H, s, NCH$_3$), 3.72 (3H, s, OCH$_3$), 4.15 (2H, s, NCH$_2$), 4.84 (2H, s, NCH$_2$), 7.04 (2H, m, aromatics), 7.32 (2H, m, aromatics). Anal. calcd for C$_{14}$H$_{15}$FN$_2$O$_4$: C, 57.14; H, 5.13; N, 9.52. Found: C, 56.87; H, 5.12; N, 9.42.

Method 44B: A solution of 2 M methylamine in tetrahydrofuran (0.58 ml, 1.16 mmol) was added to a mixture of paraformaldehyde (0.35 g, 1.16 mmol, equivalent of formaldehyde) in methanol (3 ml) and the resulting mixture was heated at 60° C. for 5 min. Then solid 2-(2,2-dimethyl-5-oxo-[1,3]dioxolan-4-ylidene)-N-(4-fluorobenzyl)-N-methoxy-acetamide (0.30 g, 0.97 mmol) was added all at once and the resulting mixture was maintained at 60° C. for another 60 min. The reaction mixture was then quenched by the addition of ethyl acetate and pH 2 phosphate buffer. The organic phase was washed with brine, dried (anhydrous magnesium sulfate) and concentrated under reduced pressure. Recrystallization of the solid residue from a mixture of ethyl acetate and hexane gave 0.181 g (64% yield) of the title material as a white solid.

EXAMPLE 45

Compound 45: 4-Hydroxy-1-(2-morpholino-4-yl-ethyl)-5-oxo-2,5-dihydro-1H-pyrrole-3-carboxylic acid (4-fluoro-benzyl)-methoxy-amide

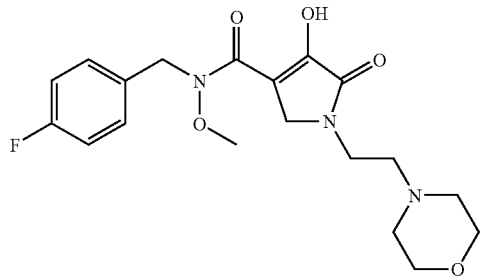

3-[(4-Fluoro-benzyl)-methoxy-carbamoyl]-2-hydroxy-acrylic acid methyl ester (Compound 44-D) was treated with paraformaldehyde and N-(2-aminoethyl)morphiline as described in the preparation of Compound 13. The reaction mixture was diluted with water and extracted the CH$_2$Cl$_2$. After concentration of the organic phase, the residue was triturated with EtOAc and the solid filtered to yield the title compound as a white solid (0.1444 g, 37% yield). $^1$H NMR (500 MHz, DMSO) δ: 3.08 (d, J=11.1 Hz, 2H), 3.41 (d, J=5.2 Hz, 2H), 3.51 (d, J=12.2 Hz, 2H), 3.69 (t, J=11.9 Hz, 2H), 3.75 (s, 3H), 3.81 (s, 2H), 3.98 (d, 1=13.2 Hz, 2H), 4.25 (s, 2H), 4.88 (s, 2H), 7.18 (t, J=8.8 Hz, 2H), 7.37 (m, 2H), 10.11 (s, 1H), 11.42 (s, 1H). HRMS (M+H) calcd for C$_{19}$H$_{24}$FN$_3$O$_5$: 392.16217. found: 392.1627.

EXAMPLE 46

Compound 46: 4-Hydroxy-5-oxo-1-(2-piperazin-1-yl-ethyl)-2,5-dihydro-1H-pyrrole-3-carboxylic acid (4-fluoro-benzyl)-methoxy-amide

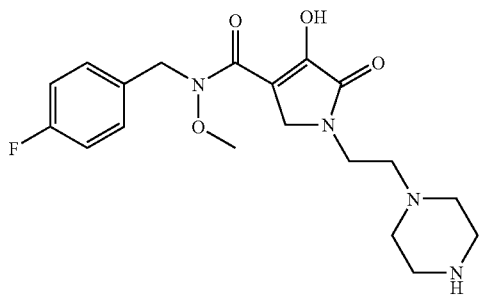

3-[(4-Fluoro-benzyl)-methoxy-carbamoyl]-2-hydroxy-acrylic acid methyl ester (Compound 44-D) was treated with paraformaldehyde and N-(2-aminoethyl)piperazine as described in the preparation of Compound 13. The mixture was purified by chromatography (YMC Combiprep ODS-A, 30 mm×50 mm, MeOH/H2O/0.1% TFA) to yield the title compound as a white powder (0.0110 g, 4.3% yield). $^1$H NMR (500 MHz, CDCl$_3$) δ: 2.55 (t, J=6.2 Hz, 2H), 2.71 (s, 4H), 2.98 (s, 4H), 3.47 (t, J=5.5 Hz, 2H), 3.57 (s, 3H), 4.03 (s, 2H), 4.68 (s, 2H), 6.87 (s, 2H), 7.17 (m, 2H), 9.72 (bs, 1H), 11.45 (bs, 1H). HRMS (M+H) calcd for C$_{19}$H$_{25}$FN$_4$O$_4$: 391.17816. found: 391.1786.

EXAMPLE 47

Compound 47-A: N-(3,4-Dichloro-benzyl)-O-methyl-hydroxylamine

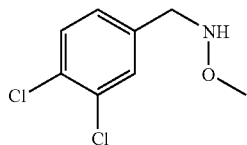

Reaction of 3,4-dichlorobenzaldehyde with methoxylamine hydrochloride followed by reduction with sodium cyanoborohydride as described in the preparation of Compound 44-A and 44-B gave the title hydroxylamine as a clear oil. $^1$HNMR 400 MHz (CDCl$_3$) δ (ppm): 3.48 (3H, s), 3.99 (2H, s), 5.74 (1H, broad s), 7.20 (1H, dd, J=2.0 Hz and J=8.1 Hz), 7.40 (1H, d, J=8.1 Hz), 7.47 (1H, d, J=2.0 Hz).

Compound 47-B: N-(3,4-Dichloro-benzyl)-2-(2,2-dimethyl-5-oxo-[1,3]dioxolan-4-ylidene)-N-methoxy-acetamide

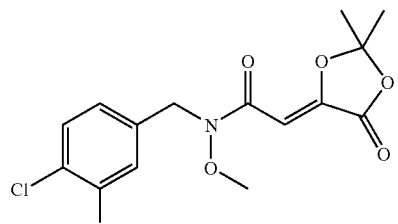

Reaction of (2,2-dimethyl-5-oxo-[1,3]dioxolan-4-ylidene)-acetyl chloride with N-3,4-dichlorobenzyl-O-methyl-hydroxylamine as described in the preparation of Compound 44-C gave the title amide as a white solid (94% yield): mp 119–120° C. (ethyl acetate-hexane). $^1$HNMR 400 MHz (CDCl$_3$) δ (ppm): 1.76 (6H, s), 3.71 (3H, s), 4.72 (2H, s), 6.38 (1H, s), 7.20 (1H, dd, J=2.0 Hz and J=8.5 Hz), 7.40 (1H, d, J=8.5 Hz), 7.46 (1H, d, J=2.0 Hz). Anal. calcd for C$_{15}$H$_{15}$Cl$_2$NO$_5$: C, 50.02; H, 4.20; N, 3.89. Found: C, 50.12; H, 4.12; N, 3.80.

Compound 47-C: 3-[(3,4-Dichloro-benzyl)-methoxy-carbamoyl]-2-hydroxy-acrylic acid methyl ester

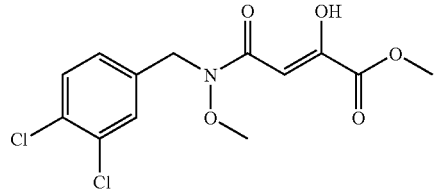

N-(3,4-Dichlorobenzyl)-2-(2,2-dimethyl-5-oxo-[1,3]-dioxolan-4-ylidene)-N-methoxy-acetamide was treated with methanol as described in the preparation of Compound 44-D and gave the title ester as white crystals (95% yield); mp 111° C. $^1$HNMR 400 MHz (CDCl$_3$) δ (ppm): 3.72 (3H, s, OCH$_3$), 3.90 (3H, s, OCH$_3$), 4.77 (2H, s, NCH$_2$), 6.46 (1H, s, CH), 7.17 (1H, dd, J=2.0 Hz, J=8.0 Hz, aromatic), 7.42 (1H, d, J=8.0 Hz, aromatic), 7.43 (1H, d, J=2.0 Hz, aromatic). Anal. calcd for C$_{13}$H$_{13}$Cl$_2$NO$_5$: C, 46.73; H, 3.92; N, 4.19. Found: C, 46.95; H, 3.82; N, 3.97.

Compound 47: 4-Hydroxy-1-methyl-5-oxo-2,5-dihydro-1H-pyrrole-3-carboxylic acid (3,4-dichloro-benzyl)-methoxy-amide

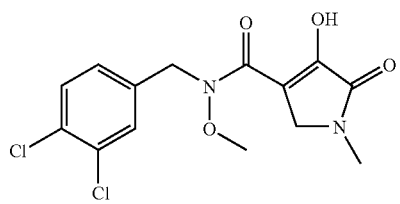

3-[(3,4-Dichlorobenzyl)-methoxy-carbamoyl]-2-hydroxy-acrylic acid methyl ester (Compound 47-C) was treated with paraformaldehyde and methylamine as described in the preparation of Compound 12, yielding the title compound as a white solid (49% yield); mp 149° C. $^1$HNMR 400 MHz (CDCl$_3$) δ (ppm): 3.11 (3H, s, NCH$_3$), 3.75 (3H, s, OCH$_3$), 4.15 (2H, s, NCH$_2$), 4.82 (2H, s, NCH$_2$), 7.18 (1H, dd, J=2.0 Hz, J=8.2 Hz, aromatic), 7.42 (1H, d, J=8.2 Hz, aromatic), 7.43 (1H, d, J=2.0 Hz, aromatic). Anal. calcd for C$_{14}$H$_{14}$Cl$_2$N$_2$O$_4$: C, 48.72; H, 4.09; N, 8.12. Found: C, 48.81; H, 4.04; N, 7.99.

EXAMPLE 48

Compound 48-A: N-(3-Chloro-4-fluoro-benzyl)-O-methyl-hydroxylamine

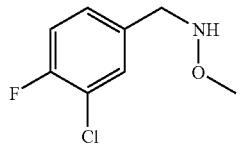

Reaction of 3-chloro-4-fluorobenzaldehyde with methoxylamine hydrochloride followed by reduction with sodium cyanoborohydride as described in the preparation of Compound 44-A and 44-B gave the title hydroxylamine as a clear oil. $^1$HNMR 400 MHz (CDCl$_3$) δ (ppm): 3.48 (3H, s), 3.98 (2H, s), 5.72 (1H, broad s), 7.10 (1H, t), 7.22 (1H, m), 7.42 (1H, m).

Compound 48-B: N-(3-Chloro-4-fluoro-benzyl)-2-(2,2-dimethyl-5-oxo-[1,3]dioxolan-4-ylidene)-N-methoxy-acetamide

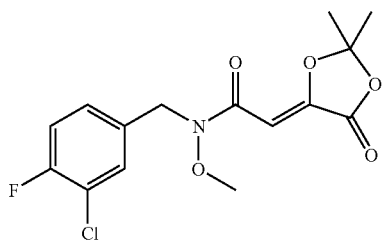

Reaction of (2,2-dimethyl-5-oxo-[1,3]dioxolan-4-ylidene)-acetyl chloride with N-(3-chloro-4-fluorobenzyl)-O-methyl-hydroxylamine as described in the preparation of Compound 44-C gave the title amide as a white solid (91% yield): mp 110–111° C. (ethyl acetate-hexane). $^1$HNMR 400 MHz (CDCl$_3$) δ (ppm): 1.76 (6H, s), 3.71 (3H, s), 4.75 (2H, s), 6.38 (1H, s), 7.09 (1H, t, J=8.8 Hz), 7.23 (1H, m), 7.41 (1H, dd, J=2.4 Hz and J=6.8 Hz). Anal. calcd for C$_{15}$H$_{15}$ClFNO$_5$: C, 52.41; H, 4.39; N, 4.07. Found: C, 52.25, H, 4.36, N, 3.87.

Compound 48-C: 3-[(3-Chloro-4-fluoro-benzyl)-methoxy-carbamoyl]-2-hydroxy-acrylic acid methyl ester

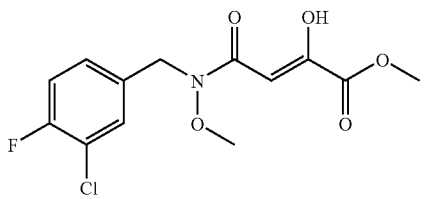

N-(3-Chloro-4-fluorobenzyl)-2-(2,2-dimethyl-5-oxo-[1,3]-dioxolan-4-ylidene)-N-methoxy-acetamide was treated with methanol as described in the preparation of Compound 44-D and gave the title ester as white crystals (54% yield); mp 97–98° C. $^1$HNMR 400 MHz (CDCl$_3$) δ (ppm): 3.72 (3H, s, OCH$_3$), 3.90 (3H, s, OCH$_3$), 4.77 (2H, s, NCH$_2$), 6.45 (1H, s, CH), 7.11 (1H, m, aromatic), 7.2 (1H, m, aromatic), 7.38 (1H, m, aromatic). Anal. calcd for C$_{13}$H$_{13}$ClFNO$_5$: C, 49.14; H, 4.12; N, 4.40. Found: C, 48.95; H, 3.96; N, 4.16.

Compound 48: 4-Hydroxy-1-methyl-5-oxo-2,5-dihydro-1H-pyrrole-3-carboxylic acid (3-chloro-4-fluoro-benzyl)-methoxy-amide

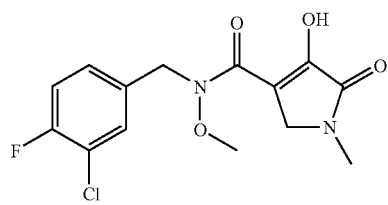

3-[(3-Chloro-4-fluorobenzyl)-methoxy-carbamoyl]-2-hydroxy-acrylic acid methyl ester (48-C) was treated with paraformaldehyde and methylamine as described in the preparation of Compound 12 to give the title compound as a white solid (60% yield); mp 148° C. dec. $^1$HNMR 400 MHz (CDCl$_3$) δ (ppm): 3.10 (3H, s, NCH$_3$), 3.75 (3H, s, OCH$_3$), 4.15 (2H, s, NCH$_2$), 4.81 (2H, s, NCH$_2$), 7.12 (1H, m, aromatic), 7.22 (1H, m, aromatic), 7.38 (1H, m, aromatic). Anal. calcd for C$_{14}$H$_{14}$Cl$_2$N$_2$O$_4$: C, 51.15; H, 4.29; N, 8.52. Found: C, 51.19; H, 4.17; N, 8.50.

EXAMPLE 49

Compound 49-A: N-(3-Fluoro-benzyl)-O-methyl-hydroxylamine

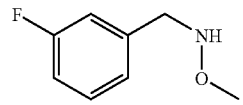

Reduction 3-fluorobenzaldehyde O-methyloxime with sodium cyanoborohydride as described in the preparation of Compounds 44-A and 44-B gave the title hydroxylamine as a clear oil (60% yield). ¹HNMR 400 MHz (CDCl₃) δ (ppm): 3.50 (3H, s, OCH₃), 4.04 (2H, s, NCH₂), 5.75 (1H, broad s, NH), 6.95–7.32 (4H, m, aromatics). The hydrochloride salt was obtained as a white solid: mp 130–131° C. (dec.). Anal. calcd for $C_8H_{10}FNO \cdot HCl$: C, 50.14; H, 5.78; N, 7.31. Found: C, 50.10; H, 5.73; N, 7.38.

Compound 49-B: 2-(2,2-Dimethyl-5-oxo-[1,3]dioxolan-4-ylidene)-N-(3-fluoro-benzyl)-N-methoxy-acetamide

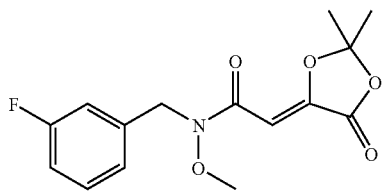

Reaction of (2,2-dimethyl-5-oxo-[1,3]dioxolan-4-ylidene)-acetyl chloride with N-(3-fluorobenzyl)-O-methyl-hydroxylamine as described in the preparation of Compound 44-C and gave the title amide as a white solid (94% yield): mp 110–111° C. (ethyl acetate-hexane). ¹HNMR 400 MHz (CDCl₃) δ (ppm): 1.76 (6H, s, CH₃), 3.70 (3H, s, OCH₃), 4.82 (2H, s, NCH₂), 6.40 (1H, s, CH), 6.96–7.32 (4H, m, aromatics). Anal. calcd. for $C_{15}H_{16}FNO_5$: C, 58.25; H, 5.21; N, 4.52. Found: C, 58.00; H, 5.30; N, 4.49.

Compound 49-C: 3-[(3-Fluoro-benzyl)-methoxy-carbamoyl]-2-hydroxy-acrylic acid methyl ester

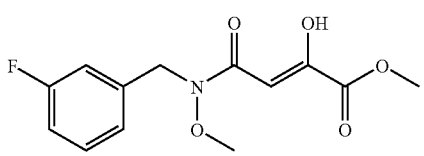

N-(3-Fluorobenzyl)-2-(2,2-dimethyl-5-oxo-[1,3]-dioxolan-4-ylidene)-N-methoxy-acetamide was treated with methanol as described in the preparation of Compound 44-D and gave the title ester as white crystals (53% yield); mp 73–75° C. ¹HNMR 400 MHz (CDCl₃) δ (ppm): 3.71 (3H, s, OCH₃), 3.90 (3H, s, OCH₃), 4.82 (2H, s, NCH₂), 6.47 (1H, s, CH), 6.98–7.34 (4H, m, aromatics). Anal. calcd for $C_{13}H_{14}FNO_5$: C, 55.12; H, 4.98; N, 4.94. Found: C, 55.18; H, 5.04; N, 5.02.

Compound 49: 4-Hydroxy-1-methyl-5-oxo-2,5-dihydro-1H-pyrrole-3-carboxylic acid (3-fluoro-benzyl)-methoxy-amide

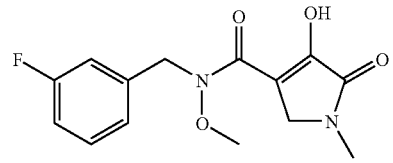

3-[(3-Fluorobenzyl)-methoxy-carbamoyl]-2-hydroxy-acrylic acid methyl ester (Compound 49-C) was reacted with paraformaldehyde and methylamine as described in the preparation of Compound 12 to give the title compound as a white solid (60% yield); mp 119° C. dec. ¹HNMR 400 MHz (CDCl₃) δ (ppm): 3.11 (3H, s, NCH₃), 3.74 (3H, s, OCH₃), 4.17 (2H, s, NCH₂), 4.87 (2H, s, NCH₂), 6.99–7.35 (4H, m, aromatics). Anal. calcd for $C_{14}H_{15}FN_2O_4$: C, 57.14; H, 5.14; N, 9.52. Found: C, 57.04; H, 5.02; N, 9.42.

EXAMPLE 50

Compound 50-A: 2-Fluorobenzaldehyde O-methyloxime

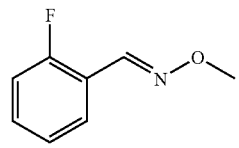

Reaction of 2-fluorobenzaldehyde with methoxylamine hydrochloride as described in the preparation of Compound 44-A gave the title oxime ether as a clear oil (98% yield). HPLC indicated a 91:9 mixture of E- to Z-isomers. ¹HNMR 400 MHz (CDCl₃) δ (ppm): (E-isomer) 3.99 (3H, s, OCH₃), 7.07 (1H, m, aromatic), 7.14 (1H, m, aromatic), 7.34 (1H, m, aromatic), 7.82 (1H, m, aromatic), 8.31 (1H, s, CH).

Compound 50-B: N-(2-Fluoro-benzyl)-O-methyl-hydroxylamine

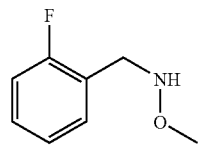

Reduction of 2-fluorobenzaldehyde O-methyloxime with sodium cyanoborohydride as described in the preparation of Compound 44-B gave the title hydroxylamine as a clear oil (74% yield). ¹HNMR 400 MHz (CDCl₃) δ (ppm): 3.52 (3H, s, OCH₃), 4.11 (2H, s, NCH₂), 5.78 (1H, broad s, NH), 7.05 (1H, m, aromatic), 7.11 (1H, m, aromatic), 7.27 (1H, m, aromatic), 7.38 (1H, m, aromatic). The hydrochloride salt was obtained as a white solid: mp 138–143° C. (dec.). Anal. calcd. for $C_8H_{10}FNO \cdot HCl$: C, 50.14; H, 5.78; N, 7.31. Found: C, 50.37; H, 5.71; N, 7.18.

Compound 50-C: 2-(2,2-Dimethyl-5-oxo-[1,3]diox-olan-4-ylidene)-N-(2-fluoro-benzyl)-N-methoxy-acetamide

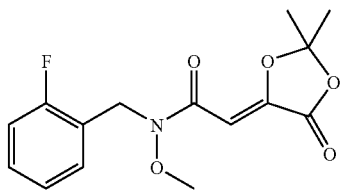

Reaction of (2,2-dimethyl-5-oxo-[1,3]dioxolan-4-ylidene)-acetyl chloride with N-(2-fluorobenzyl)-O-methyl-hydroxylamine as described in the preparation of Compound 44-C gave the title amide as a white solid (84% yield): mp 109–111° C. (ethyl acetate-hexane). $^1$HNMR 400 MHz (CDCl$_3$) δ (ppm): 1.75 (6H, s, CH$_3$), 3.72 (3H, s, OCH$_3$), 4.92 (2H, s, NCH$_2$), 6.40 (1H, s, CH), 7.03–7.12 (2H, m, aromatics), 7.24–7.30 (1H, m, aromatic), 7.4 (1H, m, aromatic). Anal. calcd. for C$_{15}$H$_{16}$FNO$_5$: C, 58.25; H, 5.21; N, 4.52. Found: C, 58.47; H, 5.16; N, 4.66.

Compound 50-D: 3-[(2-Fluoro-benzyl)-methoxy-carbamoyl]-2-hydroxy-acrylic acid methyl ester

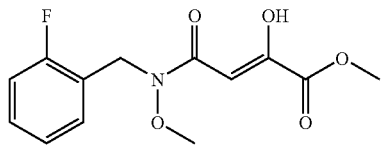

N-(2-Fluorobenzyl)-2-(2,2-dimethyl-5-oxo-[1,3]-dioxolan-4-ylidene)-N-methoxy-acetamide was treated with methanol as described in the preparation of Compound 44-D and gave the title ester as a white syrup (59% yield). $^1$HNMR 400 MHz (CDCl$_3$) δ (ppm): 3.73 (3H, s, OCH$_3$), 3.89 (3H, s, OCH$_3$), 4.93 (2H, s, NCH$_2$), 6.47 (1H, s, CH), 7.05–7.36 (4H, m, aromatics). Anal. calcd for C$_{13}$H$_{14}$FNO$_5$: C, 55.12; H, 4.98; N, 4.94. Found: C, 54.91; H, 5.23; N, 4.86.

Compound 50: 4-Hydroxy-1-methyl-5-oxo-2,5-di-hydro-1H-pyrrole-3-carboxylic acid (2-fluoro-ben-zyl)-methoxy-amide

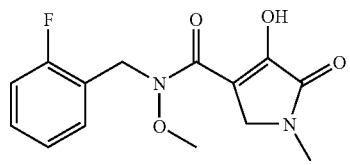

3-[(2-Fluorobenzyl)-methoxy-carbamoyl]-2-hydroxy-acrylic acid methyl ester (Compound 50-D) was treated with paraformaldehyde and methylamine as described in the preparation of Compound 12 to give the title compound as a white solid (58% yield); mp 147° C. dec. $^1$HNMR 400 MHz (CDCl$_3$) δ (ppm): 3.1 (3H, s, NCH$_3$), 3.76 (3H, s, OCH$_3$), 4.15 (2H, s, NCH$_2$), 4.97 (2H, s, NCH$_2$), 7.06–7.39 (4H, m, aromatics). Anal. calcd for C$_{14}$H$_{15}$FN$_2$O$_4$: C, 57.14; H, 5.14; N, 9.52. Found: C, 57.00; H, 5.29; N, 9.33.

EXAMPLE 51

Compound 51-A: N-(4-Chloro-benzyl)-2-(2,2-dim-ethyl-5-oxo-[1,3]dioxolan-4-ylidene)-N-methoxy-acetamide

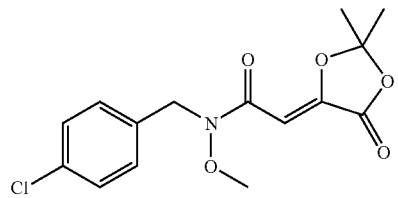

Reaction of (2,2-dimethyl-5-oxo-[1,3]dioxolan-4-ylidene)-acetyl chloride with N-(4-chlorobenzyl)-O-methyl-hydroxylamine (Kawase, M. et al., J. Chem. Soc. Perkin Trans. 1, 1979, 643–645) as described in the preparation of compound 1-A gave the title amide as white crystals (95% yield): mp 129–130° C. (ethyl acetate-hexane). $^1$HNMR 400 MHz (CDCl$_3$) δ (ppm): 1.75 (6H, s, CH$_3$), 3.69 (3H, s, OCH$_3$), 4.79 (2H, s, NCH$_2$), 6.39 (1H, s, CH), 7.4 (4H, s, aromatics). Anal. calcd. for C$_{15}$H$_{16}$ClNO$_5$: C, 55.31; H, 4.95; N, 4.30. Found: C, 55.32; H, 4.95; N, 4.27.

Compound 51-B: 3-[(4-Chloro-benzyl)-methoxy-carbamoyl]-2-hydroxy-acrylic acid methyl ester

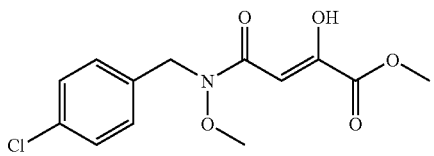

N-(4-Chlorobenzyl)-2-(2,2-dimethyl-5-oxo-[1,3]-dioxolan-4-ylidene)-N-methoxy-acetamide was treated with methanol as described in the preparation of Compound 44-D and gave the title ester as a white syrup (52% yield). $^1$HNMR 400 MHz (CDCl$_3$) δ (ppm): 3.70 (3H, s, OCH$_3$), 3.90 (3H, s, OCH$_3$), 4.80 (2H, s, NCH$_2$), 6.45 (1H, s, CH), 7.25–7.33 (4H, m, aromatics). Anal. calcd for C$_{13}$H$_{14}$ClNO$_5$: C, 52.10; H, 4.71; N, 4.67. Found: C, 51.86; H, 4.68; N, 4.45.

Compound 51: 4-Hydroxy-1-methyl-5-oxo-2,5-dihydro-1H-pyrrole-3-carboxylic acid (4-chloro-benzyl)-methoxy-amide

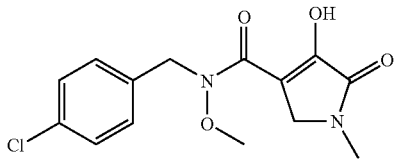

3-[(4-Chlorobenzyl)-methoxy-carbamoyl]-2-hydroxy-acrylic acid methyl ester (Compound 51-B) was treated with paraformaldehyde and methylamine as described in the preparation of Compound 12 to give the title compound as a white solid (69% yield); mp 165° C. dec. $^1$HNMR 400 MHz (CDCl$_3$) δ (ppm): 3.10 (3H, s, NCH$_3$), 3.72 (3H, s, OCH$_3$), 4.15 (2H, s, NCH$_2$), 4.84 (2H, s, NCH$_2$), 7.25–7.34 (4H, m, aromatics). Anal. calcd for C$_{14}$H$_{15}$ClN$_2$O$_4$: C, 54.11; H, 4.87; N, 9.02. Found: C, 53.88; H, 4.71; N, 8.78.

EXAMPLE 52

Compound 52-A: 4-Fluorophenylacetaldehyde O-methyloxime

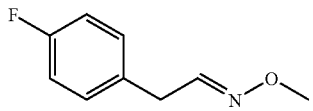

Reaction of 4-fluorophenylacetaldehyde with methoxylamine hydrochloride as described in the preparation of Compound 44-A gave the title oxime ether as a clear oil (43% yield). $^1$HNMR indicated a 1:1 mixture of E- to Z-isomers. $^1$HNMR 400 MHz (CDCl$_3$) δ (ppm): 3.51 (2H, d, J=6.7 Hz, CH$_2$), 3.66 (2H, d, J=5.5 Hz, CH$_2$), 3.88 (3H, s, OCH$_3$), 3.96 (3H, s, OCH$_3$), 6.79 (1H, t, J=5.5 Hz, CH), 7.03 (2H, m, aromatics), 7.19 (2H, m, aromatics), 7.45 (1H, t, J=6.7 Hz, CH).

Compound 52-B: N-[2-(4-Fluoro-phenyl)-ethyl]-O-methyl-hydroxylamine

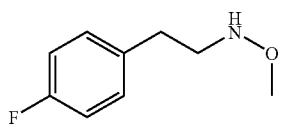

Reduction of 4-fluorophenylacetaldehyde O-methyloxime with sodium cyanoborohydride as described in the preparation of Compound 44-B gave the title hydroxylamine as a clear oil after chromatography on silica gel (62% yield). $^1$HNMR 400 MHz (C$_6$D$_6$) δ (ppm): 2.64 (2H, d, J=7.1 Hz, CH$_2$), 2.97 (2H, d, J=7.1 Hz, CH$_2$), 3.53 (3H, s, OCH$_3$), 5.24 (broad, NH), 6.9 (4H, m, aromatics).

Compound 52-C: 2-(2,2-Dimethyl-5-oxo-[1,3]dioxolan-4-ylidene)-N-[2-(4-fluoro-phenyl)-ethyl]-N-methoxy-acetamide

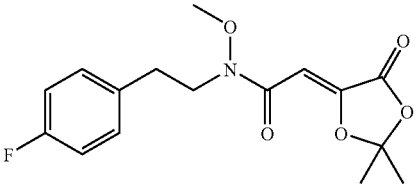

Reaction of (2,2-dimethyl-5-oxo-[1,3]dioxolan-4-ylidene)-acetyl chloride with N-[2-(4-fluorophenyl)-ethyl]-O-methyl-hydroxylamine as described in the preparation of Compound 44-C gave the title amide as white crystals (86% yield): mp 106–107° C. (ethyl acetate-hexane). $^1$HNMR 400 MHz (CDCl$_3$) δ (ppm): 1.76 (6H, s, CH$_3$), 2.95 (2H, m, CH$_2$), 3.72 (3H, s, OCH$_3$), 3.87 (2H, m, NCH$_2$), 6.38 (1H, broad s, CH), 6.99 (2H, m, aromatics), 7.20 (2H, m, aromatics). Anal. calcd for C$_{16}$H$_{18}$FNO$_5$: C, 59.43; H, 5.61; N, 4.33. Found: C, 59.39; H, 5.43; N, 4.13.

Compound 52-D: 3{[2-(4-Fluoro-phenyl)-ethyl]-methoxy-carbamoyl}-2-hydroxy-acrylic acid methyl ester

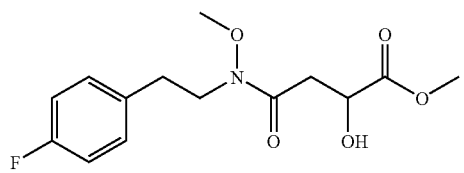

2-(2,2-Dimethyl-5-oxo-[1,3]-dioxolan-4-ylidene)-N-[2-(4-fluorophenyl)-ethyl]-N-methoxy-acetamide was treated with methanol as described in the preparation Compound 44-D and gave the title ester as a clear oil (66% yield). HRMS (MAB N$_2$) calculated for C$_{14}$H$_{16}$FNO$_5$: [M]$^+$: 297.101251. found: 297.101514. $^1$HNMR 400 MHz (CDCl$_3$) δ (ppm): 2.95 (2H, t, J=7.6 Hz, CH$_2$), 3.73 (3H, s, OCH$_3$), 3.89 (2H, t, J=7.6 Hz, CH$_2$), 3.92 (3H, s, OCH$_3$), 6.44 (1H, s, CH), 7.0 (2H, m, aromatics), 7.19 (2H, m, aromatics).

Compound 52: 4-Hydroxy-1-methyl-5-oxo-2,5-dihydro-1H-pyrrole-3-carboxylic acid [2-(4-fluoro-phenyl)-ethyl]-methoxy-amide

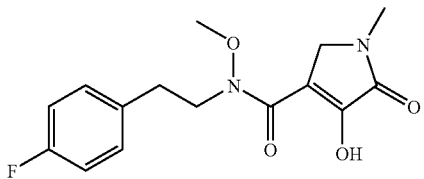

3-{[2-(4-Fluorophenyl)-ethyl]-methoxy-carbamoyl}-2-hydroxy-acrylic acid methyl ester (Compound 52-D) was treated with paraformaldehyde and methylamine as described in the preparation of Compound 12 to give the title compound as a white solid (38% yield); mp 157° C. dec. ¹HNMR 400 MHz (CDCl₃) δ (ppm): 2.96 (2H, t, J=7.6 Hz, CH₂), 3.14 (3H, s, NCH₃), 3.71 (3H, s, OCH₃), 3.93 (2H, t, J=7.6 Hz, CH₂), 4.14 (2H, s, NCH₂), 7.01 (2H, m, aromatics), 7.2 (2H, m, aromatics), 11.55 (1H, broad s, OH). Anal. calcd for C₁₅H₁₇FN₂O₄: C, 58.44; H, 5.56; N, 9.09. Found: C, 58.52; H, 5.66; N, 8.89.

EXAMPLE 53

Compound 53-A: 4-Fluorobenzaldehyde O-ethyloxime

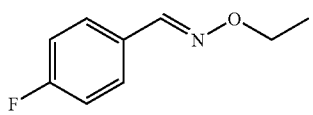

Reaction of 4-fluorobenzaldehyde with ethoxylamine hydrochloride as described in the preparation of Compound 44-A gave the title oxime ether as a clear oil after chromatography on silica gel (elution toluene-ethyl acetate 95:5) and distillation (58% yield). ¹HNMR 400 MHz (CDCl₃) δ (ppm): 1.35 (3H, t, J=7.07 Hz, CH₃), 4.24 (2H, q, J=7.07 Hz, OCH₂), 7.08 (2H, m, aromatics), 7.59 (2H, m, aromatics), 8.07 (1H, s, CH).

Compound 53-B: O-Ethyl-N-(4-fluoro-benzyl)-hydroxylamine

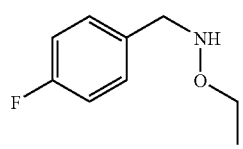

Reduction of 4-fluorobenzaldehyde O-ethyloxime with sodium cyanoborohydride as described in the preparation of Compound 44-B gave the title hydroxylamine as a clear oil after chromatography (74% yield). ¹HNMR 400 MHz (C₆D₆) δ (ppm): 1.13 (3H, t, J=7.1 Hz, CH₃), 3.70 (2H, q, J=7.1 Hz, OCH₂), 3.78 (2H, d, J=5.4 Hz, NCH₂), 5.20 (2H, broad t, NH), 6.89 (2H, m, aromatics), 7.09 (2H, m, aromatics). Anal. calcd for C₉H₁₂FNO: C, 63.88; H, 7.14; N, 8.27. Found: C, 63.68; H, 7.08; N, 8.46.

Compound 53-C: 2-(2,2-Dimethyl-5-oxo-[1,3]dioxolan-4-ylidene)-N-ethoxy-N-(4-fluoro-benzyl)-acetamide

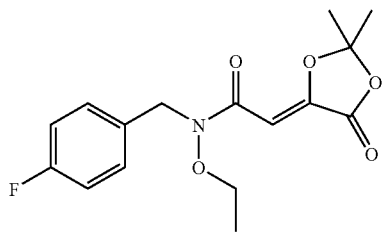

Reaction of (2,2-dimethyl-5-oxo-[1,3]dioxolan-4-ylidene)-acetyl chloride with O-ethyl-N-4-fluorobenzyl-hydroxylamine as described in the preparation of Compound 44-C gave the title amide as white crystals (92% yield): mp 95–96° C. (ethyl acetate-hexane). ¹HNMR 400 MHz (CDCl₃) δ (ppm): 1.27 (3H, t, J=7.07 Hz, CH₃), 1.77 (6H, s, CH₃), 3.90 (2H, q, J=7.07 Hz, OCH₂), 4.81 (2H, s, NCH₂), 6.41 (1H, s, CH), 7.03 (2H, m, aromatics), 7.37 (2H, m, aromatics). Anal. calcd for C₁₆H₁₈FNO₅: C, 59.43; H, 5.61; N, 4.33. Found: C, 59.50; H, 5.60; N, 4.17.

Compound 53-D: 3-[Ethoxy-(4-fluoro-benzyl)-carbamoyl]-2-hydroxy-acrylic acid methyl ester

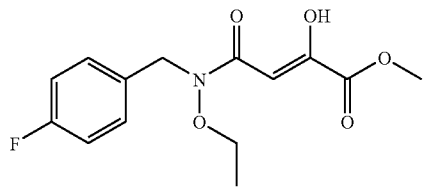

2-(2,2-Dimethyl-5-oxo-[1,3]-dioxolan-4-ylidene)-N-ethoxy-N-(4-fluorobenzyl)-acetamide was treated with methanol as described in the preparation of Compound 44-D and gave the title ester as white crystals (84% yield); mp 61–62° C. ¹HNMR 400 MHz (CDCl₃) δ (ppm): 1.28 (3H, t, J=7.1 Hz, CH₃), 3.91 (3H, s, OCH₃), 3.92 (2H, q, J=7.1 Hz, OCH₂), 4.82 (2H, s, NCH₂), 6.47 (1H, s, CH), 7.05 (2H, m, aromatics), 7.32 (2H, m, aromatics), 13.5 (1H, broad s, OH). Anal. calcd for C₁₄H₁₆FNO₅: C, 56.56; H, 5.42; N, 4.71. Found: C, 56.67; H, 5.25; N, 4.64.

Compound 53: 4-Hydroxy-1-methyl-5-oxo-2,5-dihydro-1H-pyrrole-3-carboxylic acid ethoxy-(4-fluoro-benzyl)-amide

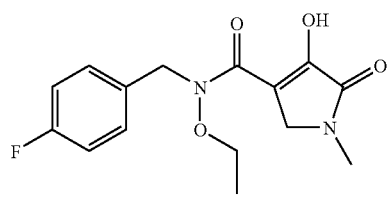

3-[Ethoxy-(4-fluorobenzyl)-carbamoyl]-2-hydroxy-acrylic acid methyl ester (Compound 53-D) was treated with paraformaldehyde and methylamine as described in the preparation of Compound 12 to give the title compound as a white solid (50% yield); mp 113–114° C. ¹HNMR 400 MHz (CDCl₃) δ (ppm): 1.30 (3H, t, J=7.1 Hz, CH₃), 3.12 (3H, s, NCH₃), 3.96 (2H, q, J=7.1 Hz, OCH₂), 4.16 (2H, s, NCH₂), 4.86 (2H, s, NCH₂), 7.06 (2H, m, aromatics), 7.33 (2H, m, aromatics), 11.65 (1H, broad s, OH). Anal. calcd for C₁₅H₁₇FN₂O₄: C, 58.43; H, 5.55; N, 9.08. Found: C, 58.30; H, 5.55; N, 9.03.

EXAMPLE 54

Compound 54-A: 3,4-Difluorobenzaldehyde O-methyloxime

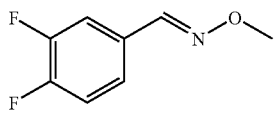

Reaction of 3,4-difluorobenzaldehyde with methoxylamine hydrochloride as described in the preparation of Compound 44-A gave the title oxime ether as a clear oil (100% yield). ¹HNMR indicated a 85:15 mixture of E- to Z-isomers. ¹HNMR 400 MHz (CDCl₃) δ (ppm): (E-isomer) 3.97 (3H, s, OCH₃), 7.12–7.26 (2H, m, aromatics), 7.44–7.52 (1H, m, aromatic), 7.97 (1H, s, CH).

Compound 54-B: N-(3,4-Difluoro-benzyl)-O-methyl-hydroxylamine

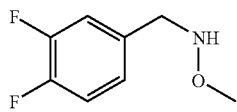

Reduction of 3,4-difluorobenzaldehyde O-methyloxime with sodium cyanoborohydride as described in the preparation of Compound 44-B gave the title hydroxylamine as a clear oil (82% yield). ¹HNMR 400 MHz (CDCl₃) δ (ppm): 3.48 (3H, s, OCH₃), 3.98 (2H, s, NCH₂), 5.73 (1H, broad s, NH), 7.04–7.23 (3H, m, aromatics). The hydrochloride salt was obtained as a white solid: mp 139–142° C. (dec.). Anal. calcd. for C₈H₉F₂NO₂—HCl: C, 45.83; H, 4.80; N, 6.68. Found: C, 45.96; H, 4.93, N, 6.67.

Compound 54-C: N-(3,4-Difluoro-benzyl)-2-(2,3-dimethyl-5-oxo-[1,3]dioxolan-4-ylidene)-N-methoxy-acetamide

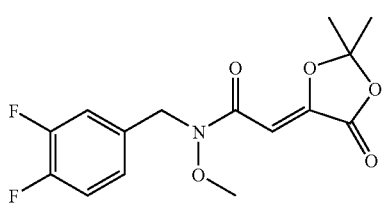

Reaction of (2,2-dimethyl-5-oxo-[1,3]dioxolan-4-ylidene)-acetyl chloride with N-3,4-difluorobenzyl-O-methyl-hydroxylamine as described in the preparation of Compound 44-C gave the title amide as a white solid (96% yield): mp 110–111° C. (ethyl acetate-hexane). ¹HNMR 400 MHz (CDCl₃) δ (ppm): 1.76 (6H, s, CH₃), 3.71 (3H, s, OCH₃), 4.72 (2H, s, NCH₂), 6.38 (1H, s, CH), 7.05–7.22 (3H, m, aromatics). Anal. calcd. for C₁₅H₁₅NO₅: C, 55.04; H, 4.62; N, 4.28. Found: C, 54.99; H, 4.55; N, 4.22.

Compound 54-D: 3-[(3,4-Difluoro-benzyl)-methoxy-carbamoyl]-2-hydroxy-acrylic acid methyl ester

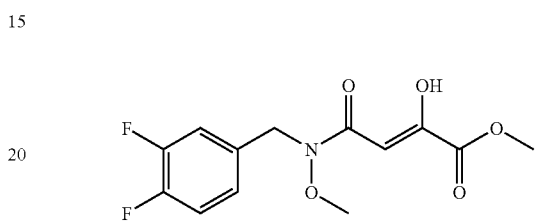

N-(3,4-Difluorobenzyl)-2-(2,2-dimethyl-5-oxo-[1,3]-dioxolan-4-ylidene)-N-methoxy-acetamide was treated with methanol as described in the preparation of Compound 44-D and gave the title ester as white crystals (53% yield); mp 76–77° C. ¹HNMR 400 MHz (CDCl₃) δ (ppm): 3.72 (3H, s, OCH₃), 3.90 (3H, s, OCH₃), 4.77 (2H, s, NCH₂), 6.45 (1H, s, CH), 7.05–7.19 (3H, m, aromatics). Anal. calcd for C₁₃H₁₃F₂NO₅: C, 51.83; H, 4.35; N, 4.65. Found: C, 51.78; H, 4.28; N, 4.53.

Compound 54: 4-Hydroxy-1-methyl-5-oxo-2,5-dihydro-1H-pyrrole-3-carboxylic acid (3,4-difluoro-benzyl)-methoxy-amide

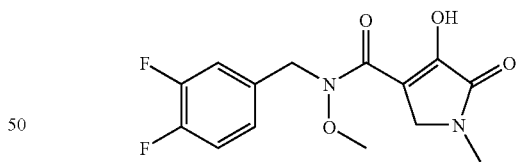

3-[(3,4-Difluorobenzyl)-methoxy-carbamoyl]-2-hydroxy-acrylic acid methyl ester (Compound 54-D) was treated with paraformaldehyde and methylamine as described in the preparation of Compound 12 to and gave the title compound as a white solid (53% yield); mp 146–147° C. ¹HNMR 400 MHz (CDCl₃) δ (ppm): 3.11 (3H, s, NCH₃), 3.74 (3H, s, OCH₃), 4.16 (2H, s, NCH₂), 4.79 (2H, s, NCH₂), 7.06–7.19 (3H, m, aromatics). Anal. calcd for C₁₄H₁₄F₂N₂O₄: C, 53.84; H, 4.51; N, 8.97. Found: C, 53.82; H, 4.41; N, 8.87.

EXAMPLE 55

Compound 55-A: 4-Methoxybenzaldehyde O-methyloxime

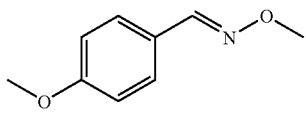

Reaction of 4-methoxybenzaldehyde with methoxylamine hydrochloride as described in the preparation of Compound 44-A gave the title oxime ether as a clear oil (100% yield). $^1$HNMR indicated a 95:5 mixture of E- to Z-isomers. $^1$HNMR 400 MHz (CDCl$_3$) δ (ppm): (E-isomer) 3.83 (3H, s, OCH$_3$), 3.94 (3H, s, OCH$_3$), 6.89 (2H, m, aromatics), 7.52 (2H, m, aromatics), 8.05 (1H, s, CH).

Compound 55-B: N-(4-Methoxy-benzyl)-O-methyl-hydroxylamine

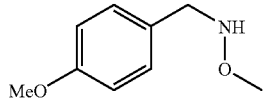

Reduction of 4-methoxybenzaldehyde O-methyloxime with sodium cyanoborohydride as described in the preparation of Compound 44-B gave the title hydroxylamine as a clear oil (96% yield). $^1$HNMR 400 MHz (CDCl$_3$) δ (ppm): 3.49 (3H, s, OCH$_3$), 3.79 (3H, s, OCH$_3$), 3.98 (2H, s, NCH$_2$), 5.62 (1H, broad s, NH), 6.86 (2H, m, aromatics), 7.25 (2H, m, aromatics). The hydrochloride salt was obtained as a white solid: mp 157–158° C. (dec.). Anal. calcd. for C$_9$H$_{13}$NO$_2$—HCl: C, 53.03; H, 6.92; N, 6.87. Found: C, 53.14; H, 6.76; N, 6.80.

Compound 55-C: 2-(2,2-Dimethyl-5-oxo-[1,3]dioxolan-4-ylidene)-N-methoxy-(4-methoxy-benzyl)-acetamide

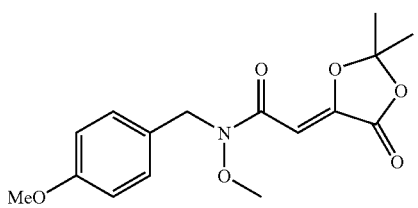

Reaction of (2,2-dimethyl-5-oxo-[1,3]dioxolan-4-ylidene)-acetyl chloride with N-(4-methoxybenzyl)-O-methyl-hydroxylamine as described in the preparation of Compound 44-C gave the title amide as white crystals (97% yield): mp 113–114° C. (ethyl acetate-hexane). $^1$HNMR 400 MHz (CDCl$_3$) δ (ppm): 1.75 (6H, s, CH$_3$), 3.66 (3H, s, OCH$_3$), 3.79 (3H, s, OCH$_3$), 4.77 (2H, s, NCH$_2$), 6.38 (1H, s, CH), 6.85 (2H, m, aromatics), 7.29 (2H, m, aromatics). Anal. calcd. for C$_{16}$H$_{19}$NO$_6$: C, 59.80; H, 5.96; N, 4.35. Found: C, 59.87; H, 5.76; N, 4.17.

Compound 55-D: 2-Hydroxy-3-[methoxy-(4-methoxy-benzyl)-carbamoyl]-acrylic acid methyl ester

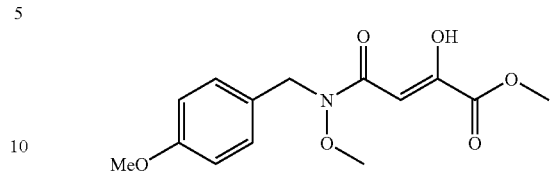

2-(2,2-Dimethyl-5-oxo-[1,3]-dioxolan-4-ylidene)-N-methoxy-N-(4-methoxybenzyl)-acetamide was treated with methanol as described in the preparation of Compound 44-D and gave the title ester as white crystals (56% yield); mp 87–89° C. $^1$HNMR 400 MHz (CDCl$_3$) δ (ppm): 3.67 (3H, s, OCH$_3$), 3.80 (3H, s, OCH$_3$), 3.89 (3H, s, OCH$_3$), 4.77 (2H, s, NCH$_2$), 6.44 (1H, s, CH), 6.87 (2H, m, aromatics), 7.26 (2H, m, aromatics). Anal. calcd for C$_{14}$H$_{17}$NO$_6$: C, 56.94; H, 5.80; N, 4.74. Found: C, 57.03; H, 5.82; N, 4.68.

Compound 55: 4-Hydroxy-1-methyl-5-oxo-2,5-dihydro-1H-pyrrole-3-carboxylic acid methoxy-(4-methoxy-benzyl)-amide

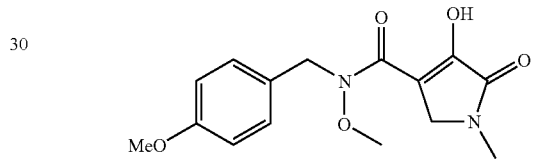

2-Hydroxy-3-[methoxy-(4-methoxybenzyl)-carbamoyl]-acrylic acid methyl ester (Compound 55-D) was treated with paraformaldehyde and methylamine as described in the preparation of Compound 12 to give the title compound as a white solid (58% yield); mp 135–137° C. $^1$HNMR 400 MHz (CDCl$_3$) δ (ppm): 3.09 (3H, s, NCH$_3$), 3.71 (3H, s, OCH$_3$), 3.80 (3H, s, OCH$_3$), 4.14 (2H, s, NCH$_2$), 4.82 (2H, s, NCH$_2$), 6.88 (2H, m, aromatics), 7.27 (2H, m, aromatics). Anal. calcd for C$_{15}$H$_{18}$N$_2$O$_5$: C, 58.81; H, 5.92; N, 9.14. Found: C, 58.62; H, 5.88; N, 9.12.

EXAMPLE 56

Compound 56-A: 2-Methylbenzaldehyde O-methyloxime

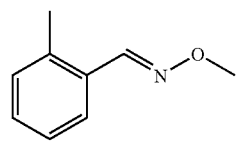

Reaction of 2-methylbenzaldehyde with methoxylamine hydrochloride as described in the preparation of Compound 44-A gave the title oxime ether as a clear oil (96% yield). HPLC indicated a 95:5 mixture of E- to Z-isomers. $^1$HNMR 400 MHz (CDCl$_3$) δ (ppm): (E-isomer) 2.44 (3H, s, CH$_3$), 4.01 (3H, s, OCH$_3$), 7.19–7.28 (3H, m, aromatics), 7.73 (1H, m, aromatic), 8.36 (1H, s, CH).

Compound 56-B: O-Methyl-N-(2-methyl-benzyl)-hydroxylamine

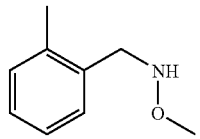

Reduction of 2-methylbenzaldehyde O-methyloxime with sodium cyanoborohydride as described in the preparation of Compound 44-B gave the title hydroxylamine as a clear oil (83% yield). $^1$HNMR 400 MHz (CDCl$_3$) δ (ppm): 2.42 (3H, s, CH$_3$), 3.55 (3H, s, OCH$_3$), 4.11 (2H, s, NCH$_2$), 5.64 (1H, s, NH), 7.19–7.32 (4H, m, aromatics). The hydrochloride salt was obtained as a white solid: mp 148–150° C. Anal. calcd. for C$_9$H$_{13}$NO—HCl: C, 57.60; H, 7.51; N, 7.46. Found: C, 57.59; H, 7.69; N, 7.52.

Compound 56-C: 2-(2,2-Dimethyl-5-oxo-[1,3]dioxolan-4-ylidene)-N-methoxy-N-(2-methyl-benzyl)-acetamide

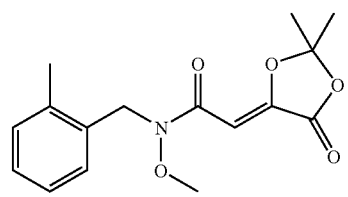

Reaction of (2,2-dimethyl-5-oxo-[1,3]dioxolan-4-ylidene)-acetyl chloride with N-(2-methylbenzyl)-O-methyl-hydroxylamine as described in the preparation of Compound 44-C gave the title amide as white crystals (100% yield): mp 96–97° C. (ethyl acetate-hexane). $^1$HNMR 400 MHz (CDCl$_3$) δ (ppm): 1.78 (6H, s, CH$_3$), 2.4 (3H, s, CH$_3$), 3.59 (3H, s, OCH$_3$), 4.89 (2H, s, NCH$_2$), 6.44 (1H, s, CH), 7.2–7.28 (4H, m, aromatics). Anal. calcd. for C$_{16}$H$_{19}$NO$_5$: C, 62.94; H, 6.27; N, 4.59. Found: C, 62.90; H, 6.21; N, 4.52.

Compound 56-D: 2-Hydroxy-3-[methoxy-(2-methyl-benzyl)-carbamoyl]-acrylic methyl ester

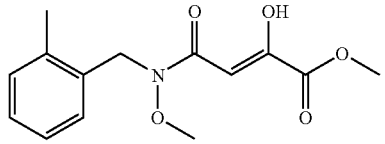

2-(2,2-Dimethyl-5-oxo-[1,3]-dioxolan-4-ylidene)-N-methoxy-N-(2-methylbenzyl)-acetamide was treated with methanol as described in the preparation of Compound 44-D and gave the title ester as white crystals (61% yield); mp 80–82° C. $^1$HNMR 400 MHz (CDCl$_3$) δ (ppm): 2.39 (3H, s, CH$_3$), 3.62 (3H, s, OCH$_3$), 3.92 (3H, s, OCH$_3$), 4.89 (2H, s, NCH$_2$), 6.5 (1H, s, CH), 7.22–7.28 (4H, m, aromatics), 13.5 (1H, broad s, OH). Anal. calcd for C$_{14}$H$_{17}$NO$_5$: C, 60.20; H, 6.13; N, 5.01. Found: C, 60.07; H, 5.88; N, 4.84.

Compound 56: 4-Hydroxy-1-methyl-5-oxo-2,5-dihydro-1H-pyrrole-3-carboxylic acid methoxy-(2-methyl-benzyl)-amide

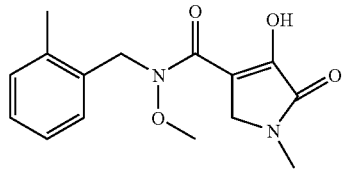

2-Hydroxy-3-[methoxy-(2-methylbenzyl)-carbamoyl]-acrylic acid methyl ester (Compound 56-D) was treated with paraformaldehyde and methylamine as described in the preparation of Compound 12 to give the title compound as a white solid (61% yield); mp 153–154° C. $^1$HNMR 400 MHz (CDCl$_3$) δ (ppm): 2.39 (3H, s, CH$_3$), 3.13 (3H, s, NCH$_3$), 3.67 (3H, s, OCH$_3$), 4.19 (2H, s, NCH$_2$), 4.95 (2H, s, NCH$_2$), 7.2–7.3 (4H, m, aromatics), 11.7 (1H, broad s, OH). Anal. calcd for C$_{15}$H$_{18}$N$_2$O$_4$: C, 62.05; H, 6.24; N, 9.65. Found: C, 61.79; H, 6.30; N, 9.58.

EXAMPLE 57

Compound 57-A: 3-Bromo-4-fluorobenzaldehyde O-methyloxime

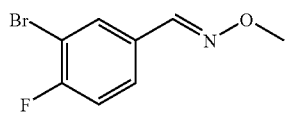

Reaction of 3-bromo-4-fluorobenzaldehyde with methoxylamine hydrochloride as described in the preparation of Compound 44-A gave the title oxime ether as a clear oil (95% yield). $^1$HNMR indicated a 95:5 mixture of E- to Z-isomers. $^1$HNMR 400 MHz (CDCl$_3$) δ (ppm): (E-isomer) 3.97 (3H, s, OCH$_3$), 7.12 (1H, m, aromatics), 7.48 (1H, m, aromatic), 7.82 (1H, m, aromatic), 7.97 (1H, s, CH).

Compound 57-B: N-(3-Bromo-4-fluoro-benzyl)-O-methyl-hydroxylamine

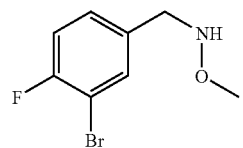

Reduction of 3-bromo-4-fluorobenzaldehyde O-methyloxime with sodium cyanoborohydride as described in the preparation of Compound 44-B gave the title hydroxylamine as a clear oil (83% yield). $^1$HNMR 400 MHz (CDCl$_3$) δ (ppm): 3.48 (3H, s, OCH$_3$), 3.99 (2H, s, NCH$_2$), 7.08 (1H, m, aromatic), 7.27 (1H, m, aromatic), 7.57 (1H, m, aromatic). The hydrochloride salt was obtained as a white solid: mp 150–151° C. Anal. calcd. for C$_8$H$_9$BrFNO—HCl: C, 35.52; H, 3.73; N, 5.18. Found: C, 35.54; H, 3.61; N, 5.12.

Compound 57-C: N-(3-Bromo-4-fluoro-benzyl)-2-(2,2-dimethyl-5-oxo-[1,3]dioxolan-4-ylidene)-N-methoxy-acetamide

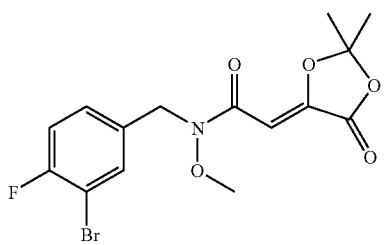

Reaction of (2,2-dimethyl-5-oxo-[1,3]dioxolan-4-ylidene)-acetyl chloride with N-3-bromo-4-fluorobenzyl-O-methyl-hydroxylamine as described in the preparation of Compound 44-C gave the title amide as a white solid (100% yield): mp 117–119° C. (ethyl acetate-hexane). $^1$HNMR 400 MHz (CDCl$_3$) δ (ppm): 1.75 (6H, s, CH$_3$), 3.71 (3H, s, OCH$_3$), 4.76 (2H, s, NCH$_2$), 6.38 (1H, s, CH), 7.07 (1H, m, aromatic), 7.28 (1H, m, aromatic), 7.56 (1H, m, aromatic). Anal. calcd. for C$_{15}$H$_{15}$BrFNO$_5$: C, 46.41; H, 3.89; N, 3.61. Found: C, 46.43; H, 4.01; N, 3.53.

Compound 57-D: 3-[(3-Bromo-4-fluoro-benzyl)-methoxy-carbamoyl]-2-hydroxy-acrylic acid methyl ester

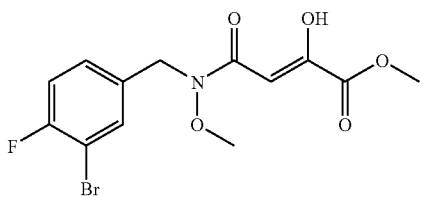

N-(3-Bromo-4-fluorobenzyl)-2-(2,2-dimethyl-5-oxo-[1,3]-dioxolan-4-ylidene)-N-methoxy-acetamide was treated with methanol as described in the preparation of Compound 44-D and gave the title ester as white crystals (44% yield); mp 107–108° C. $^1$HNMR 400 MHz (CDCl$_3$) δ (ppm): 3.72 (3H, s, OCH$_3$), 3.90 (3H, s, OCH$_3$), 4.77 (2H, s, NCH$_2$), 6.45 (1H, s, CH), 7.09 (1H, m, aromatic), 7.25 (1H, m, aromatic), 7.53 (1H, m, aromatic). Anal. calcd for C$_{13}$H$_{13}$BrFNO$_5$: C, 43.11; H, 3.62; N, 3.86. Found: C, 43.10; H, 3.54; N, 3.87.

Compound 57: 4-Hydroxy-1-methyl-5-oxo-2,5-dihydro-1H-pyrrole-3-carboxylic acid (3-bromo-4-fluoro-benzyl)-methoxy-amide

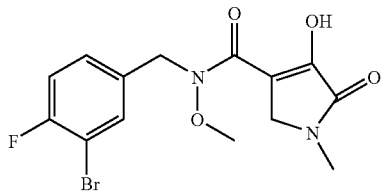

3-[(3-Bromo-4-fluorobenzyl)-methoxy-carbamoyl]-2-hydroxy-acrylic acid methyl ester (Compound 57-D) was treated with paraformaldehyde and methylamine as described in the preparation of Compound 12 to give the title compound as a white solid (35% yield); mp 154–157° C. dec. $^1$HNMR 400 MHz (CDCl$_3$) δ (ppm): 3.11 (3H, s, NCH$_3$), 3.75 (3H, s, OCH$_3$), 4.15 (2H, s, NCH$_2$), 4.81 (2H, s, NCH$_2$), 7.1 (1H, m, aromatic), 7.27 (1H, m, aromatic), 7.54 (1H, m, aromatic). Anal. calcd for C$_{14}$H$_{14}$BrFN$_2$O$_4$: C, 45.06; H, 3.78; N, 7.50. Found: C, 44.80; H, 3.81; N, 7.33.

EXAMPLE 58

Compound 58-A: 4-Fluorobenzaldehyde O-isobutyloxime

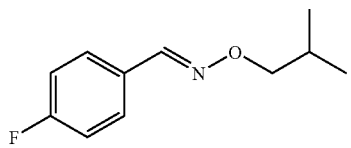

Reaction of 4-fluorobenzaldehyde with O-isobutyl-hydroxylamine hydrochloride as described in the preparation of Compound 44-A gave the title oxime ether as a clear oil after chromatography on silica gel (elution toluene-ethyl acetate 95:5), (77% yield). $^1$HNMR 400 MHz (CDCl$_3$) δ (ppm): 0.98 (6H, d, J=6.5 Hz, CH$_3$), 2.07 (1H, m, CH), 3.95 (2H, d, J=7.18 Hz, OCH$_2$), 7.08 (2H, m, aromatics), 7.59 (2H, m, aromatics), 8.08 (1H, s, CH). Anal. calcd for C$_{11}$H$_{14}$FNO: C, 67.67; H, 7.22; N, 7.17. Found: C, 67.71; H, 7.32; N, 7.38.

Compound 58-B: N-(4-Fluoro-benzyl)-O-isobutyl-hydroxylamine

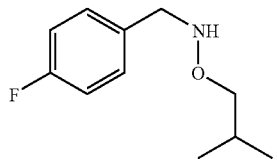

Reduction of 4-fluorobenzaldehyde O-isobutyloxime with sodium cyanoborohydride as described in the preparation of Compound 44-B gave the title hydroxylamine as a clear oil after chromatography (65% yield). $^1$HNMR 400 MHz (C$_6$D$_6$) δ (ppm): 0.87 (6H, d, J=6.75 Hz, CH$_3$), 1.88 (1H, m, CH), 3.46 (2H, d, J=6.41 Hz, OCH$_2$), 4.05 (2H, s, NCH$_2$), 7.04 (2H, m, aromatics), 7.37 (2H, m, aromatics). Anal. calcd for C$_{11}$H$_{16}$FNO: C, 66.98; H, 8.17; N, 7.10. Found: C, 66.88; H, 7.97; N, 7.32.

Compound 58-C: 2-(2,2-Dimethyl-oxo-[1,3]diox-olan-4-ylidene)-N-(4-fluoro-benzyl)-N-isobutoxy-acetamide

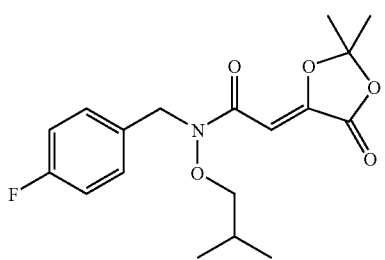

Reaction of (2,2-dimethyl-5-oxo-[1,3]dioxolan-4-ylidene)-acetyl chloride with N-(4-fluorobenzyl)-O-isobutyl-hydroxylamine as described in the preparation of Compound 44-C gave the title amide as white crystals (91% yield): mp 105–106° C. (ethyl acetate-hexane). $^1$HNMR 400 MHz (CDCl$_3$) δ (ppm): 0.98 (3H, d, J=6.45 Hz, CH$_3$), 1.77 (6H, s, CH$_3$), 1.95 (1H, m, CH), 3.64 (2H, d, J=6.63 Hz, OCH$_2$), 4.80 (2H, s, NCH$_2$), 6.41 (1H, s, CH), 7.03 (2H, m, aromatics), 7.36 (2H, m, aromatics). Anal. calcd for C$_{18}$H$_{22}$FNO$_5$: C, 61.53; H, 6.31; H, 3.98. Found: C, 61.47; H, 6.39; N, 3.97.

Compound 58-D: 3-[(4-Fluoro-benzyl)-isobutoxy-carbamoyl]-2-hydroxy-acrylic acid methyl ester

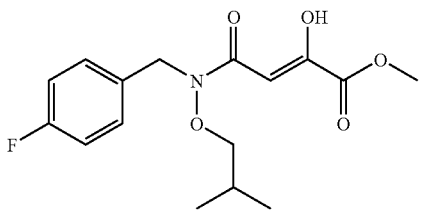

2-(2,2-Dimethyl-5-oxo-[1,3]-dioxolan-4-ylidene)-N-(4-fluorobenzyl)-N-isobutoxy-acetamide was treated with methanol as described in the preparation of Compound 44-D and gave the title ester as white crystals (48% yield); mp 55–56° C. $^1$HNMR 400 MHz (CDCl$_3$) δ (ppm): mixture of rotamers: 0.99 (6H, d, J=7.1 Hz, CH$_3$), 1.96 (1H, m, CH), 3.65 (2H, d, J=6.0 Hz, OCH$_2$), 3.91 (3H, s, OCH$_3$), 4.81 (2H, s, NCH$_2$), 6.49 (1H, s, CH), 7.05 (2H, m, aromatics), 7.33 (2H, m, aromatics), 13.4 (1H, broad s, OH). HRMS (ES+) calculated for C$_{16}$H$_{21}$FNO$_5$, [M+H]$^+$: 326.140376. found: 326.139560.

Compound 58: 4-Hydroxy-1-methyl-5-oxo-2,5-dihydro-1H-pyrrole-3-carboxylic acid (4-fluoro-benzyl)-isobutoxy-amide

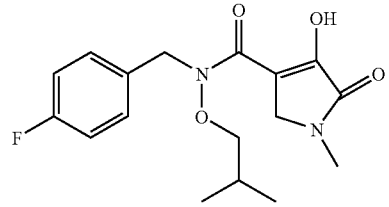

3-[(4-Fluorobenzyl)-isobutoxy-carbamoyl]-2-hydroxy-acrylic acid methyl ester (Compound 58-D) was treated with paraformaldehyde and methylamine as described in the preparation of Compound 12 to give the title compound as a white solid (40% yield); mp 96–97° C. $^1$HNMR 400 MHz (CDCl$_3$) δ (ppm): 0.98 (6H, d, J=6.5 Hz, CH$_3$), 1.96 (1H, m CH), 3.12 (3H, s, NCH$_3$), 3.69 (2H, d, J=6.4 Hz, OCH$_2$), 4.1 (2H, s, NCH$_2$), 4.85 (2H, s, NCH$_2$), 7.06 (2H, m, aromatics), 7.33 (2H, m, aromatics), 11.65 (1H, broad s, OH). HRMS (ES+) calculated for C$_{17}$H$_{22}$FN$_2$O$_4$, [M+H]$^+$: 337.156361. found: 337.156153.

EXAMPLE 59

Compound 59-A: 2-Hydroxy-3-[methoxy-(4-methyl-benzyl)-carbamoyl]-acrylic acid methyl ester

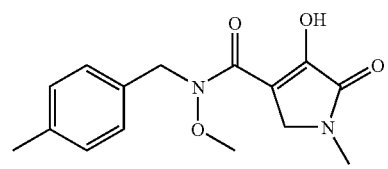

2-(2,2-Dimethyl-5-oxo-[1,3]-dioxolan-4-ylidene)-N-methoxy-N-(4-methylbenzyl)-acetamide, prepared using the methods described in the previous examples, was treated with methanol as described in the preparation of Compound 44-D to give the title ester as white crystals (69% yield); mp 83–84° C. $^1$HNMR 400 MHz (CDCl$_3$) δ (ppm): 2.59 (3H, s, CH$_3$), 3.94 (3H, s, OCH$_3$), 4.15 (3H, s, OCH$_3$), 5.05 (2H, s, NCH$_2$), 6.72 (1H, s, CH), 7.41 (2H, d, J=8.1 Hz, aromatics), 7.47 (2H, d, J=8.1 Hz, aromatics), 13.75 (1H, broad s, OH). Anal. calcd for C$_{14}$H$_{17}$NO$_5$: C, 60.20; H, 6.13; N, 5.01. Found: C, 60.24; H, 6.09; N, 4.85.

Compound 59: 4-Hydroxy-1-methyl-5-oxo-2,5-dihydro-1H-pyrrole-3-carboxylic acid methoxy-(4-methyl-benzyl)-amide 2-Hydroxy-3-[methoxy-(4-methylbenzyl)-carbamoyl]-acrylic acid methyl ester (Compound 59-A) was treated with paraformaldehyde and methylamine as described in the preparation of Compound 12 to give the title compound as a white solid (41% yield); mp 150–152° C. ¹HNMR 400 MHz (CDCl₃) δ (ppm): 2.4 (3H, s, CH₃), 3.16 (3H, s, NCH₃), 3.78 (3H, s, OCH₃), 4.21 (2H, s, NCH₂), 4.91 (2H, s, NCH₂), 7.22 (2H, d, J=8 Hz, aromatics), 7.28 (2H, d, J=8 Hz, aromatics), 11.7 (1H, broad s, OH). Anal. calcd for C₁₅H₁₈N₂O₄: C, 62.05; H, 6.24; N, 9.65. Found: C, 61.91; H, 6.30; N, 9.56.

EXAMPLE 60

Compound 60-A: 2,4-Difluorobenzaldehyde O-methyloxime

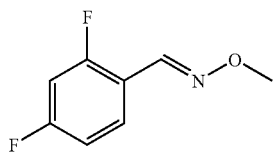

Reaction of 2,4-difluorobenzaldehyde with methoxylamine hydrochloride as described in the preparation of Compound 44-A gave the title oxime ether as a clear oil (80% yield). ¹HNMR indicated a 95:5 mixture of E- and Z-isomers. ¹HNMR 400 MHz (CDCl₃) δ (ppm): (E-isomer) 3.98 (3H, s, OCH₃), 6.79–6.91 (2H, m, aromatics), 7.79–7.85 (1H, m, aromatic), 8.24 (1H, s, CH).

Compound 60-B: N-(2,4-Difluoro-benzyl)-O-methyl-hydroxylamine

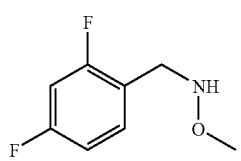

Reduction of 2,4-difluorobenzaldehyde O-methyloxime with sodium cyanoborohydride as described in the preparation of Compound 44-B gave the title hydroxylamine as a clear oil (72% yield). ¹HNMR 400 MHz (CDCl₃) δ (ppm): 3.51 (3H, s, OCH₃), 4.07 (2H, s, NCH₂), 6.78–6.88 (2H, m, aromatics), 7.32–7.38 (1H, m, aromatic). The hydrochloride salt was obtained as a white solid: mp 154–158° C. (dec.). Anal. calcd. for C₈H₉NO₂—HCl: C, 45.83; H, 4.80; N, 6.68. Found: C, 45.81; H, 4.84; N, 6.59.

Compound 60-C: N-(2,4-Difluoro-benzyl)-2-(2,2-dimethyl-5-oxo-[1,3]dioxolan-4-ylidene)-N-methoxy-acetamide

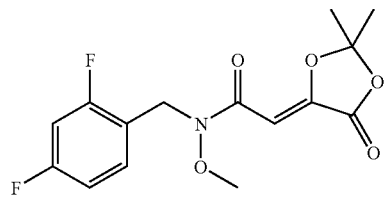

Reaction of (2,2-dimethyl-5-oxo-[1,3]dioxolan-4-ylidene)-acetyl chloride with N-2,4-difluorobenzyl-O-methyl-hydroxylamine as described in the preparation of Compound 44-C gave the title amide as a white solid (97% yield): mp 120–125° C. (ethyl acetate-hexane). ¹HNMR 400 MHz (CDCl₃) δ (ppm): 1.75 (6H, s, CH₃), 3.73 (3H, s, OCH₃), 4.86 (2H, s, NCH₂), 6.38 (1H, s, CH), 6.78–6.87 (2H, m, aromatics), 7.37–7.43 (1H, m, aromatic). Anal. calcd. for C₁₅H₁₅F₂NO₅: C, 55.04; H, 4.62; N, 4.28. Found: C, 55.03; H, 4.43; N, 4.17.

Compound 60-D: 3-[(2,4-Difluoro-benzyl)-methoxy-carbamoyl]-2-hydroxy-acrylic acid methyl ester

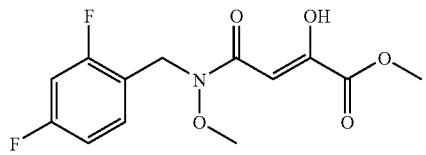

N-(2,4-Difluorobenzyl)-2-(2,2-dimethyl-5-oxo-[1,3]-dioxolan-4-ylidene)-N-methoxy-acetamide was treated with methanol as described in the preparation of Compound 44-D and gave the title ester as white crystals (55% yield); mp 104–105° C. ¹HNMR 400 MHz (CDCl₃) δ (ppm): 3.73 (3H, s, OCH₃), 3.89 (3H, s, OCH₃), 4.87 (2H, s, NCH₂), 6.45 (1H, s, CH), 6.8–6.9 (2H, m, aromatics), 7.31–7.37 (1H, m, aromatic). Anal. calcd for C₁₃H₁₃F₂NO₅: C, 51.83; H, 4.35; N, 4.65. Found: C, 51.68; H, 4.27; N, 4.53.

Compound 60: 4-Hydroxy-1-methyl-5-oxo-2,5-dihydro-1H-pyrrole-3-carboxylic acid (2,4-difluoro-benzyl)-methoxy-amide

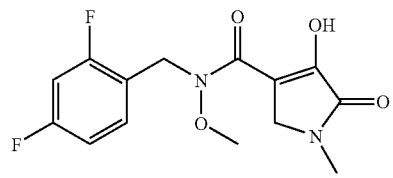

3-[(2,4-Difluorobenzyl)-methoxy-carbamoyl]-2-hydroxy-acrylic acid methyl ester (Compound 60-D) was treated with paraformaldehyde and methylamine as described in the preparation of Compound 12 to give the title compound as a white solid (55% yield); mp 141–149° C., dec. ¹HNMR 400 MHz (CDCl₃) δ (ppm): 3.1 (3H, s, NCH₃), 3.77 (3H, s, OCH₃), 4.14 (2H, s, NCH₂), 4.92 (2H, s, NCH₂), 6.8–6.9 (2H, m, aromatics), 7.35–7.41 (1H, m, aromatic).

EXAMPLE 61

Compound 61-A: 3-Cyano-4-fluorobenzaldehyde O-methyloxime

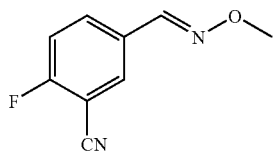

Reaction of 3-cyano-4-fluorobenzaldehyde with methoxylamine hydrochloride as described in the preparation of Compound 44-A gave the title oxime ether as a clear oil after chromatography on silica gel (elution hexane-ethyl acetate 8:2) (94% yield). ¹HNMR indicated a 93:7 mixture of E- to Z-isomers. ¹HNMR 400 MHz (CDCl₃) δ (ppm): (E-isomer) 4.02 (3H, s, OCH₃), 7.26 (1H, m, aromatic), 7.85 (2H, m, aromatics), 8.03 (1H, s, CH).

Compound 61-B: 2-Fluoro-5-(methoxyamino-methyl)-benzonitrile

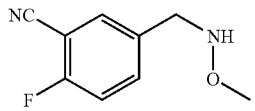

Reduction of 3-cyano-4-fluorobenzaldehyde O-methyloxime with sodium cyanoborohydride as described in the preparation of Compound 44-B gave the title hydroxylamine as a clear oil after chromatography on silica gel (elution hexane-ethyl acetate 8:2) (73% yield). ¹HNMR 400 MHz (CDCl₃) δ (ppm): 3.46 (3H, s, OCH₃), 4.02 (2H, s, NCH₂), 7.18 (1H, t, aromatic), 7.58–7.66 (2H, m, aromatics). The hydrochloride salt was obtained as a white solid: mp 152–158° C. Anal. calcd for C₉H₉FN₂O—HCl: C, 49.89; H, 4.65; N, 12.93. Found: C, 50.04; H, 4.64; N, 12.84.

Compound 61-C: N-(3-Cyano-4-fluoro-benzyl)-2-(2,2-dimethyl-5-oxo-[1,3]dioxolan-4-ylidene)-N-methoxy-acetamide

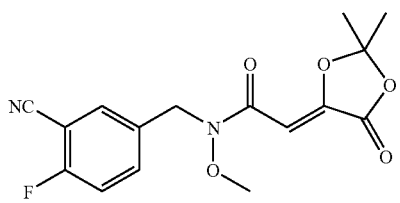

Reaction of (2,2-dimethyl-5-oxo-[1,3]dioxolan-4-ylidene)-acetyl chloride with N-(3-cyano-4-fluorobenzyl)-O-methyl-hydroxylamine as described in the preparation of Compound 44-C gave the title amide as white crystals (97% yield): mp 119–120° C. (ethyl acetate-hexane). ¹HNMR 400 MHz (CDCl₃) δ (ppm): 1.75 (6H, s, CH₃), 3.75 (3H, s, OCH₃), 4.78 (2H, s, NCH₂), 6.36 (1H, s, CH), 7.17 (1H, t, aromatic), 7.58–7.64 (2H, m, aromatics). Anal. calcd for C₁₆H₁₅F₂NO₅: C, 57.48; H, 4.52; N, 8.38. Found: C, 57.39; H, 4.61; N, 8.32.

Compound 61-D: 3-[(3-Cyano-4-fluoro-benzyl)-methoxy-carbamoyl]-2-hydroxy-acrylic acid methyl ester

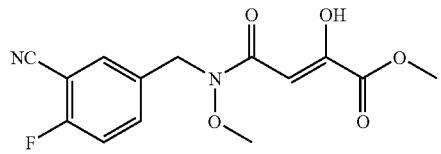

N-(3-Cyano-4-fluorobenzyl)-2-(2,2-dimethyl-5-oxo-[1,3]-dioxolan-4-ylidene)-N-methoxy-acetamide was treated with methanol as described in the preparation of Compound 44-D and gave the title ester as white crystals (47% yield); mp 125–126° C. ¹HNMR 400 MHz (CDCl₃) δ (ppm): 3.75 (3H, s, OCH₃), 3.90 (3H, s, OCH₃), 4.81 (2H, s, NCH₂), 6.44 (1H, s, CH), 7.18 (1H, m, aromatic), 7.56–7.61 (2H, m, aromatics). Anal. calcd for C₁₄H₁₃FN₂O₅: C, 54.54; H, 4.25; N, 9.08. Found: C, 54.76; H, 4.29; N, 9.04.

Compound 61: 4-Hydroxy-1-methyl-5-oxo-2,5-dihydro-1H-pyrrole-3-carboxylic acid (3-cyano-4-fluoro-benzyl)-methoxy-amide

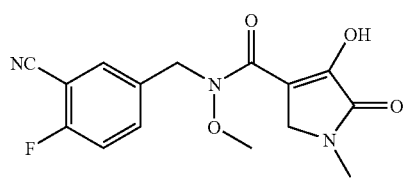

3-[(3-Cyano-4-fluorobenzyl)-methoxy-carbamoyl]-2-hydroxy-acrylic acid methyl ester (Compound 61-D) was treated with paraformaldehyde and methylamine as described in the preparation of Compound 12 to give the title compound as a white solid (69% yield); mp 175° C. dec. ¹HNMR 400 MHz (CDCl₃) δ (ppm): 3.11 (3H, s, NCH₃), 3.78 (3H, s, OCH₃), 4.16 (2H, s, NCH₂), 4.85 (2H, s, NCH₂), 7.19–7.24 (1H, m, aromatic), 7.59–7.62 (2H, m, aromatics).

EXAMPLE 62

Compound 62-A: 4-Cyanobenzaldehyde O-methyloxime

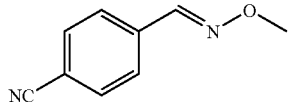

Reaction of 4-cyanobenzaldehyde with methoxylamine hydrochloride as described in the preparation of Compound 44-A gave the title oxime ether as a white solid (96% yield), (Gordon, M. S. et al., J. Org. Chem., 49, 1984, 97–100). $^1$HNMR indicated a 95:5 mixture of E- to Z-isomers. $^1$HNMR 400 MHz (CDCl$_3$) δ (ppm): (E-isomer) 4.02 (3H, s, OCH$_3$), 7.07 (4H, m, aromatics), 8.06 (1H, s, CH).

Compound 62-B: 4-(Methoxyamino-methyl)-benzonitrile)

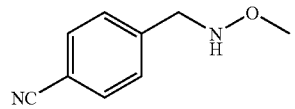

Reduction of 4-cyanobenzaldehyde O-methyloxime with sodium cyanoborohydride as described in the preparation of Compound 44-B gave the title hydroxylamine as a clear oil (75% yield). $^1$HNMR 400 MHz (CDCl$_3$) δ (ppm): 3.48 (3H, s, OCH$_3$), 4.09 (2H, s, NCH$_2$), 7.48 (2H, m, aromatics), 7.63 (2H, m, aromatics). The hydrochloride salt was obtained as a white solid: mp 168° C. (dec.). Anal. calcd. for C$_9$H$_{10}$N$_2$O—HCl: C, 54.41; H, 5.58; N, 14.10. Found: C, 54.44; H, 5.62; N, 13.94.

Compound 62-C: N-(4-Cyano-benzyl)-2-(2,2-dimethyl-5-oxo-[1,3]dioxolan-4-ylidene)-N-methoxy-acetamide

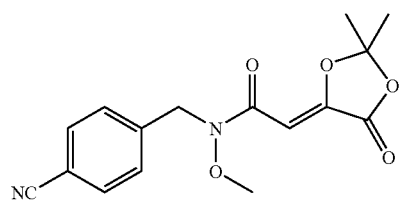

Reaction of (2,2-dimethyl-5-oxo-[1,3]dioxolan-4-ylidene)-acetyl chloride with N-(4-cyanobenzyl)-O-methyl-hydroxylamine as described in the preparation of Compound 44-C gave the title amide as white crystals (99% yield): mp 148–149° C. (ethyl acetate-hexane). $^1$HNMR 400 MHz (CDCl$_3$) δ (ppm): 1.75 (6H, s, CH$_3$), 3.72 (3H, s, OCH$_3$), 4.86 (2H, s, NCH$_2$), 6.39 (1H, s, CH), 7.46 (2H, m, aromatics), 7.63 (2H, m, aromatics). Anal. calcd. for C$_{16}$H$_{16}$N$_2$O$_5$: C, 60.75; H, 5.10; N, 8.86. Found: C, 60.60; H, 4.91; N, 8.78.

Compound 62-D: 3-[(4-Cyano-benzyl)-methoxy-carbamoyl]-2-hydroxy-acrylic acid methyl ester

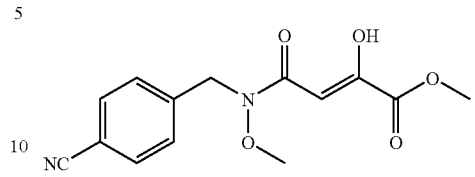

N-(4-Cyanobenzyl)-2-(2,2-dimethyl-5-oxo-[1,3]-dioxolan-4-ylidene)-N-methoxy-acetamide was treated with methanol as described in the preparation of Compound 44-D gave the title ester as white crystals (52% yield); mp 110° C. $^1$HNMR 400 MHz (CDCl$_3$) δ (ppm): 3.73 (3H, s, OCH$_3$), 3.90 (3H, s, OCH$_3$), 4.88 (2H, s, NCH$_2$), 6.47 (1H, s, CH), 7.43 (2H, d, J=8.6 Hz, aromatics), 7.64 (2H, d, J=8.6 Hz, aromatics). Anal. calcd for C$_{14}$H$_{14}$N$_2$O$_5$: C, 57.93; H, 4.86; N, 9.65. Found: C, 57.87; H, 4.80; N, 9.67.

Compound 62: 4-Hydroxy-1-methyl-5-oxo-2,5-dihydro-1H-pyrrole-3-carboxylic acid (4-cyano-benzyl)-methoxy-amide

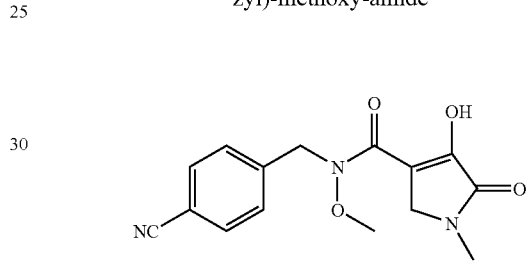

3-[(4-Cyanobenzyl)-methoxy-carbamoyl]-2-hydroxy-acrylic acid methyl ester (Compound 62-D) was treated with paraformaldehyde and methylamine as described in the preparation of Compound 12 to give the title compound as a white solid (46% yield); mp 161° C. dec. $^1$HNMR 400 MHz (CDCl$_3$) δ (ppm): 3.11 (3H, s, NCH$_3$), 3.75 (3H, s, OCH$_3$), 4.17 (2H, s, NCH$_2$), 4.93 (2H, s, NCH$_2$), 7.44 (2H, d, J=8.2 Hz, aromatics), 7.65 (2H, d, J=8.2 Hz, aromatics). Anal. calcd for C$_{15}$H$_{15}$N$_3$O$_4$: C, 59.79; H, 5.01; N, 13.94. Found: C, 59.51; H, 4.90; N, 13.69.

EXAMPLE 63

Compound 63-A: 4-Acetamidobenzaldehyde O-methyloxime

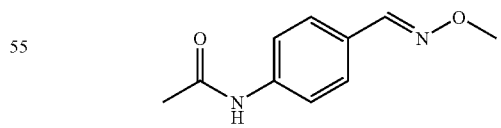

Reaction of 4-acetamidobenzaldehyde with methoxylamine hydrochloride as described in the preparation of Compound 44-A gave the title oxime ether as a white solid (98% yield), (Sakamoto, T. et al., J. Org. Chem., 57, 1992, 3245–3248). $^1$HNMR indicated a 95:5 mixture of E- to Z-isomers. $^1$HNMR 400 MHz (CDCl$_3$) δ (ppm): (E-isomer) 2.19 (3H, s, CH$_3$), 3.96 (3H, s, OCH$_3$), 7.22 (1H, broad s, NH), 7.53 (4H, m, aromatics), 8.01 (1H, s, CH).

Compound 63-B: N-[4-(Methoxyamino-methyl)-phenyl]-acetamide

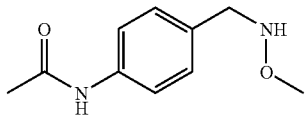

Reduction of 4-acetamidobenzaldehyde O-methyloxime with sodium cyanoborohydride as described in the preparation of Compound 44-B gave the title hydroxylamine as a waxy solid (100% yield). $^1$HNMR 400 MHz (CDCl$_3$) δ (ppm): 2.16 (3H, s, CH$_3$), 3.49 (3H, s, OCH$_3$), 4.00 (2H, s, NCH$_2$), 7.26 (1H, broad s, NH), 7.29 (2H, m, aromatics), 7.46 (2H, m, aromatics). The hydrochloride salt was obtained as a white solid: mp 186–188° C. (dec.). Anal. calcd. for C$_{10}$H$_{14}$N$_2$O$_2$—HCl—H$_2$O: C, 50.87; H, 6.66; N, 11.87. Found: C, 50.77; H, 6.44; N, 12.16.

Compound 63-C: N-(4-Acetylamino-benzyl)-2(2,2-dimethyl-5-oxo-[1,3]dioxolan-4-ylidene)-N-methoxy-acetamide

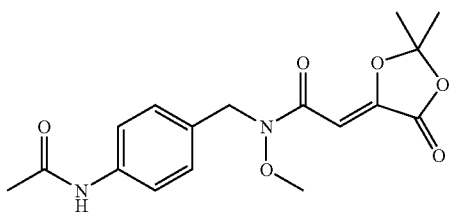

Reaction of (2,2-dimethyl-5-oxo-[1,3]dioxolan-4-ylidene)-acetyl chloride with N-(4-acetamidobenzyl)-O-methyl-hydroxylamine as described in the preparation of Compound 44-C gave the title amide as white crystals (92% yield): mp 212–215° C. (dec.) (dichloromethane-hexane). $^1$HNMR 400 MHz (CDCl$_3$) δ (ppm): 1.73 (6H, s, CH$_3$), 2.16 (3H, s, CH$_3$), 3.67 (3H, s, OCH$_3$), 4.78 (2H, s, NCH$_2$), 6.39 (1H, s, CH), 7.32 (3H, m, aromatics and NH), 7.45 (2H, m, aromatics). Anal. calcd. for C$_{17}$H$_{20}$N$_2$O$_6$: C, 57.87; H, 5.86; N, 7.94. Found: C, 57.76; H, 5.68; N, 8.51.

Compound 63-D: 3-[(4-Acetylamino-benzyl)-methoxy-carbamoyl]-2-hydroxy-acrylic acid methyl ester

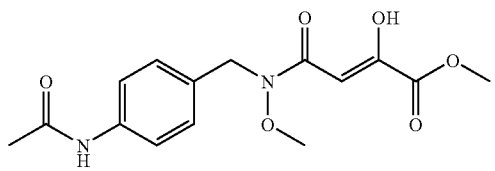

N-(4-Acetylaminobenzyl)-2-(2,2-dimethyl-5-oxo-[1,3]-dioxolan-4-ylidene)-N-methoxy-acetamide was treated with methanol as described in the preparation of Compound 44-D and gave the title ester as white crystals (35% yield); mp 125° C. $^1$HNMR 400 MHz (CDCl$_3$) δ (ppm): 2.18 (3H, s, COCH$_3$), 3.68 (3H, s, OCH$_3$), 3.89 (3H, s, OCH$_3$), 4.79 (2H, s, NCH$_2$), 6.46 (1H, s, CH), 7.16 (1H broad s, NH), 7.29 (2H, d, J=8.6 Hz, aromatics), 7.48 (2H, d, J=8.6 Hz, aromatics). Anal. Calcd for C$_{15}$H$_{18}$N$_2$O$_6$: C, 55.89; H, 5.62; N, 8.69. Found: C, 55.95; H, 5.70; N, 8.59.

Compound 63: 4-Hydroxy-1-methyl-5-oxo-2,5-dihydro-1H-pyrrole-3-carboxylic acid (4-acetylamino-benzyl)-methoxy-amide

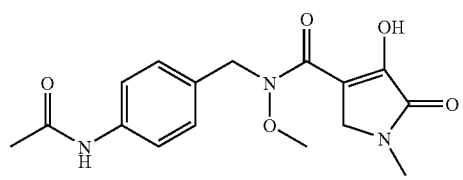

3-[(4-Acetylaminobenzyl)-methoxy-carbamoyl]-2-hydroxy-acrylic acid methyl ester (Compound 63-D) was treated with paraformaldehyde and methylamine as described in the preparation Compound 12 to give the title compound as a white solid (43% yield); mp 110° C. $^1$HNMR 400 MHz (CDCl$_3$) δ (ppm): 2.18 (3H, s, COCH$_3$), 3.1 (3H, s, NCH$_3$), 3.71 (3H, s, OCH$_3$), 4.15 (2H, s, NCH$_2$), 4.83 (2H, s, NCH$_2$), 7.29 (2H, d, J=8.6 Hz, aromatics), 7.34 (1H, broad s, NH), 7.50 (2H, d, J=8.6 Hz, aromatics). HRMS (ES+) calculated for C$_{16}$H$_{20}$N$_3$O$_5$: [M+H]$^+$: 334.140296. found: 334.139137.

EXAMPLE 64

Compound 64-A: 3-[(4-Fluoro-3-methyl-benzyl)-methoxy-carbamoyl]-2-hydroxy-acrylic acid methyl ester

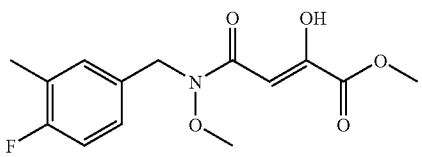

2-(2,2-Dimethyl-5-oxo-[1,3]-dioxolan-4-ylidene)-N-(4-fluoro-3-methylbenzyl)-N-methoxy-acetamide, prepared using the methods described in the previous examples, was treated with methanol as described in the preparation of Compound 44-C and gave the title ester as white crystals (32% yield); mp 60–62° C. $^1$HNMR 400 MHz (CDCl$_3$) δ (ppm): 2.27 (3H, broad s, CH$_3$), 3.70 (3H, s, OCH$_3$), 3.90 (3H, s, OCH$_3$), 4.76 (2H, s, NCH$_2$), 6.46 (1H, s, CH), 6.96 (1H, m, aromatic), 7.12 (2H, m, aromatics). Anal. calcd for C$_{14}$H$_{16}$FNO$_5$: C, 56.56; H, 5.42; N, 4.71. Found: C, 56.36; H, 5.44; N, 4.54.

Compound 64: 4-Hydroxy-1-methyl-5-oxo-2,5-dihydro-1H-pyrrole-3-carboxylic acid (4-fluoro-3-methyl-benzyl)-methoxy-amide

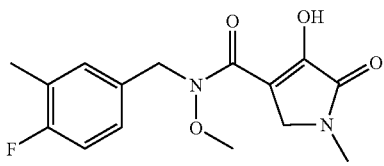

3-[(4-Fluoro-3-methylbenzyl)-methoxy-carbamoyl]-2-hydroxy-acrylic acid methyl ester (Compound 64-A) was treated with paraformaldehyde and methylamine as described in the preparation of Compound 12 to give the title compound as white crystals (76% yield); mp 160–164° C. $^1$HNMR 400 MHz (CDCl$_3$) δ (ppm): 2.27 (3H, s, CH$_3$), 3.10 (3H, s, NCH$_3$), 3.73 (3H, s, OCH$_3$), 4.15 (2H, s, NCH$_2$), 4.81 (2H, s, NCH$_2$), 6.97 (1H, m, aromatic), 7.12 (2H, m, aromatics). Anal. calcd for C$_{15}$H$_{17}$FN$_2$O$_4$: C, 58.44; H, 5.56; N, 9.09. Found: C, 58.41; H, 5.61; N, 8.90.

EXAMPLE 65

Compound 65-A: 3-[(3-Fluoro-4-methyl-benzyl)-methoxy-carbamoyl]-2-hydroxy-acrylic acid methyl ester

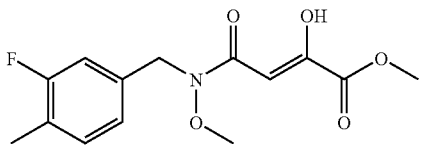

2-(2,2-Dimethyl-5-oxo-[1,3]-dioxolan-4-ylidene)-N-(3-fluoro-4-methylbenzyl)-N-methoxy-acetamide, prepared using the methods described in the previous examples, was treated with methanol as described in the preparation of Compound 44-C and gave the title ester as white crystals (49% yield); mp 88° C. $^1$HNMR 400 MHz (CDCl$_3$) δ (ppm): 2.25 (3H, d, J=1.5 Hz, CH$_3$), 3.70 (3H, s, OCH$_3$), 3.90 (3H, s, OCH$_3$), 4.78 (2H, s, NCH$_2$), 6.47 (1H, s, CH), 6.96 (2H, m, aromatics), 7.26 (1H, m, aromatic). HRMS (MAB N$_2$) calculated for C$_{14}$H$_{16}$FNO$_5$, [M]$^+$: 297.101251. found: 297.101261.

Compound 65: 4-Hydroxy-1-methyl-5-oxo-2,5-dihydro-1H-pyrrole-3-carboxylic acid (3-fluoro-4-methyl-benzyl)-methoxy-amide

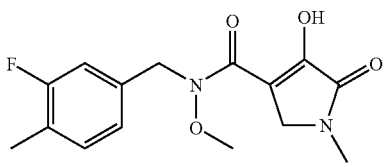

3-[(3-Fluoro-4-methylbenzyl)-methoxy-carbamoyl]-2-hydroxy-acrylic acid methyl ester (Compound 65-A) was treated with paraformaldehyde and methylamine as described in the preparation of Compound 12 to give the title compound as white crystals (54% yield); mp 145° C. $^1$HNMR 400 MHz (CDCl$_3$) δ (ppm): 2.26 (3H, broad s, CH$_3$), 3.11 (3H, s, NCH$_3$), 3.73 (3H, s, OCH$_3$), 4.16 (2H, s, NCH$_2$), 4.83 (2H, s, NCH$_2$), 6.99 (2H, m, aromatics), 7.16 (1H, m, aromatic). Anal. calcd for C$_{15}$H$_{17}$FN$_2$O$_4$: C, 58.44; H, 5.56; N, 9.09. Found: C, 58.16; H, 5.44; N, 8.88.

EXAMPLE 66

Compound 66-A: 2-Hydroxy-3-[(2-isopropoxy-benzyl)-methoxy-carbamoyl]-acrylic acid methyl ester

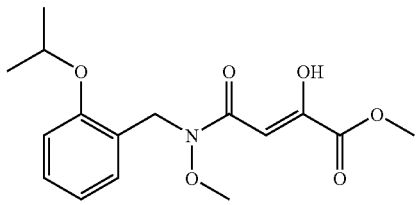

2-(2,2-Dimethyl-5-oxo-[1,3]-dioxolan-4-ylidene)-N-(2-isopropoxybenzyl)-N-methoxy-acetamide, prepared using the methods described in the previous examples, was treated with methanol as described in the preparation of Compound 44-D and gave the title ester as a white syrup (62% yield). $^1$HNMR 400 MHz (CDCl$_3$) δ (ppm): 1.33 (6H, d, J=6 Hz, CH$_3$), 3.68 (3H, s, OCH$_3$), 3.89 (3H, s, OCH$_3$), 4.59 (1H, m, CH), 4.9 (2H, s, NCH$_2$), 6.50 (1H, s, CH), 6.88 (2H, m, aromatics), 7.24 (2H, m, aromatics). HRMS (MAB N$_2$) calculated for C$_{16}$H$_{21}$NO$_6$, [M]$^+$: 323.136888. found: 323.136700.

Compound 66: 4-Hydroxy-1-methyl-5-oxo-2,5-dihydro-1H-pyrrole-3-carboxylic acid (2-isopropoxy)-methoxy-amide

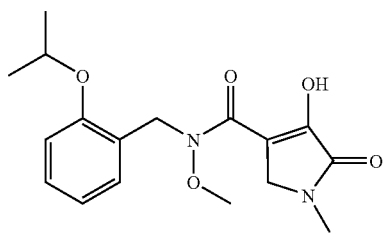

2-Hydroxy-3-[(2-isopropoxybenzyl)-methoxy-carbamoyl]-acrylic acid methyl ester (Compound 66-A) was treated with paraformaldehyde and methylamine as described in the preparation of Compound 12 to give the title compound as a tan solid (22% yield). $^1$HNMR 400 MHz (DMSO-d$_6$) δ (ppm): 1.26 (6H, d, J=6.2 Hz, CH$_3$), 2.91 (3H, s, NCH$_3$), 3.57 (3H, s, OCH$_3$), 4.03 (2H, s, NCH$_2$), 4.60 (1H, m, CH), 4.71 (2H, s, NCH$_2$), 6.66 (1H, m, aromatic), 6.95 (1H, m, aromatic), 7.15 (2H, m, aromatics). HRMS (ES+) calculated for C$_7$H$_{23}$N$_2$O$_5$, [M+H]$^+$: 335.160697. found: 335.161171.

EXAMPLE 67

Compound 67-A: 4-Carbomethoxybenzaldehyde O-methyloxime

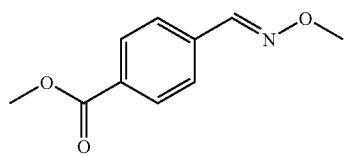

Reaction of methyl 4-formylbenzoate with methoxylamine hydrochloride as described in the preparation of Compound 44-A gave the title oxime ether (96% yield) as a white solid (mixture of E- and Z-isomers). The E-isomer was obtained as white crystals from hexane; mp 66–67° C. (Lit. mp 65–66° C., Cooks, Org. Mass Spectrum., 5, 1971, 687). $^1$HNMR 400 MHz (DMSO-$d_6$) δ (ppm): (E-isomer) 3.86 (3H, s, OCH$_3$), 3.93 (3H, s, OCH$_3$), 7.75 (2H, d, aromatics), 7.98 (2H, d, aromatics), 8.32 (1H, s, CH).

Compound 67-B: 4-(Methoxyamino-methyl)-benzoic acid methyl ester

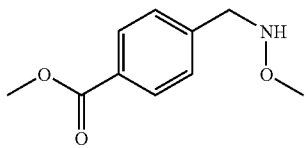

Reduction of 4-carbomethoxybenzaldehyde O-methyloxime with sodium cyanoborohydride as described in the preparation of Compound 44-B gave the title hydroxylamine as an oil (53% yield). The hydrochloride salt was obtained as a white solid: mp 166–169° C. $^1$HNMR 400 MHz (DMSO-$d_6$) δ (ppm): 3.75 (3H, s, OCH$_3$), 3.86 (3H, s, OCH$_3$), 4.39 (2H, s, NCH$_2$), 7.65 (2H, d, aromatics), 7.97 (2H, d, aromatics). Anal. calcd for $C_{10}H_{13}NO_3$—HCl: C, 51.84; H, 6.09; N, 6.04. Found: C, 51.74; H, 6.01; N, 5.50.

Compound 67-C: 4-({[2-(2,2-Dimethyl-5-oxo-[1,3]dioxolan-4-ylidene)-acetyl]-methoxy-amino}-methyl)-benzoic acid methyl ester

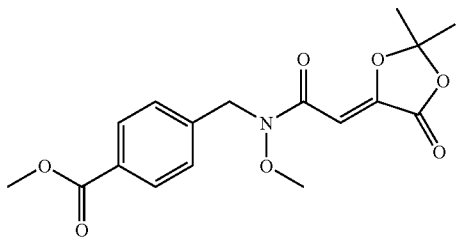

Reaction of (2,2-dimethyl-5-oxo-[1,3]dioxolan-4-ylidene)-acetyl chloride with N-4-carbomethoxybenzyl-O-methyl-hydroxylamine as described in the preparation of Compound 44-C gave the title amide as a white solid (83% yield): mp 120° C. (dichloromethane-hexane). $^1$HNMR 400 MHz (CDCl$_3$) δ (ppm): 1.75 (6H, s, CH$_3$), 3.67 (3H, s, OCH$_3$), 3.91 (3H, s, OCH$_3$), 4.88 (2H, s, NCH$_2$), 6.40 (1H, s, CH), 7.42 (2H, d, aromatics), 8.0 (2H, d, aromatics). Anal. calcd for $C_{17}H_{19}NO_7$: C, 58.45; H, 5.48; N, 4.01. Found: C, 58.54; H, 5.55; N, 3.61.

Compound 67-D: 4{[(3-Hydroxy-3-methoxycarbonyl-acryloyl)-methoxy-amino]-methyl}-benzoic acid methyl ester

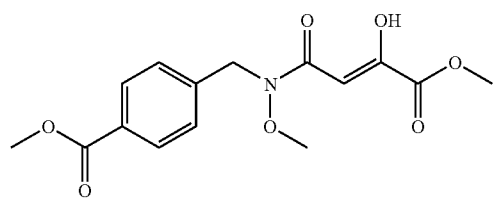

4-({[2-(2,2-Dimethyl-5-oxo-[1,3]-dioxolan-4-ylidene)-acetyl]-methoxyamino}-methyl)-benzoic acid methyl ester was treated with methanol as described in the preparation of Compound 44-D and gave the title ester as a white solid. $^1$HNMR 400 MHz (CDCl$_3$) δ (ppm): 3.70 (3H, s, OCH$_3$), 3.90 (3H, s, OCH$_3$), 3.91 (3H, s, OCH$_3$), 4.89 (2H, s, NCH$_2$), 6.5 (1H, s, CH), 7.39 (2H, d, J=8.1 Hz, aromatics), 8.02 (2H, d, J=8.1 Hz, aromatics). HRMS (ES+) calculated for $C_{15}H_{18}NO_7$, [M+H]$^+$: 324.108327. found: 324.109066.

Compound 67: 4-{[(4-Hydroxy-1-methyl-5-oxo-2,5-dihydro-1H-pyrrole-3-carbonyl)-methoxy-amino]-methyl}-benzoic acid methyl ester

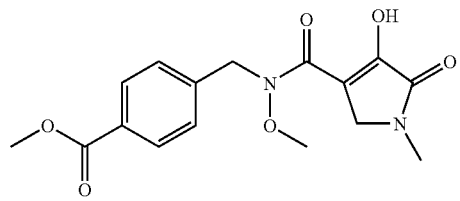

4-{[(3-Hydroxy-3-[methoxycarbonyl-acryloyl)-methoxyamino]-methyl}-benzoic acid methyl ester (Compound 67-D) was treated with paraformaldehyde and methylamine as described in the preparation of Compound 12 to give the title compound as a tan solid. $^1$HNMR 400 MHz (CDCl$_3$) δ (ppm): 3.11 (3H, s, NCH$_3$), 3.73 (3H, s, OCH$_3$), 3.92 (3H, s, OCH$_3$), 4.17 (2H, s, NCH$_2$), 4.93 (2H, s, NCH$_2$), 7.4 (2H, d, J=8.1 Hz, aromatics), 8.02 (2H, d, J=8.1 Hz, aromatics), 11.54 (1H, broad s, OH). HRMS (ES+) calculated for $C_{16}H_{19}N_2O_6$, [M+H]$^+$: 335.1249. found: 335.1243.

EXAMPLE 68

Compound 68-A: 4-{[(4-Hydroxy-1-methyl-5-oxo-2,5-dihydro-1H-pyrrole-3-carbonyl)-methoxy-amino]-methyl}-benzoic acid tert-butyl ester

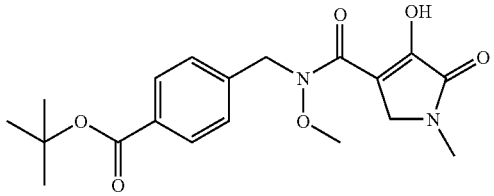

4-({[2-(2,2-dimethyl-5-oxo-[1,3]-dioxolan-4-ylidene)-acetyl]-methoxyamino}-methyl)-benzoic acid tert-butyl ester, prepared using the methods described in the previous examples, was treated in methanol with paraformaldehyde and methylamine as described in the preparation of Compound 12 to give the title compound as a white solid (40% yield); mp 157–160° C. $^1$HNMR 400 MHz (CDCl$_3$) δ (ppm): 1.58 (9H, s, t-Bu), 3.11 (3H, s, NCH$_3$), 3.72 (3H, s, OCH$_3$), 4.16 (2H, s, NCH$_2$), 4.92 (2H, s, NCH$_2$), 7.37 (2H, d, J=8 Hz, aromatics), 7.97 (2H, d, J=8 Hz, aromatics), 11.55 (1H, broad s, OH).

Compound 68: 4-{[(4-Hydroxy-1-methyl-5-oxo-2,5-dihydro-1H-pyrrole-3-carbonyl)-methoxy-amino]-methyl}-benzoic acid

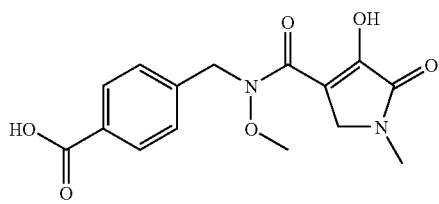

A solution of 4-{[(4-hydroxy-1-methyl-5-oxo-2,5-dihydro-1H-pyrrole-3-carbonyl)-methoxyamino]-methyl}-benzoic acid tert-butyl ester (0.062 g, 0.16 mmol) in dichloromethane (3 ml) was treated with trifluoroacetic acid (0.6 ml) and stirred at 25° C. for 2 h. The solvent was then evaporated in vacuo and the residue was triturated with acetonitrile to give 0.041 g (80% yield) of the title material as a white solid; mp 196–197° C. $^1$HNMR 400 MHz (DMSO-d$_6$) δ (ppm): 2.97 (3H, s, NCH$_3$), 3.73 (3H, s, OCH$_3$), 4.19 (2H, s, NCH$_2$), 4.96 (2H, s, NCH$_2$), 7.42 (2H, d, J=8.3 Hz, aromatics), 7.91 (2H, d, J=8.3 Hz, aromatics), 11.4 (1H, broad s, OH), 12.9 (1H, broad s, OH). Anal. calcd for C$_{15}$H$_{16}$N$_2$O$_6$.H$_2$O: C, 53.25; H, 5.36; N, 8.28. Found: C, 53.59; H, 4.79; N, 8.19.

EXAMPLE 69

Compound 69: 4-Hydroxy-1-methyl-5-oxo-2,5-dihydro-1H-pyrrole-3-carboxylic acid [1-(4-fluorophenyl)-ethyl]-methoxy-amide

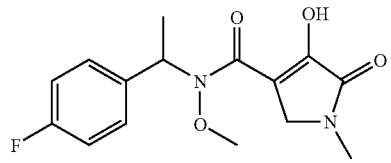

2-(2,2-Dimethyl-5-oxo-[1,3]-dioxolan-4-ylidene)-N-[1-(4-fluorophenyl)-ethyl]-N-methoxy-acetamide, prepared using the methods described in the previous examples, was treated in methanol with paraformaldehyde and methylamine as described in the preparation Compound 12 to give the title compound as a white solid (47% yield); mp 136–138° C. $^1$HNMR 400 MHz (CDCl$_3$) δ (ppm): 1.68 (3H, d, J=7.1 Hz, CH$_3$), 3.1 (3H, s, NCH$_3$), 3.49 (3H, s, OCH$_3$), 4.13 (2H, AB system, J$_{AB}$=18.2 Hz, Δv=45.7 Hz, NCH$_2$), 5.75 (1H, q, J=7.1 Hz, CH), 7.06 (2H, m, aromatics), 7.42 (2H, m, aromatics). Anal. calcd for C$_{15}$H$_{17}$FN$_2$O$_4$: C, 58.43; H, 5.55; N, 9.08. Found: C, 58.40; H, 5.38; N, 9.01.

EXAMPLE 70

Compound 70-A: (4-Fluorobenzylideneaminooxy)-acetic acid tert-butyl ester

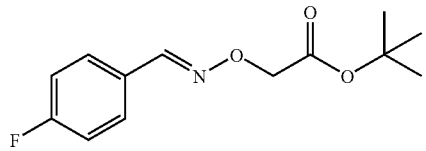

Condensation of 4-fluorobenzaldehyde with hydroxylamine hydrochloride using the same procedure as Compound 44-A followed by reaction with tert-butyl bromoacetate gave the title oxime ether as a clear oil (84% yield). $^1$HNMR 400 MHz (CDCl$_3$) δ (ppm): 1.52 (9H, s, t-Bu), 4.61 (2H, s, OCH$_2$), 7.08 (2H, m, aromatics), 7.59 (2H, m, aromatics), 8.19 (1H, s, CH).

Compound 70-B: [N-(4-Fluoro-benzyl)aminooxy]-acetic acid tert-butyl ester

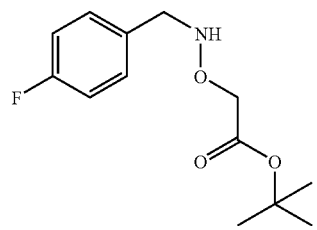

Reduction of (4-fluorobenzylideneaminooxy)-acetic acid tert-butyl ester as described in the preparation of Compound 44-B gave the title hydroxylamine as a clear oil (65% yield). $^1$HNMR 400 MHz (C$_6$D$_6$) δ (ppm): 1.43 (9H, s, t-Bu), 3.84

(2H, d, J=5.6 Hz, NCH$_2$), 4.17 (2H, s, OCH$_2$), 6.39 (1H, broad t, NH), 6.86 (2H, m, aromatics), 7.05 (2H, m, aromatics).

Compound 70-C: [[2-(2,2-Dimethyl-5-oxo-[1,3]dioxolan-4-ylidene)-acetyl]-(4-fluoro-benzyl)-aminooxy]-acetic acid tert butyl ester

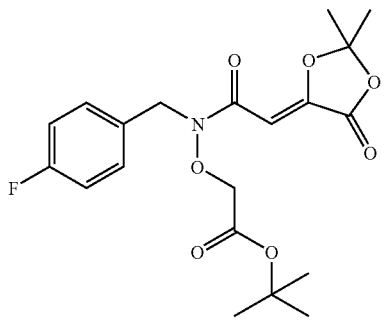

Reaction of (2,2-dimethyl-5-oxo-[1,3]dioxolan-4-ylidene)-acetyl chloride with [N-(4-fluorobenzyl)aminooxy]-acetic acid tert-butyl ester as described in the preparation of compound 1-A gave the title amide as white crystals (85% yield): mp 119–120° C. (ethyl acetate-hexane). $^1$HNMR 400 MHz (CDCl$_3$) δ (ppm): 1.48 (9H, s, t-Bu), 1.74 (6H, s, CH$_3$), 4.30 (2H, s, CH$_2$), 4.88 (2H, s, CH$_2$), 6.48 (1H, s, CH), 7.0 (2H, m, aromatics), 7.38 (2H, m, aromatics). Anal. calcd for C$_{20}$H$_{24}$FNO$_7$: C, 58.67; H, 5.91; N, 3.42. Found: C, 58.83; H, 5.92; N, 3.31.

Compound 70-D: 3-[tert-Butoxycarbonylmethoxy-(4-fluoro-benzyl)-carbamoyl]-2-hydroxy-acrylic acid methyl ester

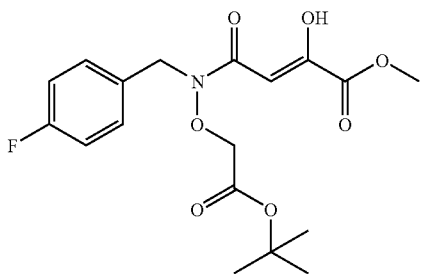

[[2-(2,2-Dimethyl-5-oxo-[1,3]-dioxolan-4-ylidene)-acetyl]-(4-fluorobenzyl)-aminooxy]-acetic acid tert-butyl ester was treated with methanol as described in the preparation of Compound 44-D and gave the title ester as a clear oil (69% yield). $^1$HNMR 400 MHz (CDCl$_3$) δ (ppm): 1.50 (9H, s, t-Bu), 3.92 (3H, s, OCH$_3$), 4.35 (2H, s, CH$_2$), 4.94 (2H, s, CH$_2$), 6.55 (1H, s, OH), 7.05 (2H, m, aromatics), 7.39 (2H, m, aromatics), 13.35 (1H, broad s, OH). HRMS (ES+) calculated for C$_{18}$H$_{23}$FNO$_7$, [M+H]$^+$: 384.145856. found: 384.146214.

Compound 70: [(4-Fluoro-benzyl)-(4-hydroxy-1-methyl-5-oxo-2,5-dihydro-1H-3-carbonyl)-aminooxy-acetic acid tert-butyl ester

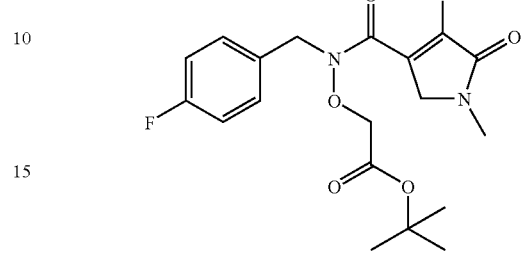

3-[tert-Butoxycarbonylmethoxy-(4-fluorobenzyl)-carbamoyl]-2-hydroxy-acrylic acid methyl ester (Compound 70-D) was treated with paraformaldehyde and methylamine as described in the preparation of Compound 12 to give the title compound as a white solid (30% yield); mp 128–130° C. $^1$HNMR 400 MHz (CDCl$_3$) δ (ppm): 1.48 (9H, s, t-Bu), 3.1 (3H, s, NCH$_3$), 4.22 (2H, s, CH$_2$), 4.35 (2H, s, CH$_2$), 4.93 (2H, s, NCH$_2$), 7.06 (2H, m, aromatics), 7.38 (2H, m, aromatics), 11.55 (1H, broad s, OH). HRMS (ES+) calculated for C$_{19}$H$_{24}$FN$_2$O$_6$, [M+H]$^+$: 395.161840. found: 395.161599.

EXAMPLE 71

Compound 71: [(4-Fluoro-benzyl)-(4-hydroxy-1-methyl-5-oxo-2,5-dihydro-1H-pyrrole-3-carbonyl)-aminooxy]-acetic acid

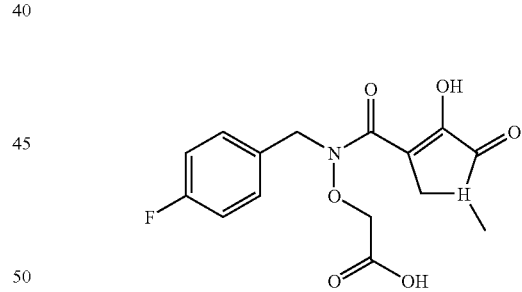

A solution of [(4-fluorobenzyl)-(4-hydroxy-1-methyl-5-oxo-2,5-dihydro-1H-pyrrole-3-carbonyl)-aminooxy]-acetic acid tert-butyl ester (0.041 g, 0.104 mmol) in dichloromethane (4 ml) was treated with trifluoroacetic acid (1 ml) and the resulting mixture was stirred at 22° C. for 2 h. The solvent was evaporated in vacuo and the residue was recrystallized from a mixture of ethyl acetate and hexane to give 0.027 g (80% yield) of the title material as white crystals; mp 147–150° C. $^1$HNMR 400 MHz (DMSO-d$_6$) δ (ppm): 2.95 (3H, s, NCH$_3$), 4.14 (2H, s, CH$_2$), 4.62 (2H, s, CH$_2$), 4.92 (2H, s, CH$_2$), 7.17 (2H, m, aromatics), 7.36 (2H, m, aromatics), 11.4 (1H, broad s, OH), 13.1 (1H, broad s, OH). HRMS (ES+) calculated for C$_{15}$H$_{16}$FN$_2$O$_6$, [M+H]$^+$: 339.099240. found: 339.100624.

EXAMPLE 72

Compound 72-A: N-Dimethylcarbamoylmethoxy-2-(2,2-dimethyl-5-oxo-[1,3]dioxolan-4-ylidene)-N-(4-fluoro-benzyl)-acetamide

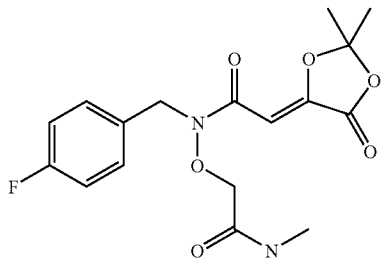

A solution of [[2-(2,2-dimethyl-5-oxo-[1,3]-dioxolan-4-ylidene)-acetyl]-(4-fluorobenzyl)-aminooxy]-acetic acid (0.681 g, 1.93 mmol) in dichloromethane (20 ml) was treated at 22° C. with oxalyl chloride (0.34 ml, 3.9 mmol) and a trace of N,N-dimethylformamide and the resulting mixture was stirred for 1 h. The solvent and excess reagent were then evaporated in vacuo. The residual material was dissolved in dry dichloromethane (10 ml) and added dropwise to a cold (0° C.) solution of dimethylamine (0.18 g, 4.0 mmol) and pyridine (0.25 ml, 3.2 mmol) in dichloromethane. After 2 h, the reaction mixture was diluted with ethyl acetate, washed with saturated sodium bicarbonate and brine and dried over anhydrous magnesium sulfate. Evaporation of the solvent in vacuo and crystallisation of the residue from a mixture of ethyl acetate and hexane gave 0.370 g (50% yield) of the title material as a white solid. $^1$HNMR 400 MHz (CDCl$_3$) δ (ppm): 1.77 (6H, s, CH$_3$), 2.91 (3H, s, CH$_3$), 2.97 (3H, s, CH$_3$), 4.53 (2H, s, CH$_2$), 4.93 (2H, s, CH$_2$), 6.43 (1H, s, CH), 7.03 (2H, m, aromatics), 7.41 (2H, m, aromatics).

Compound 72-B: 3-[Dimethylcarbamoylmethoxy-(4-fluoro-benzyl)-carbamoyl]-2-hydroxy-acrylic acid methyl ester

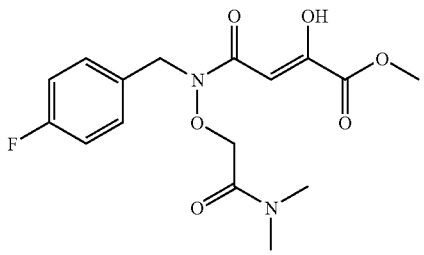

N-Dimethylcarbamoylmethoxy-2-(2,2-dimethyl-5-oxo-[1,3]-dioxolan-4-ylidene)-N-(4-fluorobenzyl)-acetamide was treated with methanol as described in the preparation of Compound 44-D and gave the title ester as white crystals (54% yield); mp 133–135° C. $^1$HNMR 400 MHz (CDCl$_3$) δ (ppm): 2.9 (3H, s, NCH$_3$), 2.98 (3H, s, NCH$_3$), 3.91 (3H, s, OCH$_3$), 4.54 (2H, s, CH$_2$), 4.96 (2H, s, CH$_2$), 6.52 (1H, s, CH), 7.06 (2H, m, aromatics), 7.39 (2H, m, aromatics), 13.38 (1H, broad s, OH). Anal. calcd for C$_{16}$H$_{19}$FN$_2$O$_6$: C, 54.24; H, 5.40; N, 7.90. Found: C, 53.62; H, 5.40; N, 7.79.

Compound 72: 4-Hydroxy-1-methyl-5-oxo-2,5-dihydro-1H-pyrrole-3-carboxylic acid dimethylcarbamoylmethoxy-(4-fluoro-benzyl)-amide

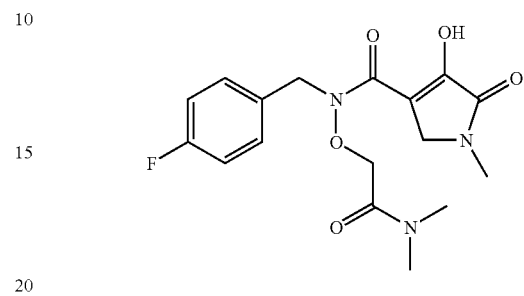

3-[Dimethylcarbamoylmethoxy-(4-fluorobenzyl)-carbamoyl]-2-hydroxy-acrylic acid methyl ester (Compound 72-B) was treated with paraformaldehyde and methylamine as described in the preparation of Compound 12 to give the title compound as a white solid (25% yield); mp 147–149° C. $^1$HNMR 400 MHz (CDCl$_3$) δ (ppm): 2.79 (3H, s, NCH$_3$), 2.96 (3H, s, NCH$_3$), 3.11 (3H, s, NCH$_3$), 4.25 (2H, s, CH$_2$), 4.51 (2H, s, CH$_2$), 4.96 (2H, s, CH$_2$), 7.06 (2H, m, aromatics), 7.38 (2H, m, aromatics), 11.54 (1H, broad s, OH). HRMS (ES+) calculated for C$_{17}$H$_{21}$FN$_3$O$_5$, [M+H]$^+$: 366.146524. found: 366.146176.

EXAMPLE 73

Compound 73: 4-Hydroxy-1-methyl-5-oxo-2,5-dihydro-1H-pyrrole-3-carboxylic acid [bis-(4-fluoro-phenyl)-methyl]-methoxy-amide

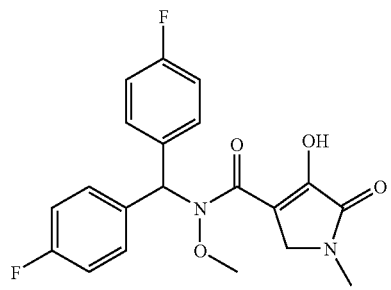

N-[Bis-(4-fluorophenyl)-methyl]-2-(2,2-dimethyl-5-oxo-[1,3]-dioxolan-4-ylidene)-N-methoxy-acetamide, prepared using the methods described in the previous examples, was treated in methanol with paraformaldehyde and methylamine as described in the preparation of Compound 44, Method 44B, to give the title compound as a tan solid (42% yield). $^1$HNMR 400 MHz (DMSO-d$_6$) δ (ppm): 2.9 (3H, broad s, NCH$_3$), 3.1 (3H, broad s, OCH$_3$), 4.2 (2H, broad, NCH$_2$), 6.9 (1H, broad s, CH), 7.0–7.4 (8H, m, aromatics). HRMS (ES+) calculated for C$_{20}$H$_{22}$F$_2$N$_3$O$_4$, [M+NH$_4$]$^+$: 406.157838. found: 406.158046.

EXAMPLE 74

Compound 74: 4-Hydroxy-1-methyl-5-oxo-2,5-dihydro-1H-pyrrole-3-carboxylic acid (2-chloro-4-fluoro-benzyl)-methoxy-amide

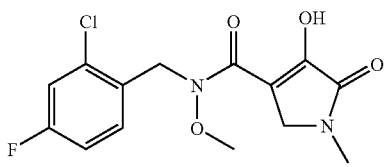

N-(2-Chloro-4-fluorobenzyl)-2-(2,2-dimethyl-5-oxo-[1,3]-dioxolan-4-ylidene)-N-methoxy-acetamide, prepared using the methods described in the previous examples, was treated in methanol with paraformaldehyde and methylamine as described in the preparation of Compound 44, Method 44B, to give the title compound as white crystals (55% yield); mp 152–155° C. $^1$HNMR 400 MHz (CDCl$_3$) δ (ppm): 3.11 (3H, s, NCH$_3$), 3.75 (3H, s, OCH$_3$), 4.17 (2H, s, NCH$_2$), 5.01 (2H, s, NCH$_2$), 6.99 (1H, m, aromatic), 7.15 (1H, dd, J=2.5 Hz, J=8.0 Hz, aromatic), 7.36 (1H, dd, J=5.7 Hz, J=8.8 Hz, aromatic). Anal. calcd for C$_{14}$H$_{14}$ClFN$_2$O$_4$: C, 51.15; H, 4.29; N, 8.52. Found: C, 50.62; H, 4.18; N, 8.40.

EXAMPLE 75

Compound 75: 4-Hydroxy-1-methyl-5-oxo-2,5-dihydro-1H-pyrrole-3-carboxylic acid [1-(4-chlorobenzyl)-2-(4-chloro-phenyl)-ethyl]-methyl-amide

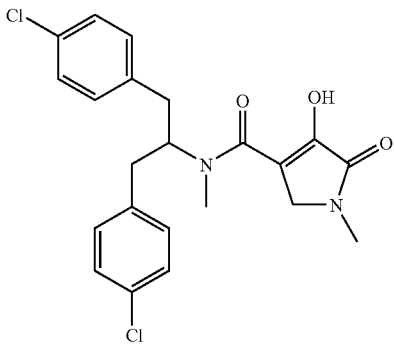

N-[1-(4-Chloro-benzyl)-2-(4-chloro-phenyl)-ethyl]-2-(2,2-dimethyl-5-oxo-[1,3]dioxolan-4-ylidene)-N-methyl-acetamide, prepared using the methods described in the previous examples, was treated in methanol with paraformaldehyde and methylamine as described in the preparation of Compound 44, Method 44B, to give the title compound as white crystals (56% yield); mp 152–154° C. $^1$HNMR 400 MHz (DMSO-d$_6$) δ (ppm): mixture of rotamers: 2.7–3.0 (4H, m, CH$_2$), 2.84 (3H, s, NCH$_3$), 2.9 (3H, broad s, NCH$_3$), 3.4 and 3.7 (2H, two broad s, NCH$_2$), 4.16 and 4.9 (1H, broad m, CH), 7.15–7.34 (8H, m, aromatics), 10.7 and 11.0 (1H, two s, OH). HRMS (MAB N$_2$) calculated for C$_{22}$H$_{22}$Cl$_2$N$_2$O$_3$: [M]$^+$: 432.100748. found: 432.100835.

EXAMPLE 76

Compound 76-A:
4-Fluoro-N-(4-fluoro-benzyl)-benzamide

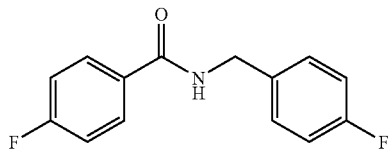

4-Flourobenzyl amine (27 grams, 0.22 mole) was dissolved in 200 mL of CH$_2$Cl$_2$. To this was added 400 mL of 1N NaOH and the resulting mixture cooled to 0° C. 4-Fluorobenzoyl chloride (33 grams, 0.21 mole) was added dropwise with stirring. The reaction was allowed to proceed for 20 min after which the organic layer was separated, dried over Na$_2$SO$_4$, filtered and the solvent removed under vacuum to yield 47 grams (92% yield) of 4-fluoro-N-(4-fluoro-benzyl)-benzamide as a solid. MS (M–H) calcd for C$_{14}$H$_{10}$F$_2$NO: 246.1. found: 246.0. Anal. Calcd for C$_{14}$H$_{11}$F$_2$NO; C, 68.01; H, 4.48; N, 5.66; found: C, 67.76; H, 4.54; N, 5.45. $^1$H NMR (500 MHz, DMSO) δ: 4.45 (d, 2, J=6), 7.15 (m, 2), 7.34 (overlapping m, 4), 7.97 (m, 2), 9.09 (t, 1, J=6). $^{13}$C NMR (125 MHz, DMSO) δ: 41.88, 114.81, 114.98, 115.06, 115.23, 129.08, 129.15, 129.76, 129.83, 130.60, 130.62, 135.66, 135.68, 160.10, 162.03, 162.83, 164.81, 165.04.

Compound 76-B: Bis-(4-fluoro-benzyl)-amine hydrochloride

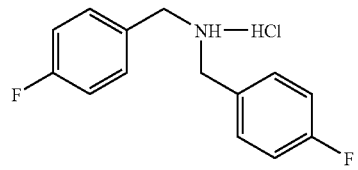

4-Fluoro-N-(4-fluoro-benzyl)-benzamide (40.0 grams, 0.16 mole) was dissolved in 240 mL of THF. To this was added BF$_3$.Et$_2$O (7.4 mL. 0.06 mole) and the resulting mixture heated to reflux for 15 min. After cooling to –30° C., BH$_3$.SMe$_2$ (22.3 mL, 0.24 mole) was added using a dropping funnel. The reaction was allowed to warm to room temperature. The reaction flask was fitted with a distillation condenser and solvent removed under reflux for 25 min. The distillation apparatus was replaced with a reflux condenser and the reaction heated to 110° C. for 2 h. After cooling to 0° C., 100 mL of 6N HCl was added and the mixture heated to reflux for 1 hr to yield a thick slurry. 300 mL of 6N NaOH was slowly added at room temperature with intermittent cooling using an ice bath. After all the solid has dissolved Et$_2$O was added and the mixture transferred to a separatory funnel. The organic layer was separated, dried over Na$_2$SO$_4$, filtered and the solvent removed under vacuum to yield an oil. The oil was dissolved in 50 mL of Et$_2$O and 4N HCl (dioxane) added resulting in the formation of a white precipitate which was isolated by filtration to yield 40 grams (93% yield) of bis-(4-fluoro-benzyl)-amine hydrochloride. MS (M+H) calcd for C$_{14}$H$_{14}$F$_2$N, 234.1. found: 234.0. Anal.

calcd for C$_{14}$H$_{14}$F$_2$NCl: C, 62.34; H, 5.23; N, 5.19. found: C, 61.89; H, 5.15; N, 5.27. $^1$H NMR (500 MHz, DMSO) δ: 4.12 (br s, 4), 7.26 (m, 4), 7.65 (m, 4), 9.91 (br s, 2).

Compound 76-C: N,N-Bis-(4-fluoro-benzyl)-acetamide

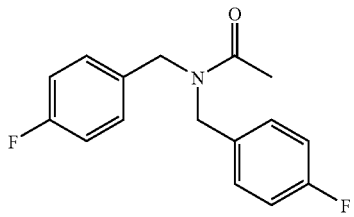

Bis-(4-fluoro-benzyl)-amine hydrochloride (43 grams, 0.16 mole) was suspended in 200 mL of CH$_2$Cl$_2$. To this was added 730 mL of 1N NaOH. The reaction mixture was stirred vigorously while AcCl (20 mL, 0.28 mole) was slowly added. The reaction was stirred for 0.5 h, then the organic layer separated, washed with 1N HCl, dried over Na$_2$SO$_4$, filtered and the solvent removed under vacuum to yield 24 grams (55% yield) of N,N-bis-(4-fluoro-benzyl)-acetamide as an oil. MS (M+H) calcd for C$_{16}$H$_{16}$F$_2$NO: 276.1. found: 276.0. Anal. calcd for C$_{16}$H$_{15}$F$_2$NO: C, 69.80; H, 5.49; N, 5.08. found: C, 69.53; H, 5.41; N, 5.06. $^1$H NMR (500 MHz, DMSO) δ: 2.10 (s, 3), 4.45 (s, 2), 4.50 (s, 2), 7.11–7.27 (overlapping m, 8). $^{13}$C NMR (125 MHz, DMSO) δ: 21.34, 50.04, 54.80, 114.90, 115.07, 115.27, 115.45, 128.51, 128.58, 129.57, 129.64, 133.32, 133.34, 133.86, 133.89, 160.25, 160.33, 162.27, 170.22.

Compound 76-D: 3-[Bis-(4-fluoro-benzyl)-carbamoyl]-2-hydroxy-acrylic acid methyl ester

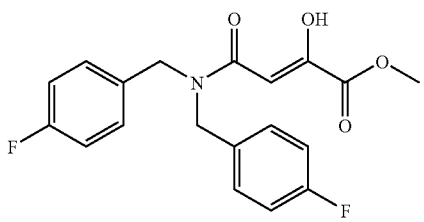

N,N-Bis-(4-fluoro-benzyl)-acetamide (15.0 grams, 54.5 mmol) and dimethyloxalate (9.6 grams, 81.3 mmol) were dissolved in 54 mL of THF. After cooling to 0° C. 108 mL of 1N LiHMDS (THF) was added dropwise. The reaction mixture was stirred 1 hr then quenched with 1N HCl. The resulting mixture was extracted with CH$_2$Cl$_2$, dried over Na$_2$SO$_4$, filtered and the solvent removed under vacuum. The product was purified by flash column chromatography (SiO$_2$, 80:20 hexanes/EtOAc) to yield 10 grams (53% yield) of 3-[bis-(4-fluoro-benzyl)-carbamoyl]-2-hydroxy-acrylic acid methyl ester as a solid. Mp=118–120° C. Anal. calcd for C$_{19}$H$_{17}$F$_2$NO$_4$: C, 63.15; H, 4.74; N, 3.87. found: C, 62.97; H, 4.72; N, 3.81. $^1$H NMR (500 MHz, CDCl$_3$) δ: 3.87 (s, 3), 4.46 (s, 2), 4.58 (s, 2), 6.32 (s, 1), 7.00–7.26 (overlapping m, 8). $^{13}$C NMR (125 MHz, CDCl$_3$) δ: 47.34, 49.35, 53.03, 93.34, 115.66, 115.83, 116.00, 116.18, 128.45, 128.52, 130.03, 130.10, 131.09, 131.93, 131.95, 160.29, 161.44, 161.51, 163.10, 163.41, 163.47, 171.36.

Compound 76: 4-Hydroxy-1-methyl-5-oxo-2,5-dihydro-1H-pyrrole-3-carboxylic acid bis-(4-fluoro-benzyl)-amide

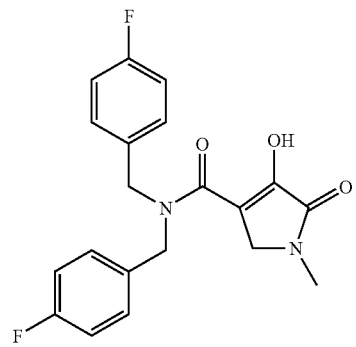

To 2 mL of AcOH at 60° C. was added 1 mL 2M MeNH$_2$ (THF) and 60 mg paraformaldehyde. After stirring for 5 min 3-[bis-(4-fluoro-benzyl)-carbamoyl]-2-hydroxy-acrylic acid methyl ester (723 mg, 2.0 mmol) was added and the resulting solution stirred at 60° C. for 2 h. The reaction mixture was then cooled to room temperature and transferred to a separatory funnel. The solution was extracted with EtOAc, the organic layer separated, washed with H$_2$O, satd NaCl, then dried over Na$_2$SO$_4$. After filtration the solvent was removed to isolate 500 mg (67% yield) of 4-hydroxy-1-methyl-5-oxo-2,5-dihydro-1H-pyrrole-3-carboxylic acid bis-(4-fluoro-benzyl)-amide as an orange solid. MS (M+H) calcd for C$_{20}$H$_{19}$F$_2$N$_2$O$_3$: 373.1. found: 373.0. $^1$H NMR (500 MHz, DMSO) δ: 2.94 (s, 3), 4.01 (s, 2), 4.46 (br s, 2), 4.55 (br s, 2), 7.13–7.22 (overlapping m, 8).

EXAMPLE 77

Compound 77-A: (4-Chloro-benzyl)-(3,4-dichloro-benzyl)-amine

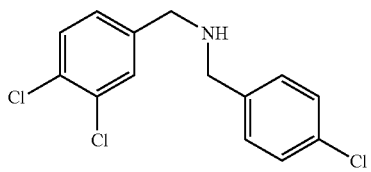

From N-(4-chlorobenzyl)-3,4-dichlorobenzamide (Borgma et al. *Farmaco Ed. Sci.* 1977, 32, 813). $^1$HNMR 400 MHz (C$_6$D$_6$) δ (ppm): 3.22 (2H, s, NCH$_2$), 3.31 (2H, s, NCH$_2$), 6.78 (1H, d, J=8.5 Hz, aromatic), 6.99 (2H, d, J=8.1 Hz, aromatics), 7.15 (2H, d, J=8.1 Hz, aromatics), 7.24–7.31 (3H, m, aromatics).

Compound 77-B: N-(4-Chloro-benzyl)-N-(3,4-dichloro-benzyl)-acetamide

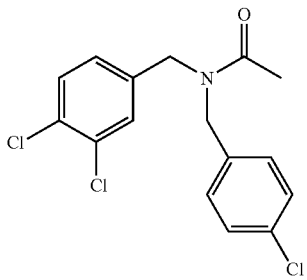

4-(Chlorobenzyl)-(3,4-dichlorobenzyl)-amine was acetylated as described in the preparation of Compound 76-C and gave the title amide as a clear oil (78% yield). $^1$HNMR 400 MHz ($C_6D_6$) δ (ppm), mixture of rotamers: 1.77 and 1.78 (3H, 2 s, $COCH_3$), 3.6 and 3.66 (2H, 2 s, $NCH_2$), 4.26. and 4.33 (2H, 2 s, $NCH_2$), 6.37–7.2 (7H, m, aromatics). Anal. calcd for $C_{16}H_{14}Cl_3NO$: C, 56.08; H, 4.12; N, 4.09. Found: C, 56.13; H, 4.07; N, 4.08.

Compound 77-C: 3-[(4-Chloro-benzyl)-(3,4-dichloro-benzyl)-carbamoyl]-2-hydroxy-acrylic acid methyl ester

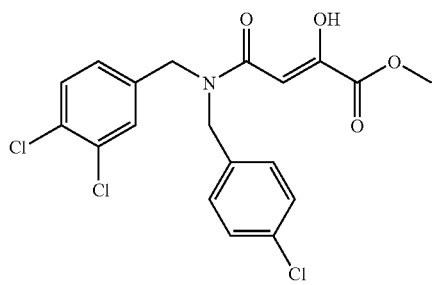

N-(4-Chlorobenzyl)-N-(3,4-dichlorobenzyl)-acetamide was reacted with dimethyl oxalate as described in the preparation of Compound 76-D and gave the title methyl ester as a clear oil (40% yield). $^1$HNMR 400 MHz ($CDCl_3$) δ (ppm): mixture of rotamers: 3.9 (3H, s, $OCH_3$), 4.47, 4.5, 4.58 and 4.62 (2×2H, 4 s, $NCH_2$), 6.27 and 6.33 (1H, 2 s, CH), 7.0–7.48 (7H, m, aromatics), 14.33 and 14.37 (1H, 2 s, OH).

Compound 77: 4-Hydroxy-1-methyl-5-oxo-2,5-dihydro-1H-pyrrole-3-carboxylic acid (4-chloro-benzyl)-(3,4-dichloro-benzyl)-amide

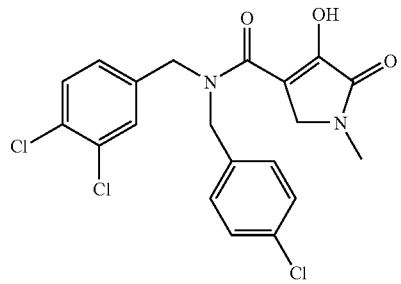

3-[(4-Chlorobenzyl)-(3,4-dichlorobenzyl)-carbamoyl]-2-hydroxy-acrylic acid methyl ester was reacted with paraformaldehyde and methylamine as described in the preparation of Compound 12 to give the title compound as a white solid (39% yield); mp 165° C., dec. $^1$HNMR 400 MHz ($CDCl_3$) δ (ppm): 3.09 (3H, s, $NCH_3$), 4.09, 4.55 and 4.56 (3×2H, 3 s, $NCH_2$), 7.05–7.45 (7H, m, aromatics), 10.3 (1H, broad, OH).

EXAMPLE 78

Compound 78-A: N-(3,4-Dichloro-phenyl)-N-(4-fluoro-benzyl)-acetamide

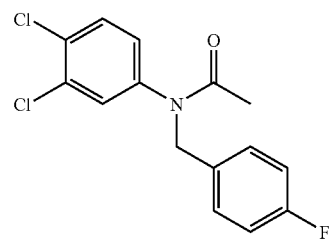

3,4-(Dichlorophenyl)-(4-fluorobenzyl)-amine was acetylated as described in the preparation of Compound 76-C and gave the title amide as a clear oil (89% yield). $^1$HNMR 400 MHz ($C_6D_6$) δ (ppm): 1.59 (3H, s, $COCH_3$), 4.56 (2H, s, $NCH_2$), 6.04 (1H, broad s, aromatic), 6.71–6.98 (6H, m, aromatics). Anal. calcd for $C_{15}H_{12}Cl_2FNO$: C, 57.71; H, 3.87; N, 4.48. Found: C, 57.85; H, 3.89; N, 4.49.

Compound 78-B: 3-[(3,4-Dichloro-phenyl)-(4-fluoro-benzyl)-carbamoyl]-2-hydroxy-acrylic acid methyl ester

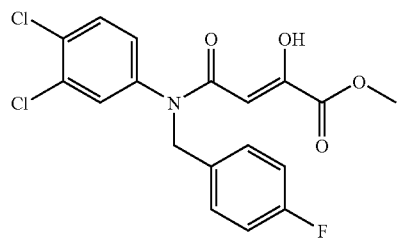

N-(3,4-Dichlorophenyl)-N-(4-fluorobenzyl)-acetamide was reacted with dimethyl oxalate as described in the preparation of Compound 76-D and gave the title methyl ester as a clear oil (40% yield). $^1$HNMR 400 MHz (CDCl$_3$) δ (ppm): 3.84 (3H, s, OCH$_3$), 4.90 (2H, s, NCH$_2$), 5.69 (1H, s, CH), 6.83 (1H, dd, J=2.0 Hz and J=8.5 Hz, aromatic), 7.02 (2H, m, aromatic), 7.19 (3H, m, aromatic), 7.47 (1H, d, J=8.5 Hz, aromatic), 13.83 (1H, s, OH).

Compound 78: 4-Hydroxy-1-methyl-5-oxo-2,5-dihydro-1H-pyrrole-3-carboxylic acid (3,4-dichlorophenyl)-(4-fluoro-benzyl)-amide

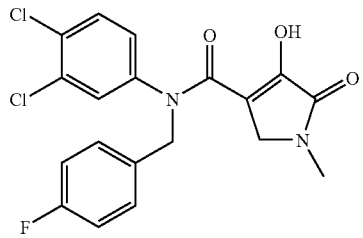

3-[(3,4-Dichlorophenyl)-(4-fluorobenzyl)-carbamoyl]-2-hydroxy-acrylic acid methyl ester (Compound 78-B) was treated with paraformaldehyde and methylamine as described in the preparation of Compound 12 to give the title compound as a white solid (68% yield); mp 195° C., dec. $^1$HNMR 400 MHz (CDCl$_3$) δ (ppm): 2.9 (3H, s, NCH$_3$), 3.03 (2H, s, NCH$_2$), 4.90 (2H, s, NCH$_2$), 6.87 (1H, dd, J=2.5 Hz and J=8.6 Hz, aromatic), 7.02 (2H, m, aromatics), 7.2 (2H, m, aromatics), 7.22 (1H, d, J=2.5 Hz, aromatic), 7.49 (1H, d, J=8.6 Hz, aromatic), 11.9 (1H, broad, OH). Anal. calcd for C$_{19}$H$_{15}$Cl$_2$FN$_2$O$_3$: C, 55.76; H, 3.69; N, 6.84. Found: C, 55.53; H, 3.61; N, 6.75.

EXAMPLE 79

Compound 79-A: N-Benzyl-N-methyl-acetamide

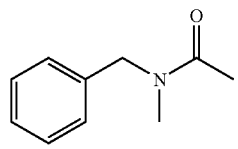

Compound 79-A was prepared using methods described in the previous examples. $^1$H NMR and $^{13}$C NMR show a mixture of rotamers at room temperature. $^1$H NMR (500 MHz, CDCl$_3$) δ: 2.20 (s), 2.95 (s), 2.97 (s), 4.56 (s), 4.62 (s), 7.19–7.41 (overlapping m). $^{13}$C NMR (125 MHz, CDCl$_3$) δ: 21.42, 21.80, 33.82, 35.58, 50.68, 54.29, 126.33, 127.41, 127.70, 128.07, 128.63, 128.99, 136.46, 137.26, 170.88, 171.19.

Compound 79-B: 3-(Benzyl-methyl-carbamoyl)-2-hydroxy-acrylic acid methyl ester

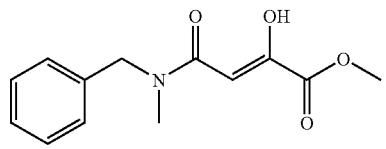

Compound 79-B was prepared using methods described in the previous examples. $^1$H NMR shows a mixture of rotamers at room temperature. $^1$H NMR (500 MHz, CDCl$_3$) δ: 3.02 (s), 3.86 (s), 3.90 (s), 4.60 (s), 4.66 (s), 6.31 (s), 6.34 (s), 7.18–7.40 (overlapping m).

Compound 79: 4-Hydroxy-1-methyl-5-oxo-2,5-dihydro-1H-pyrrole-3-carboxylic acid benzyl-methyl-amide

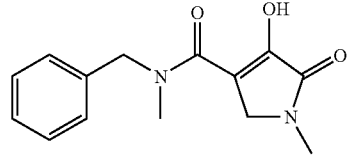

Compound 79 was prepared using methods described in the previous examples. HRMS (M–H) calcd for C$_{14}$H$_{15}$N$_2$O$_3$: 259.10827. found 259.1082. $^1$H NMR (500 MHz, CDCl$_3$) δ: 3.03 (s, 3), 3.09 (s, 3), 4.15 (s, 2), 4.65 (s, 2), 7.23–7.37 (m, 5). $^{13}$C NMR (125 MHz, CDCl$_3$) δ: 29.95, 34.67, 50.80, 52.28, 108.72, 127.38, 127.86, 128.94, 136.12, 154.15, 165.10, 166.46.

EXAMPLE 80

Method for the Preparation of Compounds 80–724

PL-FMP resin (4-formyl-3-methoxy-phenoxymethyl functionalized polystyrene), VII-1 in Scheme VII or similar aldehyde derivatized resin (approximately 40 mg, 0.048 meq.) was suspended in 2 ml of anhydrous DMF, anhydrous trimethylorthoformate and acetic acid mixture in 7:3:1 ratio. To this mixture was added a primary amine, VII-2 in scheme VII, (0.72 mmol) followed by sodium triacetoxy borohydride (0.72 mmol). The resulting mixture was agitated for 72 h at room temperature using a shaker. The resin was filtered, washed successively with (DMF, THF and DCM, 3×2 ml each), dried and used as is in the next step.

The resin (VII-3 in Scheme VII) was suspended in anhydrous dichloromethane (1 mL) and to this was added, 2,2-dimethyl-5-(carboxymethylene)-1,3-dioxalan-4-one (Compound III-A) (16.5 mg, 0.096 mmol), Pybop (50 mg, 0.096 mmol) and iPr$_2$NEt (24.8 mg, 0.192 mmol). The resulting mixture was agitated for 48 h at room temperature using a shaker. Resin was filtered, washed successively (DMF, THF and DCM, 3×2 ml each), dried and used in the next step.

Next the resin, VII-4 in Scheme VII, was suspended in 1 ml anhydrous N-methyl-2-pyrrolidinone (NMP). To thimixture was added a preformed imine mixture (preformed by heating aldehyde (18 mg, 0.55 mmol), and amine (0.5 s mmol) and 0.25 ml methanol, at 70° C. for 2 h) and the resulting mixture was heated with agitation in a sealed container at 70–80° C. for 72 h. Resin was filtered, washed successively with (DMF, DMF/MeOH (1:1), THF and DCM, 3×2 ml each), dried.

The final product, VII-6 in Scheme VII, was cleaved from the resin by treating with 1.5 ml of 1:1 mixture of trifluoroacetic acid and dichloromethane for 1 h. TFA solution was filtered and the solvent was evaporated to give the required product.

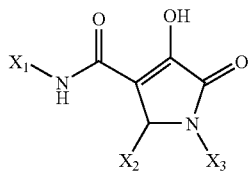

| Compd | X1 | X2 | X3 | MS obsd | LC RT (min) |
|---|---|---|---|---|---|
| 80 | -X1) | $X_2$-H | $X_3$-$CH_3$ | 261.1 | 1.3 |
| 81 | -X1) | $X_2$-H | $X_3$-$CH_3$ | 289.2 | 1.5 |
| 82 | | $X_2$-H | $X_3$-$CH_3$ | 317.0 | 1.5 |
| 83 | | $X_2$-H | $X_3$-$CH_3$ | 315.1 | 1.4 |
| 84 | | $X_2$-H | $X_3$-$CH_3$ | 265.1 | 1.1 |
| 85 | | $X_2$-H | $X_3$-$CH_3$ | 321.1 | 1.3 |
| 86 | | $X_2$-H | $X_3$-$CH_3$ | 275.2 | 1.4 |
| 87 | | $X_2$-H | $X_3$-$CH_3$ | 311.2 | 1.6 |
| 88 | | $X_2$-H | $X_3$-$CH_3$ | 275.3 | 1.3 |

-continued
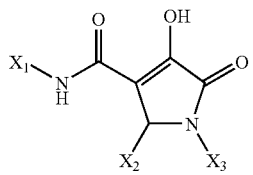
| Compd | X1 | X2 | X3 | MS obsd | LC RT (min) |
|---|---|---|---|---|---|
| 89 | 3,4-dichlorophenethyl-X₁ | X₂-H | X₃-CH₃ | 329.0 | 1.6 |
| 90 | 3-fluorophenethyl-X₁ | X₂-H | X₃-CH₃ | 279.1 | 1.4 |
| 91 | 4-fluorophenethyl-X₁ | X₂-H | X₃-CH₃ | 279.1 | 1.4 |
| 92 | 4-(F₃CS)benzyl-X₁ | X₂-H | X₃-CH₃ | 347.1 | 1.6 |
| 93 | 3,4-dimethoxybenzyl-X₁ | X₂-H | X₃-CH₃ | 307.4 | 1.1 |
| 94 | 4-methoxybenzyl-X₁ | X₂-H | X₃-CH₃ | 277.4 | 1.2 |
| 95 | 1-naphthylmethyl-X₁ | X₂-H | X₃-CH₃ | 297.3 | 1.5 |
| 96 | 2,6-dimethylbenzyl-X₁ | X₂-H | X₃-CH₃ | 275.4 | 1.5 |
| 97 | 1-phenylcyclopropylmethyl-X₁ | X₂-H | X₃-CH₃ | 287.4 | 1.5 |
| 98 | 3,4-dichlorobenzyl-X₁ | X₂-H | X₃-(2-benzyl-2-hydroxyethyl) | 435.3 | 1.6 |

-continued

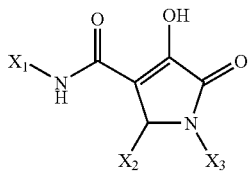

| Compd | X1 | X2 | X3 | MS obsd | LC RT (min) |
|---|---|---|---|---|---|
| 99 | 3,4-dichlorobenzyl | X₂-H | morpholinopropyl | 428.3 | 1.2 |
| 100 | 3,4-dichlorobenzyl | X₂-H | 1-(ethoxycarbonyl)piperidin-4-yl | 456.3 | 1.6 |
| 101 | 3,4-dichlorobenzyl | X₂-H | 2-(piperidin-1-yl)ethyl | 412.4 | 1.2 |
| 102 | 3,4-dichlorobenzyl | X₂-H | 4-(carboxymethyl)phenyl | 435.3 | 1.6 |
| 103 | 3,4-dichlorobenzyl | X₂-H | 1-methoxy-2-propyl | 373.3 | 1.5 |
| 104 | 3,4-dichlorobenzyl | X₂-H | 1-hydroxy-2-propyl | 359.3 | 1.4 |
| 105 | 3,4-dichlorobenzyl | X₂-H | isobutyl | 357.3 | 1.6 |
| 106 | 3,4-dichlorobenzyl | X₂-H | 2-methoxyethyl | 359.3 | 1.4 |
| 107 | 3,4-dichlorobenzyl | X₂-H | 2-(2-hydroxyethoxy)ethyl | 389.3 | 1.3 |
| 108 | 3,4-dichlorobenzyl | X₂-H | 3-(dimethylamino)propyl | 386.4 | 1.2 |

-continued

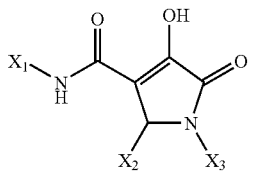

| Compd | X1 | X2 | X3 | MS obsd | LC RT (min) |
|---|---|---|---|---|---|
| 109 | 3,4-dichlorobenzyl | $X_2$-H | HO-propyl-$X_3$ | 359.3 | 1.4 |
| 110 | 3,4-dichlorobenzyl | $X_2$-H | N-acetyl lysine (HO$_2$C, AcNH, -$X_3$) | 472.3 | 1.4 |
| 111 | 3,4-dichlorobenzyl | $X_2$-H | $X_3$-propyl-imidazol-1-yl | 409.3 | 1.2 |
| 112 | 3,4-dichlorobenzyl | $X_2$-H | MeO-propyl-$X_3$ | 373.3 | 1.5 |
| 113 | 3,4-dichlorobenzyl | $X_2$-H | $X_3$-ethyl-pyridin-4-yl | 406.3 | 1.2 |
| 114 | 3,4-dichlorobenzyl | $X_2$-H | $X_3$-propyl-N(CH$_2$CH$_2$OH)$_2$ | 446.3 | 1.2 |
| 115 | 3,4-dichlorobenzyl | $X_2$-H | PhO-ethyl-$X_3$ | 421.3 | 1.7 |
| 116 | 3,4-dichlorobenzyl | $X_2$-H | morpholin-4-yl-ethyl-$X_3$ | 414.4 | 1.1 |
| 117 | 3,4-dichlorobenzyl | cyclohexyl-$X_2$ | $X_3$-CH$_3$ | 397.3 | 1.8 |
| 118 | 3,4-dichlorobenzyl | phenyl-$X_2$ | $X_3$-CH$_3$ | 391.3 | 1.7 |

-continued
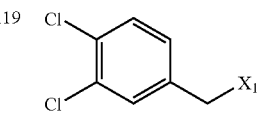
| Compd | X1 | X2 | X3 | MS obsd | LC RT (min) |
|---|---|---|---|---|---|
| 119 | 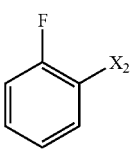 |  | X3-CH3 | 409.3 | 1.7 |
| 120 | 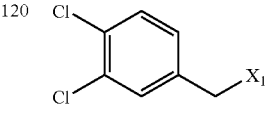 | 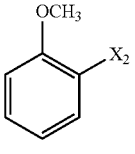 | X3-CH3 | 421.3 | 1.8 |
| 121 |  | 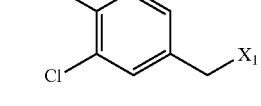 | X3-CH3 | 451.3 | 1.7 |
| 122 | 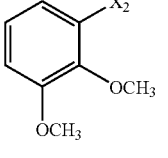 |  | X3-CH3 | 435.3 | 1.8 |
| 123 | 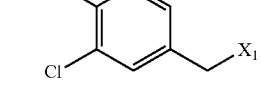 | 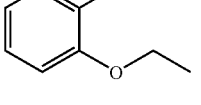 | X3-CH3 | 416.3 | 1.6 |
| 124 |  | 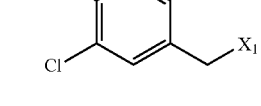 | X3-CH3 | 439.3 | 1.6 |
| 125 | 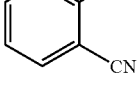 |  | X3-CH3 | 421.3 | 1.7 |
| 126 | 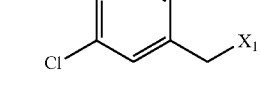 | 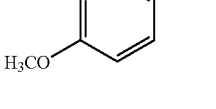 | X3-CH3 | 416.3 | 1.6 |
| 127 |  | 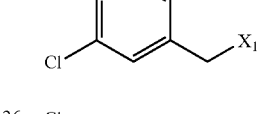 | X3-CH3 | 434.3 | 1.3 |

-continued
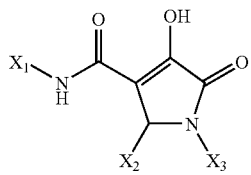
| Compd | X1 | X2 | X3 | MS obsd | LC RT (min) |
|---|---|---|---|---|---|
| 128 | 3,4-diCl-benzyl | 4-methoxyphenyl | X3-CH3 | 421.3 | 1.7 |
| 129 | 3,4-diCl-benzyl | 4-(propoxy)phenyl | X3-CH3 | 463.3 | 2.0 |
| 130 | 3,4-diCl-benzyl | 2-Cl-4-F-phenyl | X3-CH3 | 443.2 | 1.8 |
| 131 | 3,4-diCl-benzyl | 6-methylpyridin-2-yl | X3-CH3 | 406.3 | 1.3 |
| 132 | 3,4-diCl-benzyl | pyridin-3-yl | X3-CH3 | 392.3 | 1.2 |
| 133 | 3,4-diCl-benzyl | 4-(methoxycarbonyl)phenyl | X3-CH3 | 449.3 | 1.6 |
| 134 | 3,4-diCl-benzyl | 4-carboxyphenyl | X3-CH3 | 435.3 | 1.5 |
| 135 | 3,4-diCl-benzyl | 4-methylphenyl | X3-CH3 | 405.3 | 1.7 |
| 136 | 3,4-diCl-benzyl | 4-ethylphenyl | X3-CH3 | 419.3 | 1.8 |
| 137 | 3,4-diCl-benzyl | isopropyl | X3-CH3 | 357.3 | 1.6 |

-continued
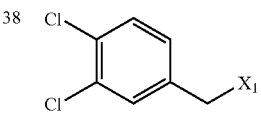
| Compd | X1 | X2 | X3 | MS obsd | LC RT (min) |
|---|---|---|---|---|---|
| 138 | 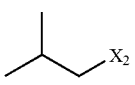 |  | $X_3$-$CH_3$ | 371.3 | 1.7 |
| 139 | 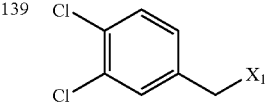 | 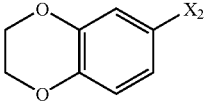 | $X_3$-$CH_3$ | 449.3 | 1.6 |
| 140 |  | 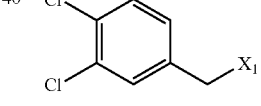 | $X_3$-$CH_3$ | 381.3 | 1.6 |
| 141 | 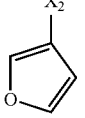 |  | $X_3$-$CH_3$ | 451.3 | 1.7 |
| 142 | 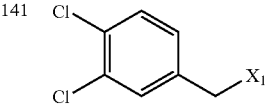 | 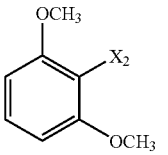 | $X_3$-$CH_3$ | 492.4 | 1.3 |
| 143 |  | 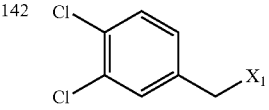 | $X_3$-$CH_3$ | 355.3 | 1.6 |
| 144 | 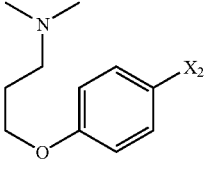 |  | $X_3$-$CH_3$ | 465.3 | 1.5 |
| 145 | 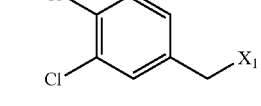 |  | $X_3$-$CH_3$ | 435.3 | 1.7 |
| 146 |  | 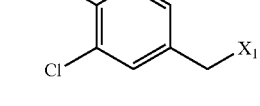 | $X_3$-$CH_3$ | 469.2 | 1.7 |

-continued

[Structure: X1-NH-C(=O)- attached to a pyrrolinone ring with OH, =O, X2 at C5, N-X3]

| Compd | X1 | X2 | X3 | MS obsd | LC RT (min) |
|---|---|---|---|---|---|
| 147 | 3,4-dichlorobenzyl | 4-tert-butylphenyl | X3-CH3 | 447.3 | 2.0 |
| 148 | 3,4-dichlorobenzyl | 2-(4-chlorophenylthio)phenyl | X3-CH3 | 533.2 | 2.0 |
| 149 | 4-methoxybenzyl | 2-carboxyphenyl | CH3OCH2CH(CH3)- | 455.4 | 1.17 |
| 150 | 4-fluorobenzyl | 2-carboxyphenyl | CH3OCH2CH2CH2- | 441.1 | 1.05 |
| 151 | 3-phenylpropyl | isobutyl (2-methylpropyl) | 1-(ethoxycarbonyl)piperidin-4-yl | 472.3 | 0.75 |
| 152 | 4-fluorobenzyl | 2-methylpropyl | CH3OCH2CH2- | 365.2 | 1.57 |
| 153 | 3-phenylpropyl | isobutyl | CH3OCH2CH2- | 375.2 | 1.32 |

-continued
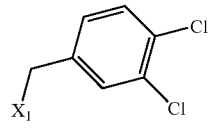
| Compd | X1 | X2 | X3 | MS obsd | LC RT (min) |
|---|---|---|---|---|---|
| 154 | 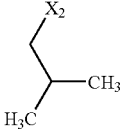 | 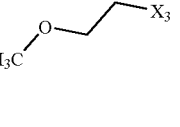 | 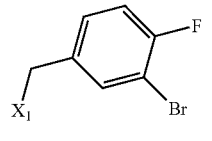 | 415.2 | 1.48 |
| 155 | 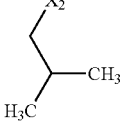 | 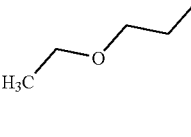 | 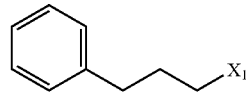 | 471.2 | 1.05 |
| 156 | 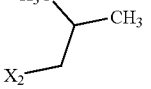 | 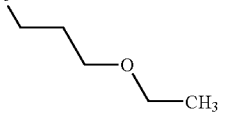 | 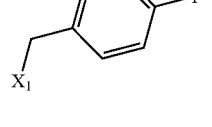 | 403.3 | 1.37 |
| 157 | 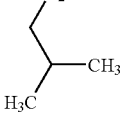 | 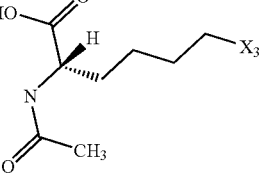 | 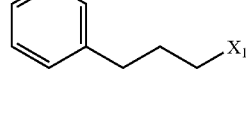 | 478.2 | 1.19 |
| 158 | 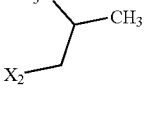 | 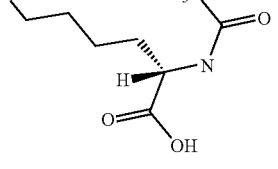 | 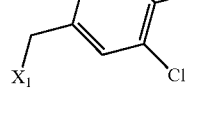 | 488.6 | 1.41 |
| 159 | 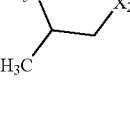 | 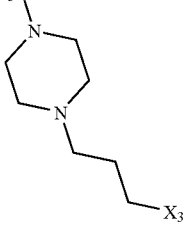 | 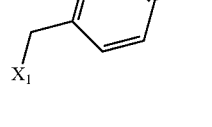 | 497.1 | 1.13 |
| 160 | 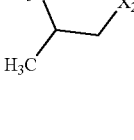 | 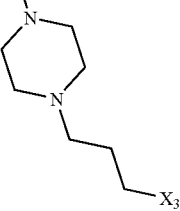 |  | 447.2 | 1.10 |

-continued

| Compd | X1 | X2 | X3 | MS obsd | LC RT (min) |
|---|---|---|---|---|---|
| 161 | 3-phenylpropyl | isobutyl | 3-(4-methylpiperazin-1-yl)propyl | 457.5 | 1.03 |
| 162 | 3,4-dichlorobenzyl | isobutyl | 3-(4-methylpiperazin-1-yl)propyl | 497.1 | 1.05 |
| 163 | 3,5-dichlorobenzyl | isobutyl | 3-methoxypropyl | 429.3 | 1.38 |
| 164 | 3-bromo-4-fluorobenzyl | isobutyl | cyclopropylmethyl | 439.1 | 1.03 |
| 165 | 4-fluorobenzyl | isobutyl | cyclopropylmethyl | 361.2 | 1.41 |
| 166 | 3,4-dichlorobenzyl | isobutyl | cyclopropylmethyl | 411.1 | 1.53 |
| 167 | 4-methoxybenzyl | 2-(allyloxy)phenyl | 2-methoxyethyl | 453.2 | 1.50 |

-continued

| Compd | X1 | X2 | X3 | MS obsd | LC RT (min) |
|---|---|---|---|---|---|
| 168 | 3,5-dichlorobenzyl | benzo[1,3]dioxol-4-yl | 1-(ethoxycarbonyl)piperidin-4-yl | 576.2 | 1.59 |
| 169 | 3-phenylpropyl | benzo[1,3]dioxol-4-yl | 1-(ethoxycarbonyl)piperidin-4-yl | 536.2 | 2.03 |
| 170 | 4-fluorobenzyl | benzo[1,3]dioxol-4-yl | 2-methoxyethyl | 429.1 | 1.23 |
| 171 | 3-phenylpropyl | benzo[1,3]dioxol-4-yl | 2-methoxyethyl | 439.2 | 1.25 |
| 172 | 3-phenylpropyl | benzo[1,3]dioxol-4-yl | 3-ethoxypropyl | 467.2 | 1.35 |
| 173 | 3,4-dichlorobenzyl | benzo[1,3]dioxol-4-yl | 3-ethoxypropyl | 507.3 | 1.33 |
| 174 | 3-bromo-4-fluorobenzyl | benzo[1,3]dioxol-4-yl | N-acetyl-L-lysine | 620.4 | 1.07 |

-continued

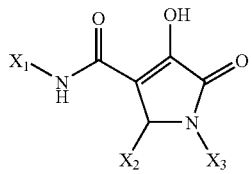

| Compd | X1 | X2 | X3 | MS obsd | LC RT (min) |
|---|---|---|---|---|---|
| 175 | 3,4-dichlorobenzyl | benzo[1,3]dioxol-4-yl | N-acetyl-lysine (HOOC-CH(NHAc)-(CH2)4-) | 592.1 | 1.21 |
| 176 | 4-fluorobenzyl | benzo[1,3]dioxol-4-yl | 4-methylpiperazin-1-yl-propyl | 511.2 | 0.94 |
| 177 | 3,4-dichlorobenzyl | benzo[1,3]dioxol-4-yl | 4-methylpiperazin-1-yl-propyl | 561.1 | 1.00 |
| 178 | 3,5-dichlorobenzyl | benzo[1,3]dioxol-4-yl | cyclopropylmethyl | 475.1 | 1.62 |
| 179 | 4-fluorobenzyl | benzo[1,3]dioxol-4-yl | cyclopropylmethyl | 425.1 | 1.24 |
| 180 | 3-phenylpropyl | benzo[1,3]dioxol-4-yl | cyclopropylmethyl | 435.3 | 2.18 |
| 181 | 3,5-dichlorobenzyl | 2-(difluoromethoxy)phenyl | 1-(ethoxycarbonyl)piperidin-4-yl | 598.2 | 1.45 |

-continued

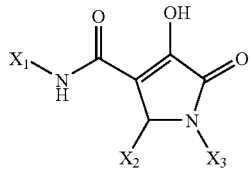

| Compd | X1 | X2 | X3 | MS obsd | LC RT (min) |
|---|---|---|---|---|---|
| 182 | 4-fluoro-3-bromobenzyl | 2-(difluoromethoxy)phenyl | cyclopropylmethyl | 525.1 | 1.04 |
| 183 | 4-fluorobenzyl | 2-methoxyphenyl | 1-methoxy-2-propyl | 429.1 | 1.26 |
| 184 | 3-phenylpropyl | 2-methoxyphenyl | 2-methoxyethyl | 425.4 | 1.27 |
| 185 | 3-phenylpropyl | 2-methoxyphenyl | 3-ethoxypropyl | 453.2 | 1.41 |
| 186 | 3,5-dichlorobenzyl | 2-methoxyphenyl | N-acetyl-lysyl | 578.2 | 1.24 |
| 187 | 4-fluorobenzyl | 2-methoxyphenyl | N-acetyl-lysyl | 528.5 | 0.27 |
| 188 | 3-phenylpropyl | 2-methoxyphenyl | N-acetyl-lysyl | 536.2 | 1.20 |

-continued

| Compd | X1 | X2 | X3 | MS obsd | LC RT (min) |
|---|---|---|---|---|---|
| 189 | 3,4-dichlorobenzyl | 2-methoxyphenyl | N-acetyl-lysine-like (HOOC-CH(NHAc)-(CH2)4-X3) | 578.1 | 1.26 |
| 190 | 3-phenylpropyl | 2-methoxyphenyl | 3-(4-methylpiperazin-1-yl)propyl | 507.2 | 1.03 |
| 191 | 3,4-dichlorobenzyl | 2-methoxyphenyl | 3-(4-methylpiperazin-1-yl)propyl | 547.1 | 1.04 |
| 192 | 3,5-dichlorobenzyl | 2-methoxyphenyl | cyclopropylmethyl | 461.1 | 1.72 |
| 193 | 3-bromo-4-fluorobenzyl | 2-methoxyphenyl | cyclopropylmethyl | 489.2 | 1.03 |
| 194 | 4-fluorobenzyl | 2-methoxyphenyl | cyclopropylmethyl | 411.2 | 1.37 |

-continued

| Compd | X1 | X2 | X3 | MS obsd | LC RT (min) |
|---|---|---|---|---|---|
| 195 | 3-phenylpropyl | 2-methoxyphenyl | cyclopropylmethyl | 421.2 | 1.45 |
| 196 | 3,4-dichlorobenzyl | 2-methoxyphenyl | cyclopropylmethyl | 461.1 | 1.77 |
| 197 | 3-phenylpropyl | 2-(carboxymethoxy)phenyl | 1-(ethoxycarbonyl)piperidin-4-yl | 566.3 | 1.35 |
| 198 | 4-methoxybenzyl | 2-(carboxymethoxy)phenyl | 1-(ethoxycarbonyl)piperidin-4-yl | 568.2 | 1.23 |
| 199 | 3,5-dichlorobenzyl | 2-(carboxymethoxy)phenyl | ethyl | 479.3 | 1.36 |
| 200 | 3-phenylpropyl | 2-(carboxymethoxy)phenyl | ethyl | 439.2 | 1.39 |

-continued

| Compd | X1 | X2 | X3 | MS obsd | LC RT (min) |
|---|---|---|---|---|---|
| 201 | 4-F, 3-Br benzyl | 2-(carboxymethoxy)phenyl | 2-methoxyethyl | 537.1 | 1.14 |
| 202 | 3-phenylpropyl | 2-(carboxymethoxy)phenyl | 2-methoxyethyl | 469.4 | 1.19 |
| 203 | 3,4-dichlorobenzyl | 2-(carboxymethoxy)phenyl | 2-methoxyethyl | 509.1 | 1.31 |
| 204 | 4-F, 3-Br benzyl | 2-(carboxymethoxy)phenyl | 3-ethoxypropyl | 565.1 | 1.11 |
| 205 | 3,5-dichlorobenzyl | 2-(carboxymethoxy)phenyl | N-acetyl-lysine side chain | 622.1 | 1.23 |
| 206 | 3-phenylpropyl | 2-(carboxymethoxy)phenyl | N-acetyl-lysine side chain | 582.3 | 1.34 |

-continued
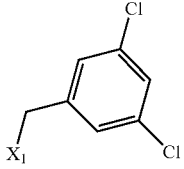
| Compd | X1 | X2 | X3 | MS obsd | LC RT (min) |
|---|---|---|---|---|---|
| 207 | 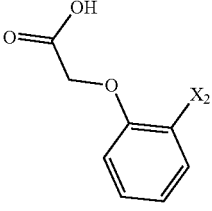 | 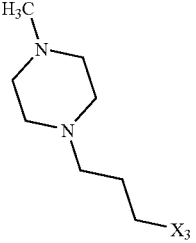 | 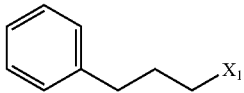 | 591.1 | 1.04 |
| 208 | 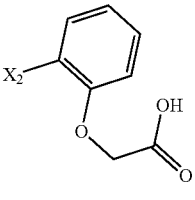 | 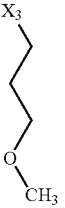 | 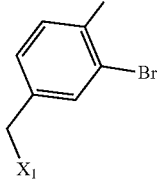 | 483.2 | 1.22 |
| 209 | 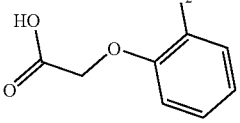 | 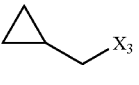 | 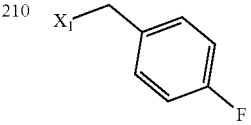 | 533.1 | 1.05 |
| 210 | 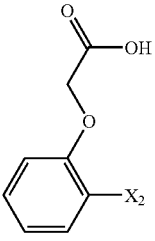 |  | 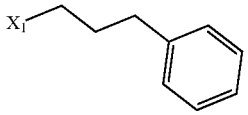 | 455.1 | 1.31 |
| 211 | 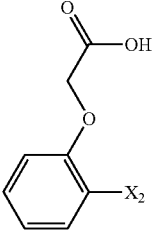 |  | | 465.2 | 1.42 |

-continued
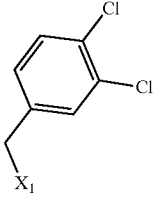
| Compd | X1 | X2 | X3 | MS obsd | LC RT (min) |
|---|---|---|---|---|---|
| 212 | 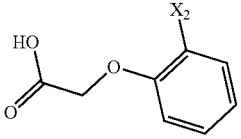 | 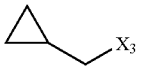 | 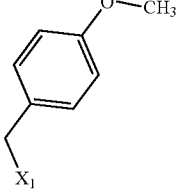 | 505.1 | 1.58 |
| 213 | 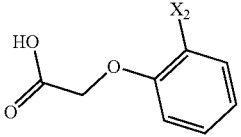 | 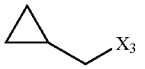 | 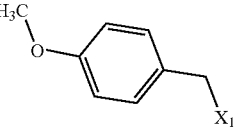 | 467.1 | 1.30 |
| 214 | 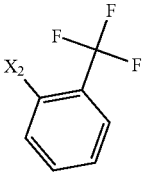 | 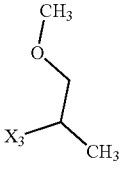 | 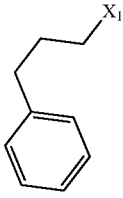 | 479.3 | 0.94 |
| 215 | 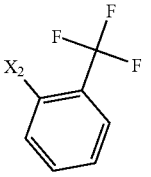 |  | 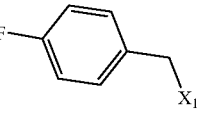 | 419.2 | 1.39 |
| 216 |  | 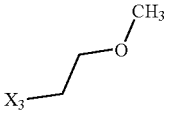 | 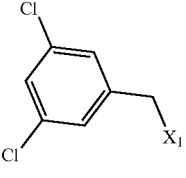 | 453.1 | 1.30 |
| 217 | 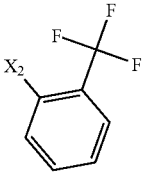 | 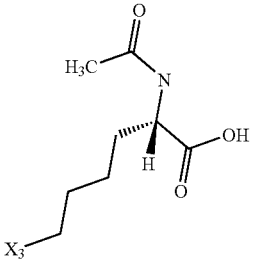 | | 616.2 | 1.30 |

-continued

| Compd | X1 | X2 | X3 | MS obsd | LC RT (min) |
|---|---|---|---|---|---|
| 218 | 4-methoxybenzyl | 2-(trifluoromethyl)phenyl | cyclopropylmethyl | 461.2 | 1.38 |
| 219 | 3,5-dichlorobenzyl | cyclopropyl | 2-methoxy-2-methylethyl (isobutyl methyl ether) | 413.2 | 1.68 |
| 220 | 3-bromo-4-fluorobenzyl | cyclopropyl | 2-methoxyethyl | 427.1 | 1.50 |
| 221 | 4-fluorobenzyl | cyclopropyl | 2-methoxyethyl | 349.1 | 1.11 |
| 222 | 3,4-dichlorobenzyl | cyclopropyl | 2-methoxyethyl | 399.1 | 1.32 |
| 223 | 3,5-dichlorobenzyl | cyclopropyl | 3-ethoxypropyl | 427.1 | 1.43 |
| 224 | 4-fluorobenzyl | cyclopropyl | 3-ethoxypropyl | 377.3 | 1.28 |
| 225 | 3-phenylpropyl | cyclopropyl | 3-ethoxypropyl | 387.3 | 1.30 |

-continued

| Compd | X1 | X2 | X3 | MS obsd | LC RT (min) |
|---|---|---|---|---|---|
| 226 | 4-fluorobenzyl | cyclopropyl | N-acetyl-lysine carboxylic acid | 462.2 | 1.10 |
| 227 | 3,4-dichlorobenzyl | cyclopropyl | N-acetyl-lysine carboxylic acid | 512.1 | 1.22 |
| 228 | 3,5-dichlorobenzyl | cyclopropyl | 3-(4-methylpiperazin-1-yl)propyl | 481.1 | 1.02 |
| 229 | 4-fluorobenzyl | cyclopropyl | 3-(4-methylpiperazin-1-yl)propyl | 431.2 | 1.01 |
| 230 | 3-phenylpropyl | cyclopropyl | 3-(4-methylpiperazin-1-yl)propyl | 441.3 | 0.96 |
| 231 | 3,4-dichlorobenzyl | cyclopropyl | 3-(4-methylpiperazin-1-yl)propyl | 481.1 | 1.04 |

-continued

| Compd | X1 | X2 | X3 | MS obsd | LC RT (min) |
|---|---|---|---|---|---|
| 232 | 4-fluorobenzyl | cyclopropyl | -CH₂CH₂CH₂-O-CH₃ | 361.1 | 0.97 |
| 233 | 3-bromo-4-fluorobenzyl | cyclopropyl | cyclopropylmethyl | 423.0 | 1.00 |
| 234 | 4-fluorobenzyl | cyclopropyl | cyclopropylmethyl | 345.2 | 1.41 |
| 235 | 3-phenylpropyl | cyclopropyl | cyclopropylmethyl | 355.2 | 1.37 |
| 236 | 3,4-dichlorobenzyl | cyclopropyl | cyclopropylmethyl | 395.1 | 1.54 |
| 237 | 4-fluorobenzyl | 2-(benzyloxy)phenyl | ethyl 4-piperidinecarboxylate | 588.4 | 1.46 |
| 238 | 3,5-dichlorobenzyl | 2-(benzyloxy)phenyl | -CH₂CH₂-O-CH₃ | 541.1 | 1.57 |

-continued
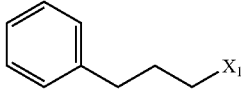
| Compd | X1 | X2 | X3 | MS obsd | LC RT (min) |
|---|---|---|---|---|---|
| 239 | 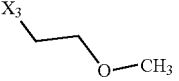 | 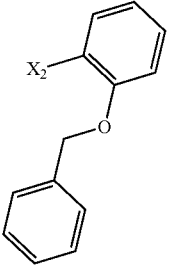 | 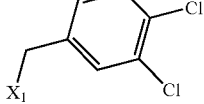 | 501.2 | 1.84 |
| 240 | 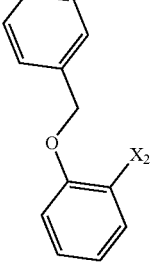 | 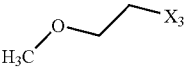 | 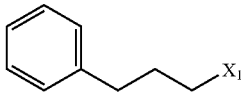 | 541.1 | 1.86 |
| 241 | 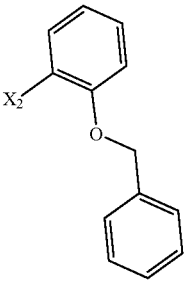 |  | 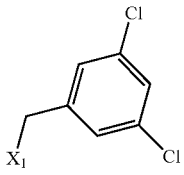 | 529.4 | 1.55 |
| 242 | 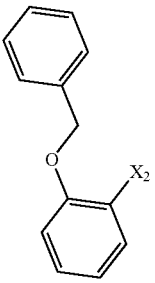 | 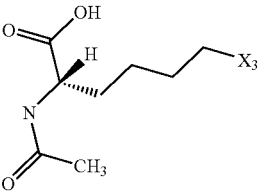 |  | 654.2 | 1.39 |

-continued
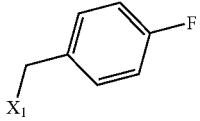
| Compd | X1 | X2 | X3 | MS obsd | LC RT (min) |
|---|---|---|---|---|---|
| 243 | 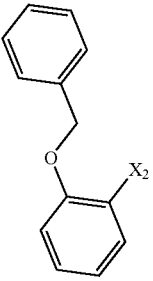 | 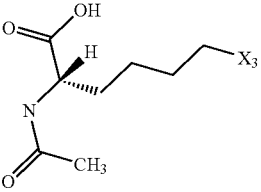 | 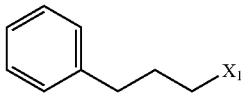 | 604.2 | 1.43 |
| 244 | 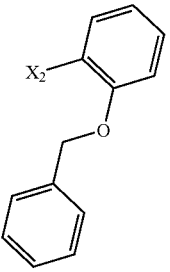 | 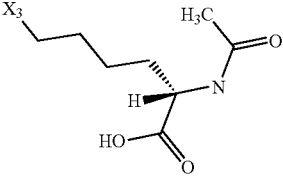 | 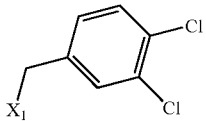 | 614.3 | 1.31 |
| 245 | 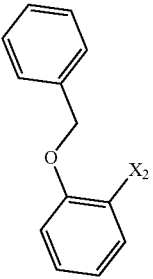 | 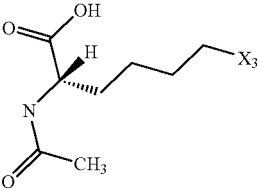 | 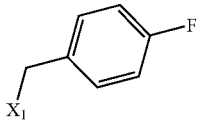 | 654.2 | 1.36 |
| 246 | 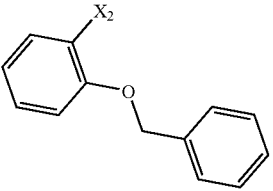 | 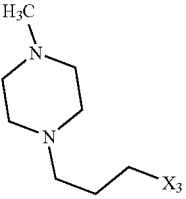 | 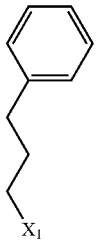 | 573.3 | 1.06 |
| 247 | 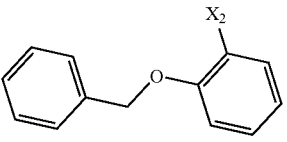 | 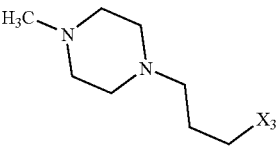 | | 583.2 | 1.14 |

-continued

| Compd | X1 | X2 | X3 | MS obsd | LC RT (min) |
|---|---|---|---|---|---|
| 248 | 4-fluorobenzyl | 2-benzyloxyphenyl | 3-methoxypropyl | 505.2 | 1.41 |
| 249 | 3-phenylpropyl | 2-benzyloxyphenyl | 3-methoxypropyl | 515.3 | 1.51 |
| 250 | 3-bromo-4-fluorobenzyl | 2-benzyloxyphenyl | cyclopropylmethyl | 565.1 | 1.04 |
| 251 | 3-phenylpropyl | 2-benzyloxyphenyl | cyclopropylmethyl | 497.2 | 1.68 |
| 252 | 4-fluorobenzyl | 2-benzyloxyphenyl | (2S)-1-hydroxy-3-methylbutan-2-yl | 519.2 | 1.59 |

-continued
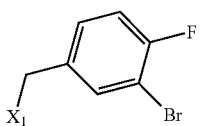
| Compd | X1 | X2 | X3 | MS obsd | LC RT (min) |
|---|---|---|---|---|---|
| 253 | 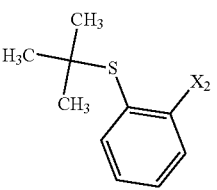 |  | 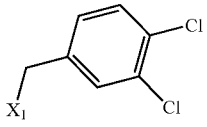 | 523.1 | 1.10 |
| 254 | 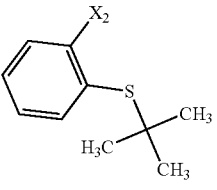 | 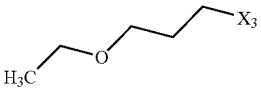 | 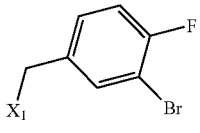 | 551.2 | 1.73 |
| 255 | 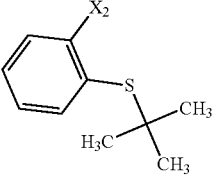 | 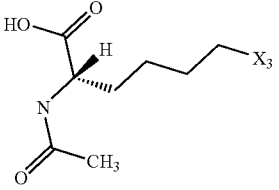 | 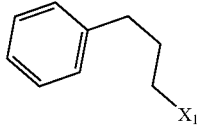 | 664.2 | 1.05 |
| 256 | 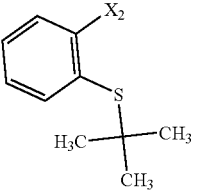 | 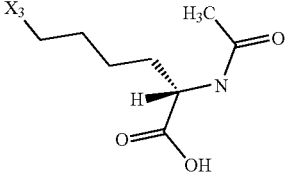 | 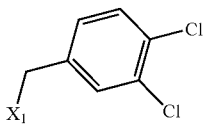 | 596.6 | 1.30 |
| 257 | 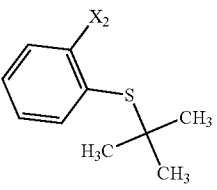 | 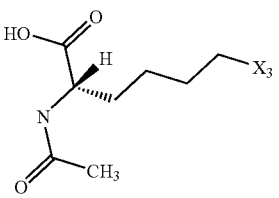 | 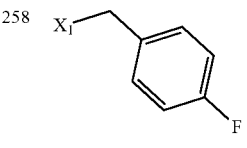 | 636.2 | 1.41 |
| 258 | 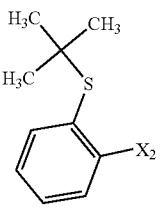 |  |  | 469.2 | 1.61 |

-continued

| Compd | X1 | X2 | X3 | MS obsd | LC RT (min) |
|---|---|---|---|---|---|
| 259 | 3,4-dichlorobenzyl | 2-(tert-butylthio)phenyl | cyclopropylmethyl | 519.1 | 1.85 |
| 260 | 4-fluoro-3-bromobenzyl | X2-H | 2-methoxyethyl | 387.2 | 1.02 |
| 261 | 4-fluorobenzyl | X2-H | 2-methoxyethyl | 309.1 | 1.05 |
| 262 | 3-phenylpropyl | X2-H | 2-methoxyethyl | 319.1 | 1.13 |
| 263 | 3-phenylpropyl | X2-H | 3-ethoxypropyl | 347.2 | 1.31 |
| 264 | 3,5-dichlorobenzyl | X2-H | (2S)-2-hydroxymethyl-3-methylbutyl | 387.1 | 1.24 |
| 265 | 4-methoxybenzyl | 2-ethoxyphenyl | 1-(ethoxycarbonyl)piperidin-4-yl | 538.3 | 1.35 |
| 266 | 4-fluoro-3-bromobenzyl | 2-ethoxyphenyl | 2-methoxyethyl | 507.4 | 1.02 |

-continued

| Compd | X1 | X2 | X3 | MS obsd | LC RT (min) |
|---|---|---|---|---|---|
| 267 | 4-fluorobenzyl | 2-ethoxyphenyl | methoxyethyl | 429.4 | 1.34 |
| 268 | 3,4-dichlorobenzyl | 2-ethoxyphenyl | methoxyethyl | 479.1 | 1.52 |
| 269 | 3,5-dichlorobenzyl | 2-ethoxyphenyl | 3-ethoxypropyl | 507.2 | 1.59 |
| 270 | 4-fluorobenzyl | 2-ethoxyphenyl | 3-ethoxypropyl | 457.2 | 1.36 |
| 271 | 4-fluorobenzyl | 2-ethoxyphenyl | N-acetyl-L-lysyl | 542.2 | 1.15 |
| 272 | 4-phenylbutyl | 2-ethoxyphenyl | N-acetyl-L-lysyl | 552.2 | 1.25 |

-continued
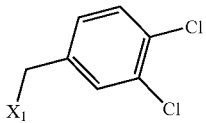
| Compd | X1 | X2 | X3 | MS obsd | LC RT (min) |
|---|---|---|---|---|---|
| 273 | 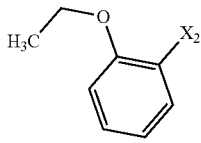 | 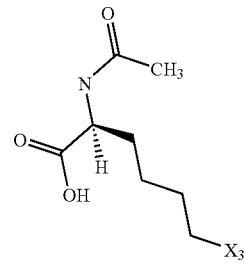 | 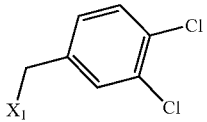 | 592.5 | 1.48 |
| 274 | 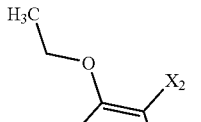 | 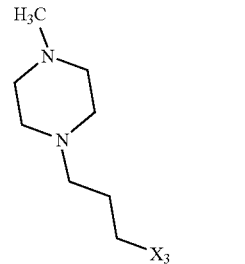 | 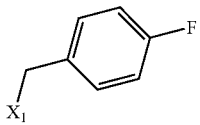 | 561.2 | 1.59 |
| 275 | 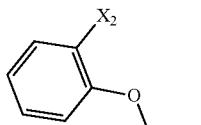 | 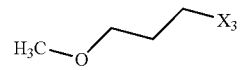 | 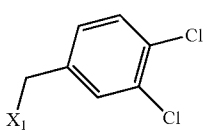 | 443.2 | 1.30 |
| 276 | 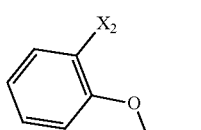 | 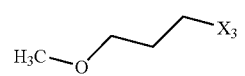 | 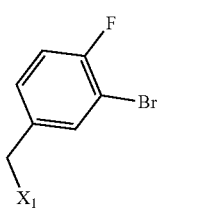 | 493.2 | 1.40 |
| 277 | 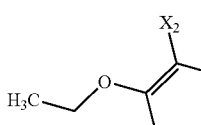 | 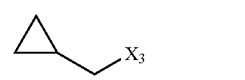 | 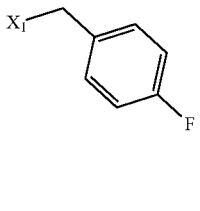 | 503.1 | 1.04 |
| 278 | 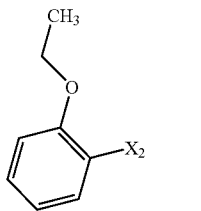 | 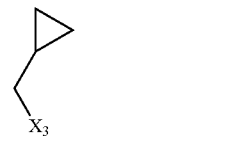 | | 425.2 | 1.91 |

-continued
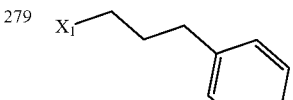
| Compd | X1 | X2 | X3 | MS obsd | LC RT (min) |
|---|---|---|---|---|---|
| 279 | 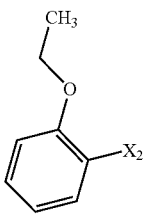 |  | 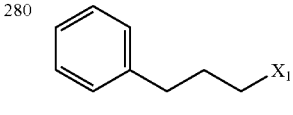 | 435.5 | 1.46 |
| 280 | 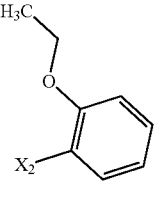 | 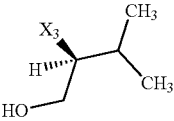 | 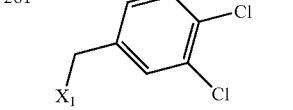 | 467.3 | 1.39 |
| 281 | 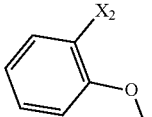 | 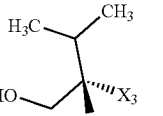 | 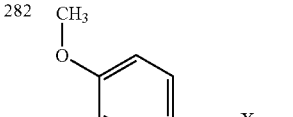 | 507.2 | 1.46 |
| 282 | 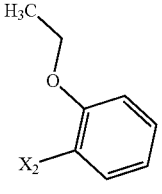 | 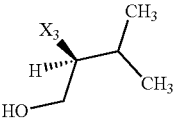 | 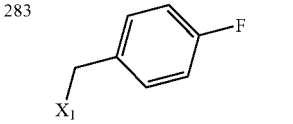 | 469.5 | 1.31 |
| 283 | 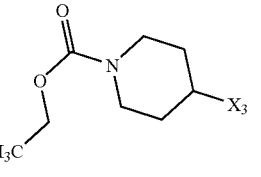 | X2—H | 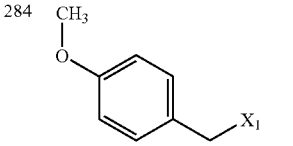 | 406.2 | 1.12 |
| 284 | 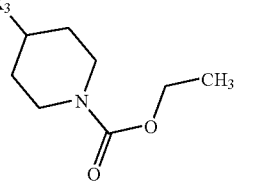 | X2—H | 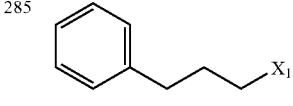 | 416.2 | 1.12 |
| 285 | 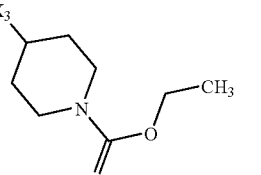 | X2—H |  | 416.2 | 1.21 |

-continued
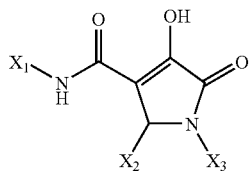
| Compd | X1 | X2 | X3 | MS obsd | LC RT (min) |
|---|---|---|---|---|---|
| 286 | 4-fluorobenzyl | X2-H | 2-methoxy-1-methylethyl | 323.2 | 1.07 |
| 287 | 3-phenylpropyl | X2-H | 1-(methoxymethyl)ethyl | 333.2 | 1.29 |
| 288 | 3-phenylpropyl | X2-H | ethyl | 289.1 | 1.16 |
| 289 | 3,4-dichlorobenzyl | X2-H | 3-ethoxypropyl | 387.3 | 1.29 |
| 290 | 4-fluorobenzyl | X2-H | 3-ethoxypropyl | 337.1 | 1.11 |
| 291 | 4-methoxybenzyl | X2-H | N-acetyl-L-lysine | 434.2 | 0.93 |
| 292 | 3-phenylpropyl | X2-H | N-acetyl-L-lysine | 432.2 | 0.53 |
| 293 | 4-fluorobenzyl | X2-H | 3-(4-methylpiperazin-1-yl)propyl | 391.2 | 0.70 |

-continued

| Compd | X1 | X2 | X3 | MS obsd | LC RT (min) |
|---|---|---|---|---|---|
| 294 | 4-F-benzyl | X2-H | H2N-C(=O)-CH(X3)-CH2OH | 336.0 | 1.22 |
| 295 | 3-phenylpropyl | X2-H | X3-CH(CH2OH)-C(=O)NH2 | 348.0 | 1.38 |
| 296 | 3,5-dichlorobenzyl | X2-H | H2N-C(=O)-CH(X3)-CH2OH | 386.0 | 1.56 |
| 297 | 4-F-benzyl | 2-methoxyphenyl | cyclopropyl | 397.2 | 1.31 |
| 298 | 3-phenylpropyl | 2-methoxyphenyl | cyclopropyl | 407.2 | 1.32 |
| 299 | 4-methoxybenzyl | 2-methoxyphenyl | CH3 | 383.2 | 1.19 |
| 300 | 3-phenylpropyl | 2-methoxyphenyl | CH3 | 381.1 | 1.23 |

-continued

| Compd | X1 | X2 | X3 | MS obsd | LC RT (min) |
|---|---|---|---|---|---|
| 301 | 3,5-dichlorobenzyl | 2-methoxyphenyl | CH₃ | 421.1 | 1.40 |
| 302 | 3-bromo-4-fluorobenzyl | 2-methoxyphenyl | CH₃ | 447.3 | 1.23 |
| 303 | 3,4-dichlorobenzyl | 2-methoxyphenyl | ethyl | 435.4 | 1.65 |
| 304 | 4-fluorobenzyl | 2-methoxyphenyl | ethyl | 385.2 | 1.26 |
| 305 | 4-methoxybenzyl | 2-methoxyphenyl | ethyl | 395.0 | 1.25 |
| 306 | 3-phenylpropyl | 2-methoxyphenyl | ethyl | 395.2 | 1.35 |
| 307 | 3-bromo-4-fluorobenzyl | 2-methoxyphenyl | ethyl | 463.1 | 1.05 |
| 308 | 4-methoxybenzyl | 2-methoxyphenyl | 2-methoxyethyl | 427.2 | 1.23 |

-continued

| Compd | X1 | X2 | X3 | MS obsd | LC RT (min) |
|---|---|---|---|---|---|
| 309 | 4-fluoro-3-bromobenzyl | 2-methoxyphenyl | 2-methoxyethyl | 493.1 | 1.17 |
| 310 | 3,4-dichlorobenzyl | 2-methoxyphenyl | 3-ethoxypropyl | 493.2 | 1.40 |
| 311 | 4-fluorobenzyl | 2-methoxyphenyl | 3-ethoxypropyl | 443.2 | 1.27 |
| 312 | 4-methoxybenzyl | 2-methoxyphenyl | 3-ethoxypropyl | 455.2 | 1.59 |
| 313 | 3,5-dichlorobenzyl | 2-methoxyphenyl | 3-ethoxypropyl | 493.1 | 1.41 |
| 314 | 4-fluorobenzyl | 2-methoxyphenyl | 3-(4-methylpiperazin-1-yl)propyl | 497.3 | 0.94 |
| 315 | 4-methoxybenzyl | 2-methoxyphenyl | 3-(4-methylpiperazin-1-yl)propyl | 509.2 | 0.94 |

-continued
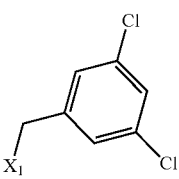
| Compd | X1 | X2 | X3 | MS obsd | LC RT (min) |
|---|---|---|---|---|---|
| 316 | 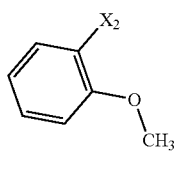 | 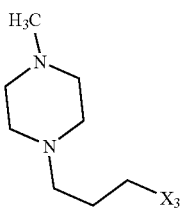 | 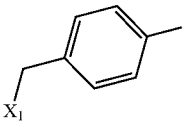 | 547.1 | 1.05 |
| 317 | 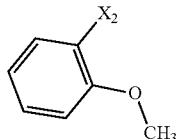 | 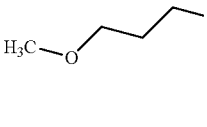 | 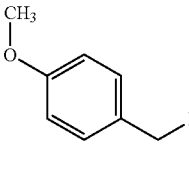 | 429.1 | 1.26 |
| 318 | 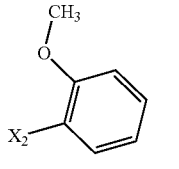 | 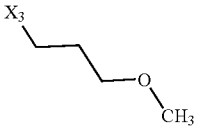 | 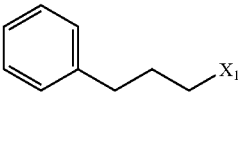 | 441.2 | 1.23 |
| 319 | 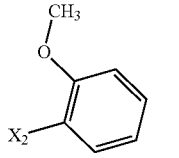 | 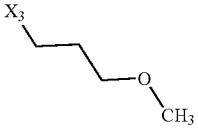 | 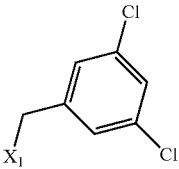 | 439.3 | 1.82 |
| 320 | 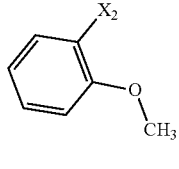 | 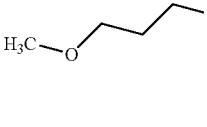 | 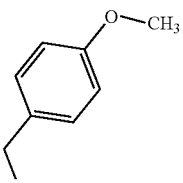 | 479.1 | 1.75 |
| 321 | 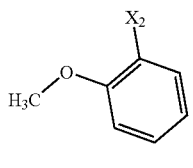 | 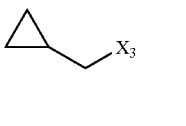 | 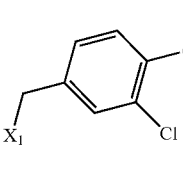 | 423.2 | 1.36 |
| 322 | 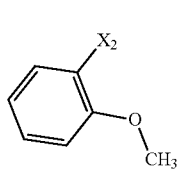 | 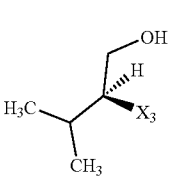 |  | 493.0 | 1.51 |

-continued

| Compd | X1 | X2 | X3 | MS obsd | LC RT (min) |
|---|---|---|---|---|---|
| 323 | 4-F-benzyl | 2-methoxyphenyl | (S)-1-hydroxymethyl-2-methylpropyl | 443.0 | 1.22 |
| 324 | 4-methoxybenzyl | 2-methoxyphenyl | (R)-1-hydroxymethyl-2-methylpropyl | 455.0 | 1.17 |
| 325 | 3-phenylpropyl | 2-methoxyphenyl | (R)-1-hydroxymethyl-2-methylpropyl | 451.0 | 1.25 |
| 326 | 3,5-dichlorobenzyl | 2-methoxyphenyl | (S)-1-hydroxymethyl-2-methylpropyl | 493.0 | 1.56 |
| 327 | 4-methoxybenzyl | 2-methoxyphenyl | (S)-1-carbamoyl-2-hydroxyethyl | 456.7 | 1.17 |
| 328 | 3,5-dichlorobenzyl | 2-methoxyphenyl | (R)-1-carbamoyl-2-hydroxyethyl | 493.7 | 1.57 |
| 329 | 3,4-dichlorobenzyl | 2-(carboxymethoxy)phenyl | cyclopropyl | 491.1 | 1.28 |

-continued

| Compd | X1 | X2 | X3 | MS obsd | LC RT (min) |
|---|---|---|---|---|---|
| 330 | 3,5-dichlorobenzyl | 2-(carboxymethoxy)phenyl | cyclopropyl | 491.1 | 1.58 |
| 331 | 3,5-dichlorobenzyl | 2-(carboxymethoxy)phenyl | 2-morpholinoethyl | 563.8 | 1.01 |
| 332 | 3-bromo-4-fluorobenzyl | 2-(carboxymethoxy)phenyl | 2-morpholinoethyl | 590.0 | 1.45 |
| 333 | 4-fluorobenzyl | 2-(carboxymethoxy)phenyl | methyl | 415.1 | 1.28 |
| 334 | 3-bromo-4-fluorobenzyl | 2-(carboxymethoxy)phenyl | methyl | 491.1 | 1.03 |
| 335 | 3-bromo-4-fluorobenzyl | 2-(carboxymethoxy)phenyl | ethyl | 507.1 | 1.04 |

-continued

| Compd | X1 | X2 | X3 | MS obsd | LC RT (min) |
|---|---|---|---|---|---|
| 336 | 4-fluorobenzyl | 2-(carboxymethoxy)phenyl | 2-methoxyethyl | 459.1 | 1.15 |
| 337 | 4-fluorobenzyl | 2-(carboxymethoxy)phenyl | N-acetyl-lysine derivative | 572.1 | 1.17 |
| 338 | 4-methoxybenzyl | 2-(carboxymethoxy)phenyl | N-acetyl-lysine derivative | 584.0 | 1.15 |
| 339 | 3-bromo-4-fluorobenzyl | 2-(carboxymethoxy)phenyl | 3-(4-methylpiperazin-1-yl)propyl | 616.7 | 1.13 |
| 340 | 3-bromo-4-fluorobenzyl | 2-(carboxymethoxy)phenyl | 3-methoxypropyl | 549.0 | 1.00 |

-continued

| Compd | X1 | X2 | X3 | MS obsd | LC RT (min) |
|---|---|---|---|---|---|
| 341 | 4-fluorobenzyl | 2-(carboxymethoxy)phenyl | (2S)-1-hydroxy-3-methylbutan-2-yl | 485.0 | 1.36 |
| 342 | 4-methoxybenzyl | 2-(carboxymethoxy)phenyl | (2S)-1-hydroxy-3-methylbutan-2-yl | 497.0 | 1.26 |
| 343 | 4-methoxybenzyl | 2-(carboxymethoxy)phenyl | (2S)-1-amino-3-hydroxy-1-oxopropan-2-yl | 500.0 | 1.17 |
| 344 | 3,4-dichlorobenzyl | 2-ethoxyphenyl | cyclopropyl | 461.1 | 1.46 |
| 345 | 4-fluorobenzyl | 2-ethoxyphenyl | cyclopropyl | 411.1 | 1.27 |
| 346 | 3-phenylpropyl | 2-ethoxyphenyl | cyclopropyl | 421.2 | 1.37 |
| 347 | 3,5-dichlorobenzyl | 2-ethoxyphenyl | cyclopropyl | 461.1 | 1.47 |

-continued

| Compd | X1 | X2 | X3 | MS obsd | LC RT (min) |
|---|---|---|---|---|---|
| 348 | 3-Br-4-F-benzyl | 2-ethoxyphenyl | cyclopropyl | 487.4 | 1.03 |
| 349 | 3-Br-4-F-benzyl | 2-ethoxyphenyl | 2-morpholinoethyl | 562.2 | 1.01 |
| 350 | 3-Br-4-F-benzyl | 2-ethoxyphenyl | 1-methoxy-2-methylpropyl | 521.6 | 1.04 |
| 351 | 4-F-benzyl | 2-ethoxyphenyl | ethyl | 385.2 | 1.28 |
| 352 | 4-methoxybenzyl | 2-ethoxyphenyl | methyl | 397.2 | 1.23 |
| 353 | 3-phenylpropyl | 2-ethoxyphenyl | methyl | 395.4 | 1.41 |
| 354 | 3-Br-4-F-benzyl | 2-ethoxyphenyl | methyl | 463.1 | 1.01 |

-continued
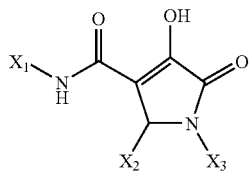
| Compd | X1 | X2 | X3 | MS obsd | LC RT (min) |
|---|---|---|---|---|---|
| 355 | 3,4-dichlorobenzyl | 2-ethoxyphenyl | ethyl | 449.1 | 1.43 |
| 356 | 3-phenylpropyl | 2-ethoxyphenyl | ethyl | 409.2 | 1.44 |
| 357 | 3,5-dichlorobenzyl | 2-ethoxyphenyl | ethyl | 449.1 | 1.64 |
| 358 | 3-bromo-4-fluorobenzyl | 2-ethoxyphenyl | ethyl | 477.2 | 1.04 |
| 359 | 4-methoxybenzyl | 2-ethoxyphenyl | 2-methoxyethyl | 441.2 | 1.29 |
| 360 | 3,5-dichlorobenzyl | 2-ethoxyphenyl | 2-methoxyethyl | 479.1 | 1.47 |

-continued
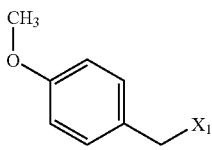
| Compd | X1 | X2 | X3 | MS obsd | LC RT (min) |
|---|---|---|---|---|---|
| 361 | 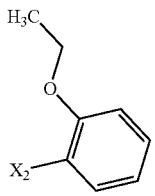 | 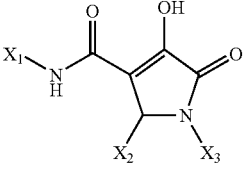 | 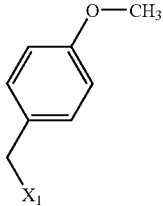 | 469.2 | 1.36 |
| 362 | 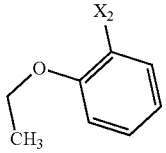 | 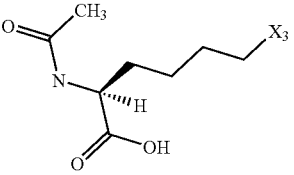 | 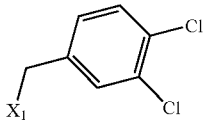 | 554.3 | 2.12 |
| 363 | 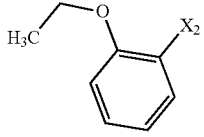 | 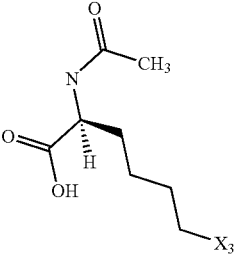 | 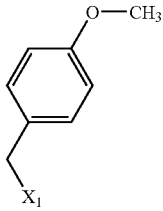 | 592.1 | 1.26 |
| 364 | 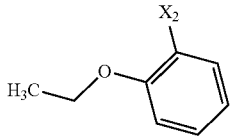 | 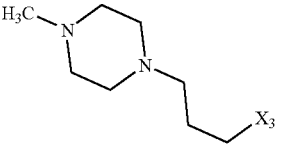 | 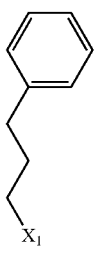 | 523.2 | 0.96 |
| 365 | 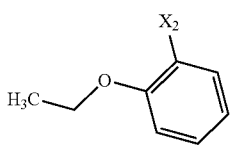 | 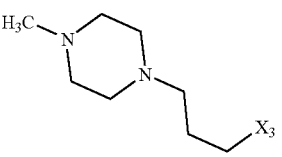 | | 521.2 | 1.12 |

-continued
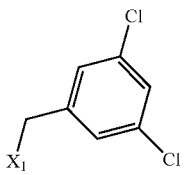
| Compd | X1 | X2 | X3 | MS obsd | LC RT (min) |
|---|---|---|---|---|---|
| 366 | 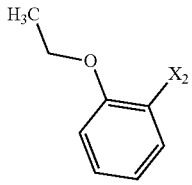 | 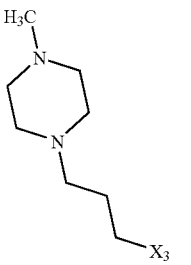 | 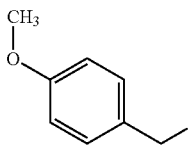 | 561.2 | 1.07 |
| 367 | 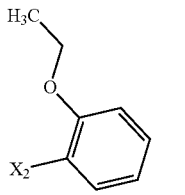 | 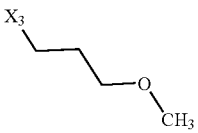 | 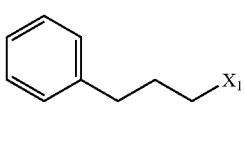 | 455.2 | 1.30 |
| 368 | 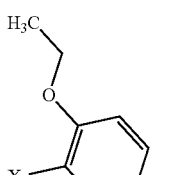 | 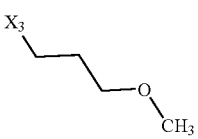 | 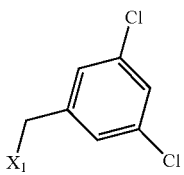 | 453.2 | 1.38 |
| 369 | 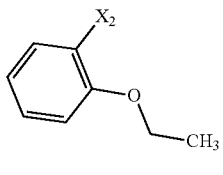 | 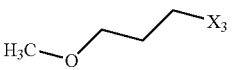 | 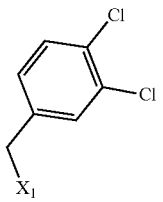 | 493.2 | 1.45 |
| 370 | 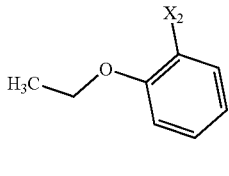 | 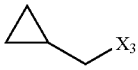 | 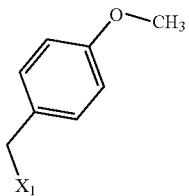 | 475.1 | 1.59 |
| 371 | 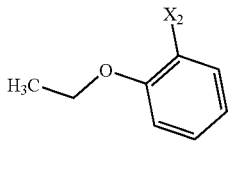 | 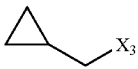 |  | 437.2 | 1.32 |

-continued

| Compd | X1 | X2 | X3 | MS obsd | LC RT (min) |
|---|---|---|---|---|---|
| 372 | 3-Br-4-F-benzyl | 2-ethoxyphenyl | (2S)-2-methyl-3-hydroxy-butan-2-yl (valinol-like) | 533.0 | 1.08 |
| 373 | 3,5-diCl-benzyl | 2-ethoxyphenyl | (2S)-1-hydroxy-3-amino-3-oxopropan-2-yl (serinamide) | 506.0 | 1.37 |
| 374 | 3,4-diCl-benzyl | 2-carboxyphenyl | cyclopropyl | 461.1 | 1.29 |
| 375 | 3-phenylpropyl | 2-carboxyphenyl | 1-methoxy-2-methylpropan-2-yl | 451.0 | 1.52 |
| 376 | 3-Br-4-F-benzyl | 2-carboxyphenyl | 1-methoxy-2-methylpropan-2-yl | 521.0 | 1.20 |
| 377 | 3,4-diCl-benzyl | 2-carboxyphenyl | methyl | 447.1 | 1.12 |
| 378 | 4-F-benzyl | 2-carboxyphenyl | ethyl | 397.1 | 1.04 |

-continued

| Compd | X1 | X2 | X3 | MS obsd | LC RT (min) |
|---|---|---|---|---|---|
| 379 | 3,4-dichlorobenzyl | 2-carboxyphenyl | -CH2CH2OCH3 | 479.1 | 1.46 |
| 380 | 3,4-dichlorobenzyl | 2-carboxyphenyl | -CH2CH2CH2OCH2CH3 | 504.6 | 1.65 |
| 381 | 3-phenylpropyl | 2-carboxyphenyl | -CH2CH2CH2-(4-methylpiperazin-1-yl) | 521.3 | 1.24 |
| 382 | 3,5-dichlorobenzyl | 2-carboxyphenyl | -CH2CH2CH2-(4-methylpiperazin-1-yl) | 561.1 | 1.10 |
| 383 | 3,4-dichlorobenzyl | 2-carboxyphenyl | cyclopropylmethyl | 475.1 | 1.30 |
| 384 | 4-fluorobenzyl | 2-carboxyphenyl | cyclopropylmethyl | 425.4 | 1.22 |
| 385 | 3-phenylpropyl | 2-carboxyphenyl | cyclopropylmethyl | 435.2 | 1.28 |

-continued

| Compd | X1 | X2 | X3 | MS obsd | LC RT (min) |
|---|---|---|---|---|---|
| 386 | 3-Br-4-F-benzyl | 2-carboxyphenyl | cyclopropylmethyl | 501.0 | 1.03 |
| 387 | 4-methoxybenzyl | 2-carboxyphenyl | (S)-CH(CH2OH)C(O)NH2 | 468.0 | 1.18 |
| 388 | 3-phenylpropyl | 2-carboxyphenyl | (S)-CH(CH2OH)C(O)NH2 | 466.0 | 1.38 |
| 389 | 3,5-dichlorobenzyl | 2-carboxyphenyl | (R)-CH(CH2OH)C(O)NH2 | 506.0 | 1.57 |
| 390 | 4-fluorobenzyl | 2-trifluoromethylphenyl | cyclopropyl | 435.3 | 1.30 |
| 391 | 3,5-dichlorobenzyl | 2-trifluoromethylphenyl | cyclopropyl | 483.0 | 1.64 |
| 392 | 3-phenylpropyl | 2-trifluoromethylphenyl | 2-morpholinoethyl | 518.0 | 2.20 |

-continued

| Compd | X1 | X2 | X3 | MS obsd | LC RT (min) |
|---|---|---|---|---|---|
| 393 | 3-phenylpropyl | 2-(trifluoromethyl)phenyl | ethyl | 431.2 | 1.37 |
| 394 | 3,5-dichlorobenzyl | 2-(trifluoromethyl)phenyl | ethyl | 471.0 | 1.94 |
| 395 | 3,4-dichlorobenzyl | 2-(trifluoromethyl)phenyl | 2-methoxyethyl | 503.4 | 1.39 |
| 396 | 4-methoxybenzyl | 2-(trifluoromethyl)phenyl | 2-methoxyethyl | 465.4 | 1.28 |
| 397 | 3-phenylpropyl | 2-(trifluoromethyl)phenyl | 2-methoxyethyl | 463.2 | 1.34 |
| 398 | 3-bromo-4-fluorobenzyl | 2-(trifluoromethyl)phenyl | 2-methoxyethyl | 531.1 | 1.00 |
| 399 | 3,4-dichlorobenzyl | 2-(trifluoromethyl)phenyl | 3-ethoxypropyl | 531.1 | 1.61 |

-continued

| Compd | X1 | X2 | X3 | MS obsd | LC RT (min) |
|---|---|---|---|---|---|
| 400 | 3-phenylpropyl | 2-(trifluoromethyl)phenyl | 3-ethoxypropyl | 491.2 | 1.40 |
| 401 | 3,5-dichlorobenzyl | 2-(trifluoromethyl)phenyl | 3-ethoxypropyl | 531.1 | 1.58 |
| 402 | 4-fluorobenzyl | 2-(trifluoromethyl)phenyl | N-acetyl-lysyl (carboxylic acid) | 566.1 | 1.18 |
| 403 | 3-phenylpropyl | 2-(trifluoromethyl)phenyl | N-acetyl-lysyl (carboxylic acid) | 576.2 | 1.25 |
| 404 | 3-bromo-4-fluorobenzyl | 2-(trifluoromethyl)phenyl | N-acetyl-lysyl (carboxylic acid) | 641.7 | 1.14 |
| 405 | 3,4-dichlorobenzyl | 2-(trifluoromethyl)phenyl | 3-(4-methylpiperazin-1-yl)propyl | 585.2 | 1.03 |

-continued
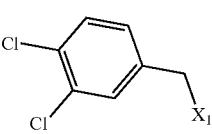
| Compd | X1 | X2 | X3 | MS obsd | LC RT (min) |
|---|---|---|---|---|---|
| 406 | 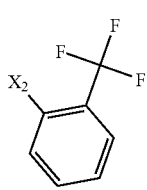 | 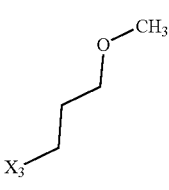 | 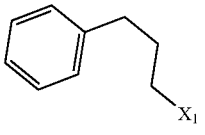 | 517.1 | 2.03 |
| 407 | 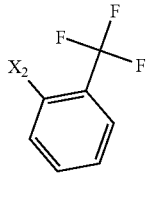 | 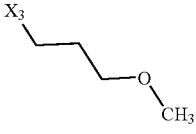 | 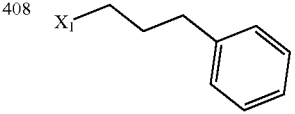 | 475.0 | 1.37 |
| 408 | 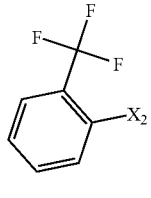 |  | 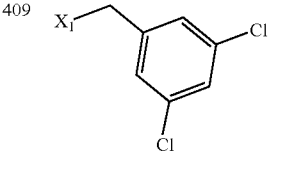 | 459.2 | 1.70 |
| 409 | 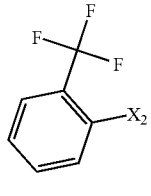 |  | 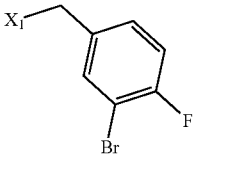 | 497.0 | 2.02 |
| 410 | 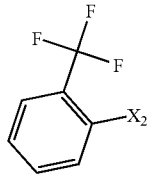 |  | 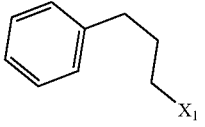 | 525.1 | 1.05 |
| 411 | 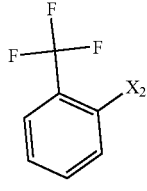 | 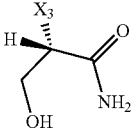 | 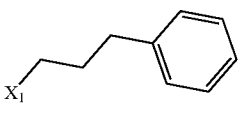 | 492.0 | 1.26 |
| 412 | 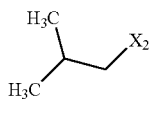 | 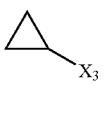 | | 357.4 | 1.34 |

-continued

| Compd | X1 | X2 | X3 | MS obsd | LC RT (min) |
|---|---|---|---|---|---|
| 413 | 3,5-dichlorobenzyl | isobutyl | cyclopropyl | 397.1 | 1.49 |
| 414 | 3,4-dichlorobenzyl | isobutyl | 2-morpholinoethyl | 470.1 | 1.16 |
| 415 | 3,4-dichlorobenzyl | isobutyl | 1-methoxy-2-propyl (CH$_3$O-CH$_2$-CH(CH$_3$)-) | 429.2 | 1.44 |
| 416 | 3-phenylpropyl | isobutyl | 1-methoxy-2-propyl | 389.2 | 1.37 |
| 417 | 3,5-dichlorobenzyl | isobutyl | 1-methoxy-2-propyl | 429.2 | 1.48 |
| 418 | 3-phenylpropyl | isobutyl | methyl | 331.2 | 1.30 |
| 419 | 3,5-dichlorobenzyl | isobutyl | methyl | 371.1 | 1.36 |
| 420 | 3,4-dichlorobenzyl | isobutyl | ethyl | 385.2 | 1.42 |

-continued

| Compd | X1 | X2 | X3 | MS obsd | LC RT (min) |
|---|---|---|---|---|---|
| 421 | 3-phenylpropyl | isobutyl | ethyl | 345.2 | 1.40 |
| 422 | 3,5-dichlorobenzyl | isobutyl | ethyl | 385.1 | 1.43 |
| 423 | 3-bromo-4-fluorobenzyl | isobutyl | ethyl | 413.1 | 1.05 |
| 424 | 4-methoxybenzyl | isobutyl | 2-methoxyethyl | 377.2 | 1.23 |
| 425 | 3,5-dichlorobenzyl | isobutyl | 2-methoxyethyl | 415.1 | 1.45 |
| 426 | 3,4-dichlorobenzyl | isobutyl | 3-ethoxypropyl | 443.1 | 1.51 |
| 427 | 4-methoxybenzyl | isobutyl | 3-methoxypropyl | 405.2 | 1.28 |
| 428 | 3,4-dichlorobenzyl | isobutyl | N-acetyl-lysine sidechain | 528.1 | 1.23 |

-continued

| Compd | X1 | X2 | X3 | MS obsd | LC RT (min) |
|---|---|---|---|---|---|
| 429 | 4-methoxybenzyl | isobutyl | N-acetyl-L-lysine (α-COOH) | 488.3 | 1.20 |
| 430 | 3-bromo-4-fluorobenzyl | isobutyl | N-acetyl-L-lysine (ε-linked) | 556.2 | 1.07 |
| 431 | 3,4-dichlorobenzyl | isobutyl | 3-methoxypropyl | 429.2 | 1.44 |
| 432 | 4-fluorobenzyl | isobutyl | 3-methoxypropyl | 379.2 | 1.22 |
| 433 | 4-methoxybenzyl | isobutyl | 3-methoxypropyl | 391.2 | 1.23 |
| 434 | 3-phenylpropyl | isobutyl | 3-methoxypropyl | 389.2 | 1.34 |
| 435 | 4-methoxybenzyl | isobutyl | cyclopropylmethyl | 373.2 | 1.34 |
| 436 | 3,4-dichlorobenzyl | cyclopropyl | cyclopropyl | 381.1 | 1.35 |

-continued
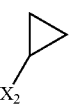
| Compd | X1 | X2 | X3 | MS obsd | LC RT (min) |
|---|---|---|---|---|---|
| 437 | 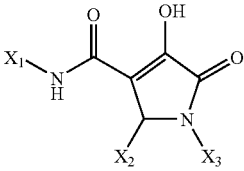 |  | 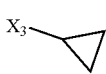 | 331.1 | 1.14 |
| 438 |  | 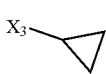 | 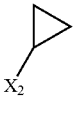 | 341.2 | 1.25 |
| 439 | 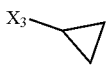 | 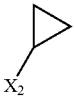 | 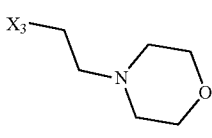 | 381.1 | 1.38 |
| 440 |  | 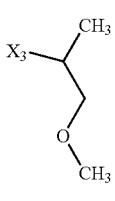 | 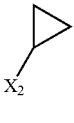 | 409.0 | 1.23 |
| 441 | 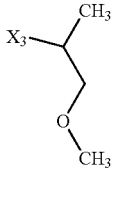 | 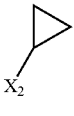 | 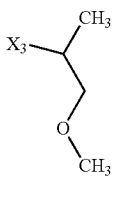 | 414.2 | 1.02 |
| 442 | | | | 363.1 | 1.19 |
| 443 | | | | 375.3 | 1.82 |
| 444 | | | | 439.1 | 1.03 |

-continued

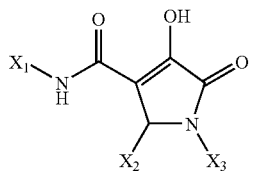

| Compd | X1 | X2 | X3 | MS obsd | LC RT (min) |
|---|---|---|---|---|---|
| 445 | 4-methoxybenzyl | cyclopropyl | CH3 | 317.2 | 1.79 |
| 446 | 3-phenylpropyl | cyclopropyl | CH3 | 315.2 | 1.42 |
| 447 | 3,5-dichlorobenzyl | cyclopropyl | CH2CH3 | 369.2 | 1.33 |
| 448 | 4-methoxybenzyl | cyclopropyl | CH2CH2OCH3 | 361.2 | 1.11 |
| 449 | 3-phenylpropyl | cyclopropyl | CH2CH2OCH3 | 359.2 | 1.23 |
| 450 | 4-fluorobenzyl | 2-allyloxyphenyl | cyclopropyl | 423.2 | 1.33 |
| 451 | 3,4-dichlorobenzyl | 2-allyloxyphenyl | 2-morpholinoethyl | 546.1 | 1.06 |
| 452 | 3-bromo-4-fluorobenzyl | 2-allyloxyphenyl | 1-(ethoxycarbonyl)piperidin-4-yl | 615.0 | 2.14 |

-continued

| Compd | X1 | X2 | X3 | MS obsd | LC RT (min) |
|---|---|---|---|---|---|
| 453 | 4-F-benzyl | 2-(allyloxy)phenyl | CH3 | 397.2 | 1.31 |
| 454 | 4-OCH3-benzyl | 2-(allyloxy)phenyl | CH3 | 409.2 | 1.26 |
| 455 | 3,5-diCl-benzyl | 2-(allyloxy)phenyl | CH3 | 447.1 | 1.59 |
| 456 | 3-Br-4-F-benzyl | 2-(allyloxy)phenyl | CH3 | 475.1 | 1.03 |
| 457 | 3,4-diCl-benzyl | 2-(allyloxy)phenyl | CH2CH3 | 461.1 | 1.42 |
| 458 | 4-F-benzyl | 2-(allyloxy)phenyl | CH2CH3 | 411.2 | 1.33 |

-continued

| Compd | X1 | X2 | X3 | MS obsd | LC RT (min) |
|---|---|---|---|---|---|
| 459 | 4-methoxybenzyl | 2-(allyloxy)phenyl | ethyl | 423.1 | 1.29 |
| 460 | 3-phenylpropyl | 2-(allyloxy)phenyl | ethyl | 421.2 | 1.45 |
| 461 | 3-bromo-4-fluorobenzyl | 2-(allyloxy)phenyl | ethyl | 489.1 | 1.05 |
| 462 | 3,4-dichlorobenzyl | 2-(allyloxy)phenyl | 2-methoxyethyl | 491.1 | 1.41 |
| 463 | 4-fluorobenzyl | 2-(allyloxy)phenyl | 2-methoxyethyl | 441.2 | 1.32 |
| 464 | 3-phenylpropyl | 2-(allyloxy)phenyl | 2-methoxyethyl | 451.2 | 1.43 |

-continued

| Compd | X1 | X2 | X3 | MS obsd | LC RT (min) |
|---|---|---|---|---|---|
| 465 | 3,5-dichlorobenzyl | 2-(allyloxy)phenyl | 2-methoxyethyl | 491.1 | 1.66 |
| 466 | 3,4-dichlorobenzyl | 2-(allyloxy)phenyl | 3-ethoxypropyl | 519.2 | 1.54 |
| 467 | 4-methoxybenzyl | 2-(allyloxy)phenyl | 3-methoxypropyl | 481.2 | 1.40 |
| 468 | 3-phenylpropyl | 2-(allyloxy)phenyl | 3-methoxypropyl | 479.3 | 1.50 |
| 469 | 3,5-dichlorobenzyl | 2-(allyloxy)phenyl | 3-ethoxypropyl | 519.5 | 1.49 |
| 470 | 3-bromo-4-fluorobenzyl | 2-(allyloxy)phenyl | 3-ethoxypropyl | 547.2 | 1.02 |

-continued
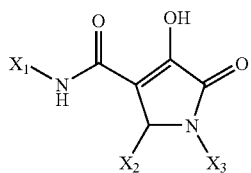
| Compd | X1 | X2 | X3 | MS obsd | LC RT (min) |
|---|---|---|---|---|---|
| 471 | 4-fluorobenzyl | 2-(allyloxy)phenyl | N-acetyl-lysine (COOH) | 554.2 | 1.21 |
| 472 | 4-methoxybenzyl | 2-(allyloxy)phenyl | N-acetyl-lysine (COOH) | 566.2 | 1.41 |
| 473 | 3-phenylpropyl | 2-(allyloxy)phenyl | N-acetyl-lysine (COOH) | 564.3 | 1.27 |
| 474 | 3-bromo-4-fluorobenzyl | 2-(allyloxy)phenyl | N-acetyl-lysine (COOH) | 632.1 | 1.05 |
| 475 | 4-fluorobenzyl | 2-(allyloxy)phenyl | 3-(4-methylpiperazin-1-yl)propyl | 523.2 | 1.00 |

-continued
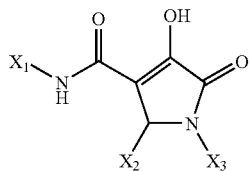
| Compd | X1 | X2 | X3 | MS obsd | LC RT (min) |
|---|---|---|---|---|---|
| 476 | 4-methoxybenzyl | 2-(allyloxy)phenyl | 3-(4-methylpiperazin-1-yl)propyl | 535.2 | 1.13 |
| 477 | 3-phenylpropyl | 2-(allyloxy)phenyl | 3-(4-methylpiperazin-1-yl)propyl | 533.6 | 1.27 |
| 478 | 3,5-dichlorobenzyl | 2-(allyloxy)phenyl | 3-(4-methylpiperazin-1-yl)propyl | 573.1 | 1.12 |
| 479 | 3-bromo-4-fluorobenzyl | 2-(allyloxy)phenyl | 3-(4-methylpiperazin-1-yl)propyl | 601.1 | 1.03 |
| 480 | 3,4-dichlorobenzyl | 2-methoxyethyl | 3-methoxypropyl | 505.1 | 1.61 |

-continued

| Compd | X1 | X2 | X3 | MS obsd | LC RT (min) |
|---|---|---|---|---|---|
| 481 | 4-methoxybenzyl-X1 | 2-(allyloxy)phenyl-X2 | X3-CH2CH2CH2-O-CH3 | 467.2 | 1.33 |
| 482 | 3-phenylpropyl-X1 | 2-(allyloxy)phenyl-X2 | X3-CH2CH2CH2-O-CH3 | 465.2 | 1.41 |
| 483 | 3,5-dichlorobenzyl-X1 | X3-CH2CH2-O-CH3 | H3C-O-CH2CH2CH2-X3 | 505.1 | 1.45 |
| 484 | 3-bromo-4-fluorobenzyl-X1 | X3-CH2CH2-O-CH3 | H3C-O-CH2CH2CH2-X3 | 533.2 | 1.03 |
| 485 | 3,4-dichlorobenzyl-X1 | 2-(allyloxy)phenyl-X2 | cyclopropylmethyl-X3 | 487.1 | 1.78 |
| 486 | 4-fluorobenzyl-X1 | 2-(allyloxy)phenyl-X2 | cyclopropylmethyl-X3 | 437.2 | 1.38 |

-continued

| Compd | X1 | X2 | X3 | MS obsd | LC RT (min) |
|---|---|---|---|---|---|
| 487 | 4-methoxybenzyl | 2-(allyloxy)phenyl | cyclopropylmethyl | 449.2 | 1.42 |
| 488 | 3-phenylpropyl | 2-(allyloxy)phenyl | cyclopropylmethyl | 447.3 | 1.50 |
| 489 | 3,5-dichlorobenzyl | 2-(allyloxy)phenyl | cyclopropylmethyl | 487.2 | 1.61 |
| 490 | 3-phenylpropyl | 2-(allyloxy)phenyl | (S)-CH(CH2OH)C(O)NH2 | 480.0 | 1.38 |
| 491 | 3,5-dichlorobenzyl | 2-(2-methoxyethoxy)phenyl | (S)-CH(CH2OH)C(O)NH2 | 518.0 | 1.57 |
| 492 | 4-fluorobenzyl | 2-(benzyloxy)phenyl | cyclopropylmethyl | 473.2 | 1.78 |

-continued

| Compd | X1 | X2 | X3 | MS obsd | LC RT (min) |
|---|---|---|---|---|---|
| 493 | 4-methoxybenzyl | 2-(benzyloxy)phenyl | cyclopropyl | 485.5 | 1.37 |
| 494 | 3-phenylpropyl | 2-(benzyloxy)phenyl | cyclopropyl | 483.2 | 1.58 |
| 495 | 3-bromo-4-fluorobenzyl | 2-(benzyloxy)phenyl | cyclopropyl | 551.1 | 1.04 |
| 496 | 3-bromo-4-fluorobenzyl | 2-(benzyloxy)phenyl | 1-methoxy-2-methylpropan-2-yl | 583.0 | 0.99 |
| 497 | 3,4-dichlorobenzyl | 2-(benzyloxy)phenyl | methyl | 497.4 | 1.47 |
| 498 | 4-fluorobenzyl | 2-(benzyloxy)phenyl | methyl | 447.2 | 1.36 |

-continued

| Compd | X1 | X2 | X3 | MS obsd | LC RT (min) |
|---|---|---|---|---|---|
| 499 | 4-methoxybenzyl | 2-benzyloxyphenyl | CH₃ | 459.2 | 1.49 |
| 500 | 3-phenylpropyl | 2-benzyloxyphenyl | CH₃ | 457.2 | 1.50 |
| 501 | 3,5-dichlorobenzyl | 2-benzyloxyphenyl | CH₃ | 497.4 | 1.52 |
| 502 | 3-bromo-4-fluorobenzyl | 2-benzyloxyphenyl | CH₃ | 525.2 | 1.02 |
| 503 | 4-methoxybenzyl | 2-benzyloxyphenyl | CH₂CH₃ | 473.3 | 1.40 |

-continued
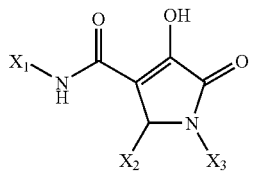
| Compd | X1 | X2 | X3 | MS obsd | LC RT (min) |
|---|---|---|---|---|---|
| 504 | 3-phenylpropyl-X1 | 2-(benzyloxy)phenyl-X2 | ethyl-X3 | 471.2 | 1.57 |
| 505 | 3,5-dichlorobenzyl-X1 | 2-(benzyloxy)phenyl-X2 | ethyl-X3 | 511.2 | 1.61 |
| 506 | 3-bromo-4-fluorobenzyl-X1 | 2-(benzyloxy)phenyl-X2 | ethyl-X3 | 539.1 | 1.03 |
| 507 | 4-methoxybenzyl-X1 | 3-(benzyloxy)phenyl-X2 | 2-methoxyethyl-X3 | 503.2 | 1.42 |
| 508 | 4-methoxybenzyl-X1 | 2-(benzyloxy)phenyl-X2 | 3-methoxypropyl-X3 | 531.3 | 1.43 |

-continued

| Compd | X1 | X2 | X3 | MS obsd | LC RT (min) |
|---|---|---|---|---|---|
| 509 | 4-fluoro-3-bromobenzyl | 2-(benzyloxy)phenyl | -CH2CH2CH2-O-CH2CH3 | 597.2 | 1.02 |
| 510 | 4-methoxybenzyl | 2-(benzyloxy)phenyl | N-acetyl-L-lysine side chain (with COOH) | 616.3 | 1.25 |
| 511 | 4-fluoro-3-bromobenzyl | 2-(benzyloxy)phenyl | N-acetyl-L-lysine side chain (with COOH) | 682.2 | 1.04 |
| 512 | 3,4-dichlorobenzyl | 2-(benzyloxy)phenyl | 2-methoxyphenyl | 623.2 | 1.15 |
| 513 | 4-methoxybenzyl | 2-(benzyloxy)phenyl | 3-(4-methylpiperazin-1-yl)propyl | 585.2 | 1.09 |

-continued
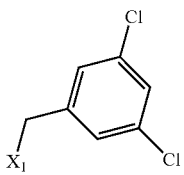
| Compd | X1 | X2 | X3 | MS obsd | LC RT (min) |
|---|---|---|---|---|---|
| 514 | 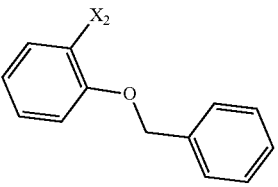 | 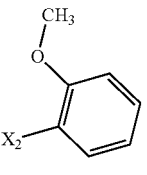 | 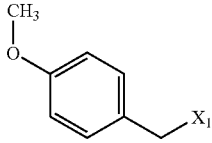 | 623.5 | 1.14 |
| 515 | 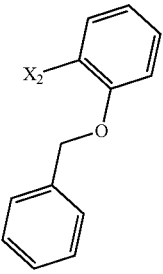 | 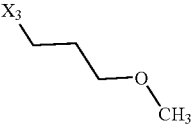 | 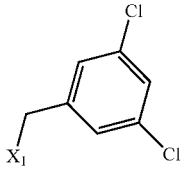 | 517.3 | 1.39 |
| 516 | 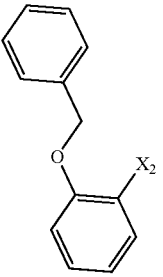 | 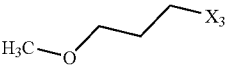 | 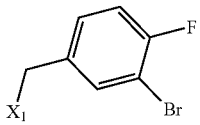 | 555.2 | 1.62 |
| 517 | 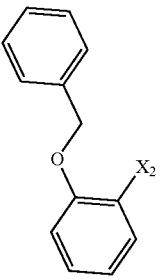 | 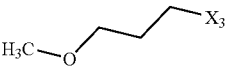 | 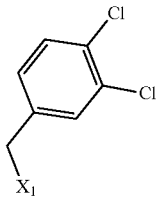 | 583.1 | 1.06 |
| 518 | 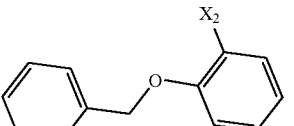 | 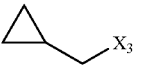 | | 537.1 | 1.69 |

-continued

| Compd | X1 | X2 | X3 | MS obsd | LC RT (min) |
|---|---|---|---|---|---|
| 519 | 4-methoxybenzyl | 2-(benzyloxy)phenyl | cyclopropylmethyl | 499.2 | 1.69 |
| 520 | 3,5-dichlorobenzyl | 2-(benzyloxy)phenyl | cyclopropylmethyl | 537.2 | 1.75 |
| 521 | 3,5-dichlorobenzyl | 2-(benzyloxy)phenyl | (2S)-1-hydroxy-3-methylbutan-2-yl | 569.2 | 1.04 |
| 522 | 3,4-dichlorobenzyl | 2-(benzyloxy)phenyl | (2S)-1-amino-3-hydroxy-1-oxopropan-2-yl | 570.0 | 1.50 |
| 523 | 3,4-dichlorobenzyl | benzo[d][1,3]dioxol-4-yl | cyclopropyl | 461.1 | 1.30 |
| 524 | 4-fluorobenzyl | benzo[d][1,3]dioxol-4-yl | cyclopropyl | 411.4 | 1.33 |
| 525 | 4-methoxybenzyl | benzo[d][1,3]dioxol-4-yl | cyclopropyl | 423.1 | 1.21 |

-continued

| Compd | X1 | X2 | X3 | MS obsd | LC RT (min) |
|---|---|---|---|---|---|
| 526 | 3-phenylpropyl | benzo[1,3]dioxol-4-yl | cyclopropyl | 421.2 | 1.34 |
| 527 | 3,5-dichlorobenzyl | benzo[1,3]dioxol-4-yl | cyclopropyl | 461.1 | 1.35 |
| 528 | 3-bromo-4-fluorobenzyl | benzo[1,3]dioxol-4-yl | cyclopropyl | 489.1 | 1.05 |
| 529 | 3,4-dichlorobenzyl | benzo[1,3]dioxol-4-yl | 1-(ethoxycarbonyl)piperidin-4-yl | 576.1 | 1.73 |
| 530 | 3,4-dichlorobenzyl | benzo[1,3]dioxol-4-yl | 1-methoxypropan-2-yl | 493.1 | 1.37 |
| 531 | 4-fluorobenzyl | benzo[1,3]dioxol-4-yl | 1-methoxypropan-2-yl | 443.1 | 1.24 |
| 532 | 4-methoxybenzyl | benzo[1,3]dioxol-4-yl | 1-methoxypropan-2-yl | 455.2 | 1.26 |
| 533 | 4-fluorobenzyl | benzo[1,3]dioxol-4-yl | methyl | 385.1 | 1.12 |

-continued

| Compd | X1 | X2 | X3 | MS obsd | LC RT (min) |
|---|---|---|---|---|---|
| 534 | 4-methoxybenzyl | benzo[1,3]dioxol-4-yl | CH₃ | 395.5 | 0.97 |
| 535 | 3-phenylpropyl | benzo[1,3]dioxol-4-yl | CH₃ | 395.2 | 2.06 |
| 536 | 3,4-dichlorobenzyl | benzo[1,3]dioxol-4-yl | CH₂CH₃ | 449.1 | 1.34 |
| 537 | 4-methoxybenzyl | benzo[1,3]dioxol-4-yl | CH₂CH₃ | 411.1 | 1.22 |
| 538 | 3,5-dichlorobenzyl | benzo[1,3]dioxol-4-yl | CH₂CH₃ | 449.1 | 1.65 |
| 539 | 3-bromo-4-fluorobenzyl | benzo[1,3]dioxol-4-yl | CH₂CH₃ | 477.1 | 1.01 |
| 540 | 3,4-dichlorobenzyl | benzo[1,3]dioxol-4-yl | CH₂CH₂OCH₃ | 479.1 | 1.34 |
| 541 | 4-methoxybenzyl | benzo[1,3]dioxol-4-yl | CH₂CH₂OCH₃ | 439.5 | 1.68 |

-continued

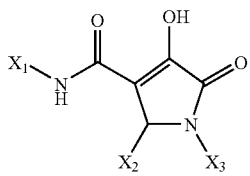

| Compd | X1 | X2 | X3 | MS obsd | LC RT (min) |
|---|---|---|---|---|---|
| 542 | 4-fluorobenzyl | benzo[1,3]dioxol-4-yl | ethoxypropyl | 457.1 | 1.24 |
| 543 | 4-methoxybenzyl | benzo[1,3]dioxol-4-yl | methoxypropyl | 469.1 | 1.20 |
| 544 | 3,5-dichlorobenzyl | benzo[1,3]dioxol-4-yl | ethoxypropyl | 507.1 | 1.42 |
| 545 | 3-phenylpropyl | benzo[1,3]dioxol-4-yl | N-acetyl lysine | 550.0 | 1.14 |
| 546 | 3,5-dichlorobenzyl | benzo[1,3]dioxol-4-yl | N-acetyl lysine | 592.1 | 1.23 |
| 547 | 4-methoxybenzyl | benzo[1,3]dioxol-4-yl | 3-(4-methylpiperazin-1-yl)propyl | 523.2 | 1.04 |
| 548 | 3,5-dichlorobenzyl | benzo[1,3]dioxol-4-yl | 2-methoxyphenyl | 561.2 | 1.43 |

-continued

| Compd | X1 | X2 | X3 | MS obsd | LC RT (min) |
|---|---|---|---|---|---|
| 549 | 4-F-benzyl | benzo[1,3]dioxol-4-yl | 3-methoxypropyl | 443.1 | 1.23 |
| 550 | 4-methoxybenzyl | benzo[1,3]dioxol-4-yl | 3-methoxypropyl | 455.1 | 1.22 |
| 551 | 3,5-dichlorobenzyl | benzo[1,3]dioxol-4-yl | 3-methoxypropyl | 493.1 | 1.39 |
| 552 | 4-methoxybenzyl | benzo[1,3]dioxol-4-yl | cyclopropylmethyl | 437.4 | 2.03 |
| 553 | 3,5-dichlorobenzyl | benzo[1,3]dioxol-4-yl | (S)-1-carbamoyl-2-hydroxyethyl | 508.0 | 1.56 |
| 554 | 3-bromo-4-fluorobenzyl | 2-(tert-butylthio)phenyl | cyclopropylmethyl | 533.0 | 1.04 |
| 555 | 4-methoxybenzyl | 2-(tert-butylthio)phenyl | 2-methyl-3-methoxypropyl | 499.4 | 0.93 |

-continued

| Compd | X1 | X2 | X3 | MS obsd | LC RT (min) |
|---|---|---|---|---|---|
| 556 | 4-F, 3-Br benzyl | 2-(tert-butylthio)phenyl | 1-methoxypropan-2-yl | 565.0 | 1.00 |
| 557 | 4-F benzyl | 2-(tert-butylthio)phenyl | CH3 | 429.2 | 1.40 |
| 558 | 4-methoxybenzyl | 2-(tert-butylthio)phenyl | CH3 | 441.5 | 2.09 |
| 559 | 3-phenylpropyl | 2-(tert-butylthio)phenyl | CH3 | 439.2 | 1.72 |
| 560 | 3,5-dichlorobenzyl | 2-(tert-butylthio)phenyl | CH3 | 479.1 | 1.67 |
| 561 | 4-F, 3-Br benzyl | 2-(tert-butylthio)phenyl | CH3 | 507.0 | 1.07 |
| 562 | 3,5-dichlorobenzyl | 2-(tert-butylthio)phenyl | ethyl | 493.1 | 1.64 |

-continued

| Compd | X1 | X2 | X3 | MS obsd | LC RT (min) |
|---|---|---|---|---|---|
| 563 | 4-fluorobenzyl | 2-(tert-butylthio)phenyl | ethyl | 441.0 | 0.83 |
| 564 | 4-methoxybenzyl | 2-(tert-butylthio)phenyl | ethyl | 455.2 | 1.51 |
| 565 | 3-phenylpropyl | 2-(tert-butylthio)phenyl | ethyl | 453.5 | 1.52 |
| 566 | 3,5-dichlorobenzyl | 2-(tert-butylthio)phenyl | 2-methoxyethyl | 523.1 | 1.07 |
| 567 | 3-bromo-4-fluorobenzyl | 2-(tert-butylthio)phenyl | 2-methoxyethyl | 553.0 | 1.04 |
| 568 | 4-methoxybenzyl | 2-(tert-butylthio)phenyl | N-acetyl-lysine side chain | 598.2 | 1.73 |

-continued

| Compd | X1 | X2 | X3 | MS obsd | LC RT (min) |
|---|---|---|---|---|---|
| 569 | 3-phenylpropyl | 2-(tert-butylthio)phenyl | 3-(4-methylpiperazin-1-yl)propyl | 563.0 | 2.02 |
| 570 | 3,5-dichlorobenzyl | 2-(tert-butylthio)phenyl | 3-methoxypropyl | 537.2 | 1.70 |
| 571 | 4-fluorobenzyl | 2-(tert-butylthio)phenyl | 3-methoxypropyl | 487.2 | 1.63 |
| 572 | 3-phenylpropyl | 2-(tert-butylthio)phenyl | 3-methoxypropyl | 495.7 | 1.82 |
| 573 | 3,5-dichlorobenzyl | 2-(tert-butylthio)phenyl | 3-methoxypropyl | 537.2 | 1.69 |
| 574 | 3-bromo-4-fluorobenzyl | 2-(tert-butylthio)phenyl | 3-methoxypropyl | 564.8 | 1.02 |

-continued

| Compd | X1 | X2 | X3 | MS obsd | LC RT (min) |
|---|---|---|---|---|---|
| 575 | 3-phenylpropyl | 2-(tert-butylthio)phenyl | cyclopropylmethyl | 479.2 | 1.80 |
| 576 | 3,5-dichlorobenzyl | 2-(tert-butylthio)phenyl | (S)-1-hydroxy-3-methylbutan-2-yl | 548.6 | 1.92 |
| 577 | 4-fluorobenzyl | 2-(tert-butylthio)phenyl | (S)-1-amino-3-hydroxy-1-oxopropan-2-yl | 500.0 | 1.22 |
| 578 | 3,5-dichlorobenzyl | 2-(tert-butylthio)phenyl | (S)-1-amino-3-hydroxy-1-oxopropan-2-yl | 550.0 | 1.56 |
| 579 | 4-methoxybenzyl | 2-(difluoromethoxy)phenyl | cyclopropylmethyl | 445.2 | 2.08 |
| 580 | 3-phenylpropyl | 2-(difluoromethoxy)phenyl | cyclopropylmethyl | 443.2 | 1.43 |

-continued
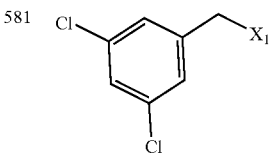
| Compd | X1 | X2 | X3 | MS obsd | LC RT (min) |
|---|---|---|---|---|---|
| 581 | 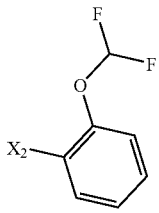 | 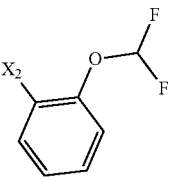 | 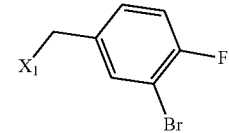 | 482.6 | 1.56 |
| 582 | 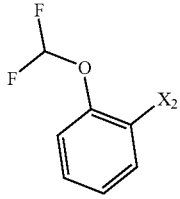 |  | 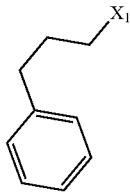 | 511.1 | 1.05 |
| 583 | 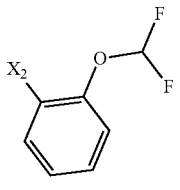 | 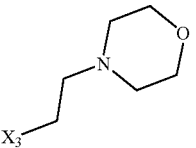 | 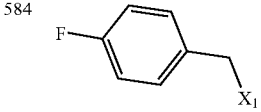 | 516.3 | 1.10 |
| 584 | 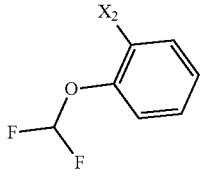 | 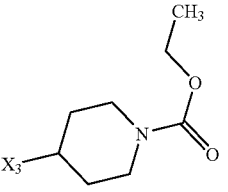 | 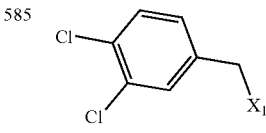 | 546.7 | 1.15 |
| 585 |  | 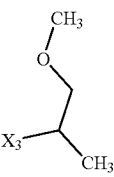 | 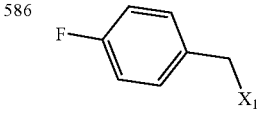 | 513.0 | 0.42 |
| 586 |  |  | X$_3$—CH$_3$ | 407.1 | 1.26 |

-continued
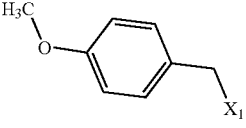
| Compd | X1 | X2 | X3 | MS obsd | LC RT (min) |
|---|---|---|---|---|---|
| 587 | 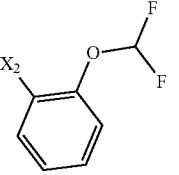 |  | 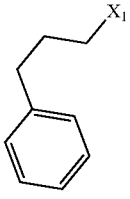 | 419.1 | 1.23 |
| 588 | 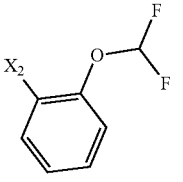 |  | 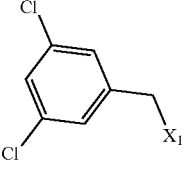 | 417.2 | 1.32 |
| 589 | 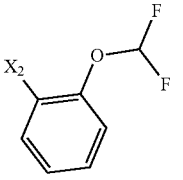 |  | 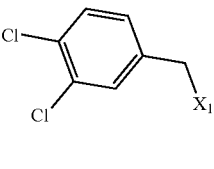 | 457.1 | 1.45 |
| 590 | 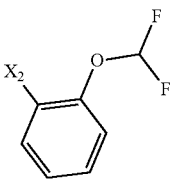 |  | 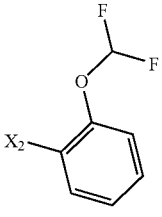 | 471.4 | 1.39 |
| 591 | 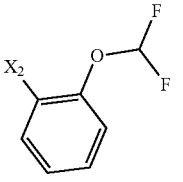 |  | 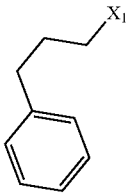 | 433.4 | 1.27 |
| 592 | 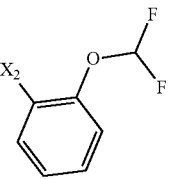 |  | | 431.2 | 1.44 |

-continued

| Compd | X1 | X2 | X3 | MS obsd | LC RT (min) |
|---|---|---|---|---|---|
| 593 | 3,5-dichlorobenzyl | 2-(OCHF₂)phenyl | ethyl | 471.1 | 1.43 |
| 594 | 3,4-dichlorobenzyl | 2-(OCHF₂)phenyl | 2-methoxyethyl | 501.1 | 1.41 |
| 595 | 4-fluorobenzyl | 2-(OCHF₂)phenyl | 2-methoxyethyl | 451.1 | 1.26 |
| 596 | 3-phenylpropyl | 2-(OCHF₂)phenyl | 2-methoxyethyl | 461.2 | 1.39 |
| 597 | 3,5-dichlorobenzyl | 2-(OCHF₂)phenyl | 2-methoxyethyl | 501.2 | 1.42 |
| 598 | 2-(OCHF₂)phenyl | 2-(OCHF₂)phenyl | 3-ethoxypropyl | 489.0 | 1.29 |

-continued
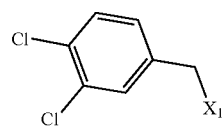
| Compd | X1 | X2 | X3 | MS obsd | LC RT (min) |
|---|---|---|---|---|---|
| 599 | 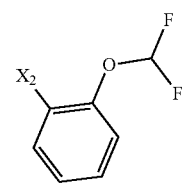 | 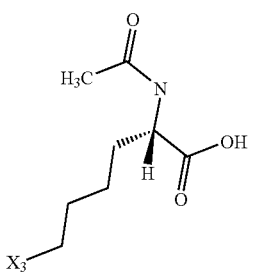 | 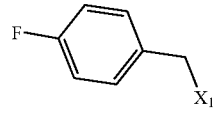 | 611.6 | 1.19 |
| 600 | 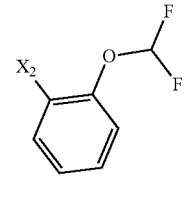 | 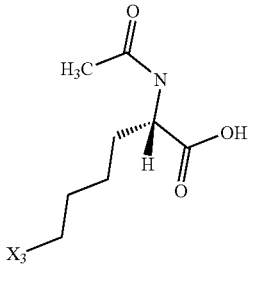 | 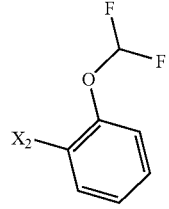 | 564.1 | 1.18 |
| 601 | 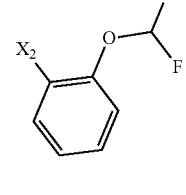 | 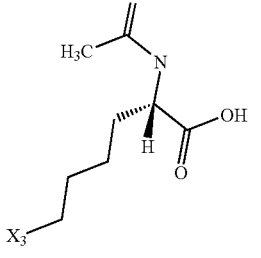 | 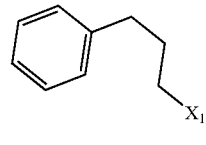 | 576.2 | 1.17 |
| 602 | 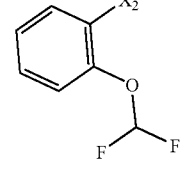 | 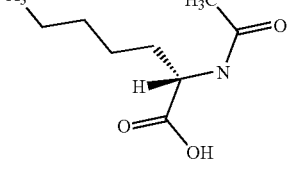 | 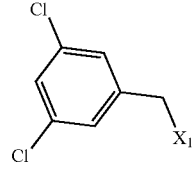 | 574.2 | 1.25 |
| 603 | 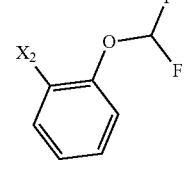 | 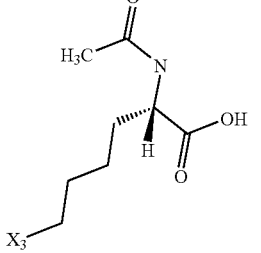 | | 614.1 | 1.31 |

-continued

| Compd | X1 | X2 | X3 | MS obsd | LC RT (min) |
|---|---|---|---|---|---|
| 604 | 3-bromo-4-fluorobenzyl | 2-(difluoromethoxy)phenyl | N-acetyl-lysine side chain (HOOC-CH(NHAc)-(CH2)4-) | 642.2 | 1.20 |
| 605 | 3,4-dichlorobenzyl | 2-(difluoromethoxy)phenyl | 3-(4-methylpiperazin-1-yl)propyl | 583.1 | 1.10 |
| 606 | 4-fluorobenzyl | 2-(difluoromethoxy)phenyl | 3-(4-methylpiperazin-1-yl)propyl | 533.2 | 1.00 |
| 607 | 3-phenylpropyl | 2-(difluoromethoxy)phenyl | 3-(4-methylpiperazin-1-yl)propyl | 543.3 | 1.02 |
| 608 | 3-phenylpropyl | 2-(difluoromethoxy)phenyl | 3-methoxypropyl | 475.2 | 1.41 |
| 609 | 3,5-dichlorobenzyl | 2-(difluoromethoxy)phenyl | 3-methoxypropyl | 515.1 | 1.42 |

-continued
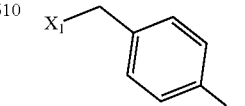
| Compd | X1 | X2 | X3 | MS obsd | LC RT (min) |
|---|---|---|---|---|---|
| 610 | 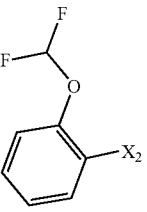 |  | 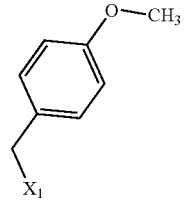 | 447.2 | 1.31 |
| 611 | 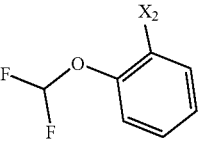 |  | 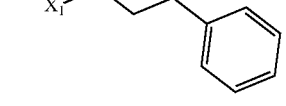 | 459.2 | 1.53 |
| 612 | 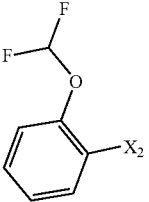 |  | 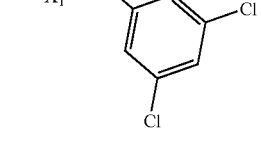 | 457.2 | 1.46 |
| 613 | 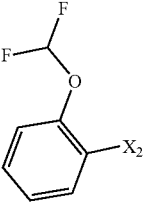 | 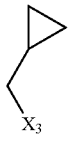 | 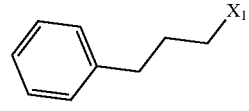 | 496.6 | 1.67 |
| 614 | 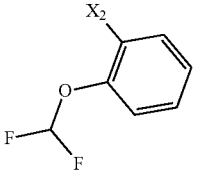 | 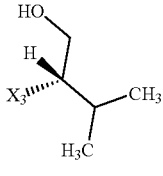 | 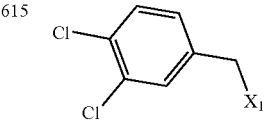 | 489.0 | 1.33 |
| 615 | 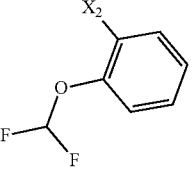 | 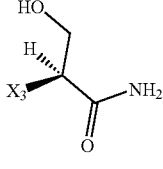 |  | 528.0 | 1.51 |

-continued
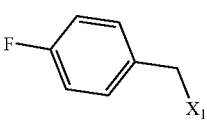
| Compd | X1 | X2 | X3 | MS obsd | LC RT (min) |
|---|---|---|---|---|---|
| 616 | 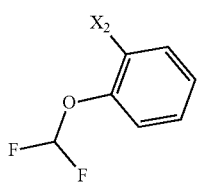 | 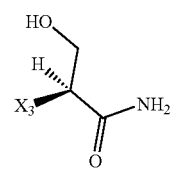 | 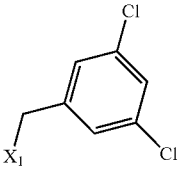 | 478.0 | 1.22 |
| 617 | 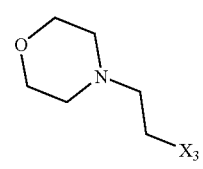 | X₂-H | 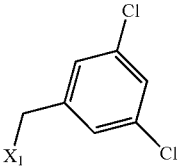 | 414.0 | 1.10 |
| 618 | 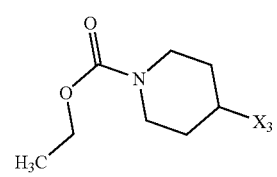 | X₂-H | 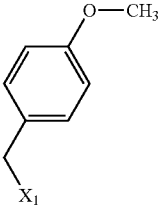 | 456.1 | 1.39 |
| 619 | 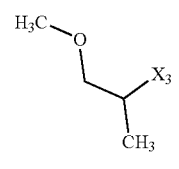 | X₂-H | 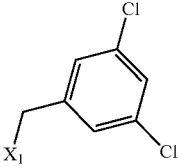 | 335.1 | 1.15 |
| 620 | 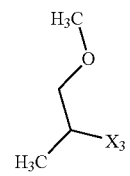 | X₂-H | 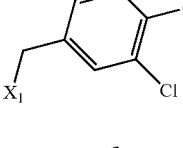 | 373.1 | 1.33 |
| 621 | 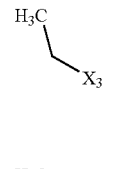 | X₂-H | 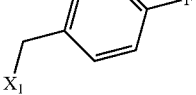 | 329.0 | 1.26 |
| 622 | 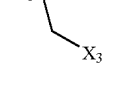 | X₂-H | 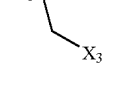 | 279.1 | 1.13 |

-continued

| Compd | X1 | X2 | X3 | MS obsd | LC RT (min) |
|---|---|---|---|---|---|
| 623 | 4-methoxybenzyl | X₂-H | ethyl (H₃C-CH₂-X₃) | 291.1 | 1.11 |
| 624 | 3,5-dichlorobenzyl | X₂-H | isopropyl | 329.0 | 1.33 |
| 625 | 4-fluorobenzyl | X₂-H | 3-methoxypropyl (H₃C-O-CH₂CH₂CH₂-X₃) | 323.1 | 1.14 |
| 626 | 3-phenylpropyl | X₂-H | 3-methoxypropyl | 333.1 | 1.20 |
| 627 | 4-fluorobenzyl | X₂-H | cyclopropylmethyl | 305.1 | 1.23 |
| 628 | 3,4-dichlorobenzyl | 2-methoxyphenyl | cyclopropylmethyl | 447.1 | 1.49 |
| 629 | 3,5-dichlorobenzyl | 2-methoxyphenyl | cyclopropylmethyl | 447.1 | 1.55 |

-continued
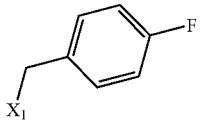
| Compd | X1 | X2 | X3 | MS obsd | LC RT (min) |
|---|---|---|---|---|---|
| 630 | 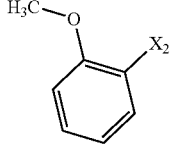 | 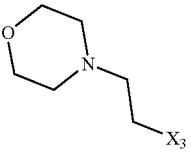 | 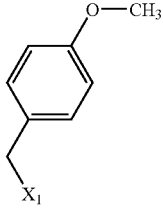 | 470.1 | 1.11 |
| 631 | 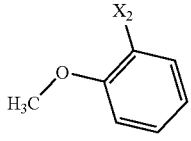 | 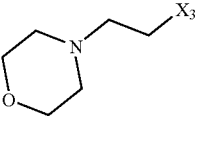 | 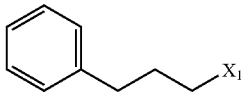 | 482.1 | 1.06 |
| 632 | 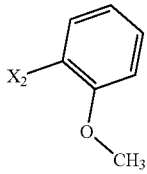 | 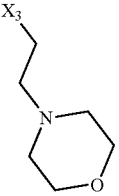 | 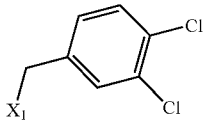 | 480.1 | 1.14 |
| 633 | 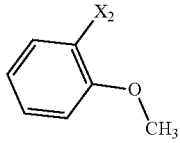 | 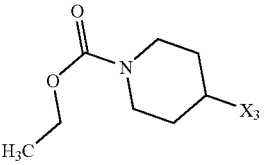 | 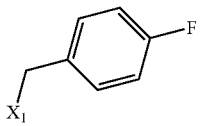 | 562.2 | 1.50 |
| 634 | 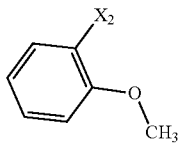 | 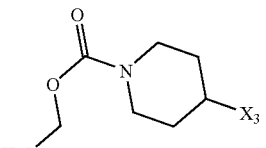 | 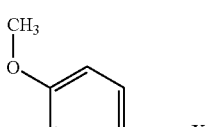 | 512.2 | 1.40 |
| 635 | 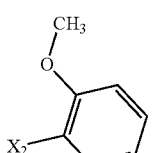 | 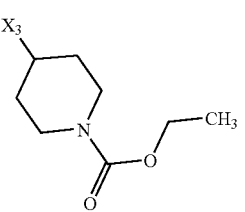 | 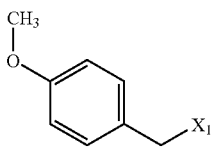 | 524.2 | 1.37 |
| 636 | 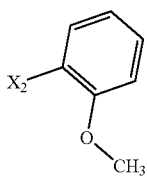 | 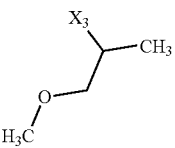 | | 441.2 | 1.33 |

-continued

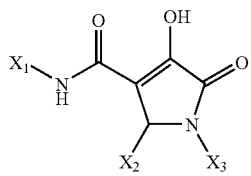

| Compd | X1 | X2 | X3 | MS obsd | LC RT (min) |
|---|---|---|---|---|---|
| 637 | 3,5-dichlorobenzyl | 2-methoxyphenyl | 2-methoxyethyl | 465.1 | 1.44 |
| 638 | 3,4-dichlorobenzyl | 2-(carboxymethoxy)phenyl | 2-morpholinoethyl | 564.0 | 1.18 |
| 639 | 3-phenylpropyl | 2-(carboxymethoxy)phenyl | 2-methoxy-1-methylethyl | 483.2 | 1.32 |
| 640 | 3,4-dichlorobenzyl | 2-(carboxymethoxy)phenyl | 3-ethoxypropyl | 537.1 | 1.38 |
| 641 | 3,5-dichlorobenzyl | 2-(carboxymethoxy)phenyl | 3-ethoxypropyl | 537.1 | 1.50 |
| 642 | 3,4-dichlorobenzyl | 2-(carboxymethoxy)phenyl | 3-(4-methylpiperazin-1-yl)propyl | 591.1 | 1.09 |

-continued
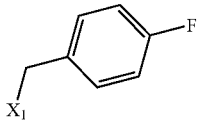
| Compd | X1 | X2 | X3 | MS obsd | LC RT (min) |
|---|---|---|---|---|---|
| 643 | 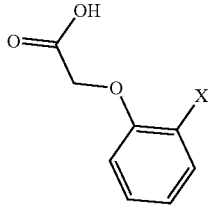 | 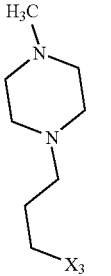 | 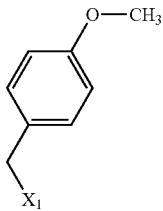 | 541.1 | 1.00 |
| 644 | 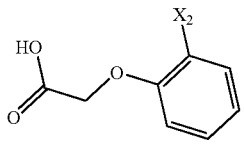 | 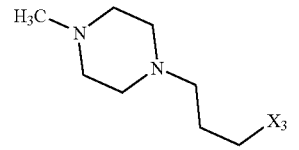 | 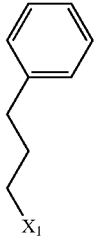 | 553.2 | 0.99 |
| 645 | 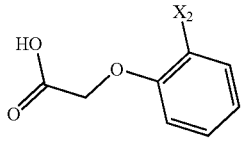 | 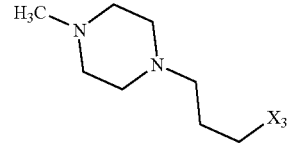 | 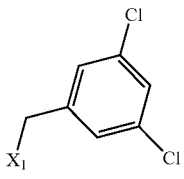 | 551.2 | 1.07 |
| 646 | 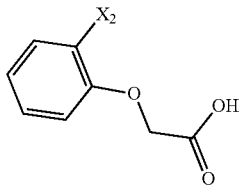 | 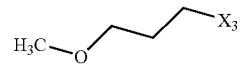 | 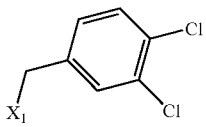 | 523.1 | 1.37 |
| 647 | 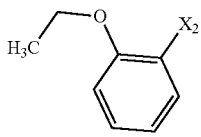 | 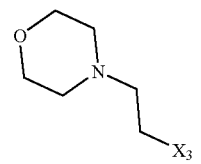 | 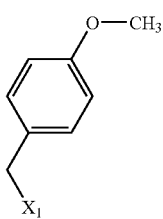 | 534.1 | 1.23 |
| 648 | 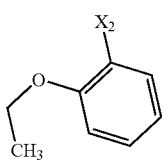 | 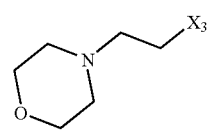 | | 496.2 | 1.13 |

-continued

| Compd | X1 | X2 | X3 | MS obsd | LC RT (min) |
|---|---|---|---|---|---|
| 649 | 3-phenylpropyl | 2-ethoxyphenyl | 2-morpholinoethyl | 494.2 | 1.17 |
| 650 | 3,5-dichlorobenzyl | 2-ethoxyphenyl | 2-morpholinoethyl | 534.1 | 1.25 |
| 651 | 4-fluorobenzyl | 2-ethoxyphenyl | 1-(ethoxycarbonyl)piperidin-4-yl | 526.2 | 1.45 |
| 652 | 3-phenylpropyl | 2-ethoxyphenyl | 1-(ethoxycarbonyl)piperidin-4-yl | 536.3 | 1.52 |
| 653 | 3,4-dichlorobenzyl | 2-ethoxyphenyl | 1-methoxy-2-propyl | 493.1 | 1.59 |
| 654 | 4-fluorobenzyl | 2-ethoxyphenyl | 1-methoxy-2-propyl | 443.2 | 1.42 |
| 655 | 4-methoxybenzyl | 2-carboxyphenyl | cyclopropylmethyl | 423.1 | 1.25 |

-continued
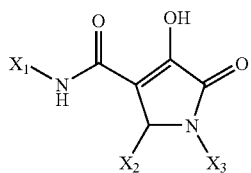
| Compd | X1 | X2 | X3 | MS obsd | LC RT (min) |
|---|---|---|---|---|---|
| 656 | 3,4-dichlorobenzyl | 2-carboxyphenyl | 2-morpholinoethyl | 534.0 | 1.16 |
| Compd | X1 | X2 | X3 | MS obsd | LC RT (min) |
|---|---|---|---|---|---|
| 657 | 3-phenylpropyl | 2-carboxyphenyl | 2-morpholinoethyl | 494.2 | 1.14 |
| 658 | 3,5-dichlorobenzyl | 2-carboxyphenyl | 2-morpholinoethyl | 534.0 | 1.16 |
| 659 | 4-methoxybenzyl | 2-carboxyphenyl | CH$_3$ | 397.1 | 1.21 |
| 660 | 4-fluorobenzyl | 2-carboxyphenyl | 2-methoxyethyl | 429.1 | 1.25 |
| 661 | 4-methoxybenzyl | 2-carboxyphenyl | 2-methoxyethyl | 441.1 | 1.25 |

-continued

| Compd | X1 | X2 | X3 | MS obsd | LC RT (min) |
|---|---|---|---|---|---|
| 662 | 3-phenylpropyl-X1 | 2-(HOOC)C6H4-X2 | X3-CH2CH2-O-CH3 | 439.2 | 1.33 |
| 663 | 3,5-dichlorobenzyl-X1 | 2-(HOOC)C6H4-X2 | CH3-O-CH2CH2-X3 | 479.1 | 1.38 |
| 664 | 4-fluorobenzyl-X1 | 2-(HOOC)C6H4-X2 | 4-methylpiperazin-1-yl-propyl-X3 | 511.1 | 1.00 |
| 665 | 3,4-dichlorobenzyl-X1 | 2-(HOOC)C6H4-X2 | H3C-O-CH2CH2CH2-X3 | 493.1 | 1.41 |
| 666 | 4-methoxybenzyl-X1 | 2-(HOOC)C6H4-X2 | cyclopropylmethyl-X3 | 437.2 | 1.34 |
| 667 | 3,4-dichlorobenzyl-X1 | 2-(CF3)C6H4-X2 | cyclopropyl-X3 | 485.1 | 1.58 |
| 668 | 4-methoxybenzyl-X1 | 2-(CF3)C6H4-X2 | cyclopropyl-X3 | 447.1 | 1.38 |
| 669 | 3,4-dichlorobenzyl-X1 | 2-(CF3)C6H4-X2 | 2-morpholinoethyl-X3 | 558.0 | 1.20 |

-continued
| Compd | X1 | X2 | X3 | MS obsd | LC RT (min) |
|---|---|---|---|---|---|
| 670 | 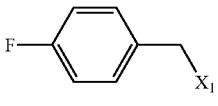 | 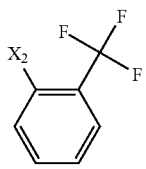 | 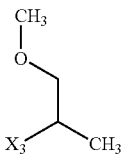 | 467.2 | 1.47 |
| 671 | 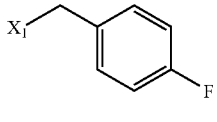 | 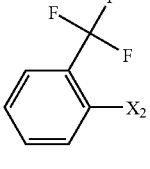 |  | 449.1 | 1.52 |
| 672 | 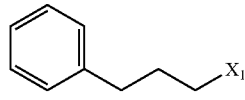 | 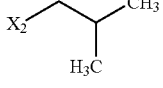 | 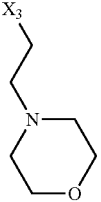 | 430.2 | 1.16 |
| 673 | 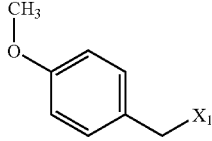 | 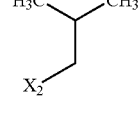 | 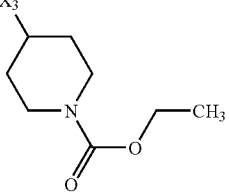 | 474.3 | 1.38 |
| 674 | 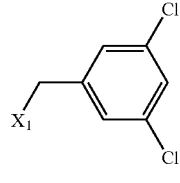 | 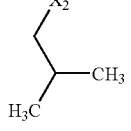 | 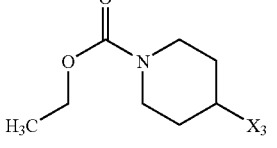 | 512.2 | 1.64 |
| 675 | 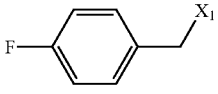 | 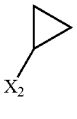 | 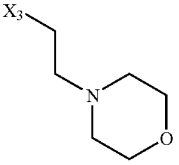 | 404.1 | 1.05 |
| 676 | 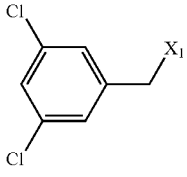 | 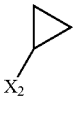 | 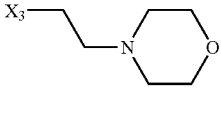 | 454.1 | 1.12 |
| 677 | 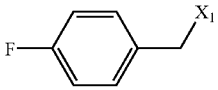 |  | 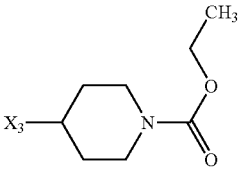 | 446.2 | 1.32 |

-continued
| Compd | X1 | X2 | X3 | MS obsd | LC RT (min) |
|---|---|---|---|---|---|
| 678 | 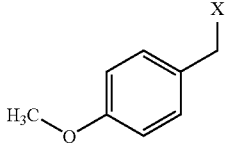 |  | 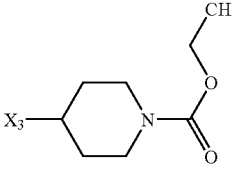 | 458.2 | 1.30 |
| 679 | 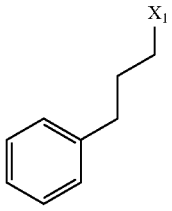 |  | 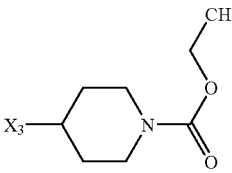 | 456.2 | 1.36 |
| 680 | 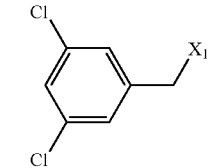 |  | 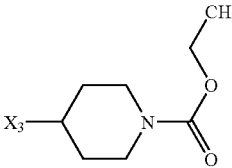 | 496.1 | 1.47 |
| 681 | 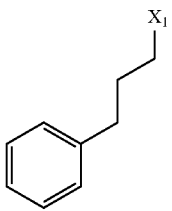 |  | 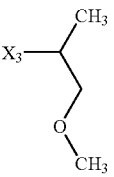 | 373.2 | 1.36 |
| 682 | 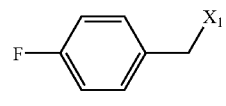 |  |  | 305.1 | 1.22 |
| 683 | 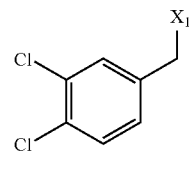 |  | 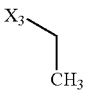 | 369.1 | 1.40 |
| 684 | 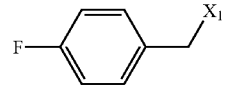 |  |  | 319.1 | 1.28 |
| 685 | 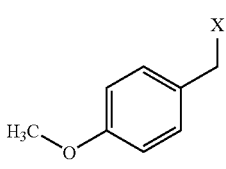 |  |  | 331.1 | 1.25 |
| 686 | 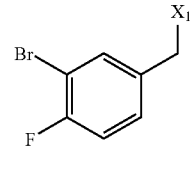 |  |  | 397.1 | 1.35 |

-continued
| Compd | X1 | X2 | X3 | MS obsd | LC RT (min) |
|---|---|---|---|---|---|
| 687 | 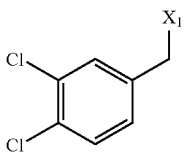 |  | 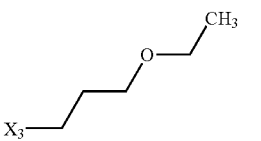 | 427.1 | 1.45 |
| 688 | 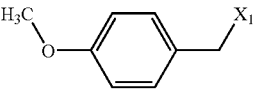 |  | 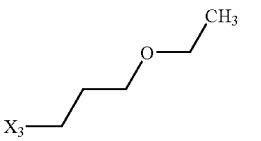 | 389.1 | 1.28 |
| 689 | 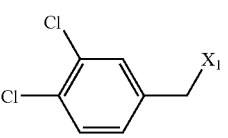 |  | 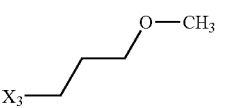 | 413.1 | 1.36 |
| 690 | 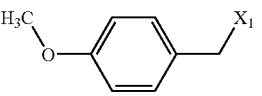 |  | 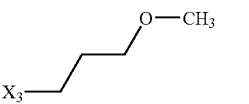 | 375.1 | 1.24 |
| 691 | 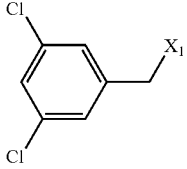 |  |  | 395.1 | 1.55 |
| 692 | 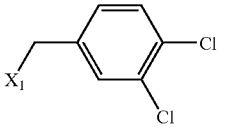 | 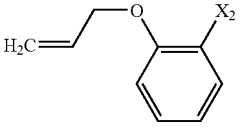 |  | 473.1 | 1.59 |
| 693 | 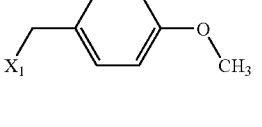 | 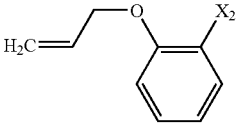 |  | 435.2 | 1.40 |
| 694 | 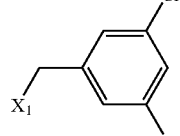 | 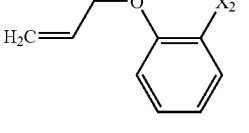 |  | 473.1 | 1.61 |
| 695 | 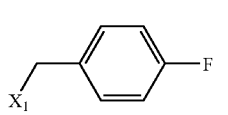 | 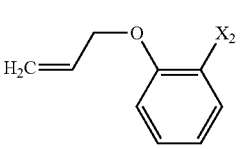 | 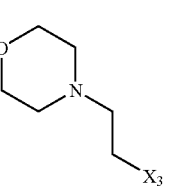 | 496.1 | 1.12 |

-continued
| Compd | X1 | X2 | X3 | MS obsd | LC RT (min) |
|---|---|---|---|---|---|
| 696 | 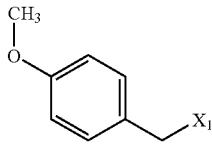 | 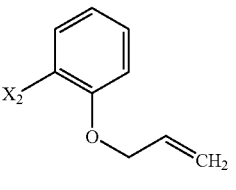 | 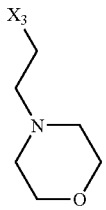 | 508.2 | 1.15 |
| 697 | 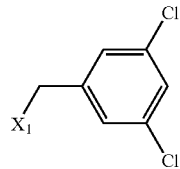 | 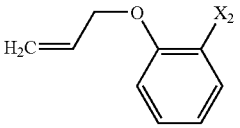 | 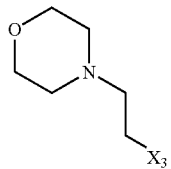 | 546.1 | 1.28 |
| 698 | 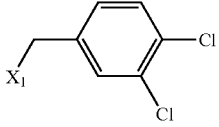 | 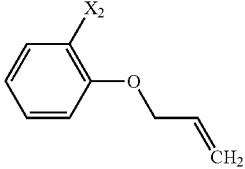 | 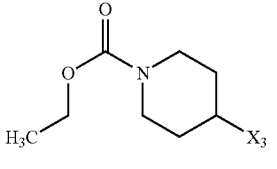 | 588.1 | 1.60 |
| 699 | 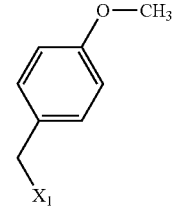 | 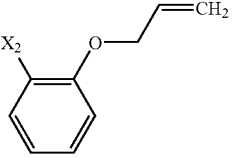 | 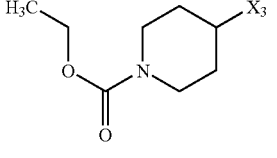 | 550.3 | 1.43 |
| 700 | 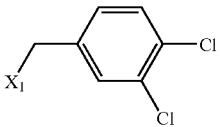 | 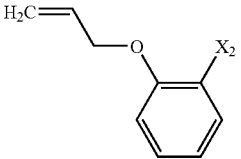 | 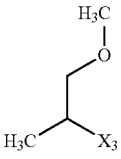 | 505.1 | 1.62 |
| 701 | 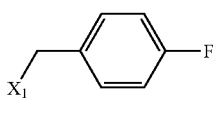 | 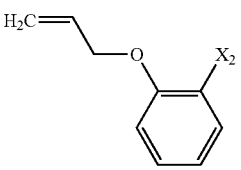 | 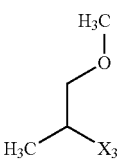 | 455.2 | 1.43 |
| 702 | 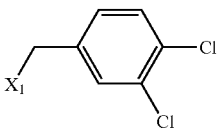 | 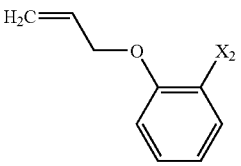 | 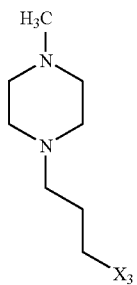 | 573.1 | 1.11 |

-continued
| Compd | X1 | X2 | X3 | MS obsd | LC RT (min) |
|---|---|---|---|---|---|
| 703 | 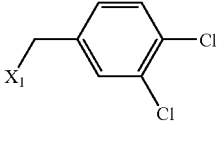 | 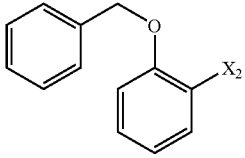 | 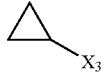 | 523.1 | 1.71 |
| 704 | 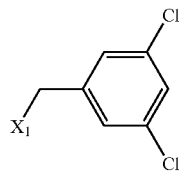 | 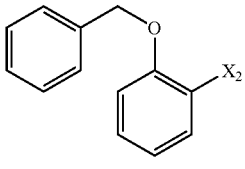 | 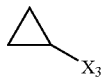 | 523.1 | 1.76 |
| 705 | 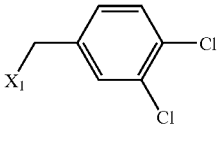 | 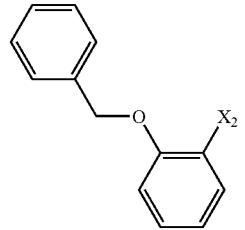 | 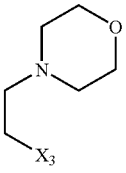 | 596.1 | 1.30 |
| 706 | 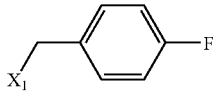 | 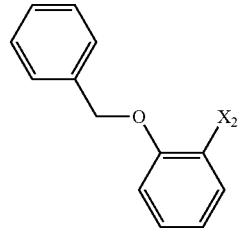 | 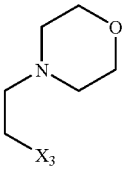 | 546.1 | 1.19 |
| 707 | 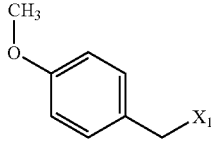 | 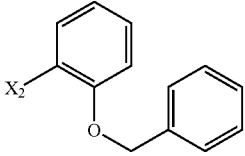 | 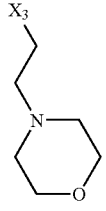 | 558.3 | 1.19 |
| 708 | 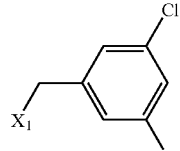 | 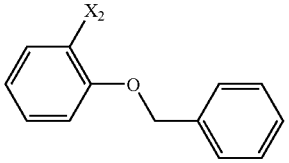 | 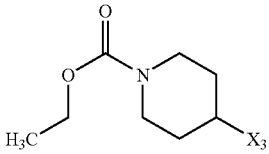 | 638.2 | 1.76 |
| 709 | 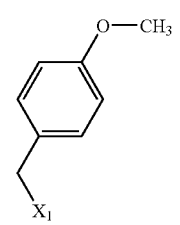 | 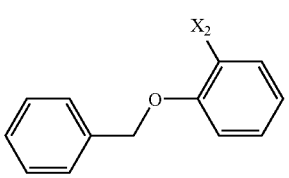 | 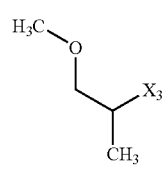 | 517.2 | 1.52 |

-continued
| Compd | X1 | X2 | X3 | MS obsd | LC RT (min) |
|---|---|---|---|---|---|
| 710 | 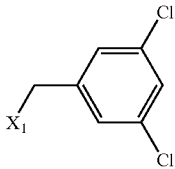 | 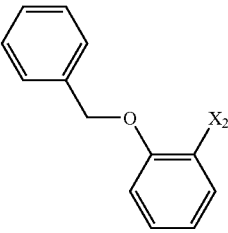 | 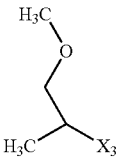 | 555.1 | 1.81 |
| 711 | 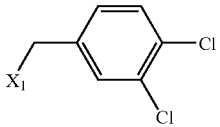 | 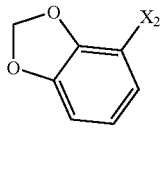 | 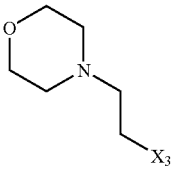 | 534.0 | 1.19 |
| 712 | 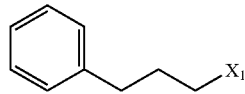 | 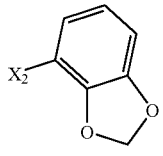 | 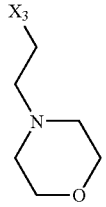 | 494.1 | 1.15 |
| 713 | 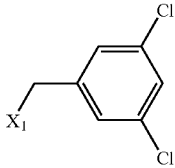 | 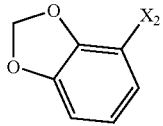 | 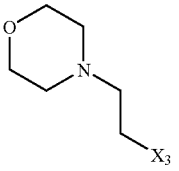 | 534.0 | 1.18 |
| 714 | 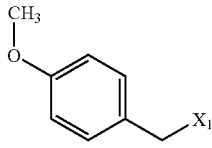 | 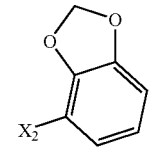 | 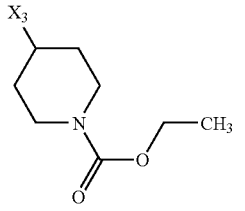 | 538.2 | 1.31 |
| 715 | 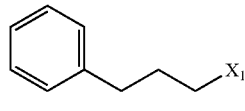 | 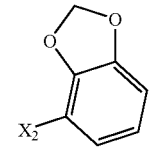 | 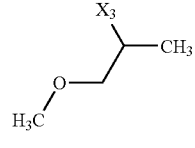 | 453.2 | 1.44 |
| 716 | 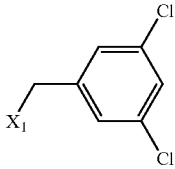 | 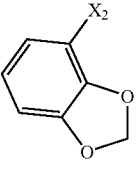 | 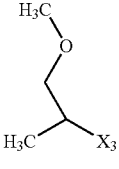 | 493.1 | 1.49 |

-continued

| Compd | X1 | X2 | X3 | MS obsd | LC RT (min) |
|---|---|---|---|---|---|
| 717 | 3,5-dichlorobenzyl-X₁ | benzo[1,3]dioxol-4-yl-X₂ | H₃C–X₃ | 435.1 | 1.42 |
| 718 | 3,4-dichlorobenzyl-X₁ | benzo[1,3]dioxol-4-yl-X₂ | H₃CO-CH₂CH₂CH₂-X₃ | 493.1 | 1.43 |
| 719 | 3,4-dichlorobenzyl-X₁ | 2-(tert-butylthio)phenyl-X₂ | morpholin-4-yl-CH₂CH₂-X₃ | 578.1 | 1.33 |
| 720 | 4-fluorobenzyl-X₁ | 2-(tert-butylthio)phenyl-X₂ | morpholin-4-yl-CH₂CH₂-X₃ | 528.1 | 1.24 |
| 721 | 3,4-dichlorobenzyl-X₁ | 2-(difluoromethoxy)phenyl-X₂ | X₃-CH₂CH₂-morpholin-4-yl | 556.0 | 1.24 |
| 722 | 4-methoxybenzyl-X₁ | 2-(difluoromethoxy)phenyl-X₂ | ethyl 4-piperidinecarboxylate-X₃ | 560.2 | 1.44 |
| 723 | 3,5-dichlorobenzyl-X₁ | 2-(difluoromethoxy)phenyl-X₂ | 1-methyl-4-(3-propyl)piperazine-X₃ | 583.1 | 1.13 |

-continued

| Compd | X1 | X2 | X3 | MS obsd | LC RT (min) |
|---|---|---|---|---|---|
| 724 | 3,4-dichlorobenzyl (X1 at benzyl position) | 2-(difluoromethoxy)phenyl-X2 | cyclopropylmethyl-X3 | 497.1 | 1.67 |

EXAMPLE 81

Method for the Preparation of Compounds 725–746

Compounds 81-A to 81-V were synthesized from [[2-(2,2-dimethyl-5-oxo-[1,3]dioxolan-4-ylidene)-acetyl]-(4-fluorobenzyl)-aminooxy]-acetic acid according to Scheme VIII. Amines VIII-3 (0.165 mmol) in 1,2-dichloroethane (1 ml) were treated at 5° C. with 2-(2-pyridyl)ethyl functionalized silica gel (0.38 mmol) followed by a solution of [[2-(2,2-dimethyl-5-oxo-[1,3]-dioxolan-4-ylidene)-acetyl]-(4-fluorobenzyl)-aminooxy]-acetyl chloride, VIII-2, (0.165 mmol) in 1,2-dichloroethane (1 ml). After one hour at 25° C., the reaction mixtures were filtered and purified on a Shimadzu automated preparative HPLC system (column Waters X Terra C-8, 5μ, 19×100 mm, elution H$_2$O$_5$ mM NH$_4$Oac-acetonitrile). The collected compounds were analysed using the following LC/MS conditions.

| | |
|---|---|
| Column: | X Terra 5μ C-8, 4.6 × 30 mm |
| Solvent: | Solvent A: 10% CH$_3$CN - 90% H$_2$O, 5 mM NH$_4$OAc |
| | Solvent B: 90% CH$_3$CN - 10% H$_2$O, 5 mM NH$_4$OAc |
| Gradient: | 100% solvent A/0% solvent B to 0% solvent A/100% solvent B |
| Gradient time: | 2 minutes, hold time 1 minute. |
| Flow rate: | 4 ml/min. |
| Detector wavelength: | 220 nm. |

Spectrometry (MS) data were determined with a Micromass ZMD Platform TSQ 7000 LC/MS in positive electrospray mode.

| Compound | X$_1$ | HPLC Retention time (min) | MS Data (M + H)$^+$ |
|---|---|---|---|
| 81-A | morpholin-4-yl (N-X$_1$) | 1.34 | 423 |
| 81-B | 3-(10,11-dihydro-5H-dibenzo[b,f]azepin-5-yl)propyl-N(methyl)-X$_1$ | 1.95 | 602 |

-continued
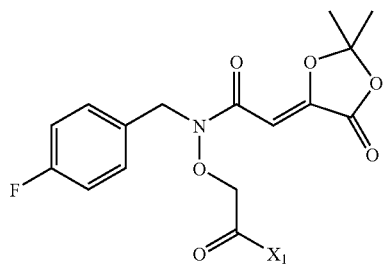
| Compound | X₁ | HPLC Retention time (min) | MS Data (M + H)⁺ |
|---|---|---|---|
| 81-C | phenyl-CH(CH₃)-NH-X₁ | 1.69 | 457 |
| 81-D | 4-F-C₆H₄-CH₂-NH-X₁ | 1.68 | 461 |
| 81-E | 4-Cl-C₆H₄-CH₂-NH-X₁ | 1.75 | 477 |
| 81-F | 4-H₃CO-C₆H₄-CH₂-NH-X₁ | 1.64 | 473 |
| 81-G | 4-CH₃-C₆H₄-CH₂-NH-X₁ | 1.71 | 457 |
| 81-H | 4-F₃C-C₆H₄-CH₂-NH-X₁ | 1.79 | 511 |
| 81-I | 4-F-C₆H₄-CH(CH₃)-NH-X₁ | 1.72 | 475 |
| 81-J | bis(4-Cl-C₆H₄)CH-CH₂CH₂-N(CH₃)-X₁ | 2.08 | 643 |

-continued
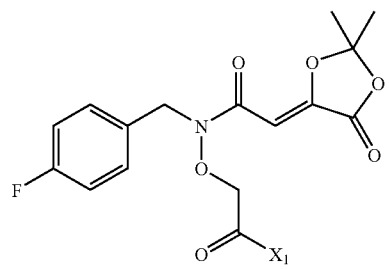
| Compound | X₁ | HPLC Retention time (min) | MS Data (M + H)⁺ |
|---|---|---|---|
| 81-K | benzyl(butyl)N-X₁ | 1.87 | 499 |
| 81-L | propyl(cyclopropylmethyl)N-X₁ | 1.72 | 449 |
| 81-M | 2,6-dimethylmorpholin-4-yl (X₁) | 1.53 | 451 |
| 81-N | (1,2-dimethoxyethyl)(methyl)N-X₁ | 1.48 | 455 |
| 81-O | diisobutyl-N-X₁ | 1.81 | 465 |
| 81-P | dihexyl-N-X₁ | 2.08 | 521 |

-continued

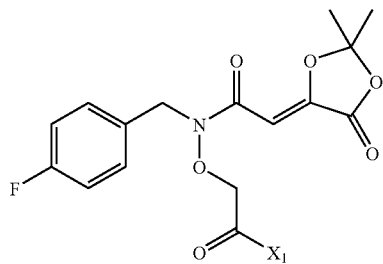

| Compound | X₁ | HPLC Retention time (min) | MS Data (M + H)⁺ |
|---|---|---|---|
| 81-Q | (structure) | 1.53 | 453 |
| 81-R | (structure) | 1.47 | 472 |
| 81-S | (structure) | 1.49 | 469 |
| 81-T | (structure) | 1.31 | 478 |
| 81-U | (structure) | 1.43 | 381 |
| 81-V | (structure) | 1.59 | 409 |

According to the method illustrated in Scheme VIII, the dioxolanes 81-A to 81-V, VIII-4 in the scheme, (approximately 0.06 mmol) were treated with a solution of formaldehyde-methyl amine adduct (0.12 mmol) in methanol (1 ml) as described in the preparation of Compound 44 (Method 44B) and the resulting mixtures were heated at 50° C. for 45 min. The reaction mixture was then diluted with acetonitrile (1 ml) and purified on a Shimadzu automated preparative HPLC system (column Waters X Terra C-8, 5 μ, 19×100 mm, elution water 0.05% TFA-acetonitrile). The collected compounds were analysed using the following LC/MS conditions.

| | |
|---|---|
| Column: | X Terra 5μ C-8, 4.6 × 30 mm |
| Solvent: | Solvent A: 10% CH₃CN - 90% H₂O, 0.05% TFA |
| | Solvent B: 90% CH₃CN - 10% H₂O, 0.05% TFA |
| Gradient: | 100% solvent A/0% solvent B to 0% solvent A/100% solvent B |
| Gradient time: | 2 minutes, hold time 1 minute. |
| Flow rate: | 4 ml/min. |
| Detector wavelength: | 220 nm. |

Spectrometry (MS) data were determined with a Micromass ZMD Platform TSQ 7000 LC/MS in positive electrospray mode.

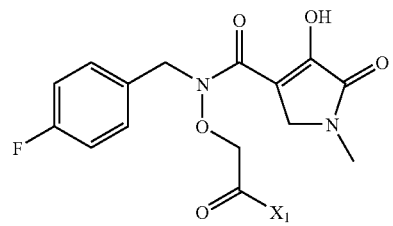
| Compound | X1 | HPLC Retention time (min) | MS Data (M + H)+ |
|---|---|---|---|
| 725 | morpholine-N-X1 | 1.12 | 408 |
| 726 | 10,11-dihydro-5H-dibenzo[b,f]azepine-N-CH2CH2CH2-N(CH3)-X1 | 1.77 | 587 |
| 727 | PhCH(CH3)-NH-X1 | 1.48 | 442 |
| 728 | 4-F-C6H4-CH2-NH-X1 | 1.47 | 446 |
| 729 | 4-Cl-C6H4-CH2-NH-X1 | 1.54 | 462 |
| 730 | 4-CH3O-C6H4-CH2-NH-X1 | 1.43 | 458 |
| 731 | 4-CH3-C6H4-CH2-NH-X1 | 1.51 | 442 |
| 732 | 4-CF3-C6H4-CH2-NH-X1 | 1.60 | 496 |

-continued
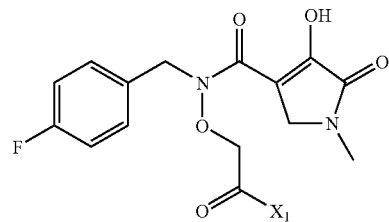
| Compound | X1 | HPLC Retention time (min) | MS Data (M + H)+ |
|---|---|---|---|
| 733 | ![structure: 1-(4-fluorophenyl)ethyl-NH-X1] | 1.52 | 460 |
| 734 | ![structure: bis(4-chlorophenyl)propyl-N(CH3)-X1] | 1.93 | 628 |
| 735 | ![structure: benzyl-N(butyl)-X1] | 1.68 | 484 |
| 736 | ![structure: propyl-N(cyclopropylmethyl)-X1] | 1.51 | 434 |
| 737 | ![structure: 2,6-dimethylmorpholine-N-X1] | 1.27 | 436 |
| 738 | ![structure: (dimethoxypropyl)-N(CH3)-X1] | 1.23 | 440 |
| 739 | ![structure: diisobutyl-N-X1] | 1.62 | 450 |
| 740 | ![structure: dihexyl-N-X1] | 1.93 | 506 |

-continued
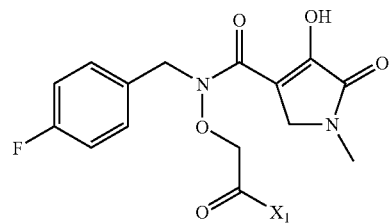
| Compound | X1 | HPLC Retention time (min) | MS Data (M + H)+ |
|---|---|---|---|
| 741 | X1-N(CH3)-CH2-C(=O)-O-Et | 1.29 | 438 |
| 742 | 4-pyridyl-CH2-N(Et)-X1 | 0.98 | 457 |
| 743 | MeO-CH2CH2-N(CH2CH2-OMe)-X1 | 1.26 | 454 |
| 744 | 1-acetyl-4-X1-homopiperazine | 1.11 | 463 |
| 745 | Et-NH-X1 | 1.16 | 366 |
| 746 | iBu-NH-X1 | 1.35 | 394 |

EXAMPLE 82

Method for the Preparation of Compounds 747–750

The general method for the synthesis of compounds 747–750 is outlined in Scheme X.

Compound 82-A: 1-(2,2-Dimethoxy-ethyl)-4-hydroxy-5-oxo-2,5-dihydro-1H-pyrrole-3-carboxylic acid (3,4-dichloro-benzyl)-methyl-amide

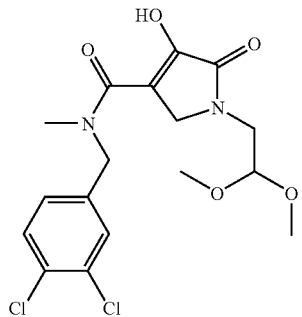

To a solution of 2-aminoacetaldehyde dimethylacetal (0.526 g mL, 5.0 mmol) and paraformaldehyde 90.15 g, 5 mmol) in MeOH (10 mL) at 55° C. was added N-(3,4-dichloro-benzyl)-2-(2,2-dimethyl-5-oxo-[1,3]dioxolan-4-ylidene)-N-methyl-acetamide (1.715 g, 5.0 mmol). After 45 min, the reaction mixture was cooled and purified by preparative HPLC on a C18 reverse phase column using acetonitrile (40–50%)/water (0.1% TFA) as eluent. The fractions containing the desired product were combined, concentrated and lyophilized to yield the title compound as an amber oil (0.68 g, 34% yield). $^1$H NMR (300 MHz, CDCl$_3$) δ: 10.81 (bs, 1H), 7.42 (d, 1H, J=8.1), 7.35 (d, 1H, J=1.8), 7.10 (dd, 1H, J=8.1, J=1.8), 4.59 (s, 2H), 4.47 (t, 1H, J=5.1), 4.27 (s, 2H), 3.59 (d, 2H, J=5.1), 3.38 (s, 6H), 3.02 (s, 3H). HRMS (M+Na) calcd for C$_{17}$H$_{20}$N$_2$Cl$_2$O$_5$Na: 425.0647. found: 425.0647.

Compound 747: 4-Hydroxy-5-oxo-1-[2-(4-pyridin-4-yl-piperazine-1-yl)-ethyl]-2,5-dihydro-1H-pyrrole-3-carboxylic acid (3,4-dichloro-benzyl)-methyl-amide

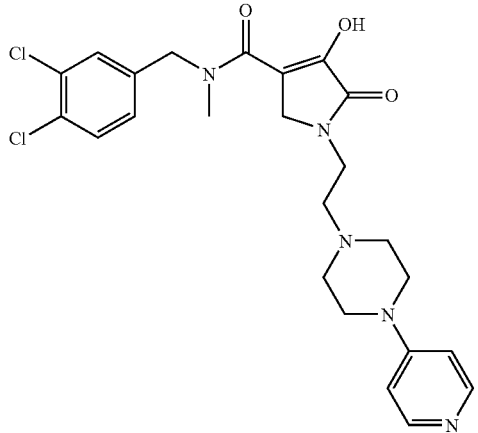

A solution of 1-(2,2-dimethoxy-ethyl)-4-hydroxy-5-oxo-2,5-dihydro-1H-pyrrole-3-carboxylic acid (3,4-dichloro-benzyl)-methyl-amide (0.29 g, 0.71 mmol) in acetonitrile/ water (10 mL, 2.5:1) was stirred with trifluoroacetic acid (1 mL) overnight at room temp. The mixture was concentrated then dissolved in MeOH (3 mL). 1-(4-pyridyl)-piperazine (0.42 g, 2.6 mmol) was added and the resulting mixture was stirred at room temp 30 min. Sodium cyanoborohydride (0.013 g, 0.2 mmol) was added and the mixture was stirred an additional 5 h at room temp. The crude product was purified by preparative HPLC (YMC Combiprep ODS-A, 30 mm×50 mm, MeOH/H2O/0.1% TFA) to yield the title compound as an amber foam (0.0042 g, 12% yield). HRMS (M+H) calcd for C$_{24}$H$_{28}$N$_5$Cl$_2$O$_3$: 504.15693; found: 504.1564.

Compound 748: 1-{2-[4-(4-Fluoro-phenyl)piperazine-1-yl]-ethyl}-4-hydroxy-5-oxo-2,5-dihydro-1H-pyrrole-3-carboxylic acid (3,4-dichloro-benzyl)-methyl-amide

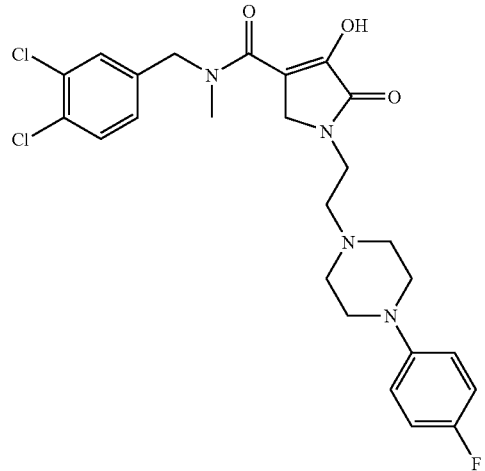

Compound 748 was prepared from 1-(2,2-dimethoxy-ethyl)-4-hydroxy-5-oxo-2,5-dihydro-1H-pyrrole-3-carboxylic acid (3,4-dichloro-benzyl)-methyl-amide and 1-(4-fluoro-phenyl)-piperazine using the method described for compound 747. The title compound was isolated as an amber foam (0.009 g, 25% yield). HRMS (M+H) calcd for C$_{24}$H$_{28}$N$_4$Cl$_2$O$_3$F: 521.15226. found: 521.1531.

Compound 749: 1-[2-(4-Benzo[1,3]dioxol-5-ylmethyl-piperazin-1-yl)-ethyl]-4-hydroxy-5-oxo-2,5-dihydro-1H-pyrrole-3-carboxylic acid (3,4-dichloro-benzyl)-methyl-amide

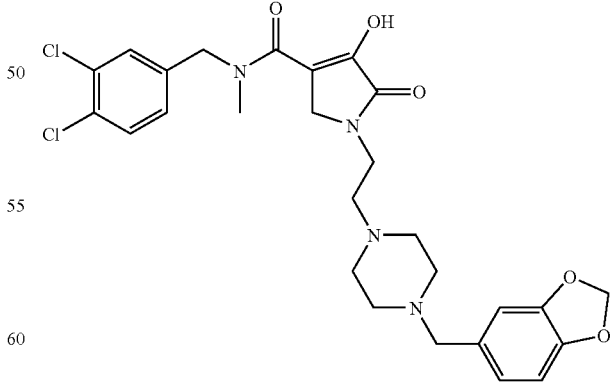

Compound 749 was prepared from 1-(2,2-dimethoxy-ethyl)-4-hydroxy-5-oxo-2,5-dihydro-1H-pyrrole-3-carboxylic acid (3,4-dichloro-benzyl)-methyl-amide and 1-benzo[1,3]dioxol-5-ylmethyl-piperazine using the method described for compound 747. The title compound was isolated as a white solid (0.0068 g, 17% yield). HRMS (M+H) calcd for $C_{27}H_{31}N_4Cl_2O_5$: 561.16716. found: 561.1674.

Compound 750: 1-[2-(2,6-Dimethyl-morpholin-4-yl)-ethyl]-4-hydroxy-5-oxo-2,5-dihydro-1H-pyrrole-3-carboxylic acid (3,4-dichloro-benzyl)-methyl-amide

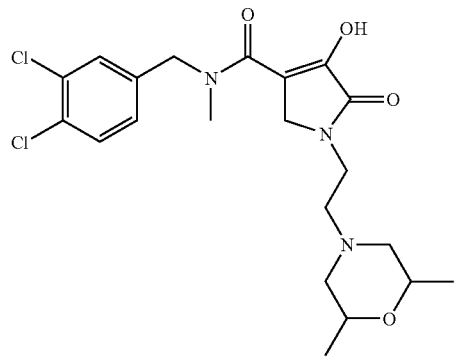

Compound 750 was prepared from 1-(2,2-dimethoxy-ethyl)-4-hydroxy-5-oxo-2,5-dihydro-1H-pyrrole-3-carboxylic acid (3,4-dichloro-benzyl)-methyl-amide and 2,6-dimethyl-morpholine using the method described for compound 747. The title compound was isolated as a pale yellow powder (0.014 g, 14% yield). HRMS (M+H) calcd for $C_{21}H_{28}N_3Cl_2O_4$: 456.14570. found: 456.1472.

EXAMPLE 83

Method for the Preparation of Compounds 751–758

The general method for the synthesis of compounds 751–758 is outlined in Scheme XI.

Compound 751: 1-(3-Dimethylcarbamoyl-propyl)-4-hydroxy-5-oxo-2,5-dihydro-1H-pyrrole-3-carboxylic acid (3,4-dichloro-benzyl)-methyl-amide

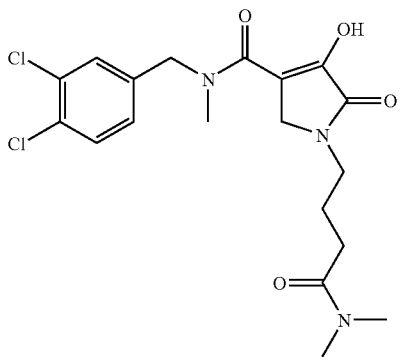

To a solution of 4-{4-[(3,4-dichloro-benzyl)-methyl-carbamoyl]-3-hydroxy-2-oxo-2,5-dihydro-pyrrol-1-yl}-butyric acid, Compound 24, (0.06 g, 0.15 mmol) in dichloromethane (1 mL) was added EDC (0.057 g, 0.3 mmol), HOBT (0.0020 g, 0.015 mmol) and dimethyl amine (0.15 mL, 2 M solution in THF, 0.30 mmol). The mixture was stirred at room temp for 6 h then concentrated and the crude product purified by preparative HPLC (YMC Combiprep ODS-A, 30 mm×50 mm, MeOH/H2O/0.1% TFA) to yield the title compound as an amber oil (0.0147 g, 23% yield). HRMS (M+H) calcd for $C_{19}H_{24}N_3Cl_2O_4$: 428.11440. found: 428.1143.

Compound 752: 4-Hydroxy-1-(4-morpholin-4-yl-4-oxo-butyl)-oxo-2,5-dihydro-1H-pyrrole-3-carboxylic acid (3,4-dichloro-benzyl)-methyl-amide

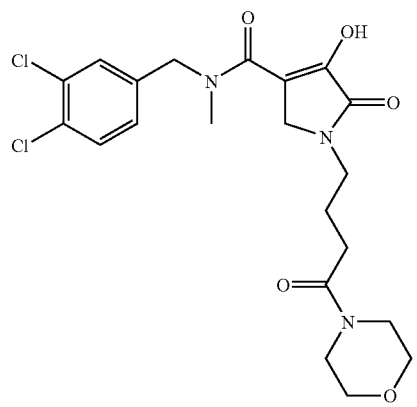

Compound 752 was prepared from 4-{4-[(3,4-dichloro-benzyl)-methyl-carbamoyl]-3-hydroxy-2-oxo-2,5-dihydro-pyrrol-1-yl}-butyric acid and morpholine using the method described for compound 751. The title compound was isolated as an amber oil (0.0148 g, 21% yield). HRMS (M+H) calcd for $C_{21}H_{26}N_3Cl_2O_5$: 470.12496. found: 470.1256.

Compound 753: 4-Hydroxy-1-[4-(4-methyl-piperazin-1-yl)-4-oxo-butyl]-5-oxo-2,5-dihydro-1H-pyrrole-3-carboxylic acid (3,4-dichloro-benzyl)-methyl-amide

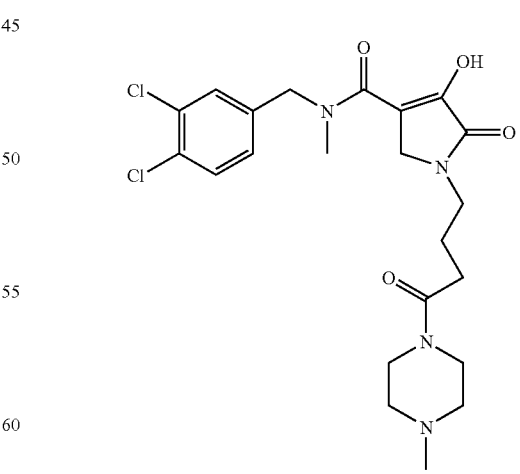

Compound 753 was prepared from 4-{4-[(3,4-dichloro-benzyl)-methyl-carbamoyl]-3-hydroxy-2-oxo-2,5-dihydro-pyrrol-1-yl}-butyric acid and 4-methyl-piperazine using the method described for compound 751. The title compound was isolated as a white powder (0.0508 g, 42% yield). HRMS (M+H) calcd for $C_{22}H_{29}N_4Cl_2O_4$: 483.1566. found: 483.1581.

Compound 754: 4-Hydroxy-1-(3-methylcarbamoyl-propyl)-5-oxo-2,5-dihydro-1H-pyrrole-3-carboxylic acid (3,4-dichloro-benzyl)-methyl-amide

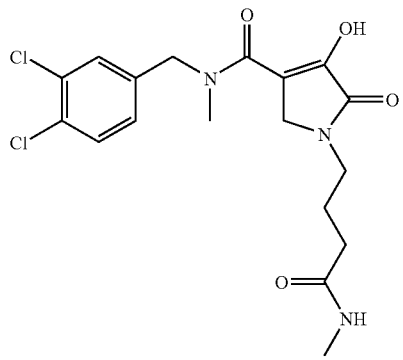

Compound 754 was prepared from 4-{4-[(3,4-dichloro-benzyl)-methyl-carbamoyl]-3-hydroxy-2-oxo-2,5-dihydro-pyrrol-1-yl}-butyric acid and methylamine using the method described for compound 751. The title compound was isolated as a white powder (0.0192 g, 18% yield). HRMS (M+H) calcd for $C_{18}H_{22}N_3Cl_2O_4$: 414.09875. found: 414.0969.

Compound 755: 4-Hydroxy-1-(4-methanesulfony-lamino-4-oxo-butyl)-5-oxo-2,5-dihydro-1H-pyrrole-3-carboxylic acid (3,4-dichloro-benzyl)-methyl-amide

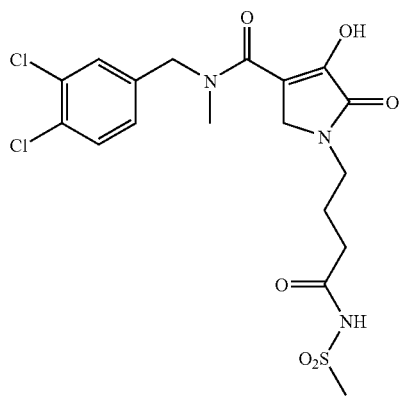

Compound 755 was prepared from 4-{4-[(3,4-dichloro-benzyl)-methyl-carbamoyl]-3-hydroxy-2-oxo-2,5-dihydro-pyrrol-1-yl}-butyric acid and methane sulfonamide using the method described for compound 751. The title compound was purified by preparative HPLC (C18, ODS-A, S-75 μm, 30%–40% acetonitrile/water/0.5% TFA) and iso-lated as a white powder (0.0158 g, 13% yield). HRMS (M−H) calcd for $C_{18}H_{20}N_3Cl_2O_6S$: 476.04499; found: 476.0431.

Compound 756: 1-[4-(3,5-Dimethyl-isoxazole-4-sulfonylamino)-4-oxo-butyl]-4-hydroxy-5-oxo-2,5-dihydro-1H-pyrrole-3-carboxylic acid (3,4-dichloro-benzyl)-methyl-amide

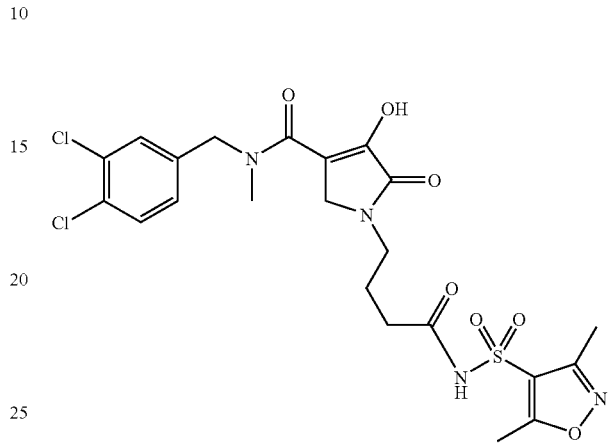

Compound 756 was prepared from 4-{4-[(3,4-dichloro-benzyl)-methyl-carbamoyl]-3-hydroxy-2-oxo-2,5-dihydro-pyrrol-1-yl}-butyric acid and 3,5-dimethyl-isoxazole-4-sulfonic acid amide using the method described for compound 751. The title compound was purified by preparative HPLC (C18, ODS-A, S-75 μm, 40% acetonitrile/water/0.5% TFA) and isolated as a white powder (0.0296 g, 21% yield). HRMS (M−H) calcd for $C_{22}H_{23}N_4Cl_2O_7S$: 557.06645. found: 557.0663.

Compound 757: 4-Hydroxy-5-oxo-1-[4-oxo-4-(1-phenyl-cyclopropanesulfonylamino)-butyl]-2,5-dihydro-1H-pyrrole-3-carboxylic acid (3,4-dichloro-benzyl)-methyl-amide

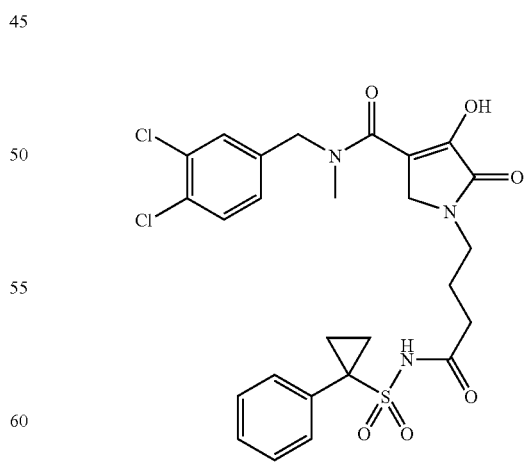

Compound 757 was prepared from 4-{4-[(3,4-dichloro-benzyl)-methyl-carbamoyl]-3-hydroxy-2-oxo-2,5-dihydro-pyrrol-1-yl}-butyric acid and 1-phenyl-cyclopropanesulfonic acid amide using the method described for compound 751. The title compound was purified by preparative HPLC (C18, ODS-A, S-75 μm, 50% acetonitrile/water/0.5% TFA) and isolated as a white powder (0.0026 g, 3% yield). HRMS (M−H) calcd for $C_{26}H_{30}N_3Cl_2O_6S$: 582.12324. found: 582.1215.

Compound 758: 4-Hydroxy-1-(2-morpholin-4-yl-2-oxo-ethyl)-5-oxo-2,5-dihydro-1H-pyrrole-3-carboxylic acid (3,4-dichloro-benzyl)-methyl-amide

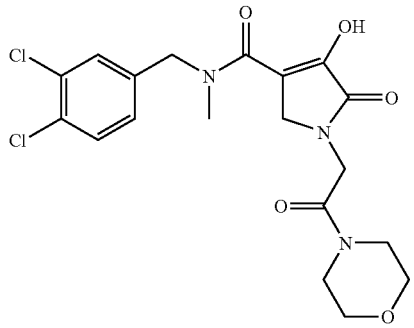

Compound 758 was prepared from {4-[(3,4-dichloro-benzyl)-methyl-carbamoyl]-3-hydroxy-2-oxo-2,5-dihydro-pyrrol-1-yl}-acetic acid, Compound 20, and morpholine using the method described for compound 751. The title compound was isolated as a white powder (0.0088 g, 20% yield). HRMS (M+H) calcd for $C_{19}H_{22}N_3Cl_2O_5$: 442.09366. found: 442.0951.

EXAMPLE 84

Method for the Preparation of Compounds 759–765

The general method for the synthesis of compounds 759–765 is outlined in Scheme XII.

Compound 84-A: 4-Hydroxy-5-oxo-1-(2-piperazin-1-yl-ethyl)-2,5-dihydro-1H-pyrrole-3-carboxylic acid (3,4-dichloro-benzyl)-methyl-amide

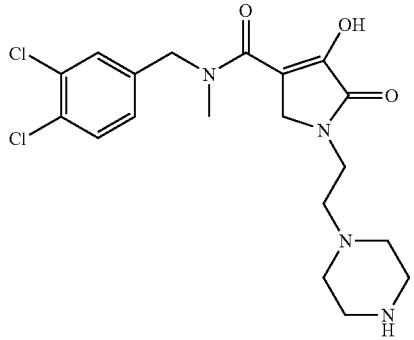

Compound 84-A was prepared from N-(3,4-dichloro-benzyl)-2-(2,2-dimethyl-5-oxo-[1,3]dioxolan-4-ylidene)-N-methyl-acetamide and 2-piperazin-1-yl-ethylamine using the method described for compound 37. The title compound was isolated as a white solid (0.183 g, 86% yield). HRMS (M+H) calcd for $C_{19}H_{25}N_3Cl_2O_4$: 427.13038. found: 427.1307.

Compound 759: 1-[2-(4-Benzoyl-piperazin-1-yl)-ethyl]-4-hydroxy-5-oxo-2,5-dihydro-1H-pyrrole-3-carboxylic acid (3,4-dichloro-benzyl)-methyl-amide

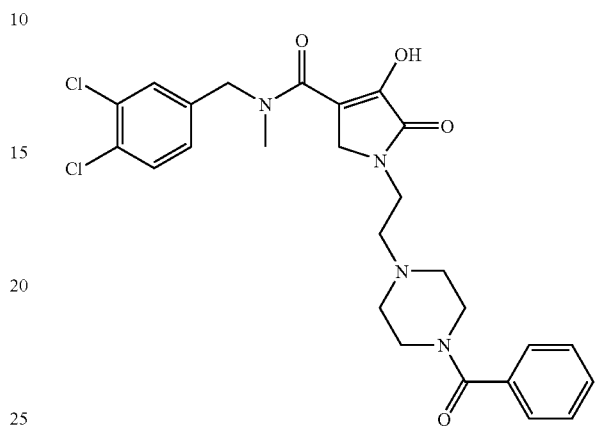

To a solution of benzoyl chloride (0.023 mL, 0.23 mmol) in dichloromethane (1 mL) cooled to 0° C. was added dropwise a solution of 4-hydroxy-5-oxo-1-(2-piperazin-1-yl-ethyl)-2,5-dihydro-1H-pyrrole-3-carboxylic acid (3,4-dichloro-benzyl)-methyl-amide (0.10 g, 0.20 mmol) in pyridine/dichloromethane (4 mL, 1:1). The resulting mixture was stirred at room temp 18 h and quenched with 1N HCl. The organic phase was washed with 1N HCl (3 times). The aqueous washings were combined and purified by preparative HPLC (C18, ODS-A, S-75 μm, 30% acetonitrile/water/0.5% TFA) to give the title compound as a white powder (0.0215 g, 20% yield). HRMS (M+H) calcd for $C_{26}H_{29}N_4Cl_2O_4$: 531.1566; found: 531.1563.

Compound 760: 1-{2-[4-(4-Fluoro-benzoyl)-piperazin-1-yl]-ethyl}-4-hydroxy-5-oxo-2,5-dihydro-1H-pyrrole-3-carboxylic acid (3,4-dichloro-benzyl)-methyl-amide

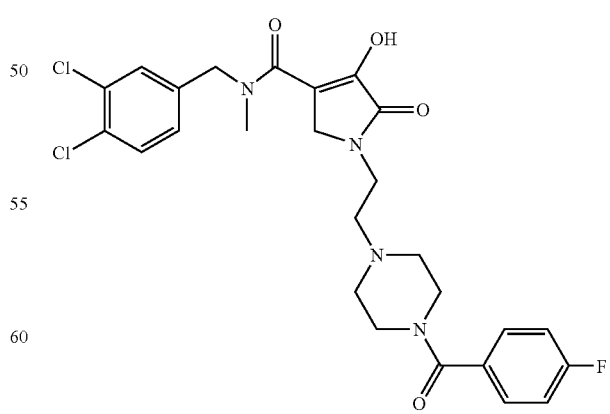

Compound 760 was prepared from 4-hydroxy-5-oxo-1-(2-piperazin-1-yl-ethyl)-2,5-dihydro-1H-pyrrole-3-carboxylic acid (3,4-dichloro-benzyl)-methyl-amide and 4-fluoro-benzoyl chloride using the method described for compound 759. The title compound was purified by preparative HPLC (C18, ODS-A, S-75 μm, 30% acetonitrile/water/0.5% TFA) and isolated as a white powder (0.0098 g, 2% yield). HRMS (M−H) calcd for $C_{26}H_{26}N_4Cl_2O_4F$: 547.13151. found: 547.1310.

Compound 761: 4-Hydroxy-1-{2-[4-(4-methyl-benzoyl)-piperazin-1-yl]-ethyl}-5-oxo-2,5-dihydro-1H-pyrrole-3 carboxylic acid (3,4-dichloro-benxyl)-methyl-amide

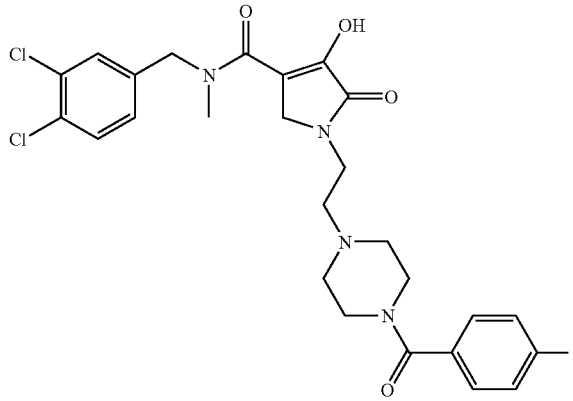

Compound 761 was prepared from 4-hydroxy-5-oxo-1-(2-piperazin-1-yl-ethyl)-2,5-dihydro-1H-pyrrole-3-carboxylic acid (3,4-dichloro-benzyl)-methyl-amide and 4-methyl-benzoyl chloride using the method described for compound 759. The title compound was purified by preparative HPLC (C18, ODS-A, S-75 μm, 30%–40% acetonitrile/water/0.5% TFA) and isolated as a white powder (0.0210 g, 17% yield). HRMS (M+H) calcd for $C_{27}H_{31}N_4Cl_2O_4$: 545.17225. found: 545.1720.

Compound 762: 4-Hydroxy-5-oxo-1-{2-[4-(pyridine-2-carbonyl)-piperazin-1-yl]-ethyl}-2,5-dihydro-1H-pyrrole-3-carboxylic acid (3,4-dichloro-benzyl)-methyl-amide

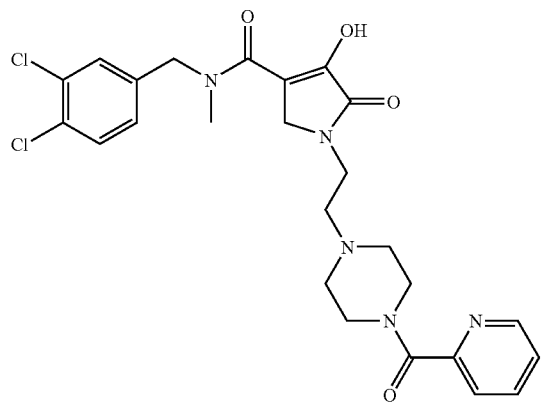

Compound 762 was prepared from 4-hydroxy-5-oxo-1-(2-piperazin-1-yl-ethyl)-2,5-dihydro-1H-pyrrole-3-carboxylic acid (3,4-dichloro-benzyl)-methyl-amide and pyridine-2-carbonyl chloride using the method described for compound 759. The title compound was purified by preparative HPLC (C18, ODS-A, S-75 μm, 10%-20%-30% acetonitrile/water/0.5% HCl) and isolated as a brown solid (0.0476 g, 39% yield). HRMS (M+H) calcd for $C_{25}H_{28}N_4Cl_2O_5$: 532.15184. found: 532.1514.

Compound 763: 4-Hydroxy-1-{2-[4-(isoxazole-5-carbonyl)-piperazin-1-yl]-ethyl}-5-oxo-2,5-dihydro-1H-pyrrole-3-carboxylic acid (3,4-dichloro-benzyl)-methyl-amide

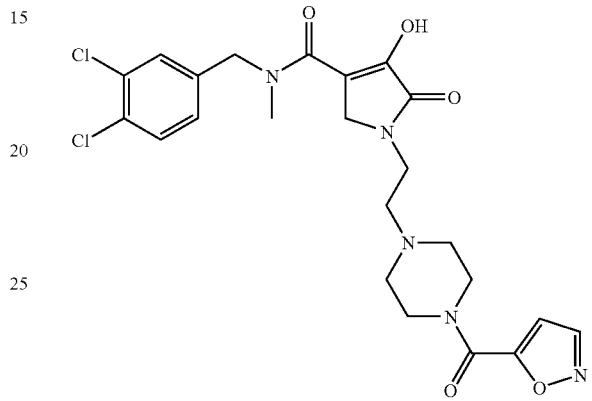

Compound 763 was prepared from 4-hydroxy-5-oxo-1-(2-piperazin-1-yl-ethyl)-2,5-dihydro-1H-pyrrole-3-carboxylic acid (3,4-dichloro-benzyl)-methyl-amide and isoxazole-5-carbonyl chloride using the method described for compound 759. The title compound was purified by preparative HPLC (C18, ODS-A, S-75 μm, 10%–20%–30% acetonitrile/water/0.5% HCl) and isolated as a brown solid (0.0268 g, 22% yield). HRMS (M+H) calcd for $C_{23}H_{26}N_5Cl_2O_5$: 522.13111. found: 522.1312.

Compound 764: 4-Hydroxy-1-[2-(4-methanesulfonyl-piperazin-1-yl)-ethyl]-5-oxo-2,5-dihydro-1H-pyrrole-3-carboxylic acid (3,4-dichloro-benzyl)-methyl-amide

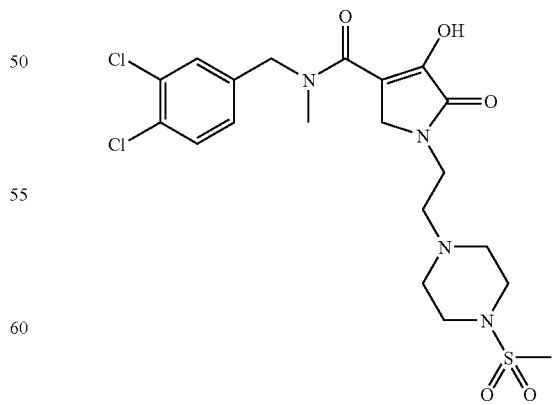

Compound 764 was prepared from 4-hydroxy-5-oxo-1-(2-piperazin-1-yl-ethyl)-2,5-dihydro-1H-pyrrole-3-carboxylic acid (3,4-dichloro-benzyl)-methyl-amide and methanesulfonyl chloride using the method described for compound 759. The title compound was purified by preparative HPLC (C18, ODS-A, S-75 μm, 10%–20%–30% acetonitrile/water/0.5% HCl) and isolated as a brown solid (0.0140 g, 12% yield). HRMS (M+H) calcd for $C_{20}H_{27}N_4Cl_2O_5S$: 505.10793. found: 505.1095.

Compound 765: 1-[2-(4-Dimethylsulfamoyl-piperazin-1-yl)-ethyl]-4-hydroxy-5-oxo-2,5-dihydro-1H-pyrrole-3-carboxylic acid (3,4-dichloro-benzyl)-methyl-amide

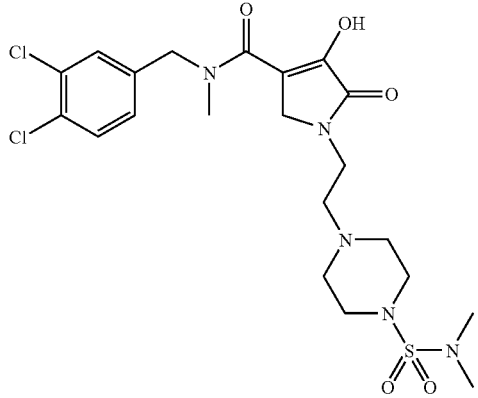

Compound 765 was prepared from 4-hydroxy-5-oxo-1-(2-piperazin-1-yl-ethyl)-2,5-dihydro-1H-pyrrole-3-carboxylic acid (3,4-dichloro-benzyl)-methyl-amide and dimethylsulfamoyl chloride using the method described for compound 759. The title compound was purified by preparative HPLC (C18, ODS-A, S-75 μm, 30% acetonitrile/water/0.5% HCl) and isolated as a brown solid (0.0231 g, 19% yield). HRMS (M+H) calcd for $C_{21}H_{30}N_5Cl_2O_5S$: 534.13448. found: 534.1322.

EXAMPLE 85

Compound 766: 4-Hydroxy-5-oxo-1-[2-(4-oxy-morpholin-4-yl)-ethyl]-2,5-dihydro-1H-pyrrole-3-carboxylic acid (3,4-dichloro-benzyl)-methyl-amide

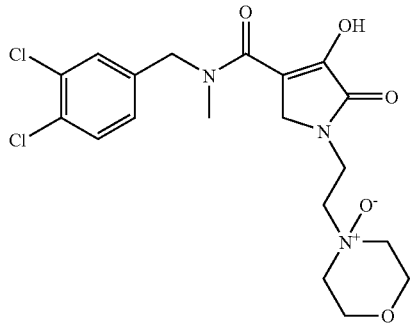

To a solution of 4-hydroxy-1-(2-morpholin-4-yl-ethyl)-5-oxo-2,5-dihydro-1H-pyrrole-3-carboxylic acid (3,4-dichloro-benzyl)-methyl-amide (0.069 g, 0.16 mmol) in dichloromethane (1 mL), was added meta-chloro-peroxybenzoic acid (MCPBA) (0.036 g, 0.21 mmol). The mixture was stirred for 24 h then concentrated. Purification using preparative HPLC (C18, ODS-A, S-75 μm, 30% acetonitrile/water/0.5% HCl) gave the title compound as a white solid (0.03 g, 94% yield). HRMS (M+H) calcd for $C_{19}H_{24}N_3Cl_2O_5$: 444.10931. found: 444.1073.

EXAMPLE 86

Method for the Preparation of Compounds 767–777

The general method for the preparation of compounds 767–777 is outlined in Scheme XIII.

Compound 86-A: 2-Methyleneamino-ethanol

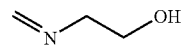

2-Aminoethanol (0.061 g, 1.0 mmol) and paraformaldehyde (0.03 g, 1.0 mmol) were stirred in methanol (10 mL) at 55° C. until the solids dissolved (approximately 20 min). The solution was cooled and used without further purification Compound 767: 4-Hydroxy-1-(2-hydroxy-ethyl)-5-oxo-2,5 dihydro-1H-pyrrole-3-carboxylic acid (3,4-dichloro-benzyl)-methyl-amide

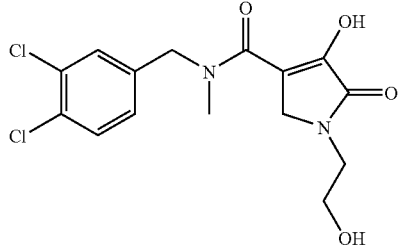

To a solution of 2-methyleneamino-ethanol (1 mL, 0.1 mmol) in MeOH (1 mL) was added N-(3,4-dichloro-benzyl)-2-(2,2-dimethyl-5-oxo-[1,3]dioxolan-4-ylidene)-N-methyl-acetamide (0.036 g, 0.1 mmol). The mixture was stirred at 55° C. for 1 h, cooled and purified by preparative HPLC (YMC Combiprep ODS-A, 30 mm×50 mm, MeOH/H2O/0.1% TFA). The title compound was isolated as a white foam (0.018 g, 49% yield). HRMS (M–H) calcd for $C_{15}H_{15}N_2Cl_2O_4$: 357.04089. found: 357.0396.

Compound 768: 4-Hydroxy-1-[1-hydroxymethyl-2-(1H-indol-3-yl)-ethyl]-5-oxo-2,5-dihydro-1H-pyrrole-3-carboxylic acid (3,4-dichloro-benzyl)-methyl-amide

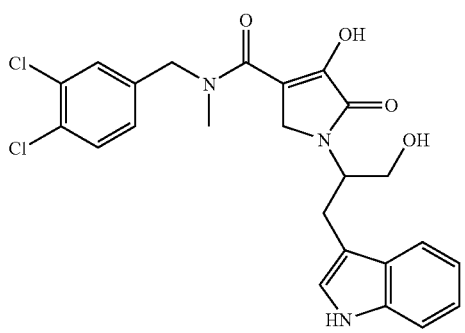

Compound 768 was prepared from N-(3,4-dichloro-benzyl)-2-(2,2-dimethyl-5-oxo-[1,3]dioxolan-4-ylidene)-N-methyl-acetamide, paraformaldehyde and 2-amino-3-(1H-indol-3-yl)-propan-1-ol according to the procedures described for compound 86-A and compound 767. The title compound was isolated as a yellow solid (0.0038 g, 8% yield). ¹HNMR (300 MHz, CDCl₃) δ: 7.52 (1H, d, J=8.05 Hz), 7.36–7.29 (3H, m), 7.14–6.98 (4H, m), 4.46 (2H, s), 4.40–4.36 (1H, m), 3.99 (2H, s), 3.81–3.78 (2H, m), 3.11–3.08 (3H, m), 2.85 (3H, s).

Compounds 769–777

As illustrated in Scheme XII, compounds 769–777 were prepared from N-(3,4-chloro-benzyl)-2-(2,2-dimethyl-5-oxo-[1,3]dioxolan-4-ylidene)-N-methyl-acetamide, paraformaldehyde and an amine, I-7, according to the procedures described for compound 86-A and compound 767.

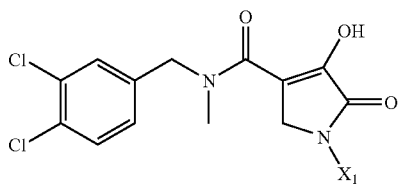

| Compound | X1 | LC/MS Retention time (min) | MS calcd (M + H) | MS found |
|---|---|---|---|---|
| 769 | 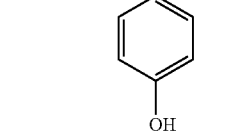 | 1.5 | 451.3 | 433.3 |
| 770 | 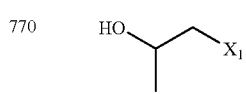 | 1.4 | 373.2 | 373.3 |
| 771 | 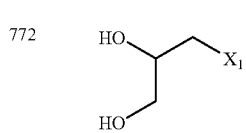 | 1.6 | 401.3 | 401.3 |
| 772 | 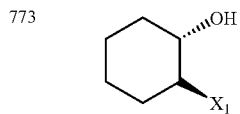 | 1.4 | 389.2 | 389.3 |
| 773 | 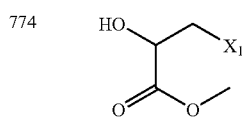 | 1.6 | 413.3 | 413.3 |
| 774 | 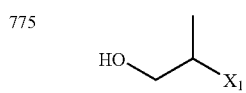 | 1.4 | 417.3 | 417.3 |
| 775 | | 1.4 | 373.2 | 373.3 |

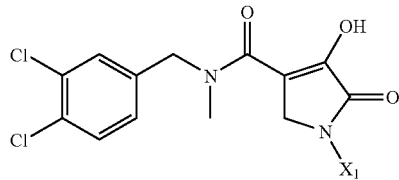

| Compound | X1 | LC/MS Retention time (min) | MS calcd (M + H) | MS found |
|---|---|---|---|---|
| 776 | | 1.3 | 389.2 | 389.3 |
| 777 | | 1.4 | 373.2 | 373.3 |

EXAMPLE 87

Method for the Preparation of Compounds 778–781

Compound 87-A: 2-(2,2-Dimethyl-5-oxo-[1,3]dioxolan-4-ylidene)-N-methyl-N-naphthalen-1-ylmethyl-acetamide

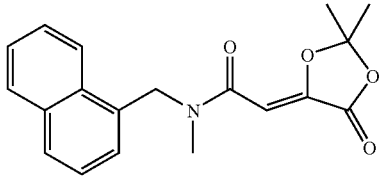

Reaction of (2,2-dimethyl-5-oxo-[1,3]dioxolan-4-ylidene)-acetyl chloride with methyl-naphthalen-1-yl-methyl-amine as described in the preparation of Compound 44-C gave the title amide as a, pale yellow oil (0.4931 g, 26% yield). ¹HNMR (300 MHz, CDCl₃) δ: 8.18 (0.6H, d), 7.88–7.80 (2.4H, m), 7.54–7.38 (4H, m), 6.17 (0.6H, s), 6.08 (0.4H, s), 5.13 (1.2H, s), 5.06 (0.8H, s), 3.08 (1.2H, s), 2.90 (1.8H, s), 1.73 (3.6H, s), 1.67 (2.4H, s).

Compound 87-B: 2-Hydroxy-3-(methyl-naphthalen-1-ylmethyl-carbamoyl-acrylic acid methyl ester

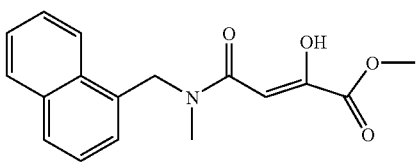

2-(2,2-Dimethyl-5-oxo-[1,3]dioxolan-4-ylidene)-N-methyl-N-naphthalen-1-ylmethyl-acetamide was treated with methanol as described in the preparation of Compound 44-D and gave the title ester as a colorless oil (0.04 g, 33% yield). ¹HNMR (300 MHz, CDCl₃) δ: 14.65 (1H, bs), 7.89–7.82

(3H, m), 7.57–7.20 (4H, m), 6.31 (0.6H, s), 6.21, (0.4H, s), 5.15 (1.2H, s), 5.07 (0.8H, s), 3.89 (1.8H, s), 3.80 (1.2H, s), 3.11 (1.2H, s), 2.94 (1.8H, s).

Compounds 778–781

2-Hydroxy-3-(methyl-naphthalen-1-ylmethyl-carbamoyl)-acrylic acid methyl ester was treated with paraformaldehyde and an amine according to the procedure described in the preparation of compound 12 to yield compounds 778–781.

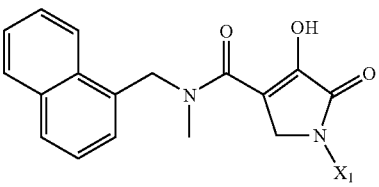

| Compound | X1 | LC/MS retention time (min) | MS calculated (M + H) | MS found |
|---|---|---|---|---|
| 778 | X₁⌒⌒ | 1.4 | 325.4 | 325.4 |
| 779 | X₁⌒⌒N(morpholine) | 1.1 | 410.5 | 410.4 |
| 780 | X₁⌒⌒OH | 1.3 | 341.4 | 341.4 |
| 781 | X₁⌒CH(OH)CH₂OH | 1.2 | 371.4 | 371.4 |

EXAMPLE 88

Compound 782: 4-[3-Hydroxy-4-(methyl-naphthalen-1-ylmethyl-carbamoyl)-2-oxo-2,5-dihydro-pyrrol-1-yl]-butyric acid

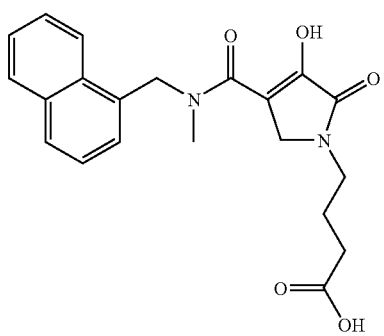

2-Hydroxy-3-(methyl-naphthalen-1-ylmethyl-carbamoyl)-acrylic acid methyl ester was treated with paraformaldehyde and 4-amino-butyric acid according to the procedure described in the preparation of compound 12 to give the title compound as a white powder (0.0210 g, 55% yield). ¹HNMR (300 MHz, CDCl₃) δ: 7.93–7.81 (2H, m), 7.55–7.42 (4H, m), 7.42–7.28 (1H, m), 5.13 (2H, s), 4.14 (2H, s), 3.52–3.50 (2H, m), 2.36–2.29 (2H, m), 1.90–1.87 (2H, m).

EXAMPLE 89

Method for the Preparation of Compounds 783–791

The general method for the preparation of compounds 783–791 is illustrated in Scheme XV.

Compound 89-A: (4-Fluoro-2-methylsulfanyl-benzyl)-methyl-amine

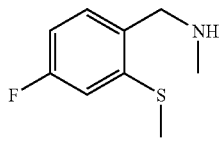

A suspension of 2,4-difluorobenzaldehyde (16 mL, 146 mmol) and sodium thiomethoxide (14 g, 200 mmol) in toluene (200 mL) was stirred at 80° C. for 7 h and 14 h at room temperature. The reaction mixture was diluted with ether (300 mL), washed with water (100 mL), saturated aqueous NaHCO3 (100 mL) and brine (50 mL). The aqueous layers were combined and extracted with ether (2×100 mL). The organic layers were combined and dried over anhydrous Na₂SO₄, filtered and concentrated to give a viscous oil. This viscous oil was dissolved in ether/hexanes (1:1, v/v) and slowly concentrated on under vacuum. The precipitated white solid was separated by filtration and dried to give 2-methylthio-4-fluorobenzaldehyde (18.7 g, 75% yield). ¹HNMR (500 MHz, CDCl₃) δ: 10.11 (1H, s), 7.78 (1H, dd, J=8.55, 6.11 Hz), 6.97 (1H, dd, J=10.07, 2.44 Hz), 6.91 (1H, td, J=8.54, 2.44 Hz), 2.45 (3H, s). MS calcd for C₈H₇FOS (M+H): 171.2. found: 171.6.

A solution of 2-methylthio-4-fluorobenzaldehyde (2.04 g, 12 mmol) and 2M methylamine in methanol (24 mL, 48 mmol) was stirred at room temperature for 2 h. To this was added a solution of ZnCl₂ (0.818 g, 6 mmol) and NaCNBH₃ (0.754 g, 12 mmol) in methanol (30 mL). After stirring for 20 h, the reaction mixture was concentrated and the resulting residue was taken up in aqueous NaOH (0.5 M, 20 mL), extracted with CH₂Cl₂ (5×50 mL). The combined organic layers were concentrated and the resulting residue was taken up in 1N HCl (25 mL). This solution was extracted with ethyl acetate (3×25 mL). The organic layers were discarded and aqueous layer was brought to pH 9 by adding Na₂CO₃ and extracted with CH₂Cl₂ (3×50 mL). The combined CH₂Cl₂ layers were dried over MgSO₄, filtered and concentrated to give the desired benzylamine as a viscous pale yellow oil (1.4 g, 60% pure).

Compound 89-B: 2-(2,2-Dimethyl-5-oxo-[1,3]diox-olan-4-ylidene)-N-(4-fluoro-2-methylsulfanyl-ben-zyl)-N-methyl-acetamide

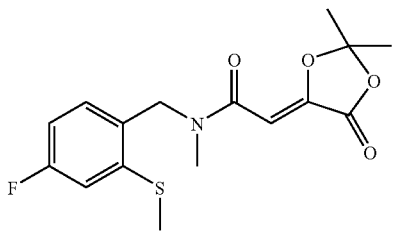

To a stirred solution of (4-fluoro-2-methylsulfanyl-benzyl)-methyl-amine (1.3 g) and diisopropylethylamine (1.74 mL, 10 mmol) in CH$_2$Cl$_2$ (60 mL) was added (2,2-dimethyl-5-oxo-[1,3]dioxolan-4-ylidene)-acetyl chloride (1.1 g, 6 mmol). After 1 h, the reaction mixture was concentrated and the resulting residue was taken up in ether (100 mL), washed with 1N HCl (10 mL) and brine (10 mL). The organic layer was dried over anhydrous Na$_2$SO$_4$, filtered and concentrated to give a viscous yellow oil. Flash chromatography on a silica gel column with 3:2 hexanes/EtOAc followed by 2:3 hexanes/EtOAc gave the desired product as a 1:1 mixture of E and Z isomers 1.8123 g, 89% yield). $^1$HNMR (500 MHz, CDCl$_3$) δ: 7.17 (0.5H, dd, J=8.54, 6.11 Hz), 7.00 (0.5H, dd, J=8.55, 5.8 Hz), 6.94–6.89 (1H, m), 6.83–6.77 (1H, m), 6.17 (0.5H, s), 6.04 (0.5H, s), 4.68 (1H, s), 4.51 (1H, s), 2.98 (1.5H, s), 2.97 (1.5H, s), 2.48 (1.5H, s), 2.45 (1.5H, s), 1.72 (3H, s), 1.67 (3H, s). MS calcd for C$_{16}$H$_{19}$FNO$_4$S (M+H): 340.1. found: 340.3.

Compound 89-C: 2-(2,2-Dimethyl-5-oxo-[1,2]diox-olan-4-ylidene)-N-(4-fluoro-2-methanesulfinyl-ben-zyl)-N-methoxy-acetamide

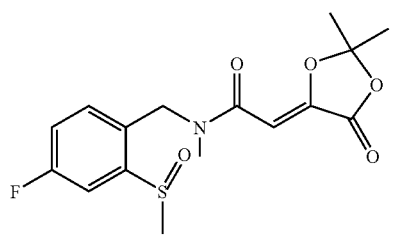

To a stirred solution of 4-fluoro-2-methylsulfanylbenzaldehyde (9.7 g, 57 mmol) in CH$_2$Cl$_2$ (300 mL) was added in small portions m-chloroperbenzoic acid (60%, 20.71 g, 120 mmol) over 20 minutes. After 24 h, mL of dimethylsulfoxide followed by saturated NaHCO$_3$ (100 mL) was added and stirred for additional 2 h. The organic layer separated and washed with saturated NaHCO$_3$ (2×100 mL). The combined aqueous layers were saturated with NaCl and extracted with CH$_2$Cl$_2$ (2×100 mL). The combined organic phases were dried over anhydrous Na$_2$SO$_4$, filtered and concentrated to give a viscous yellow oil. This residue was purified by flash chromatography on a silica gel column using hexanes/ether/ethyl acetate (gradient elution). The fractions containing the desired product are combined and concentrated to give 4-fluoro-2-methylsulfonylbenzaldehyde (3.85 g, 33%) and 4-fluoro-2-methylsulfinylbenzaldehyde (5.61 g, 53% yield) as a white solid. 4-fluoro-2-methylsulfonylbenzaldehyde: $^1$HNMR (500 MHz, CDCl$_3$) δ: 10.41 (1H, s), 8.08–8.06 (1H, M), 7.85–7.71 (2H, m), 3.09 (3H, s). HRMS calcd for C$_8$H$_6$FO$_3$S (M–H): 201.0022. found: 201.0025. 4-fluoro-2-methylsulfinyl-benzaldehyde: $^1$HNMR (500 MHz, CDCl$_3$) δ: 9.97 (1H, s), 8.07–8.05 (1H, M), 7.99–7.94 (1H, m), 7.36–7.33 (1H, m), 2.80 (3H, s). MS calcd for C$_8$H$_8$FO$_2$S (M+H): 187.02. found: 187.02.

To a stirred solution of 4-fluoro-2-methylsulfinylbenzaldehyde (2.234 g, 12 mmol) in 2M methylamine in methanol (24 mL, 48 mmol) was added a solution of ZnCl$_2$ (0.818 g, 6 mmol) and NaCNBH$_3$ (0.754 g, 12 mmol) in methanol (30 mL). After stirring for 16 h an additional methyl amine (1 equiv) and NaCNBH$_3$ (1 equiv) every 24 h for 5 days. After seven days, the reaction mixture was concentrated and the resulting residue was taken up into aqueous NaOH (1 M, 100 mL), extracted with CH$_2$Cl$_2$ (5×50 mL). The combined organic layers were concentrated to give a yellow oil which was a mixture of aldehyde and the desired (4-Fluoro-2-methanesulfinyl-benzyl)-methyl-amine. This material was used in the next step without further purification.

To a stirred solution of above amine and diisopropylethylamine (1.75 mL, 10 mmol) in CH$_2$Cl$_2$ (30 mL) was added (2,2-dimethyl-5-oxo-[1,3]dioxolan-4-ylidene)-acetyl chloride (0.95 g, 5 mmol). After 1 h, the reaction mixture was concentrated and the resulting residue was taken up into ether (150 mL), washed with 1N HCl (10 mL), water (20 mL) and brine (20 mL). The organic layer was dried over anhydrous Na$_2$SO$_4$, filtered and concentrated to give a yellow residue which was purified by flash column chromatography on silica gel column using 1:1 v/v hexanes/ethyl acetate, ethyl acetate and 2–5% methanol/ethyl acetate. The fractions containing the compound were combined and concentrated to give the product (1.65 g, 93% yield based on acid chloride used). $^1$HNMR (500 MHz, CDCl$_3$) δ: 7.76–7.72 (1H, m), 7.28 (1H,dd, J=8.3, 5.0 Hz), 7.13 (1H, td, J=8.2, 2.7 Hz), 6.14 (1H, s), 4.88 (1H, d, J=15.3 Hz), 4.46 (1H, d, J=15.3 Hz), 3.03 (3H, s), 2.71 (3H, s), 1.72 (6H, s). LRMS calcd for C16H$_{19}$FNO$_5$S (M+H): 356.1. found: 356.3.

Compound 89-D: 2-(2,2-Dimethyl-5-oxo-[1,3]diox-olan-4-ylidene)-N-(4-fluoro-2-methanesulfonyl-ben-zyl)-N-methyl-acetamide

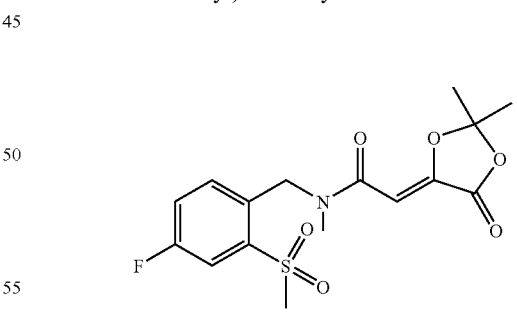

To a solution of 2-(2,2-Dimethyl-5-oxo-[1,3]dioxolan-4-ylidene)-N-(4-fluoro-2-methylsulfanyl-benzyl)-N-methyl-acetamide (0.5 g, 1.475 mmol) in CH$_2$Cl$_2$ (10 mL) was added 50% m-chloroperbenzoic acid (1.035 g, 3 mmol) and the resulting mixture stirred at room temperature for 4 h, then, taken up into EtOAc, washed successively with saturated NaHSO$_4$, saturated NaHCO$_3$ and brine. The organic layer was dried over anhydrous Na$_2$SO$_4$, filtered, concentrated and the residue purified on a silica gel column using hexanes/EtOAc (0–75%) to afford the desired product as a mixture of E/Z isomers (0.4977 g, 91%). ¹HNMR (300 MHz, CDCl₃) δ: 7.76 (1H, dd, J=8.2, 2.7 Hz), 7.38–7.27 (2H, m), 6.21 (0.8H, s), 5.93 (0.2H, s), 5.05 (1.6H, s), 5.01 (0.4H, s), 3.19 (2.4H, s), 3.16 (2.4H, s), 3.11 (0.6H, s), 3.03 (0.6H, s), 1.72 (4.8H, s), 1.69 (1.2H, s). LRMS calcd for $C_{16}H_{19}FNO_6S$ (M+H): 372. found: 372.

Compound 783: 4-{4-[(4-Fluoro-2-methylsulfanyl-benzyl)-methyl-carbamoyl]-3-hydroxy-2-oxo-2,5-dihydro-pyrrol-1-yl}-butyric acid

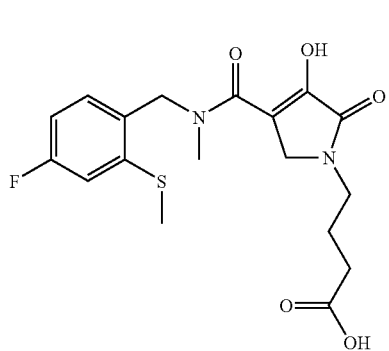

2-(2,2-Dimethyl-5-oxo-[1,3]dioxolan-4-ylidene)-N-(4-fluoro-2-methylsulfanyl-benzyl)-N-methyl-acetamide was reacted with paraformaldehyde and 4-amino-butyric acid as described in Method 44B to give the title compound as a white solid (0.05 g, 49% yield). ¹HNMR (300 MHz, CDCl₃) δ: 7.11 (1H, dd, J=8.42, 5.85 Hz), 6.91 (1H, dd, J=9.52, 2.57 Hz), 6.82 (1H, td, J=8.41, 2.56 Hz), 4.64 (2H, s), 4.15 (2H, s), 3.55 (2H, t, J=6.96 Hz), 2.98 (3H, s), 2.47 (3H, s), 2.38 (2H, t, J=6.95 Hz), 1.96–1.88 (2H, m).

Compound 784: 4-{4-[(4-Fluoro-2-methanesulfinyl-benzyl)-methyl-carbamoyl]-3-hydroxy-2-oxo-2,5-dihydro-pyrrol-1-yl}-butyric acid

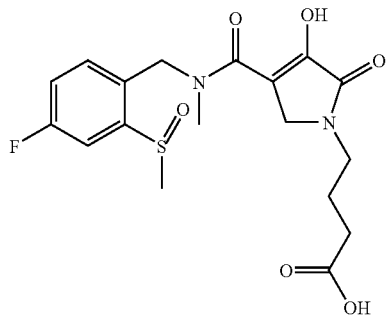

2-(2,2-Dimethyl-5-oxo-[1,3]dioxolan-4-ylidene)-N-(4-fluoro-2-methanesulfinyl-benzyl)-N-methyl-acetamide was reacted with paraformaldehyde and 4-amino-butyric acid as described in Method 44B to give the title compound as a colorless oil (0.015 g, 18% yield). ¹HNMR (300 MHz, CDCl₃) δ: 7.76 (1H, dd, J=8.05, 2.20 Hz), 7.34 (1H, dd, J=8.41, 5.12 Hz), 7.19 (1H, td, J=8.05, 2.56 Hz), 4.85 (2H, d, J=15.01 Hz), 4.18 (2H, s), 3.58 (2H, t, J=5.86), 3.01 (3H, s), 2.76 (3H, s), 2.39 (2H, t, J=5.86 Hz), 1.95 (2H, t, J=6.22 Hz).

Compound 785: 4-{4-[(4-Fluoro-2-methanesulfonyl-benzyl)-methyl-carbamoyl]-3-hydroxy-2-oxo-2,5-dihydro-pyrrol-1-yl}-butyric acid

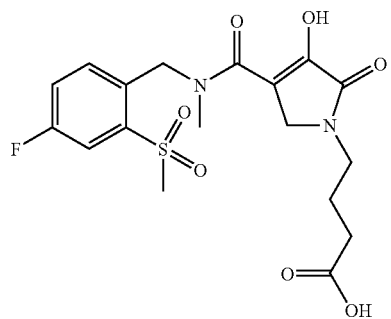

2-(2,2-Dimethyl-5-oxo-[1,3]dioxolan-4-ylidene)-N-(4-fluoro-2-methanesulfonyl-benzyl)-N-methyl-acetamide was reacted with paraformaldehyde and 4-amino-butyric acid as described in Method 44B to give the title compound as a colorless oil (0.01 g, 9% yield). ¹HNMR (300 MHz, CDCl₃) δ: 7.78 (1H, dd, J=8.06, 2.57 Hz), 7.43 (1H, dd, J=8.60, 4.94 Hz), 7.36–7.30 (1H, m), 5.08 (2H, s), 4.20 (2H, s), 3.58 (2H, t, J=5.85 Hz), 3.16 (6H, s), 2.42 (2H, t, J=6.22 Hz), 1.95 (2H, t, J=6.59).

Compound 786: 4-Hydroxy-1-(2-morpholin-4-yl-ethyl)-5-oxo-2,5-dihydro-1H-pyrrole-3-carboxylic acid (4-fluoro-2-methylsulfanyl-benzyl)-methyl-amide

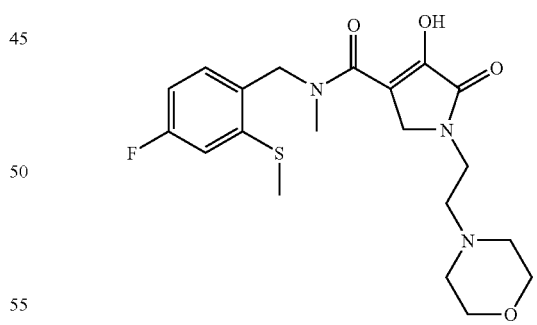

2-(2,2-Dimethyl-5-oxo-[1,3]dioxolan-4-ylidene)-N-(4-fluoro-2-methylsulfanyl-benzyl)-N-methyl-acetamide was reacted with paraformaldehyde and 2-morpholin-4-yl-ethylamine as described in Method 44B to give the title compound as a white solid (0.032 g, 76% yield). ¹HNMR (300 MHz, CDCl₃) δ: 7.07 (1H, dd, J=9.52, 6.23 Hz), 6.92 (1H, dd, J=9.52, 2.56 Hz), 6.82 (1H, td, J=8.06, 2.57 Hz), 4.61 (2H, s), 4.27 (2H, s), 3.95–3.90 (8H, m), 3.76–3.72 (2H, m), 3.39 (2H, t, J=5.85 Hz), 2.97 (3H, s), 2.47 (3H, s).

Compound 787: 4-Hydroxy-1-(2-hydroxy-ethyl)-5-oxo-2,5-dihydro-1H-pyrrole-3-carboxylic acid (4-fluoro-2-methylsulfanyl-benzyl)-methyl-amide

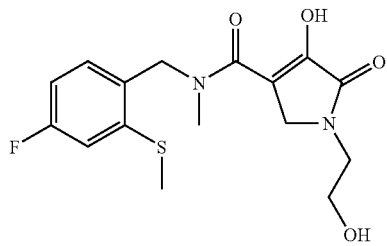

2-(2,2-Dimethyl-5-oxo-[1,3]dioxolan-4-ylidene)-N-(4-fluoro-2-methylsulfanyl-benzyl)-N-methyl-acetamide was reacted with paraformaldehyde and amino-ethanol as described in Method 44 B to give the title compound as a white solid (0.28 g, 79% yield). $^1$HNMR (300 MHz, MeOD) δ: 7.21 (1H, dd, J=8.42, 5.86 Hz), 7.06 (1H, dd, J=9.88, 2.57 Hz), 6.88 (1H, td, J=8.41, 2.56 Hz), 4.69 (2H, s), 4.23 (2H, s), 3.72 (2H, t, J=10.24, 5.12H), 3.61–3.57 (2H, m), 3.02 (3H, s), 2.50 (3H, s).

Compound 788: 4-Hydroxy-1-(2-morpholin-4-yl-ethyl)-5-oxo-2,5-dihydro-1H-pyrrole-3-carboxylic acid (4-fluoro-2-methanesulfinyl-benzyl)-methyl-amide

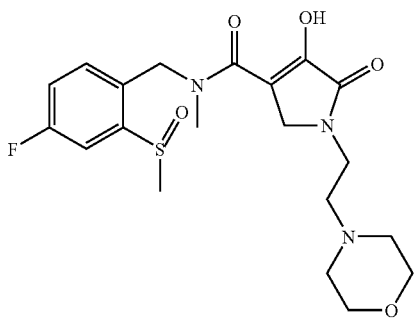

2-(2,2-Dimethyl-5-oxo-[1,3]dioxolan-4-ylidene)-N-(4-fluoro-2-methanesulfinyl-benzyl)-N-methyl-acetamide was reacted with paraformaldehyde and 2-morpholin-4-yl-ethylamine as described in Method 44 B to give the title compound as a yellow solid (0.04 g, 88% yield). $^1$HNMR (300 MHz, MeOD) δ: 7.72 (1H, dd, J=8.42, 2.56 Hz), 7.49 (1H, dd, J=8.79, 5.13 Hz), 7.32–7.26 (1H, m), 4.19 (2H, s), 4.09–3.46 (10H, m), 3.30–3.21 (2H, m), 3.12 (3H, s), 2.81 (3H, s).

Compound 789: 4-Hydroxy-1-(2-hydroxy-ethyl)-5-oxo-2,5-dihydro-1H-pyrrole-3-carboxylic acid (4-fluoro-2-methylsulfinyl-benzyl)-methyl-amide

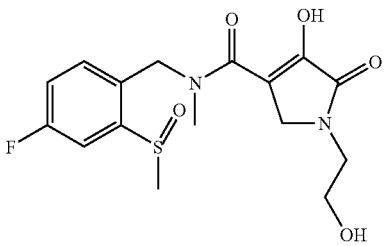

2-(2,2-Dimethyl-5-oxo-[1,3]dioxolan-4-ylidene)-N-(4-fluoro-2-methanesulfinyl-benzyl)-N-methyl-acetamide was reacted with paraformaldehyde and amino-ethanol as described in Method 44B to give the title compound as a colorless oil (0.015 g, 40% yield). $^1$HNMR (300 MHz, MeOD) δ: 7.71 (1H dd, J=8.42, 2.56 Hz), 7.47 (1H, dd, J=8.42, 5.12 Hz), 7.31 (1H, td, J=8.41, 2.56 Hz), 4.95 (2H, s), 4.23 (2H, s), 3.73 (2H, t, J=5.12 Hz), 3.59 (2H, t, J=4.76 Hz), 3.11 (3H, s), 2.80 (3H, s).

Compound 790: 4-Hydroxy-1-(2-morpholin-4-yl-ethyl)-5-oxo-2,5-dihydro-1H-pyrrole-3-carboxylic acid (4-fluoro-2-methanesulfonyl-benzyl)-methyl-amide

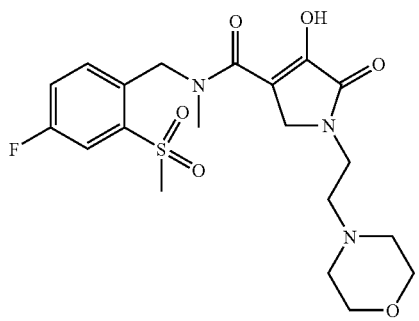

2-(2,2-Dimethyl-5-oxo-[1,3]dioxolan-4-ylidene)-N-(4-fluoro-2-methanesulfonyl-benzyl)-N-methyl-acetamide was reacted with paraformaldehyde and 2-morpholin-4-yl-ethylamine as described in Method 44B to give the title compound as a white solid (0.032 g, 69% yield). $^1$HNMR (300 MHz, DMSO) δ: 9.65 (1H, bs), 7.74 (1H, dd, J=8.41, 2.56 Hz), 7.64–7.59 (1H, m), 7.43–7.38 (1H, m), 4.99 (2H, s), 4.15 (2H, s), 4.00–3.53 (10H, m), 3.43 (2H, s), 3.38 (3H, s), 3.11 (3H, s).

Compound 791: 4-Hydroxy-1-(2-hydroxy-ethyl)-5-oxo-2,5-dihydro-1H-pyrrole-3-carboxylic acid (4-fluoro-2-methylsulfonyl-benzyl)-methyl-amide

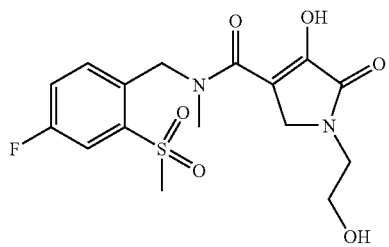

2-(2,2-Dimethyl-5-oxo-[1,3]dioxolan-4-ylidene)-N-(4-fluoro-2-methanesulfonyl-benzyl)-N-methyl-acetamide was reacted with paraformaldehyde and amino-ethanol as described in Method 44 B to give the title compound as a colorless oil (0.02 g, 41% yield). $^1$HNMR (300 MHz, MeOD) δ: 7.77 (1H, dd, J=8.42, 2.57 Hz), 7.56–7.45 (2H, m), 5.10 (2H, s), 4.26 (2H, s), 3.73 (2H, bs), 3.59 (2H, bs), 3.23 (6H, s).

EXAMPLE 90

Method for the Preparation of Compounds 792–808

Compound 90-A:
N-(3,4-dichloro-benzyl)-O-methyl-hydroxylamine

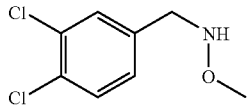

To methoxylamine hydrochloride (20 g, 0.24 mol) in water (200 mL) and THF (74 mL) was added sodium acetate (16.3 g, 0.2 mol) followed by 3,4-dichlorobenzaldehyde (25 g, 0.14 mol). The mixture was stirred at room temp for 6 h and diluted with diethyl ether. The aqueous phase was extracted with ethyl acetate, dried (sodium sulfate) and concentrated to give a colorless oil. The oil was dissolved in glacial acetic acid (200 mL) and cooled to 0° C. Sodium cyanoborohydride (18.8 g, 0.26 mol) was added over 30 min. The mixture was stirred at room temp for 4 days, cooled to 0° C. and made basic with 10 N NaOH. The mixture was extracted with EtOAc (3x's) and the combined organic extracts were washed with water and brine and concentrated to give an oil that solidifies upon standing. This residue was stirred in diethyl ether and the resulting title compound was filtered as a white solid (9.61 g, 33% yield). $^1$HNMR (300 MHz, DMSO) δ: 10.12 (1H, bs), 7.74 (1H, s), 7.67 (1H, d, J=8.42 Hz), 7.44 (1H, d, J=8.05 Hz), 4.21 (2H, s), 3.59 (3H, s).

Compound 90-B: N-(3,4-Dichloro-benzyl)-2-(2,2-dimethyl-5-oxo-[1,3]dioxolane-4-ylidene)-N-methoxy-acetamide

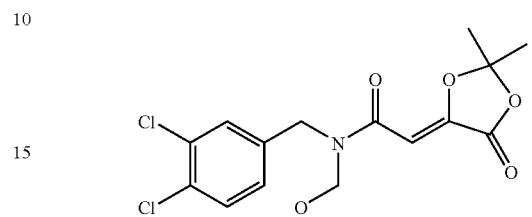

A suspension of (2,2-dimethyl-5-oxo-[1,3]dioxolan-4-ylidene)-acetic acid (4.37 g, 25.4 mmol) in benzene (30 mL) was refluxed for 1 h with oxalyl chloride (15 mL). The resulting solution was cooled and concentrated. The residue was dissolved in dichloromethane (30 mL) and cooled to 0° C. and N-(3,4-dichloro-benzyl)-O-methyl-hydroxylamine (5.3 g, 22 mmol) in dichloromethane (30 mL) and pyridine (18 mL) was added dropwise. The resulting mixture was stirred at room temp for 18 h. The mixture was diluted with 1N HCl and extracted with EtOAc. The organic phase was washed with 1N HCl, dried (sodium sulfate) and concentrated to give the title compound as a yellow solid (7.59 g, 83% yield). $^1$HNMR (300 MHz, CDCl$_3$) δ: 7.44 (1H, s), 7.39 (2H, d, J=8.05 Hz), 7.19 (2H, d, J=8.05 Hz), 6.37 (1H, s), 4.75 (2H, s), 3.70 (3H, s), 1.74 (6H, s).

Compound 90-C: 3-[(3,4-Dichloro-benzyl)-methoxy-carbamoyl]-2-hydroxy-acrylic acid methyl ester

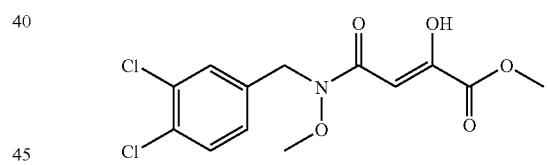

A mixture of N-(3,4-dichloro-benzyl)-2-(2,2-dimethyl-5-oxo-[1,3]dioxolane-4-ylidene)-N-methoxy-acetamide (1.0 g, 2.8 mmol) and potassium carbonate (0.39 g, 2.8 mmol) in MeOH (20 mL) was stirred at room temp for 1 h. The suspension was diluted with EtOAc and washed with 1N HCl followed by brine. The organic phase was dried (sodium sulfate) and concentrated. The title compound was purified by flash chromatography eluting with 100% hexane followed by 25% EtOAc/hexane to give a white solid (0.3107 g, 33% yield). $^1$HNMR (300 MHz, CDCl$_3$) δ: 13.28 (1H, s), 7.41 (2H, m), 7.15 (1H, dd, J=9.52, 1.47 Hz), 6.45 (1H, s), 4.77 (2H, s), 3.89 (3H, s), 3.72 (3H, s).

Compounds 792–808

Amine (0.1 mmol) was reacted with paraformaldehyde according to the method described for the preparation of compound 86-A. This was combined with 3-[(3,4-dichloro-benzyl)-methoxy-carbamoyl]-2-hydroxy-acrylic acid methyl ester (0.036 g, 0.1 mmol), in MeOH (1.0 mL) and the resulting mixture stirred at 55° C. for 1 h. The resulting solution was cooled and purified by preparative HPLC (YMC Combiprep ODS-A, 30 mm×50 mm, MeOH/H₂O/ 0.1% TFA) to give the title compounds. Compounds were evaluated by LC/MS (Waters XTERRA, 4.6 mm×30 mm, MeOH/H₂O/0.1% TFA, 10%–90% MeOH, 2 min gradient, 5 mL/min flow rate; ESI⁺).
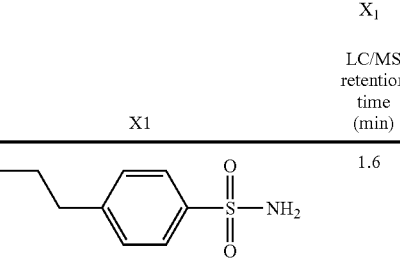
| Compound | X1 | LC/MS retention time (min) | MS calcd (M + H) | MS found |
|---|---|---|---|---|
| 792 | 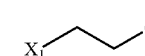 | 1.6 | 514.1 | 514.2 |
| 793 | 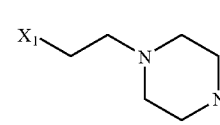 | 1.50 | 375.2 | 375.2 |
| 794 | 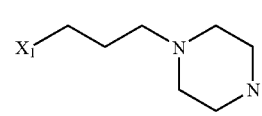 | 1.3 | 443.3 | 443.3 |
| 795 | 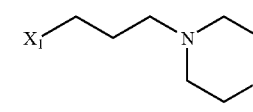 | 1.3 | 471.4 | 471.3 |
| 796 | 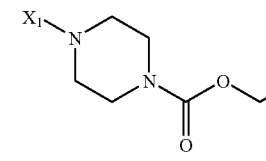 | 1.3 | 458.3 | 458.3 |
| 797 | 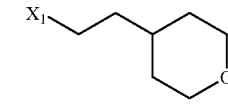 | 1.8 | 486.4 | 486.3 |
| 798 | 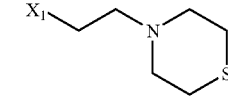 | 1.7 | 443.3 | 443.3 |
| 799 | 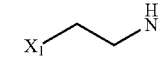 | 1.3 | 460.4 | 460.3 |
| 800 |  | 1.3 | 388.3 | 388.2 |
| 801 | X₁—CH₂CH₃ | 1.7 | 359.2 | 359.3 |
| 802 | 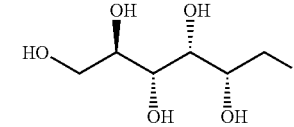 | 1.4 | 495.3 | 495.3 |

-continued
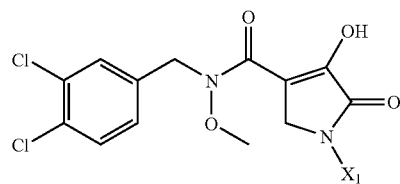
| Compound | X1 | LC/MS retention time (min) | MS calcd (M + H) | MS found |
|---|---|---|---|---|
| 803 | HO-CH(CH3)-CH2-X1 | 1.5 | 389.2 | 389.3 |
| 804 | (CH3)(CH2OH)C(CH3)-CH2-X1 | 1.7 | 417.3 | 417.3 |
| 805 | HOCH2-CH(OH)-CH2-X1 | 1.4 | 405.2 | 405.3 |
| 806 | CH3OOC-CH(CH2OH)-X1 | 1.5 | 433.2 | 433.3 |
| 807 | HOCH2-CH(CH3)-X1 | 1.5 | 389.2 | 389.3 |
| 808 | (HOCH2)2CH-X1 | 1.4 | 405.2 | 405.3 |

EXAMPLE 91

Compound 809: 4-Hydroxy-1-(4-hydroxy-butyl)-5-oxo-2,5-dihydro-1H-pyrrole-3-carboxylic acid (3,4-dichloro-benzyl)-methoxy-amide

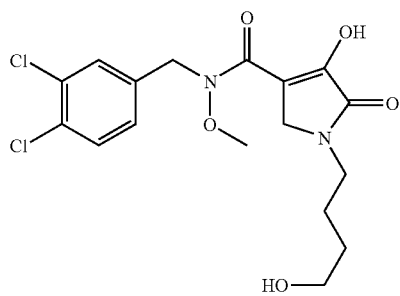

3-[(3,4-Dichloro-benzyl)-methoxy-carbamoyl]-2-hydroxy-acrylic acid methyl ester, paraformaldehyde and 4-amino-butanol were reacted according to the method described for compounds 792–808 to give the tile compound as a yellow oil (0.015 g, 36% yield). $^1$HNMR (300 MHz, CDCl$_3$) δ: 7.43–7.40 (2H, m), 7.18 (1H, dd, J=8.42,1.83 Hz), 4.81 (2H, s), 4.14 (2H, s), 3.74 (3H, s), 3.63 (2H, t, J=6.40 Hz), 3.51 (2H, t, J=4.01 Hz), 1.68–1.53 (4H, M), 1.43–1.33 (2H, m).

EXAMPLE 92

Compound 810: 4-{4-[(3,4-Dichloro-benzyl)-methoxy-carbamoyl]-3-hydroxy-2-oxo-2,5-dihydro-pyrrol-1-yl}-butyric acid

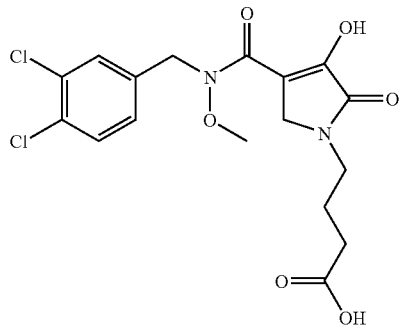

To a solution of 4-amino butyric acid (0.093 g, 0.90 mmol) in acetic acid (0.5 mL) at 55° C. was added paraformaldehyde (0.027 g, 0.90 mmol). After stirring for 10 min, 3-[(3,4-dichloro-benzyl)-methoxy-carbamoyl]-2-hydroxy-acrylic acid methyl ester (0.2978 g, 0.89 mmol) was added and the mixture was stirred at 55° C. for 1 h. The clear yellow solution was cooled, concentrated and purified by preparative HPLC (C18, ODS-A, S-75 μm, 10%–40% acetonitrile/water/0.5% HCl) to give the title compound as a yellow foam (0.129 g, 34% yield). HRMS (M+H) calcd for C$_{17}$H$_{19}$N$_2$Cl$_2$O$_6$: 417.06203; found: 417.0607.

EXAMPLE 93

Method for the Preparation of Compounds 811–814

The general method for the synthesis of compounds 811–814 is illustrated in Scheme XIV.

Compound 93-A: 2-(2,2-Dimethyl-5-oxo-[1,3]dioxolane-4-ylidene)-N-methoxy-N-naphthalen-1-ylm-ethyl-acetamide

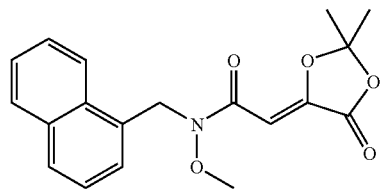

O-Methyl-N-naphthalen-1-ylmethyl-hydroxylamine was reacted with (2,2-dimethyl-5-oxo-[1,3]dioxolan-4-ylidene)-acetic acid according to the method described for the preparation of compound 90-B to give the title compound as a pale yellow solid (0.826 g, 56% yield). $^1$HNMR (300 MHz, CDCl$_3$) δ: 8.18 (1H, d, J=8.05 Hz), 7.85 (2H, t, J=9.15 Hz), 7.56–7.41 (4H, m), 6.40 (1H, s), 5.30 (2H, s), 3.43 (3H, s), 1.77 (6H, s).

Compound 93-B: 2-Hydroxy-3-(methoxy-naphthalen-1-ylmethyl-carbamoyl-acrylic acid methyl ester

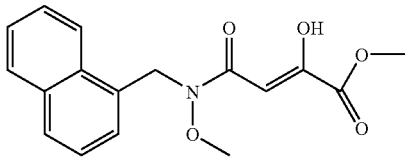

Compound 93-B was prepared using the same procedure described for the preparation of compound 90-C and isolated as an orange powder (0.022 g, 45% yield). $^1$HNMR (300 MHz, CDCl$_3$) δ: 8.09 (1H, d, J=8.05 Hz), 7.87 (2H, t, J=7.68 Hz), 7.57–7.41 (4H, m), 5.35 (2H, s), 4.16 (2H, s), 3.56 (3H, s), 3.54 (2H, t, J=6.33 Hz), 2.38 (2H, t, J=6.58 Hz), 1.91 (2H, t, J=6.22 Hz).

Compounds 811–814

As illustrated in Scheme XIV, compounds 811–814 were prepared from 2-hydroxy-3-(methoxy-naphthalen-1-ylm-ethyl-carbamoyl)-acrylic acid methyl ester, paraformaldehyde and an amine, I-7 using the same method described for the preparation of compounds 792–808.

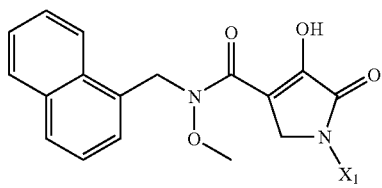

| Compound | X1 | LC/MS retention time (min) | MS calcd (M + H) | MS found |
|---|---|---|---|---|
| 811 | X₁⌒⌒ | 1.5 | 341.4 | 341.4 |
| 812 | X₁⌒⌒N(morpholine) | 1.2 | 426.5 | 426.4 |
| 813 | X₁⌒⌒OH | 1.4 | 357.4 | 357.3 |
| 814 | X₁⌒⌒(OH)(OH) | 1.3 | 387.4 | 387.3 |

EXAMPLE 94

Compound 815: 4-[3-Hydroxy-4(methoxy-naphthalen-1-yl methyl-carbamoyl)-2-oxo-2,5-dihydro-pyrrol-1-yl]-butyric acid

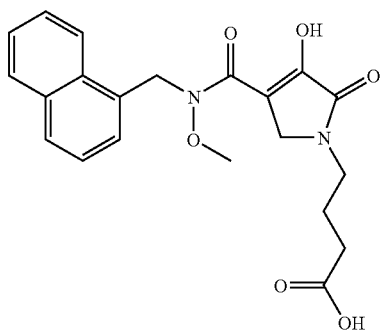

2-Hydroxy-3-(methoxy-naphthalen-1-ylmethyl-carbamoyl)-acrylic acid methyl ester, paraformaldehyde and 4-amino-butyric acid were reacted using the method described for the synthesis of Compound 810 to give the title compound as an orange powder (0.0217 g, 45% yield). $^{1}$HNMR (300 MHz, CDCl$_3$) δ: 8.09 (1H, d, J=8.05 Hz), 7.87 (2H, t, J=768 Hz), 7.57–7.41 (4H, m), 5.35 (2H, s), 4.16 (2H, s), 3.56 (3H, s), 3.54 (2H, t, J=6.33 Hz), 2.38 (2H, t, J=6.58 Hz) 1.91 (2H, t, J=6.22 Hz).

EXAMPLE 95

Compound 95-A: N-(4-fluoro-2-methylsulfanyl-benzyl)-O-methyl-hydroxylamine hydrochloride

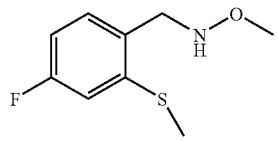

A 250 mL round bottom flask was charged with 4-fluoro-2-methylsulfanylbenzaldehyde (5.106 g, 30 mmol), O-methylhydroxylamine hydrochloride (3.758 g, 45 mmol), sodium acetate (6.124 g, 45 mmol), water (50 mL) and THF (75 mL). The reaction mixture was stirred at room temperature for 4 h and taken up into ether (300 mL), washed with water (2×50 mL) and brine (50 mL). The organic phase was dried over anhydrous Na$_2$SO$_4$, filtered and concentrated to give 4-fluoro-2-methylsulfanyl-benzaldehyde-O-methyl-oxime (5.892 g, 99%) as a white solid.

To a stirred solution of 4-fluoro-2-methylsulfanyl-benzaldehyde-O-methyl-oxime (5.982 g, 29.58 mmol) in CH$_2$Cl$_2$ (30 mL) was added trifluoroacetic acid (30 mL) followed by triethylsilane (14 mL, 90 mmol). After stirring for 6 h, the reaction mixture was concentrated and the resulting residue was taken up in saturated aqueous NaHCO$_3$ (100 mL) and extracted with ethyl acetate (3×75 mL). The combined organic extracts were dried over anhydrous Na$_2$SO$_4$, filtered, and concentrated to give a viscous oil. The crude product was re-dissolved in anhydrous ether and 2M HCl/ether w (18 mL) was added. The resulting white solid was filtered and dried to yield the desired product as the HCl salt (6.666 g, 93% yield). $^{1}$HNMR (500 MHz, DMSO-d6) δ: 11.44 (1H, br s), 7.66–7.59 (1H, m), 7.24 (1H, dd, J=10.1, 2.1 Hz), 7.08 (1H, td, J=8.6, 2.4 Hz), 4.85 (2H, s), 3.82 (3H, s), 2.53 (3H, s). MS calcd for C$_9$H$_{13}$FNOS (M+H): 202.07. found: 202.07.

Compound 95-B: 2-(2,2-Dimethyl-5-oxo-[1,3]dioxolan-4-ylidene)-N-(4-fluoro-2-methylsulfanyl-benzyl)-N-methoxy-acetamide

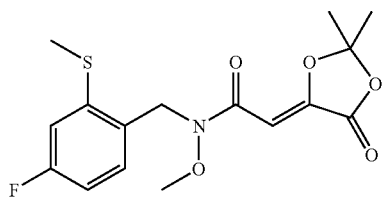

To a stirred solution of N-(4-fluoro-2-methylsulfanyl-benzyl)-O-methyl-hydroxylamine hydrochloride (1.19 g, 5 mmol) and (2,2-Dimethyl-5-oxo-[1,3]dioxolan-4-ylidene)-acetyl chloride (0.953 g, 5 mmol) in CH$_2$Cl$_2$ (20 mL) was added diisopropyethylamine (1.9 mL, 11 mmol) at room temperature. After 1 h, the reaction mixture was concentrated and the resulting residue was taken up into ether (150 mL), washed with 1N HCl (10 mL), water (20 mL) and brine (20 mL). The organic layer was dried over anhydrous Na$_2$SO$_4$, filtered and concentrated to give product as a white solid (1.77 g, 99%). ¹HNMR (300 MHz, CDCl₃) δ: 7.28–7.23 (1H, m), 6.90 (1H, dd, J=9.5, 2.6 Hz), 6.78 (1H, td, J=8.4, 2.6 Hz), 6.37 (1H, s), 4.88 (2H, s), 3.62 (3H, s), 2.44 (3H, s), 1.71 (6H, s). MS calcd for $C_{16}H_{18}FNO_5S$ Na (M+Na): 378.078; found: 378.18.

Compound 816: 4-{4-[(4-Fluoro-2-methylsulfanyl-benzyl)-methoxy-carbamoyl]-3-hydroxy-2-oxo-2,5-dihydro-pyrrol-1-yl}-butyric acid

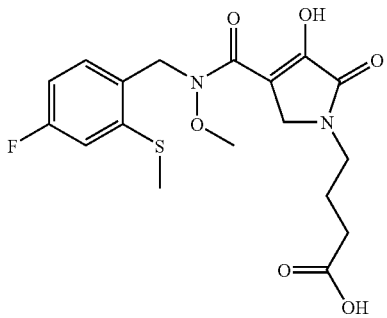

2(2,2-Dimethyl-5-oxo-[1,3]dioxolan-4-ylidene)-N-(4-fluoro-2-methylsulfanyl-benzyl)-N-methoxy-acetamide was reacted with methanol to give 3-[(4-fluoro-2-methylsulfanyl-benzyl)-methoxy-carbamoyl]-2-hydroxy-acrylic acid methyl ester as a white sticky solid (0.0807 g, 88% yield). This was then reacted with paraformaldehyde and 4-amino butyric acid following the procedure described for Compound 810 to give the title compound as an orange solid (0.0360 g, 64% yield). ¹HNMR (300 MHz, DMSO) δ: 12.10 (1H, bs), 11.35 (1H, bs), 7.30 (1H, m), 7.14 (1H, dd, J=12.44, 2.20 Hz), 6.97 (1H, td, J=8.41, 2.65 Hz), 4.86 (2H, s), 4.18 (2H, s), 3.69 (3H, s), 3.42 (2H, t, J=6.73 Hz), 2.50 (3H, t, J=1.83 Hz), 2.22 (2H, t, J=6.73 Hz), 1.78 (2H, m).

EXAMPLE 96

Compound 96-A: 2-(2,2-Dimethyl-5-oxo-[1,2]dioxolan-4-ylidene)-N-(4-fluoro-2-methanesulfinyl-benzyl)-N-methoxy-acetamide

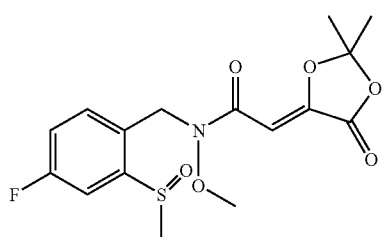

MCPBA (0.49 g, 1.41 mmol) was added to a solution of 2-(2,2-dimethyl-5-oxo-[1,3]dioxolan-4-ylidene)-N-(4-fluoro-2-methylsulfanyl-benzyl)-N-methoxy acetamide (0.50 g, 1.41 mmol) in dichloromethane (10 mL) and the mixture was stirred at room temp for 4 h. After diluting with EtOAc and washing with saturated NaHSO₄, NaHCO₃ and brine, the organic phase was dried (sodium sulfate) and concentrated. The title compound was purified by flash chromatography eluting with 100% hexane to 100% EtOAc to give a white foamy solid (0.4789 g, 92% yield). ¹HNMR (300 MHz, CDCl₃) δ: 7.75 (1H, dd, J=8.42, 2.92 Hz), 7.49 (1H, dd, J=8.42, 5.12 Hz), 7.15 (1H, td, J=8.42, 2.93 Hz), 6.34 (1H, s), 4.88 (2H, d, J=8.05 Hz), 3.70 (3H, s), 2.76 (3H, s), 1.74 (6H, s).

Compound 817: 4-{4-[(4-Fluoro-2-methanesulfinyl-benzyl)-methoxy-carbamoyl]-3-hydroxy-2-oxo-2,5-dihydro-pyrrol-1-yl}-butyric acid

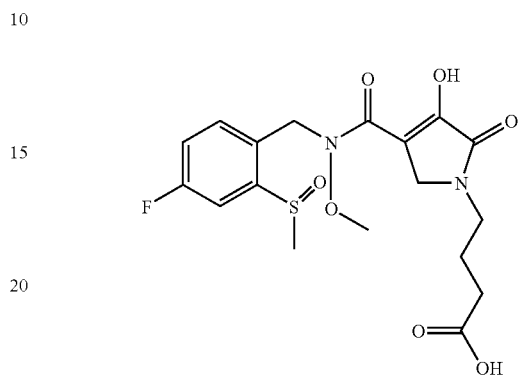

2-(2,2-Dimethyl-5-oxo-[1,3]dioxolan-4-ylidene)-N-(4-fluoro-2-methanesulfinyl-benzyl)-N-methoxy-acetamide was reacted with methanol using the procedure described for the synthesis of compound 90-C to yield 3-[(4-fluoro-2-methanesulfinyl-benzyl)-methoxy-carbamoyl]-2-hydroxy-acrylic acid methyl ester as a white sticky solid (0.1020 g, 100% yield). This crude was reacted with paraformaldehyde and 4-amino-butyric acid using the procedure described for Compound 810 to give the title compound as an orange solid (0.0360 g, 64% yield). ¹HNMR (300 MHz, CDCl₃) δ: 7.75 (1H, dd, J=8.05, 2.56 Hz), 7.48 (1H, dd, J=8.42, 4.76 Hz), 7.21 (1H, td, J=8.05, 2.56 Hz), 4.96 (2H, q), 4.19 (2H, s), 3.78 (3H, s), 3.58 (2H, td, J=6.95, 1.83 Hz), 2.82 (3H, s), 2.39 (2H, t, J=6.95 Hz), 1.97–1.92 (2H, m).

EXAMPLE 97

Compound 97-A: 2-(2,2-Dimethyl-5-oxo-[1,3]dioxolan-4-ylidene)-N-(4-fluoro-2-methanesulfonyl-benzyl)-N-methoxy-acetamide

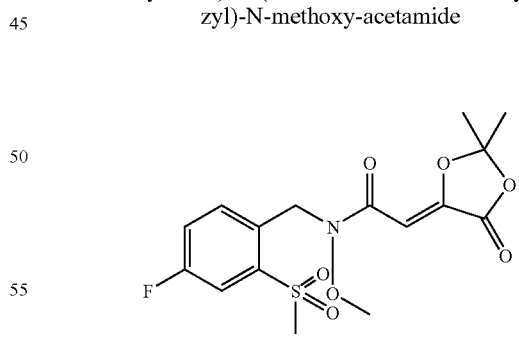

2-(2,2-Dimethyl-5-oxo-[1,3]dioxolan-4-ylidene)-N-(4-fluoro-2-methylsulfanyl-benzyl)-N-methoxy-acetamide was reacted with 2 equivalents of MCPBA using the method described for the synthesis of Compound 96-A to give the title compound as a white solid (0.263 g, 48% yield). ¹HNMR (300 MHz, CDCl₃) δ: 7.74 (1H, dd, J=8.06, 2.57 Hz), 7.60 (1H, dd, J=8.78, 5.12 Hz), 7.27 (1H, td, 7.68, 2.56 Hz), 6.45 (1H, s), 5.26 (2H, s), 3.81 (3H, s), 3.22 (3H, s), 1.74 (6H, s).

Compound 818: 4-{4-[(4-Fluoro-2-methanesulfonyl-benzyl)-methoxy-carbamoyl-3-hydroxy-2-oxo-2,5-dihydro-pyrrol-1-yl}-butyric acid

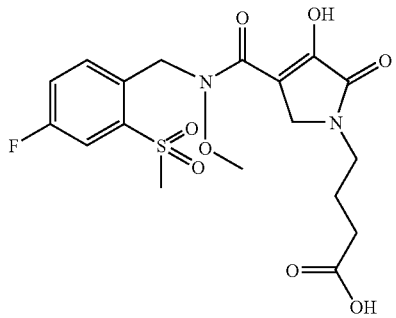

2-(2,2-Dimethyl-5-oxo-[1,3]dioxolan-4-ylidene)-N-(4-fluoro-2-methanesulfonyl-benzyl)-N-methoxy-acetamide was reacted with methanol using the procedure described for the synthesis of compound 90-C to yield 3-[(4-fluoro-benzyl)-methoxy-carbamoyl]-2-hydroxy-acrylic acid methyl ester as a white sticky solid (0.102 g, 100% yield). This was reacted with paraformaldehyde and 4-amino-butyric acid using the procedure described for Compound 810 to give the title compound as an orange solid (0.018 g, 14% yield). $^1$HNMR (300 MHz, CDCl$_3$) δ: 7.78 (1H, dd, J=8.05, 2.56 Hz), 7.59–7.54 (1H, m), 7.36–7.29 (1H, m), 5.35 (2H, s), 4.25 (2H, s), 3.83 (3H, s), 3.60 (2H, t, J=6.95 Hz), 3.22 (3H, s), 2.43 (2H, t, J=6.95 Hz), 2.00–1.96 (2H, m).

EXAMPLE 98

Compound 819: 4-Hydroxy-1-(2-morpholin-4-yl-ethyl)-5-oxo-2,5-dihydro-1H-pyrrole-3-carboxylic acid (4-fluoro-2-methylsulfanyl-benzyl)-methoxy-amide

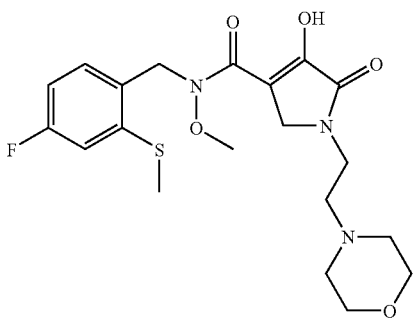

2-(2,2-Dimethyl-5-oxo-[1,3]dioxolan-4-ylidene)-N-(4-fluoro-2-methylsulfanyl-benzyl)-N-methoxy-acetamide was reacted with paraformaldehyde and 2-morpholin-4-yl-ethylamine using the method described for the preparation of Compound 767 to give the title compound as a white solid (0.012 g, 18% yield). $^1$HNMR (300 MHz, CDCl$_3$) δ: 7.27–7.22 (1H, m), 6.94 (1H, dd, J=9.51, 2.56 Hz), 6.83 (1H, td, J=8.42, 2.56 Hz), 4.95 (2H, s), 4.28 (2H, s), 3.97–3.75 (8H, m), 3.68 (3H, s), 3.40 (2H, t, J=5.85 Hz), 2.95 (2H, bs), 2.49 (3H, s).

EXAMPLE 99

Compound 820: 4-Hydroxy-1-(2-hydroxy-ethyl)-5-oxo-2,5-dihydro-1H-pyrrole-3-carboxylic acid (4-fluoro-2-benzyl)-methoxy-amide

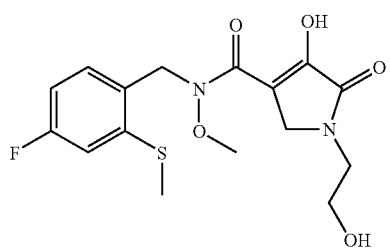

2-(2,2-Dimethyl-5-oxo-[1,3]dioxolan-4-ylidene)-N-(4-fluoro-2-methylsulfanyl-benzyl)-N-methoxy-acetamide was reacted with paraformaldehyde and amino-ethanol using the method described for the synthesis of Compound 767 to give the title compound as a yellow oil (0.021 g, 56% yield). $^1$HNMR (300 MHz, MeOD) δ: 7.35–7.29 (1H, m), 7.08 (1H, d, J=8.05 Hz), 6.92–6.84 (1H, m), 4.99 (2H, s), 4.39 (2H, s), 3.76–3.70 (5H, m), 3.63–360 (2H, m), 2.51 (3H, s).

EXAMPLE 100

Compound 821: 4-Hydroxy-1-(2-morpholin-4-yl-ethyl)-5-oxo-2,5-dihydro-1H-pyrrole-3-carboxylic acid (4-fluoro-2-methanesulfinyl-benzyl)-methoxy-amide

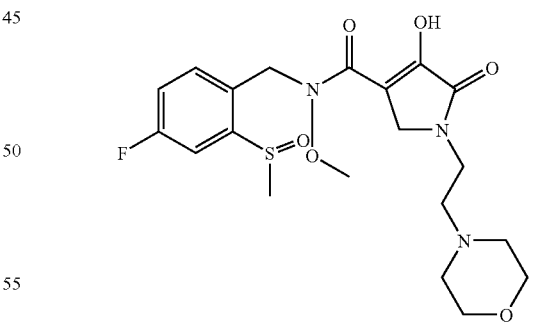

2-(2,2-Dimethyl-5-oxo-[1,2]dioxolan-4-ylidene)-N-(4-fluoro-2-methanesulfinyl-benzyl)-N-methoxy-acetamide was reacted with paraformaldehyde and 2-morpholin-4-yl-ethylamine using the method described for the preparation of Compound 767 to give the title compound as a yellow solid (0.045 g, 99% yield). $^1$HNMR (300 MHz, MeOD) δ: 7.27 (1H, dd, J=8.42, 2.56 Hz), 7.62 (1H, dd, J=8.79, 5.49 Hz), 7.32 (1H, td, J=8.41, 2.93 Hz), 5.06 (2H, s), 4.03–3.92

(4H, m), 3.83 (3H, s), 3.80–3.63 (4H, m), 3.51–3.46 (2H, m), 3.19 (2H, bs), 2.84 (3H, s).

EXAMPLE 101

Compound 822: 4-Hydroxy-1-(2-hydroxy-ethyl)-5-oxo-2,5-dihydro-1H-pyrrole-3-carboxylic acid (4-fluoro-2-methanesulfinyl-benzyl)-methoxy-amide

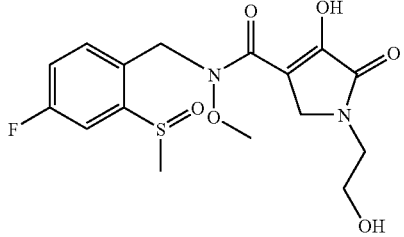

2-(2,2-Dimethyl-5-oxo-[1,3]dioxolan-4-ylidene)-N-(4-fluoro-2-methanesulfonyl-benzyl)-N-methoxy-acetamide was reacted with paraformaldehyde and amino-ethanol using the method described for the preparation of compound 767 to give the title compound as a colorless oil (0.015 g, 40% yield). $^1$HNMR (300 MHz, MeOD) δ: 7.71 (1H, dd, J=8.78, 2.93 Hz), 7.61 (1H, dd, J=8.78, 5.12 Hz), 7.31 (1H, td, J=8.42, 2.56 Hz), 5.05 (2H, d, J=9.15 Hz), 4.38 (2H, s), 3.81 (3H, s), 3.74 (2H, t, J=5.12 Hz), 3.60 (2H, t, J=5.49 Hz), 2.84 (3H, s).

EXAMPLE 102

Compound 823: 4-Hydroxy-1-(2-morpholin-4-yl-ethyl)-5-oxo-2,5-dihydro-1H-pyrrole-3-carboxylic acid (4-fluoro-2-methanesulfonyl-benzyl)-methoxy-amide

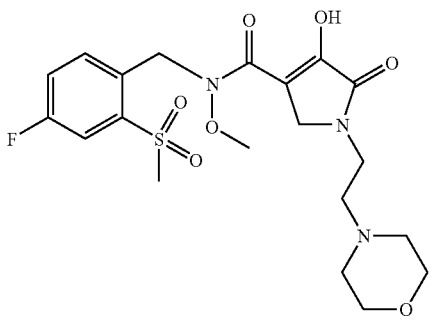

2-(2,2-Dimethyl-5-oxo-[1,3]dioxolan-4-ylidene)-N-(4-fluoro-2-methanesulfonyl-benzyl)-N-methoxy-acetamide was reacted with paraformaldehyde and 2-morpholin-4-yl-ethylamine using the method described for the preparation of compound 767 to give the title compound as a white solid (0.021 g, 45% yield). $^1$HNMR (300 MHz, MeOD) δ: 7.75 (1H, dd, J=8.78, 2.93 Hz), 7.63–7.54 (2H, m), 5.34 (2H, s), 4.29 (2H, s), 4.01–3.99 (2H, m), 3.84–3.81 (2H, m), 3.77 (3H, s), 3.63–3.45 (6H, m), 3.39 (3H, s), 3.16–3.08 (2H, m).

EXAMPLE 103

Compound 824: 4-Hydroxy-1-(2-hydroxy-ethyl)-5-oxo-2,5-dihydro-1H-pyrrole-3-carboxylic acid (4-fluoro-2-methanesulfonyl-benzyl)-methoxy-amide

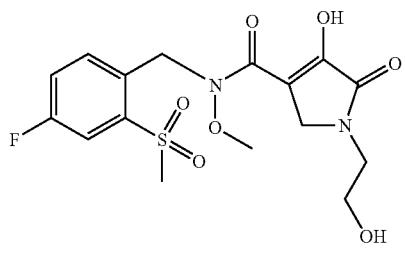

2-(2,2-Dimethyl-5-oxo-[1,3]dioxolan-4-ylidene)-N-(4-fluoro-2-methanesulfonyl-benzyl)-N-methoxy-acetamide was reacted with paraformaldehyde and amino-ethanol using the method described for the preparation of compound 767 to give the title compound as a colorless oil (0.100 g, 25% yield). $^1$HNMR (300 MHz, MeOD) δ: 7.77 (1H, dd, J=8.42, 2.56 Hz), 7.66 (1H, dd, J=8.79, 5.13 Hz), 7.45 (1H td, J=8.42, 2.93 Hz), 5.41 (2H, s), 4.46 (2H, s), 3.84 (3H, s), 3.76 (2H, t, J=5.12 Hz), 3.63 (2H, t, J=5.13 Hz), 3.28 (3H, s).

EXAMPLE 104

Compound 104-A: N-(3,4-Dichloro-benzyl)-2-(2,2-dimethyl-5-oxo-[1,3]dioxolan-4-ylidene)-acetamide

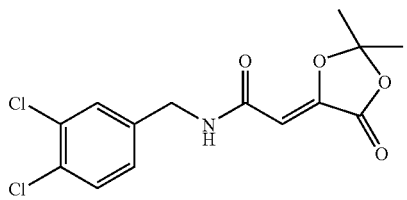

To a stirred suspension of 3,4-dichlorobenzylamine (17.6 mg, 0.1 mmol) and resin bound morpholine (100 mg, 2.5–4.0 mmol/1 g) in CH$_2$Cl$_2$ (2 mL) was added (2,2-dimethyl-5-oxo-[1,3]dioxolan-4-ylidene)-acetyl chloride (20 mg, 0.11 mmol) and the mixture stirred for 1 h. The mixture filtered and the filtrate concentrated to give the product as a white solid (33 mg, 100% yield). $^1$H NMR (500 MHz, CDCl$_3$) δ: 7.39 (2H, m), 7.15 (1H, m), 6.60 (1H, s), 5.89 (1H, s), 4.50 (2H, d, J=6.0 Hz), 1.74 (6H, s). MS calcd for C$_{14}$H$_{14}$Cl$_2$NO$_4$ [M+H]$^+$: 330.03. found: 330.1.

Compound 104-B: Methylene-(2-morpholin-4-yl-ethyl)-amine

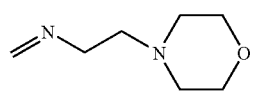

2-Aminoethanol (0.8712 g, 10.0 mmol) and paraformaldehyde (0.3 g, 10.0 mmol) were stirred in methanol (50 mL) at 55° C. until the solids dissolved (approximately 20 min). The solution was cooled and used without further purification

Compound 825: 4-Hydroxy-1-(2-morpholin-4-yl-ethyl)-5-oxo-2,5-dihydro-1H-pyrrole-3-carboxylic acid 3,4-dichloro-benzylamide

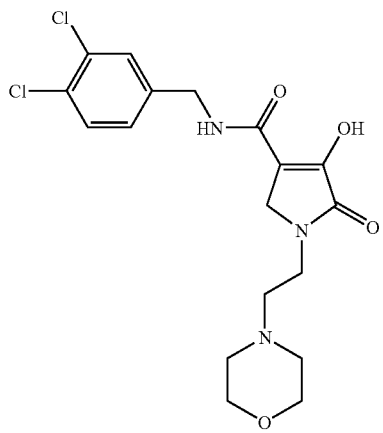

A mixture of N-(3,4-dichloro-benzyl)-2-(2,2-dimethyl-5-oxo-[1,3]dioxolan-4-ylidene)-acetamide (66 mg, 0.2 mmol) and a 0.2 mmol solution of methylene-(2-morpholin-4-yl-ethyl)-amine in methanol (1.5 mL, 0.3 mmol) was heated at 70° C. for 1.5 h. The reaction mixture was then cooled to room temperature and purified by preparative HPLC using methanol/water (0.1% TFA) as eluent. The fractions containing the product were combined and concentrated to give a white powder (23.3 mg, 22% yield). $^1$H NMR (500 MHz, DMSO) δ: 9.50 (1H, br s), 8.08 (1H, t, J=6.2 Hz), 7.59 (1H, d, J=8.2 Hz), 7.53 (1H, d, J=1.8 Hz), 7.28 (1H, dd, J=8.2, 1.8 Hz), 4.42 (2H, d, J=6.1 Hz), 4.04 (2H, s), 4.02–3.95 (2H, m), 3.81–3.77 (2H, m), 3.73–3.37 (6H, m), 3.15–3.06 (2H, m). HRMS calcd for $C_{18}H_{22}Cl_2N_3O_4$ (M+H): 414.09875. found: 414.0987.

EXAMPLE 105

Compound 105-A: N-(3,5-Difluoro-benzyl)-2-(2,2-dimethyl-5-oxo-[1,3]dioxolan-4-ylidene)-acetamide

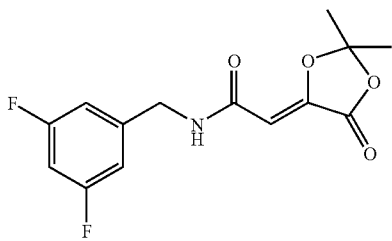

To a stirred suspension of 3,4-difluorobenzylamine (0.43 mg, 0.3 mmol) and resin bound morpholine (200 mg, 2.5–4.0 mmol/1 g) was added a solution of (2,2-dimethyl-5-oxo-[1,3]dioxolan-4-ylidene)-acetyl chloride (60 mg, 0.31 mmol) in CH$_2$Cl$_2$ (3 mL) and the mixture stirred for 1 h. The mixture was filtered and the filtrate concentrated to give the product as a white solid (85 mg, 95% yield). MS calcd for $C_{14}H_{13}F_2NO_4Na$ (M+Na): 320.29; found: 320.27.

Compound 826: 4-Hydroxy-1-(2-morpholin-4-yl-ethyl)-5-oxo-2,5-dihydro-1H-pyrrole-3-carboxylic acid 3,5-difluoro-benzylamide

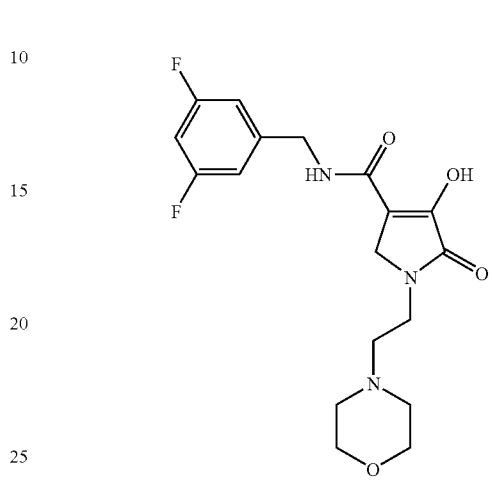

A mixture of N-(3,5-difluoro-benzyl)-2-(2,2-dimethyl-5-oxo-[1,3]dioxolan-4-ylidene)-acetamide (60 mg, 0.2 mmol) and a 0.2 mmol solution of methylene-(2-morpholin-4-yl-ethyl)-amine in methanol (1.25 mL, 0.25 mmol) was heated at 70° C. for 1 h. The reaction mixture was cooled to room temperature and purified by preparative HPLC using methanol/water (0.1% TFA) as the eluent. The fractions containing the product were combined and concentrated to give the title compound as a white powder (22 mg, 22% yield). $^1$H NMR (500 MHz, DMSO) δ: 11.95 (1H, br s), 9.54 (1H, br s), 8.08 (1H, t, J=6.1 Hz), 7.12–7.08 (1H, m), 7.00–6.94 (2H, m), 4.45 (2H, d, J=6.1 Hz), 4.05 (2H, s), 4.02–3.94 (2H, m), 3.83–3.77 (2H, m), 3.69–3.38 (6H, m), 3.16–3.05 (2H, m). HRMS calcd for $C_{18}H_{20}F_2N_3O_4$ (M–H): 380.1422. found: 380.1422.

EXAMPLE 106

Compound 106-A: 2-(2,2-Dimethyl-5-oxo-[1,3]dioxolan-4-ylidene)-N-(4-fluoro-benzyl)-acetamide

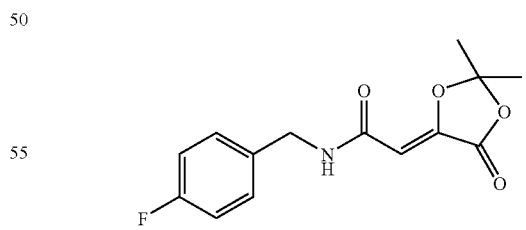

To a stirred suspension of 4-fluorobenzylamine (37.5 mg, 0.3 mmol) and resin bound morpholine (200 mg, 2.5–4.0 mmol/1 g) was added a solution of (2,2-dimethyl-5-oxo-[1,3]dioxolan-4-ylidene)-acetyl chloride (60 mg, 0.31 mmol) in CH$_2$Cl$_2$ (3 mL) and the mixture shaken for 1 h. The mixture was filtered and the filtrate concentrated to give the title product as a white solid (84.4 mg, 100% yield). MS calc for $C_{14}H_{14}FNO_4$ (M+Na): 302.29; found: 302.29.

Compound 827: 4-Hydroxy-1-(2-morpholin-4-yl-ethyl)-5-oxo-2,5-dihydro-1H-pyrrole-3-carboxylic acid 4-fluoro-benzylamide

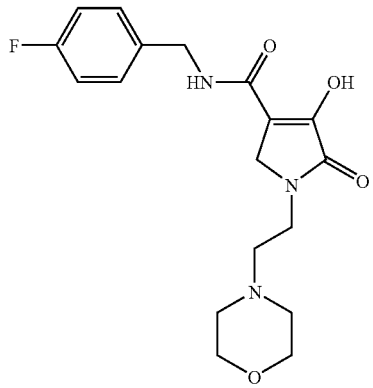

A mixture of 2-(2,2-dimethyl-5-oxo-[1,3]dioxolan-4-ylidene)-N-(4-fluoro-benzyl)-acetamide (77 mg, 0.275 mmol) and a 0.2 mmol solution of methylene-(2-morpholin-4-yl-ethyl)-amine in methanol (1.5 mL, 0. mmol) was heated at 70° C. for 1 h. The reaction mixture was cooled to room temperature and purified by preparative HPLC using methanol/water (0.1% TFA) as the eluent. The fractions containing the product were combined and concentrated to give the title compound as a pale yellow powder (42 mg, 32% yield). $^1$H NMR (500 MHz, DMSO) δ: 11.92 (1H, br s), 9.48 (1H, br s), 7.95 (1H, t, J=4.9 Hz), 7.34–7.31 (2H, m), 7.17–7.13 (2H, m), 4.42 (2H, d, J=4.9 Hz), 4.04 (2H, s), 4.01–3.95 (2H, m), 3.80–3.77 (2H, m), 3.66–3.39 (6H, m), 3.15–3.06 (2H, m). HRMS calcd for $C_{18}H_{21}FN_3O_4$ (M+H): 362.1516. found: 362.1505.

EXAMPLE 107

Compound 107-A: N-(3,4-Difluoro-benzyl)-2-(2,2-dimethyl-5-oxo-[1,3]dioxolan-4-ylidene)-acetamide

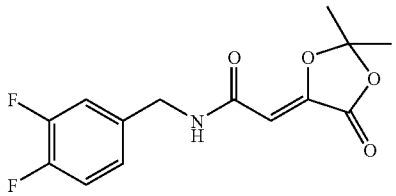

To a stirred suspension of 3,4-difluorobenzylamine (0.43 mg, 0.3 mmol) and resin bound morpholine (200 mg, 2.5–4.0 mmol/1 g) was added a solution of (2,2-dimethyl-5-oxo-[1,3]dioxolan-4-ylidene)-acetyl chloride (60 mg, 0.31 mmol) in $CH_2Cl_2$ (3 mL) and the mixture stirred for 1 h. The mixture was filtered and the filtrate concentrated to give the title product as a white solid (81.8 mg, 92% yield). MS calcd for $C_{14}H_{13}F_2NO_4Na$ (M+Na): 320.29. found: 320.27.

Compound 828: 4-Hydroxy-1-(2-morpholin-4-yl-ethyl)-5-oxo-2,5-dihydro-1H-pyrrole-3-carboxylic acid 3,4-difluoro-benzylamide

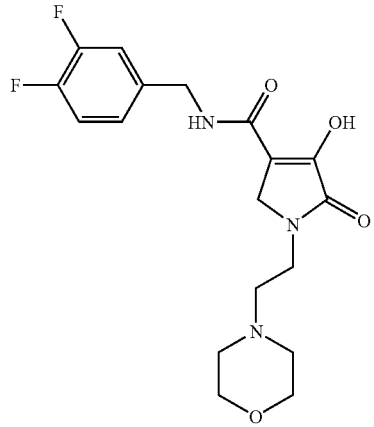

A mixture of N-(3,4-difluoro-benzyl)-2-(2,2-dimethyl-5-oxo-[1,3]dioxolan-4-ylidene)-acetamide (58 mg, 0.195 mmol) and a 0.2 mmol solution of methylene-(2-morpholin-4-yl-ethyl)-amine in methanol (1.1 mL, 0.22 mmol) was heated at 70° C. for 1 h. The reaction mixture was cooled to room temperature and purified by preparative HPLC using methanol/water (0.1% TFA) as the eluent. The fractions containing the product were combined and concentrated to give the title compound as a hydroscopic yellow powder (30 mg, 31% yield). $^1$H NMR (500 MHz, DMSO) δ: 11.95 (1H, br s), 9.56 (1H, br s), 8.03 (1H, t, J=6.1 Hz), 7.41–7.30 (2H, m), 7.15–7.12 (1H, m), 4.41 (2H, d, J=6.1 Hz), 4.04 (2H, s), 4.02–3.93 (2H, m), 3.82–3.77 (2H, m), 3.65–3.51 (4H, m), 3.45–3.41 (2H, m), 3.15–3.06 (2H, m). HRMS calcd for $C_{18}H_{20}F_2N_3O_4$ (M+H): 380.1422. found: 380.1424.

EXAMPLE 108

Compound 108-A: (3,4-Dichloro-benzyl)-isopropyl-amine; compound hydrochloride

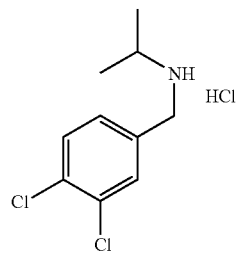

To a stirred solution of 3,4-dichlorobenzaldehyde (3.50 g, 20 mmol) and isopropylamine (2.40 g, 40 mmol) in methanol (20 mL) was added a freshly prepared solution zinc chloride (1.36 g, 10 mmol) and sodium cyanoborohydride (1.25 g, 20 mmol) in methanol (50 mL) at room temperature. The resulting clear reaction mixture was stirred overnight, then concentrated. The residue was taken up into aq NaOH (0.2N, 100 mL), extracted with ethyl acetate (3×100 mL). The combined organic extracts were dried over $Na_2SO_4$, filtered and concentrated to give viscous yellow oil. The residue was dissolved into ether and converted to hydrochloride salt (4.75 g, 93% yield). ¹H NMR (500 MHz, DMSO) δ: 9.54 (2H, s), 8.00 (1H, d, J=2 Hz), 7.70 (1H, d, J=8 Hz), 7.65 (1H, m), 4.13 (2H, t, J=6 Hz), 3.25–3.22 (1H, m), 1.30 (3H, d, J=6.5 Hz). MS calcd for C10H14Cl2N (M+H): 218.04. found: 218.04.

Compound 108-B: N-(3,4-Dichloro-benzyl)-2-(2,2-dimethyl-5-oxo-[1,3]dioxolan-4-ylidene)-N-isopropyl-acetamide

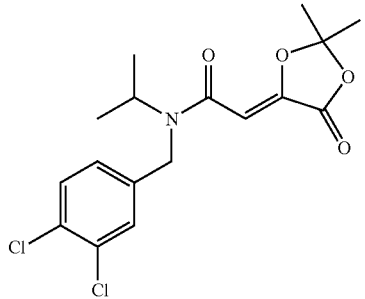

To a stirred mixture of (3,4-dichloro-benzyl)-isopropyl-amine; compound hydrochloride (260 mg, 1.024 mmol) and (2,2-dimethyl-5-oxo-[1,3]dioxolan-4-ylidene)-acetyl chloride (190 mg, 1.0 mmol) in CH₂Cl₂ (20 mL) at room temperature was added diisopropylethylamine (350 μL, 2.0 mmol). After 30 min, the reaction mixture was diluted with ethyl acetate (50 mL), washed with dilute aqueous HCl (1×5 mL), water (1×10 mL), and saturated aq. NaCl (1×5 mL). The organic layer was dried over Na₂SO₄, filtered and concentrated to give viscous yellow oil. Purification on a silica gel column using hexanes/ethyl acetate (3:2) gave pure product as a viscous yellow oil (372 mg, 93% yield). ¹H NMR (500 MHz, CDCl₃) δ: 7.41–7.30 (2H, m), 7.11 (0.67H, d, J=10.1 Hz), 7.10 (0.33H, d, J=10.1 Hz), 6.22 (0.67H, s), 5.87 (0.33H, s), 4.87–4.81 (0.33H, m), 4.51 (1.34H, s), 4.47 (0.66H, s), 4.30–4.24 (0.67H, m), 1.73 (4H, s), 1.71 (2H, s), 1.21 (4H, d, J=6.2 Hz), 1.11 (2H, d, J=6.7 Hz). MS calcd for C₁₇H₂₀Cl₂NO₄ (M+H): 372.24. found: 372.18.

Compound 829: 4-Hydroxy-1-(2-morpholin-4-yl-ethyl)-5-oxo-2,5-dihydro-1H-pyrrole-3-carboxylic acid (3,4-dichloro-benzyl)-isopropyl-amide

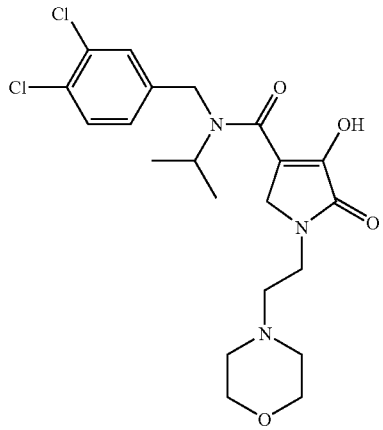

Compound 829 was prepared according to the methods described in the previous examples to yield 217 mg (47% yield) of the title compound as the corresponding TFA salt. ¹H NMR (300 MHz, DMSO) δ: 11.02 (1H, s), 9.62 (1H, br s), 7.57 (1H, d, J=8.1 Hz), 7.48 (1H, s), 7.22 (1H, d, J=7.7 Hz), 4.55 (2H, s), 4.33–4.24 (1H, br m), 4.11 (2H, s), 4.02–3.96 (2H, br m), 3.77 (2H, s), 3.64–3.54 (4H, m), 3.42 (2H, br s), 3.19–3.04 (2H, br m), 1.12 (6H, d, J=6.6 Hz). HRMS calcd for C₂₁H₂₈Cl₂N₃O₄ (M+H): 456.1457. found: 456.1470.

EXAMPLE 109

Compound 109-A: (3,4-Dichloro-benzyl)-(3-phenyl-propyl)-amine; hydrochloride

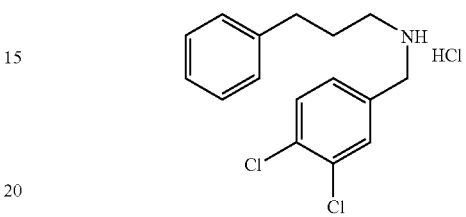

To a stirred solution of 3,4-dichlorobenzaldehyde (3.50 g, 20 mmol) and 3-phenylpropylamine (5.40 g, 40 mmol) in methanol (20 mL) was added a freshly prepared solution of zinc chloride (1.36 g, 10 mmol) and sodium cyanoborohydride (1.25 g, 20 mmol) in methanol (50 mL) at room temperature. The resulting clear reaction mixture was stirred overnight, then concentrated. The residue was taken up into aq NaOH (0.2N, 100 mL) and extracted with ethyl acetate (3×100 mL). The combined organic extracts were dried over Na₂SO₄, filtered and concentrated to give a viscous yellow oil. The residue was purified on silica gel column using 30–40% ethyl acetate in hexanes. The product was dissolved in Et₂O and treated with HCl (in ether) to form the corresponding hydrochloride salt as a precipitate which was isolated by filtration (5.40 g, 98% yield). ¹H NMR (500 MHz, DMSO) δ: 9.66 (2H,s), 7.94 (1H, d, J=2.0 Hz), 7.69 (1H, d, J=8.5 Hz), 7.59 (1H, m), 7.30–7.18 (5H, m), 4.13 (2H, s), 2.89–2.5 (2H, br s), 2.65 (2H, t, J=7.5 Hz), 1.99 (2H, m). MS calcd for C₁₆H₁₇Cl₂N (M+1): 294.08. found: 294.08.

Compound 109-B: N-(3,4-Dichloro-benzyl)-2-(2,2-dimethyl-5-oxo-[1,3]dioxolan-4-ylidene)-N-(3-phenyl-propyl)-acetamide

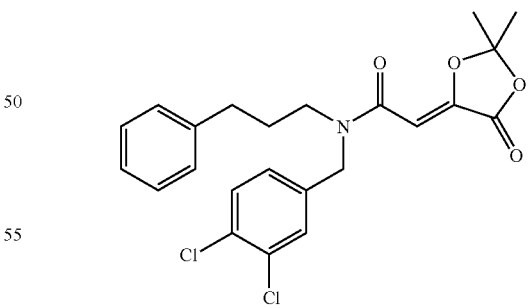

To a stirred mixture of (3,4-dichloro-benzyl)-(3-phenyl-propyl)-amine; hydrochloride (330 mg, 1.0 mmol) and (2,2-dimethyl-5-oxo-[1,3]dioxolan-4-ylidene)-acetyl chloride (206 mg, 1.08 mmol) in CH₂Cl₂ (10 mL) at room temperature was added diisopropylethylamine (386 μL, 2.2 mmol). After 30 min, the reaction mixture was diluted with ether (50 mL), washed with dilute aqueous HCl (1×5 mL), water (1×10 mL), and saturated aq. NaCl (1×5 mL). The organic layer was dried over Na₂SO₄, filtered and concentrated to give the desired amide (447 mg, 100% yield) as a viscous oil. $^{1}$H NMR (300 MHz, CDCl$_3$) δ: 7.41–6.94 (8H, m), 6.08 (0.66H, s), 6.01 (0.34H, s), 4.53 (1.33H, s), 4.48 (0.67H, s), 3.41 (0.67H, t, J=7.5 Hz), 3.26 (1.33H, t, J=7.8 Hz), 2.61 (2H, t, J=7.3 Hz), 1.95–1.85 (2H, m), 1.71 (6H,s). MS calcd for C$_{23}$H$_{23}$Cl$_2$NO$_4$Na (M+Na): 470.09. Found: 470.09.

Compound 830: 4-Hydroxy-1-(2-morpholin-4-yl-ethyl)-5-oxo-2,5-dihydro-1H-pyrrole-3-carboxylic acid (3,4-dichloro-benzyl)-(3-phenyl-propyl)-amide

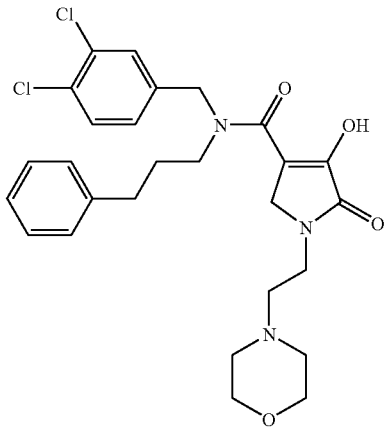

Compound 830 was prepared according to the methods described in the previous examples to yield 207 mg (38% yield) of the title compound as the corresponding TFA salt. $^{1}$HNMR (500 MHz, DMSO-d6) δ: 11.04 (1H, s), 9.64 (1H, s), 7.59 (1H, d, J=8.2 Hz), 7.50 (1H, s), 7.28–7.21 (3H, m), 7.17–7.11 (3H, m), 4.63 (2H, s), 4.07 (2H, s), 4.04–3.96 (2H, br s), 3.79–3.73 (2H, br s), 3.68–3.51 (4H, br m), 3.46–3.35 (4H, br m), 3.28 (1H, br s), 3.16–3.05 (2H, br s), 1.88–1.71 (2H, br s). HRMS calcd for C$_{27}$H$_{32}$Cl$_2$N$_3$O$_4$ (M+H): 532.1770. found: 532.1758.

EXAMPLE 110

Compound 110-A: (3,4-Dichloro-benzyl)-(3-methyl-butyl)-amine hydrochloride

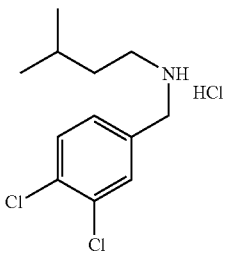

To a stirred solution of 3,4-dichlorobenzaldehyde (3.50 g, 20 mmol) and 3-methylbutylamine (2.62 g, 40 mmol) in methanol (20 mL) was added a freshly prepared solution zinc chloride (1.36 g, 10 mmol) and sodium cyanoborohydride (1.25 g, 20 mmol) in methanol (50 mL) at room temperature. The resulting clear reaction mixture was stirred overnight, then concentrated. The residue was taken up into aq NaOH (0.2N, 100 mL), extracted with ethyl acetate (3×100 mL). The combined organic extracts were dried over Na$_2$SO$_4$, filtered and concentrated to give viscous yellow oil. The residue was purified on silica gel column using 1:4, 3:7 and 2:3 ethyl acetate/hexanes as eluent. The product was dissolved in Et$_2$O and treated with HCl (in ether) to form the corresponding hydrochloride salt as a precipitate which was isolated by filtration (4.924 g, 73% yield). $^{1}$H NMR (500 MHz, DMSO) δ: 9.57 (2H,s), 7.95 (1H, d, J=2 Hz), 7.70 (1H, d, J=8.5 Hz), 7.60 (1H, m), 4.13 (2H, s), 2.87–2.85 (2H, br m), 1.63–1.54 (3H, m), 0.86 (6H, d, J=6.5 Hz). MS calcd for C$_{12}$H$_{18}$Cl$_2$N (M+H): 246.08. found: 246.31.

Compound 110-B: N-(3,4-Dichloro-benzyl)-2-(2,2-dimethyl-5-oxo-[1,3]dioxolan-4-ylidene)-N-(3-methyl-butyl)-acetamide

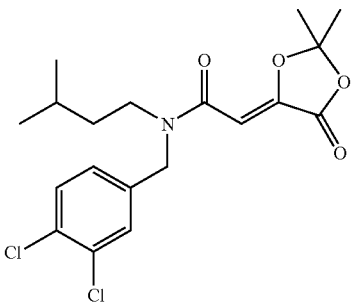

To a stirred mixture of (3,4-dichloro-benzyl)-(3-methyl-butyl)-amine hydrochloride (283 mg, 1.0 mmol) and (2,2-dimethyl-5-oxo-[1,3]dioxolan-4-ylidene)-acetyl chloride (206 mg, 1.08 mmol) in CH$_2$Cl$_2$ (10 mL) at room temperature was added diisopropylethylamine (386 μL, 2.2 mmol). After 30 min, the reaction mixture was diluted with ether (50 mL), washed with dilute aqueous HCl (1×5 mL), water (1×10 mL), and saturated aq. NaCl (1×5 mL). The organic layer was dried over Na$_2$SO$_4$, filtered and concentrated to give viscous yellow oil. Purification on a Silica gel column using hexanes/ethyl acetate (20–40% EtOAc) as the eluent gave the title compound as a viscous yellow oil (400 mg, 100% yield). $^{1}$H NMR (500 MHz, CDCl$_3$) δ: 7.42–7.26 (2H, m), 7.11 (0.67H, d, J=8.2 Hz), 7.01 (0.33H, d, J=8.2 Hz), 6.14 (0.67H, s), 6.00 (0.33H, s), 4.56 (1.34H, s), 4.52 (0.66H, s), 3.39–3.36 (0.67H, m), 3.29–3.26 (1.33H, m), 1.74 (4H, s), 1.70 (2H, s), 1.59–1.50 (1H, m), 1.47–1.42 (2H, m), 0.90–0.88 (6H, m). MS calcd for C$_{19}$H$_{24}$Cl$_2$NO$_4$ (M+H): 400.1. found: 400.07.

Compound 831: 4-Hydroxy-1-(2-morpholin-4-yl-ethyl)-5-oxo-2,5-dihydro-1H-pyrrole-3-carboxylic acid (3,4-dichloro-benzyl)-(3-methyl-butyl)-amide

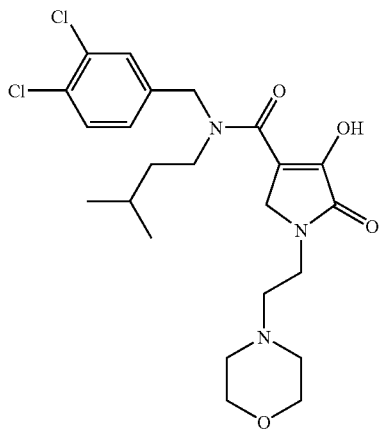

Compound 831 was prepared according to the methods described in the previous examples to yield 213 mg (38%

359 yield) of the title compound as the corresponding TFA salt. ¹HNMR (500 MHz, DMSO-d6) δ: 11.08 (1H, s), 9.73 (1H, s), 7.61 (1H, d, J=8.2 Hz), 7.52 (1H, s), 7.25 (1H, br s), 4.61 (2H, s), 4.11 (2H, s), 4.05–3.95 (2H, br m), 3.78 (2H, br s), 3.70–3.48 (4H, m), 3.46–3.31 (4H, br m), 3.26 (1H, br s), 3.17–3.02 (2H, br m), 1.57–1.27 (3H, br m), 0.80 (6H, br s). HRMS calcd for $C_{23}H_{32}Cl_2N_3O_4$ (M+H): 484.177. found: 484.1793.

EXAMPLE 111

Compound 832: 4-Hydroxy-5-oxo-1-[2-(tetrahydro-pyran-4-yl)-ethyl]-2,5-dihydro-1H-pyrrole-3-carboxylic acid (3,4-dichloro-benzyl)-methyl-amide

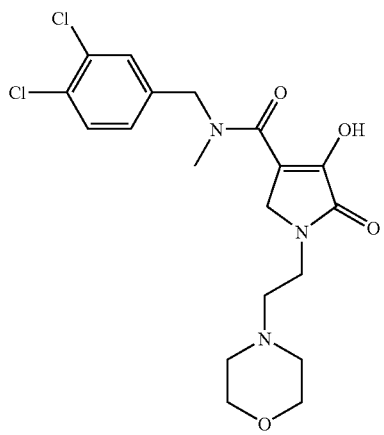

A mixture of paraformaldehyde (18 mg, 0.563 mmol) and 4-(2-aminoethyl)tetrahydropyran (65 mg, 0.5 mmol) in anhydrous methanol (3 mL) was warmed to 60° C. To the resulting clear homogeneous solution was added N-(3,4-dichloro-benzyl)-2-(2,2-dimethyl-5-oxo-[1,3]dioxolan-4-ylidene)-N-methyl-acetamide (172 mg, 0.5 mmol) and stirring continued for 18 h at 60° C. and an additional 6 h at room temperature. The crude reaction mixture was purified by preparative HPLC on a C18 column using water/methanol (0.1% TFA) as the eluent. The fractions containing the desired product were combined, the methanol removed under vacuum and the remaining aqueous solution extracted with ethyl acetate. The combined ethyl acetate extracts were dried over anhydrous $Na_2SO_4$, filtered and concentrated to give the title compound as a white solid (164 mg, 77% yield). ¹HNMR (500 MHz, CDCl₃) δ: 10.15 (1H, br s), 7.41 (1H, d, J=8.2 Hz), 7.35 (1H, s), 7.11 (1H, d, J=8.2 Hz), 4.60 (2H, s), 4.13 (2H, s), 3.93 (2H, dd, J=11, 3.7 Hz), 3.54 (2H, t, J=7.1 Hz), 3.34 (2H, t, J=11.9 Hz), 3.03 (3H, s), 1.65–1.24 (7H, m). HRMS calcd for $C_{20}H_{25}Cl_2N_2O_4$ (M+H): 427.1191. found: 427.1179.

360

EXAMPLE 112

Compound 833: 4-Hydroxy-5-oxo-1-(2-thiomorpholin-4-yl-ethyl)-2,5-dihydro-1H-pyrrole-3-carboxylic acid (3,4-dichloro-benzyl)-methyl-amide

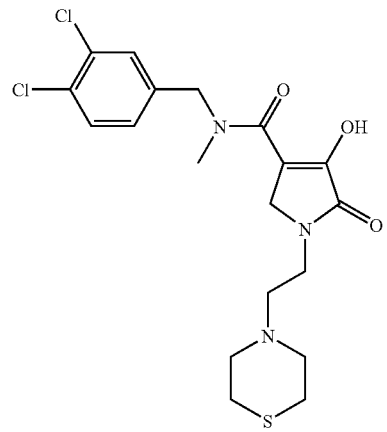

A mixture of paraformaldehyde (56 mg, 1.75 mmol) and 1-(2-aminoethyl)thiomorpholine (219 mg, 1.5 mmol) in anhydrous methanol (5 mL) was warmed to 60° C. To the resulting clear homogeneous solution was added N-(3,4-dichloro-benzyl)-2-(2,2-dimethyl-5-oxo-[1,3]dioxolan-4-ylidene)-N-methyl-acetamide (516 mg, 1.5 mmol) and stirring continued for 18 h at 60° C. and an additional 6 h at room temperature. The crude reaction mixture was purified on C18 column using water/acetonitrile (contains 0.05% TFA) as the eluent. The fractions containing the desired product were combined, concentrated and lyophilized to give the corresponding TFA salt of the title compound as a white solid (555 mg, 66% yield). ¹HNMR (500 MHz, DMSO-d6) δ: 11.10 (1H, s), 9.53 (1H, br s), 7.62 (1H, d, J=8.2 Hz), 7.50 (1H, s), 7.28–7.20 (1H, br s), 4.59 (2H, s), 4.12 (2H, s), 3.85–3.73 (4H, m), 3.45–3.37 (2H, br s), 3.25–3.14 (2H, br m), 3.02–2.95 (2H, br m), 2.94–2.85 (4H, br m). HRMS calcd for $C_{19}H_{24}Cl_2N_3O_3S$: 444.0915. found: 444.0909.

EXAMPLE 113

Compound 834: 4-Hydroxy-1-[2-(2-hydroxy-ethylamino)-ethyl]-5-oxo-2,5-dihydro-1H-pyrrole-3-carboxylic acid (3,4-dichloro-benzyl)-methyl-amide

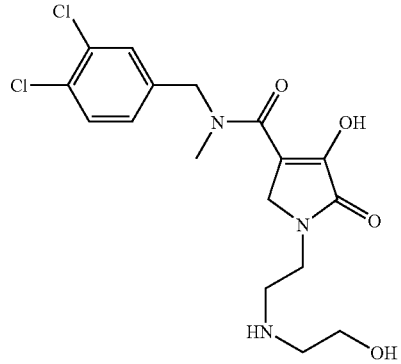

A mixture of paraformaldehyde (18 mg, 0.563 mmol) and 2-(2-aminoethylamino)ethanol (54 mg, 0.5 mmol) in anhy drous methanol (3 mL) was warmed to 60° C. To the resulting clear homogeneous solution was added N-(3,4-dichloro-benzyl)-2-(2,2-dimethyl-5-oxo-[1,3]dioxolan-4-ylidene)-N-methyl-acetamide (175 mg, 0.5 mmol) and the mixture stirred for 30 min at 60° C. The crude product was purified by preparative HPLC on a C18 column using water/methanol (0.1% TFA) as the eluent. The fractions containing the desired product were combined, concentrated and lyophilized to give the corresponding TFA salt of the title compound as a white powder (156 mg, 61%.yield). $^1$HNMR (500 MHz, CDCl$_3$) δ: 9.08 (2H, br s), 7.39 (1H, d, J=8.2 Hz), 7.32 (1H, s), 7.08 (1H, d, J=8.2 Hz), 4.55 (2H, s), 4.24 (2H, s), 3.93–3.80 (5H, br m), 3.40 (2H, br s), 3.21 (2H, br s), 2.98 (3H, s). HRMS calcd for $C_{17}H_{22}C_2N_3O_4$ (M+H): 402.0987. found: 402.1311.

EXAMPLE 114

Compound 835: 4-Hydroxy-5-oxo-1-[2-(1-oxo-1λ$^4$-thiomorpholin-4-yl)-ethyl]-2,5-dihydro-1H-pyrrole-3-carboxylic acid (3,4-dichloro-benzyl)-methyl-amide

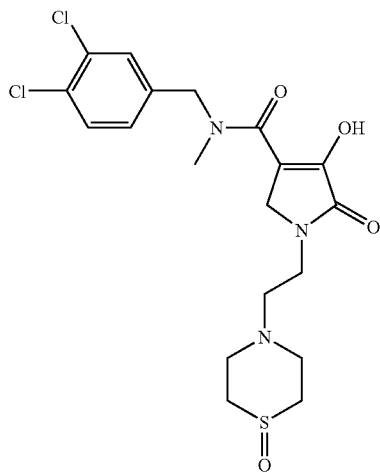

To a stirred solution of 4-hydroxy-5-oxo-1-(2-thiomorpholin-4-yl-ethyl)-2,5-dihydro-1H-pyrrole-3-carboxylic acid (3,4-dichloro-benzyl)-methyl-amide (108 mg, 0.243 mmol) in water (20 mL) was added 30% hydrogen peroxide (0.3 mL). After stirring overnight the reaction mixture was lyophilized to give the title compound as a white powder. $^1$HNMR (500 MHz, CDCl$_3$) δ: 7.42 (1H, d, J=8.5 Hz), 7.34 (1H, s), 7.10 (1H, d, J=8.2 Hz), 4.59 (2H, s), 4.28 (2H, s), 3.89 (2H, t, J=5.8 Hz), 3.74–3.70 (2H, m), 3.63 (2H, t, J=11.9 Hz), 3.29–3.24 (2H, m), 3.18 (2H, t, J=11.9 Hz), 3.07–2.99 (2H, m), 3.01 (3H, s). HRMS calcd for $C_{19}H_{24}Cl_2N_3O_4S$ (M+H): 460.0865. found: 460.0884.

EXAMPLE 115

Compound 836: [(2-{4-[(3,4-Dichloro-benzyl)-methyl-carbamoyl]-3-hydroxy-2-oxo-2,5-dihydro-pyrrol-1-yl}-ethyl)-(2-hydroxy-ethyl)-amino]-acetic acid methyl ester

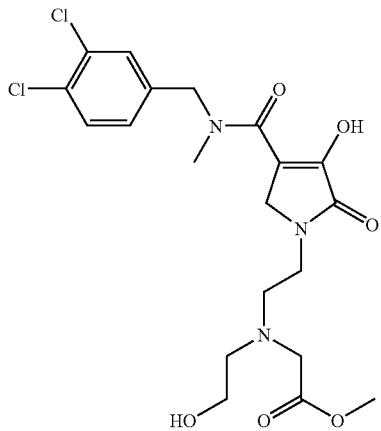

To a stirred warm (approximately 60° C.) solution of 2-(2-aminoethylamino)ethanol (104 mg, 1.0 mmol) and paraformaldehyde (32 mg, 1.0 mmol) in anhydrous methanol was added N-(3,4-dichloro-benzyl)-2-(2,2-dimethyl-5-oxo-[1,3]dioxolan-4-ylidene)-N-methyl-acetamide (344 mg, 1 mmol). After 30 min, the mixture was cooled to room temperature and methyl bromoacetate (104 μL, 1.1 mmol) followed by K$_2$CO$_3$ was added. The resulting suspension was stirred overnight at 40° C., then filtered and purified by preparative HPLC on a C18 column using water/methanol (0.1% TFA) as the eluent. The fractions containing the desired product were combined, concentrated and lyophilized to yield the corresponding TFA salt of the title compound as a white powder (248 mg, 42% yield). $^1$HNMR (500 MHz, CDCl$_3$) δ: 7.38 (1H, d, J=8.2 Hz), 7.32 (1H, s), 7.07 (1H, d, J=8 Hz), 4.56 (3H, s), 4.20 (2H, s), 4.01 (2H, s), 3.86–3.78 (4H, m), 3.59–2.55 (2H, m), 3.38–3.34 (2H, m), 3.01–2.94 (4H, m), 2.73 (3H, s). HRMS calcd for $C_{20}H_{26}Cl_2N_3O_5$ (M+H): 474.1199. found: 474.1295.

EXAMPLE 116

Compound 837: 4-{4-[(3,4-Dichloro-benzyl)-methyl-carbamoyl]-3-hydroxy-2-oxo-2,5-dihydro-pyrrol-1-yl}-piperidine-1-carboxylic acid ethyl ester

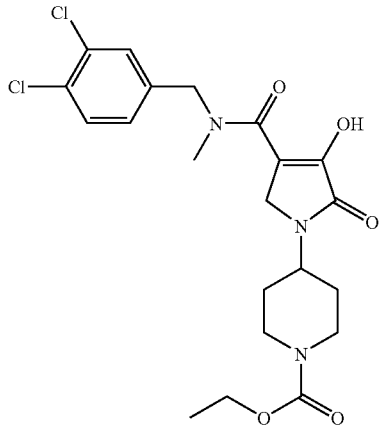

To a stirred warm (60° C.) solution of ethyl 4-amino-1-piperidinecarboxylate (86.1 mg, 0.5 mmol) and paraformaldehyde (16 mg, 0.5 mmol) in methanol (2 mL) was added N-(3,4-dichloro-benzyl)-2-(2,2-dimethyl-5-oxo-[1,3]dioxolan-4-ylidene)-N-methyl-acetamide (175 mg, 0.5 mmol). After 2 h, the reaction mixture was cooled and purified using preparative HPLC on a C18 column using water/methanol-(0.1% TFA) as the eluent. The fractions containing the desired product were combined, concentrated and lyophilized to give the title compound as a white powder (64 mg, 27% yield). $^1$HNMR (500 MHz, CDCl$_3$) δ: 10.16 (2H, br s), 7.40 (1H, d, J=8.2 Hz), 7.35 (1H, s), 7.10 (1H, d, J=8.0 Hz), 4.59 (2H, s), 4.34–4.18 (3H, m), 4.13 (2H, q, J=7.0 Hz), 4.09 (2H, s), 2.06 (2H, s), 2.87–2.80 (2H, br m), 1.82–1.76 (2H, br m), 1.63–1.55 (2H, m), 1.25 (3H, t, J=7.0 Hz). MS calcd for $C_{21}H_{26}Cl_2N_3O_5$ (M+H): 470.36. found: 470.02.

EXAMPLE 117

Compound 838: 4-Hydroxy-5-oxo-1-piperidin-3-yl-2,5-dihydro-1H-pyrrole-3-carboxylic acid (3,4-dichloro-benzyl)-methyl-amide

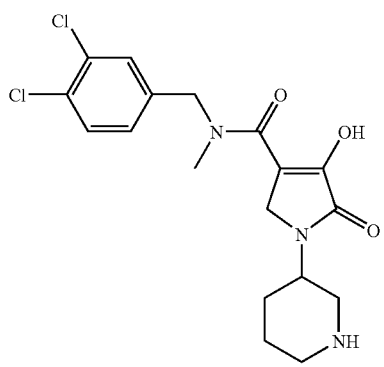

To a stirred warm (60° C.) solution of 3-aminopiperidine dihydrochloride (150 mg, 0.867 mmol), paraformaldehyde (34 mg, 1.04 mmol) and triethylamine (0.3 mL, 2.14 mmol) in methanol (5 mL) was added N-(3,4-dichloro-benzyl)-2-(2,2-dimethyl-5-oxo-[1,3]dioxolan-4-ylidene)-N-methyl-acetamide (300 mg, 0.872 mmol). After 1 h, the reaction mixture was cooled and purified by preparative HPLC using a C18 column and water/methanol (0.001 mM HCl) as eluent. The fractions containing the desired product were combined, concentrated and lyophilized to give the corresponding hydrochloride salt of the title compound as a white powder (162 mg, 43% yield). $^1$HNMR (500 MHz, DMSO-d6) δ: 11.06 (1H, br s), 9.35 (1H, d, J=10.1 Hz), 9.10–8.99 (1H, m), 7.62 (1H, d, J=8.2 Hz), 7.52 (1H, s), 7.29–7.20 (1H, br s), 4.59 (2H, d, $J_{AB}$=15.7 Hz), 4.34–3.88 (4H, m), 3.40–2.73 (6H, m), 1.90–1.74 (4H, m). HRMS calcd for $C_{18}H_{22}Cl_2N_3O_3$ (M+H): 398.1038; found: 398.1042.

EXAMPLE 118

Compound 839: 4-Hydroxy-5-oxo-1-(2,2,2-trifluoro-ethyl)-2,5-dihydro-1H-pyrrole-3-carboxylic acid (3,4-dichloro-benzyl)-methyl-amide

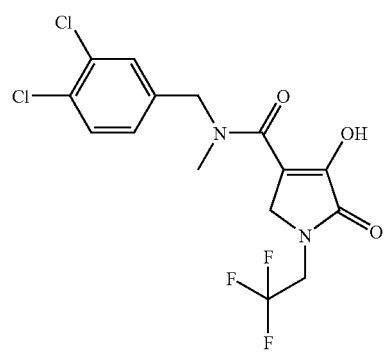

To a stirred warm (60° C.) solution of 2,2,2-trifluoroethylamine hydrochloride (100 mg, 1.0 mmol) paraformaldehyde (32 mg, 1.0 mmol) and triethylamine (0.14 mL, 1.0 mmol) in methanol (5 mL) was added N-(3,4-dichloro-benzyl)-2-(2,2-dimethyl-5-oxo-[1,3]dioxolan-4-ylidene)-N-methyl-acetamide (344 mg, 1.0 mmol). After 24 h, the reaction mixture was cooled and purified by preparative HPLC using a C18 column and water/methanol-(0.1% TFA) as eluent. The fractions containing the desired product were combined, concentrated and lyophilized to give the title compound as a white powder (81.4 mg, 21% yield). $^1$HNMR (500 MHz, CDCl$_3$) δ: 10.05 (1H, br s), 7.42 (1H, d, J=8.2 Hz), 7.36 (1H, s), 7.11 (1H, d, J=8.2 Hz), 4.60 (2H, s), 4.32 (2H, s), 4.10 (2H, q, 8.9 Hz), 3.04 (3H, s). HRMS calcd for $C_{15}H_{12}Cl_2F_3N_2O_3$ (M−H): 395.0177. found: 395.0192.

EXAMPLE 119

Compound 840: 4-Hydroxy-5-oxo-1-piperidin-4-yl-2,5-dihydro-1H-pyrrole-3-carboxylic acid (3,4-dichloro-benzyl)-methyl-amide

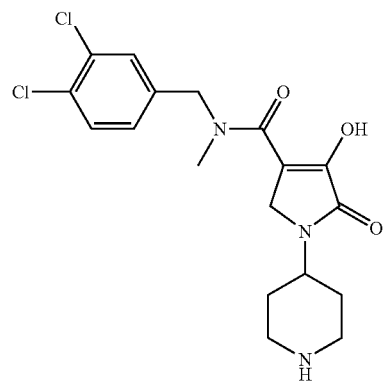

To a stirred warm (60° C.) solution of 4-aminopiperidine (36 mg, 0.25 mmol) and paraformaldehyde (8 mg, 0.25 mmol) in methanol (1.5 mL) was added N-(3,4-dichloro-benzyl)-2-(2,2-dimethyl-5-oxo-[1,3]dioxolan-4-ylidene)-N-methyl-acetamide (93 mg, 0.27 mmol). After 1 h, the reaction mixture was cooled and purified by preparative HPLC on a C18 column using water/methanol-(0.1% TFA) as the eluent. The fractions containing the desired product were combined, concentrated and lyophilized to give the corresponding TFA salt of the title compound as white powder (46.3 mg, 36% yield). ¹HNMR (300 MHz, CDCl₃) δ: 9.65 (1H, br s), 9.17 (1H, br s), 7.42 (1H, d, J=8.1 Hz), 7.34 (1H, s), 7.10 (1H, d, J=8.1 Hz), 4.60 (2H, s), 4.40–4.29 (1H, m), 4.20 (2H, s), 3.65–3.52 (2H, m), 3.10–2.82 (2H, m), 3.04 (3H, s), 2.43–1.97 (4H, m). HRMS calcd for $C_{18}H_{22}Cl_2N_3O_3$ (M+H): 398.1038. found: 398.1044.

EXAMPLE 120

Method for the Preparation of Compounds 857–862

The general method for the preparation of compounds 857–862 is illustrated in Scheme XVI.

Compound 120-A: 3,5-Dichlorobenzyl-methyl amine hydrochloride

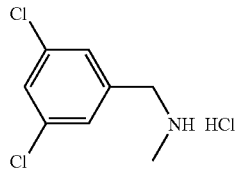

To a stirred solution of 3,5-dichlorobenzaldehyde (9.0 g, 51 mmol) in methanol (100 mL) was added methanolic methylamine (2M, 100 mL, 200 mmol) and the resulting mixture stirred for 2 h at room temperature. To this was added a solution of ZnCl₂ (3.402 g, 25 mmol) slowly and NaCNBH₃ (3.142 g, 50 mmol) in methanol (100 mL). After 24 h, the reaction mixture was concentrated, and the resulting residue taken up in dilute aq NaOH (0.5 N, 200 mL) and extracted with CH₂Cl₂ (5×50 mL). The combined CH₂Cl₂ extracts were dried over anhydrous Na₂SO₄, filtered and concentrated to give a yellow viscous liquid. The crude product was dissolved in ether (200 mL) to which was added 29 mL of 2N HCl (in ether). The resulting white 3,5-dichlorobenzyl-methylamine hydrochloride salt was filtered and dried under vacuum to give 11.20 g (97% yield) of product. ¹HNMR (300 MHz, DMSO-d6) δ: 9.48 (2H, s), 7.68 (3H, s), 4.13 (2H, s), 2.50 (3H, s). MS calcd for $C_8H_{10}Cl_2N$ (M+H): 190.02. found: 190.05.

Compound 120-B: N-(3,5-Dichloro-benzyl)-2-(2,2-dimethyl-5-oxo-[1,3]dioxolan-4-ylidene)-N-methyl-acetamide

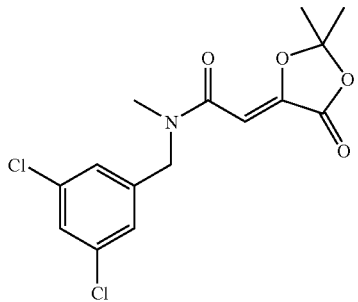

To a stirred solution of (2,2-dimethyl-5-oxo-[1,3]dioxolan-4-ylidene)-acetyl chloride (0.96 g, 5 mmol) in CH₂Cl₂ (20 mL) was added a solution of 3,5-dichlorobenzyl-methylamine hydrochloride (1.133 g, 5 mmol) and Et₃N (2 mL) in CH₂Cl₂ (25 mL). The addition flask was rinsed with CH₂Cl₂ (5 mL) and added to the reaction mixture. After 2 h, the reaction mixture was concentrated and the resulting residue was triturated with ether (100 mL), filtered and concentrated to give the desired product as a viscous brown oil (1.70 g, 100% yield). ¹HNMR (300 MHz, CDCl₃) δ: 7.30–7.27 (1H, m), 7.16 (1.5H, br s), 7.06 (0.5H, s), 6.17 (0.66H, s), 6.07 (0.34H, s), 4.59 (1.33H, s), 4.53 (0.67H, s), 3.03 (2H, s), 2.97 (1H, s), 1.74 (4H, s), 1.70 (2H,s).

General Procedure for the Preparation of Compounds 857–862

As illustrated in Scheme XVI, a 0.2 mM solution of amine, I-7, and paraformaldehyde in methanol (1 mL) are added to 0.1 mM solution of N-(3,5-dichloro-benzyl)-2-(2,2-dimethyl-5-oxo-[1,3]dioxolan-4-ylidene)-N-methyl-acetamide in methanol (2 mL). The mixture is warmed to 60° C. and kept at this temperature until the reaction is complete (1–24 h). The reaction mixture is purified by preparative HPLC on a C18 column using water/methanol-(0.1% TFA) as eluent. The fractions containing the desired product were combined, concentrated and lyophilized.

Compound 841: 4-Hydroxy-1-methyl-5-oxo-2,5-dihydro-1H-pyrrole-3-carboxylic acid (3,5-dichloro-benzyl)-methyl-amide

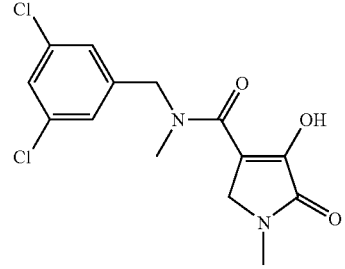

Reaction time 1 h. Obtained 47 mg (53% yield). ¹HNMR (500 MHz, CDCl₃) δ: 7.29 (1H, s), 7.13 (2H, s), 4.59 (2H, s), 4.16 (2H, s), 3.11 (3H, s), 3.03 (3H, s). HRMS calcd for $C_{14}H_{15}Cl_2N_2O_3$ (M+H): 329.04598. found: 329.0456.

Compound 842: 1-Ethyl-4-hydroxy-5-oxo-2,5-dihydro-1H-pyrrole-3-carboxylic acid (3,5-dichloro-benzyl)-methyl-amide

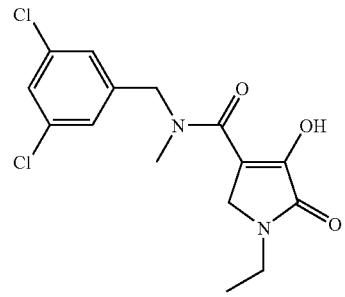

Reaction time 1 h. Obtained 39.8 mg (44% yield). ¹HNMR (500 MHz, CDCl₃) δ: 7.29 (1H, s), 7.14 (2H, s), 4.60 (2H, s), 4.17 (2H, s), 3.36 (2H, q, J=7.3 Hz), 3.04 (3H, s), 1.22 (3H, t, J=7.3 Hz). HRMS calcd for $C_{15}H_{17}Cl_2N_2O_3$ (M+H): 343.0616. found: 343.0609.

Compound 843: 1-(2-Fluoro-ethyl)-4-hydroxy-5-oxo-2,5-dihydro-1H-pyrrole-3-carboxylic acid (3,5-dichloro-benzyl)-methyl-amide Compound 845: 4-Hydroxy-1-(2-morpholin-4-yl-ethyl)-5-oxo-2,5-dihydro-1H-pyrrole-3-carboxylic acid (3,5-dichloro-benzyl)-methyl-amide

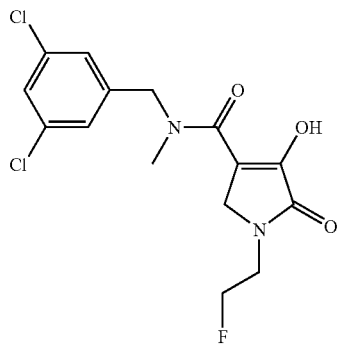

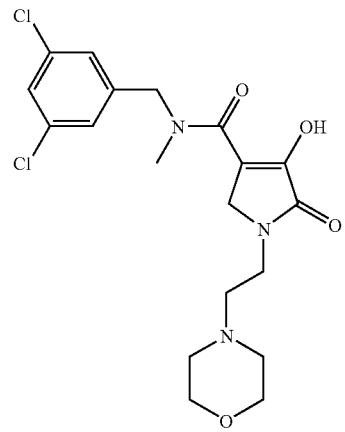

Reaction time 24 h. Obtained 13.6 mg (14% yield). $^1$HNMR (500 MHz, CDCl$_3$) δ: 7.29 (1H, s), 7.14 (2H, s), 4.65 (1H, t, J=4.6 Hz), 4.59 (2H, s), 4.56 (1H, t, J=4.6 Hz), 4.33 (2H, s), 3.84 (1H, t, J=4.6 Hz), 3.78 (1H, t, J=4.6 Hz), 3.04 (3H, s). HRMS calcd for C$_{15}$H$_{14}$Cl$_2$FN$_2$O$_3$ (M−H): 359.0366. found: 359.0374.

Reaction time 1 h. Obtained 61.1 mg (56% yield) as the corresponding TFA salt. $^1$HNMR (500 MHz, CDCl$_3$) δ: 9.15 (1H, br s), 7.29 (1H, s), 7.12 (2H, s), 4.57 (2H, s), 4.28 (2H, s), 4.06–3.72 (8H, m), 3.45–3.37 (2H, br s), 3.00 (3H, s), 2.98–2.91 (2H, m). HRMS calcd for C$_{19}$H$_{24}$Cl$_2$N$_3$O$_4$ (M+H): 428.1144. found: 428.1135.

Compound 844: 4-Hydroxy-5-oxo-1-piperidin-4-yl-2,5-dihydro-1H-pyrrole-3-carboxylic acid (3,5-dichloro-benzyl)-methyl-amide Compound 846: 1-(2-Amino-ethyl)-4-hydroxy-5-oxo-2,5-dihydro-1H-pyrrole-3-carboxylic acid (3,5-dichloro-benzyl)-methyl-amide

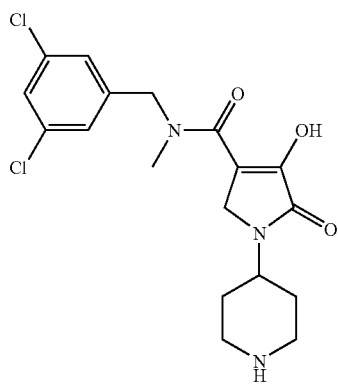

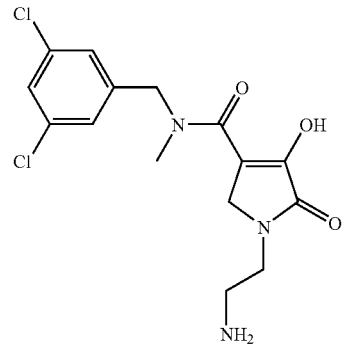

Reaction time 1 h. Obtained 42.3 mg (41% yield) as the corresponding TFA salt. $^1$HNMR (500 MHz, CDCl$_3$) δ: 9.66 (1H, s), 9.17 (1H, s), 7.30 (1H, s), 7.14 (2H, s), 4.60 (2H, s), 4.37 (1H, m), 4.21 (2H, s), 3.56–3.53 (2H, m), 3.08–3.03 (2H, m), 3.06 (3H, s), 2.27–2.19 (2H, m), 2.03–1.97 (2H, m). HRMS calcd for C$_{18}$H$_{22}$Cl$_2$N$_3$O$_3$ (M+H): 398.1038. found: 398.1040.

$^1$HNMR (500 MHz, DMSO-d6) δ: 11.01 (1H, s), 7.53 (1H, s), 7.32 (2H, s), 4.60 (2H, s), 4.10 (2H, s), 3.64 (2H, t, J=5.35 Hz), 3.43 (3H, br s), 3.07–3.00 (4H, m). HRMS calcd for C$_{15}$H$_{18}$Cl$_2$N$_3$O$_3$ (M+H): 358.0725. found: 358.0719.

EXAMPLE 121

Compound 847: 4-Hydroxy-1-(2-(dimethylsulfamidoyl-methyl-amino)-ethyl)-5-oxo-2,5-dihydro-1H-pyrrole-3-carboxylic acid (3,4-dichloro-benzyl)-methyl-amide

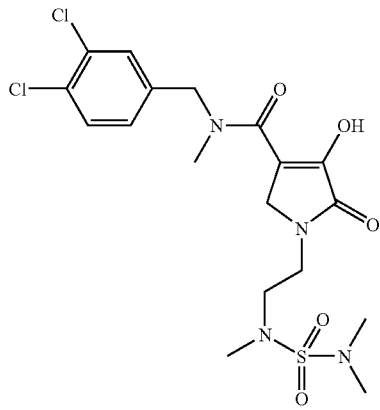

To a stirred solution of 4-hydroxy-1-(2-methylamino-ethyl)-5-oxo-2,5-dihydro-1H-pyrrole-3-carboxylic acid (3,4-dichloro-benzyl)-methyl-amide (Compound 15) (150 mg, 0.367 mmol) in $CH_2Cl_2$ (5 mL) was added $Et_3N$ (0.14 mL, 1.0 mmol) followed by dimethylsulfamoyl chloride (53 μL, 0.5 mmol) at room temperature. After 4 h, the reaction mixture was concentrated and the resulting residue was dissolved in methanol and purified by preparative HPLC on a C18 column using water/methanol-(0.1% TFA) as eluent. The fractions containing the desired product were combined, concentrated and lyophilized to give the title compound as a white solid (134.3 mg, 62% yield). $^1$HNMR (500 MHz, $CDCl_3$) δ: 10.38 (1H, br s), 7.42 (1H, d, J=8.2 Hz), 7.35 (1H, s), 7.10 (1H, d, J=8.2 Hz), 4.58 (2H, s), 4.29 (2H, s), 3.69 (2H, t, J=5.8 Hz), 3.43 (2H, t, J=5.8 Hz), 3.02 (3H, s), 2.81 (3H, s), 2.73 (6H, s). HRMS calcd for $C_{18}H_{25}Cl_2N_4O_5S$ (M+H): 479.0923. found: 479.0941.

EXAMPLE 122

Compound 848: 4-Hydroxy-1-[2-(methanesulfonyl-methyl-amino)-ethyl]-5-oxo-2,5-dihydro-1H-pyrrole-3-carboxylic acid (3,4-dichloro-benzyl)-methyl-amide

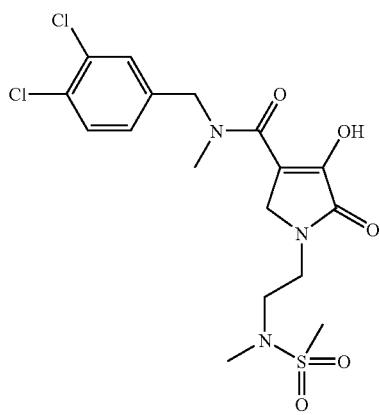

To a stirred solution of 4-hydroxy-1-(2-methylamino-ethyl)-5-oxo-2,5-dihydro-1H-pyrrole-3-carboxylic acid (3,4-dichloro-benzyl)-methyl-amide (Compound 15) (150 mg, 0.367 mmol) in $CH_2Cl_2$ (5 mL) was added $Et_3N$ (0.14 mL, 1.0 mmol) followed by methanesulfonyl chloride (38 μL, 0.5 mmol) at room temperature. After 1 h, the reaction mixture was concentrated and the resulting residue was dissolved in methanol and purified by preparative HPLC on a C18 column using water/methanol-(0.1% TFA) as eluent. The fractions containing the desired product were combined, concentrated and lyophilized to give the title compound as a white powder (21.3 mg, 13% yield). $^1$HNMR (500 MHz, $CDCl_3$) δ: 7.42 (1H, d, J=8.2 Hz), 7.35 (1H, s), 7.11 (1H, d, J=8.2 Hz), 4.58 (2H, s), 4.29 (2H, s), 3.71 (2H, t, J=5.8 Hz), 3.38 (2H, t, J=5.8 Hz), 3.02 (3H, s), 2.89 (3H, s), 2.78 (3H, s). HRMS calcd for $C_{17}H_{22}Cl_2N_3O_5S$ (M+H): 450.0657. found: 450.0658.

EXAMPLE 123

Compound 849: 1-[2-(1,3-Dimethyl-ureido)-ethyl]-4-hydroxy-5-oxo-2,5-dihydro-1H-pyrrole-3-carboxylic acid (3,4-dichloro-benzyl)-methyl-amide

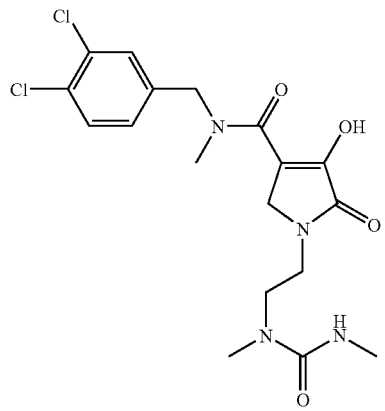

To a stirred solution of 4-hydroxy-1-(2-methylamino-ethyl)-5-oxo-2,5-dihydro-1H-pyrrole-3-carboxylic acid (3,4-dichloro-benzyl)-methyl-amide (Compound 15) (155 mg, 0.379 mmol) in $CH_2Cl_2$ (5 mL) was added $Et_3N$ (0.14 mL, 1.0 mmol) followed by methyl isocyanate (29 μL, 0.5 mmol) at room temperature. After 1 h, the reaction mixture was concentrated and the resulting residue was dissolved in methanol and purified by preparative HPLC on a C18 column using water/methanol (0.1% TFA) as eluent. The fractions containing the product were combined, concentrated and lyophilized to give the title compound as a white powder (107.6 mg, 52% yield). $^1$HNMR (500 MHz, $CDCl_3$) δ: 11.56 (1H, br s), 7.41 (1H, d, J=8.2 Hz), 7.34 (1H, s), 7.10 (1H, d, J=8.2 Hz), 4.66 (1H, br s), 4.57 (2H, s), 4.28 (2H, s), 3.62 (2H, t, J=5.8 Hz), 3.56 (2H, t, J=5.8 Hz), 3.02 (3H, s), 2.89 (3H, s), 2.70 (3H, s). HRMS calcd for $C_{18}H_{23}Cl_2N_4O_4$ (M+H): 429.1096. found: 429.1082.

EXAMPLE 124

Compound 850: 4-Hydroxy-1-[2-(1-methyl-ureido)-ethyl]-5-oxo-2,5-dihydro-1H-pyrrole-3-carboxylic acid (3,4-dichloro-benzyl)-methyl-amide

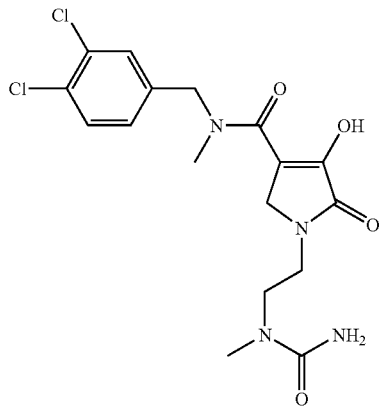

To a stirred solution of 4-hydroxy-1-(2-methylamino-ethyl)-5-oxo-2,5-dihydro-1H-pyrrole-3-carboxylic acid (3,4-dichloro-benzyl)-methyl-amide (Compound 15) (153 mg, 0.374 mmol) in $CH_2Cl_2$ (5 mL) was added $Et_3N$ (0.14 mL, 1.0 mmol) followed by trimethylsilyl isocyanate (68 μL, 0.5 mmol) at room temperature. After 2 h, the reaction mixture was concentrated and the resulting residue was dissolved in methanol and purified by preparative HPLC on a C18 column using water/methanol-(0.1% TFA) as eluent. The fractions containing the product were combined, concentrated and lyophilized to yield the title compound as a white powder (120 mg, 61% yield). $^1$HNMR (500 MHz, $CDCl_3$) δ: 10.37 (1H, br s), 7.41 (1H, d, J=8.2H), 7.34 (1H, s), 7.10 (1H, d, J=8.2 Hz), 5.78 (2H, br s), 4.56 (2H, s), 4.22 (2H, s), 3.64 (2H, t, J=5.2 Hz), 3.55 (2H, t, J=5.2 Hz), 2.99 (3H, s), 2.94 (3H, s). HRMS calcd for $C_{17}H_{21}Cl_2N_4O_4$ (M+H): 415.094. found: 415.0941.

EXAMPLE 125

Compound 851: 4-Hydroxy-1-[2-(2-((N-tert-butyl-carbamoyl-sulfamidoyl)-methyl-amino)-ethyl]-5-oxo-2,5-dihydro-1H-pyrrole-3-carboxylic acid (3,4-dichloro-benzyl)-methyl-amide

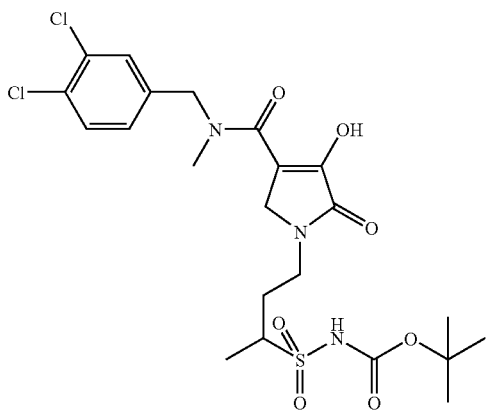

To a stirred solution of 4-hydroxy-1-(2-methylamino-ethyl)-5-oxo-2,5-dihydro-1H-pyrrole-3-carboxylic acid (3,4-dichloro-benzyl)-methyl-amide (Compound 15) (110 mg, 0.269 mmol) in $CH_2Cl_2$ (5 mL) was added $Et_3N$ (0.14 mL, 1.0 mmol) followed by a freshly prepared solution of t-butanol and chlorosulfonyl isocyanate (concentration=0.2 mM, 2 mL, 0.4 mmol) at room temperature. After 1 h, the reaction mixture was concentrated and the resulting residue dissolved in methanol and purified by preparative HPLC on a C18 column using water/methanol-(0.1% TFA) as eluent. The fractions containing the product were combined, concentrated and lyophilized to give the title compound as a white powder (77 mg, 43% yield). $^1$HNMR (500 MHz, $CDCl_3$) δ: 7.68 (1H, s), 7.41 (1H d, J=8.2 Hz), 7.35 (1H, s), 7.10 (1H, d, J=8.2 Hz), 4.57 (2H, s), 4.26 (2H, s), 3.68 (2H, t, J=5.2 Hz), 3.54 (2H, t, J=5.2 Hz), 3.00 (3H, s), 2.92 (3H, s), 1.45 (9H, s). HRMS calcd for $C_{21}H_{27}Cl_2N_4O_7S$ (M+H): 549.0978. found: 549.0988.

EXAMPLE 126

Compound 852: 1-(2-Amino-ethyl)-4-hydroxy-5-oxo-2,5-dihydro-1H-pyrrole-3-carboxylic acid (3,4-dichloro-benzyl)-methyl-amide

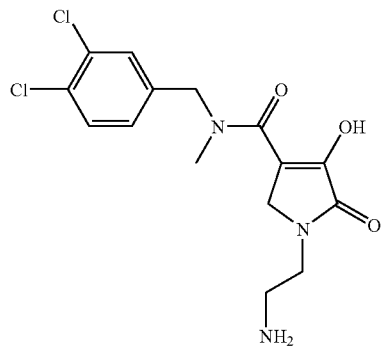

Compound 852 was prepared according to the methods described in the previous examples. $^1$HNMR (500 MHz, DMSO-d6) δ: 10.98 (1H, br s), 7.62 (1H, d, J=8.24 Hz), 7.52 (1H, d, J=2.14 Hz), 7.25 (1H, d, J=7.33 Hz), 4.59 (2H, s), 4.10 (2H, s), 3.64 (5H, br s), 3.06–3.00 (4H, m). HRMS calcd for $C_{15}H_{18}Cl_2N_3O_3$ (M+H): 358.0725. found: 358.0717.

EXAMPLE 127

Compound 853: 4-Hydroxy-1-(2-methylamino-ethyl)-5-oxo-2,5-dihydro-1H-pyrrole-3-carboxylic acid (3,5-dichloro-benzyl)-methyl-amide

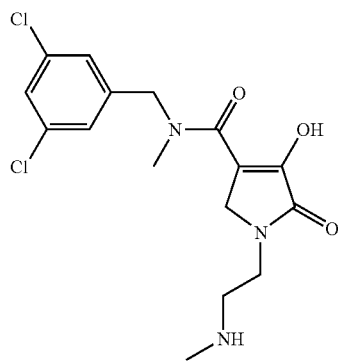

Compound 853 was prepared according to the methods described in the previous examples. ¹HNMR (500 MHz, CDCl₃) δ: 11.96 (1H, br s), 8.92 (2H, s), 7.53 (1H, s), 7.31 (2H, s), 4.60 (2H, s), 4.11 (2H, s), 3.89 (3H, br s), 3.70 (2H, br s), 3.15 (2H, m), 2.55 (3H, t, J=5.19 Hz). HRMS calcd for C₁₆H₂₀Cl₂N₃O₃ (M+H): 372.0882. found: 372.0884.

EXAMPLE 128

Compound 854: 4-Hydroxy-1-(2-(dimethylsulfamidoyl-methyl-amino)-ethyl)-5-oxo-2,5-dihydro-1H-pyrrole-3-carboxylic acid (3,5-dichloro-benzyl)-methyl-amide

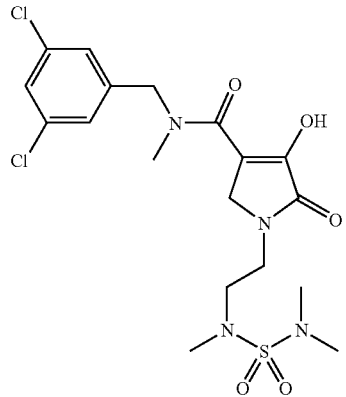

To a stirred solution of 4-hydroxy-1-(2-methylamino-ethyl)-5-oxo-2,5-dihydro-1H-pyrrole-3-carboxylic acid (3,5-dichloro-benzyl)-methyl-amide (82 mg, 0.2 mmol) and Et₃N (0.084 mL, 0.6 mmol) in CH₂Cl₂ (3 mL) was added dimethylsulfamoyl chloride (0.028 mL, 0.26 mmol). After stirring for 2 h at room temperature, the reaction mixture was concentrated and purified by preparative HPLC using MeOH/Water as the eluent. The fractions containing the product were combined and concentrated to give the title compound as a paste (70 mg, 59% yield). ¹HNMR (500 MHz, CDCl₃) δ: 10.68 (1H, br s), 7.27 (1H, s), 7.13 (2H, s), 4.58 (2H, s), 4.29 (2H, s), 3.71–3.65 (2H, m), 3.45–3.40 (2H, m), 3.02 (3H, s), 2.80 (3H, s), 2.71 (6H, s). HRMS calcd for C₁₈H₂₅Cl₂N₄O₅S (M+H): 479.0923. found: 479.0918.

EXAMPLE 129

Compound 855: 1-Carbamoylmethyl-4-hydroxy-5-oxo-2,5-dihydro-1H-pyrrole-3-carboxylic acid (3,4-dichloro-benzyl)-methyl-amide

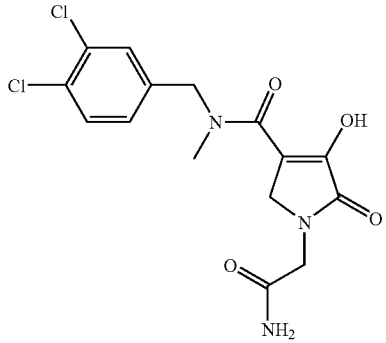

Compound 855 was prepared according to the methods described in the previous examples. ¹HNMR (500 MHz, CDCl₃) δ: 7.84 (1H, d, J=8.24 Hz), 7.28 (1H, br s), 7.05–7.01 (1H, m), 4.52 (2H, s), 4.17 (2H, s), 4.03 (2H, s), 3.43 (3H, br s), 2.94 (3H, s). HRMS calcd for C₁₅H₁₄Cl₂N₃O₄ (M–H): 370.0361; found: 370.0361.

EXAMPLE 130

Compound 856: 4-Hydroxy-1-(2-morpholin-4-yl-ethyl)-5-oxo-2,5-dihydro-1H-pyrrole-3-carboxylic acid methoxy-(4-methylbenzyl)-amide

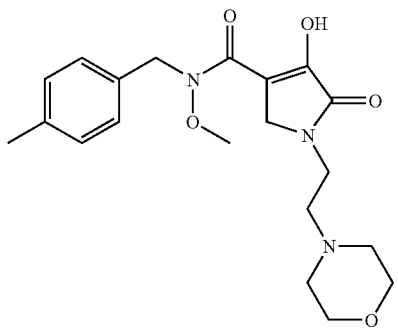

Reaction of 2-(2,2-dimethyl-5-oxo-[1,3]-dioxolan-4-ylidene)-N-methoxy-N-(4-methylbenzyl)-acetamide (0.30 g, 0.98 mmol) with the paraformaldehyde-N-(2-aminoethyl) morpholine adduct in methanol using a procedure similar to the one described in the preparation of compound 13 gave 0.17 g (45% yield) of the title compound as a solid. ¹HNMR 400 MHz (CDCl₃) δ (ppm); 2.35 (3H, s, CH₃), 2.47 (4H, m, 2×NCH₂), 2.56 (2H, t, J=6.2 Hz, NCH₂), 3.62 (2H, t, J=6.2 Hz, NCH₂), 3.66 (4H, m, 2×OCH₂), 3.71 (3H, s, OCH₃), 4.27 (2H, s, NCH₂), 4.85 (2H, s, NCH₂), 7.14–7.24 (4H, m, aromatics). HRMS (FAB+) calculated for C₂₀H₂₈N₃O₅: [M+H]⁺: 390.202896. found: 390.203567.

EXAMPLE 131

Compound 857: 4-Hydroxy-1-methyl-5-oxo-2,5-dihydro-1H-pyrrole-3-carboxylic acid methyl-(4-trifluoromethyl-benzyl)-amide

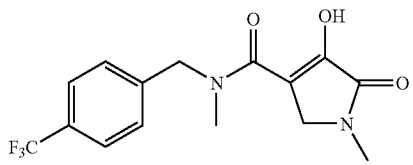

Reaction of 2-(2,2-dimethyl-5-oxo-[1,3]-dioxolan-4-ylidene)-N-methyl-N-(4-trifluoromethylbenzyl)-acetamide (0.50 g, 1.45 mmol) with the paraformaldehyde-methylamine adduct in methanol using a procedure similar to the one described in the preparation of compound 44 (method 44B) gave 0.31 g (64% yield) of the title compound as white crystals; mp 126–128° C. (ethyl acetate-hexane). ¹HNMR 400 MHz (CDCl₃) δ (ppm); 3.07 (3H, s, NCH₃), 3.13 (3H, s, NCH₃), 4.18 (2H, s, NCH₂), 4.74 (2H, s, NCH₂), 7.41 (2H, d, J=8.1 Hz, aromatics), 7.64 (2H, d, J=8.1 Hz, aro-

EXAMPLE 132

Compound 858: 4-Hydroxy-1-(2-morpholin-4-yl-ethyl)-5-oxo-2,5-dihydro-1H-pyrrole-3-carboxylic acid methyl-(4-trifluoromethyl-benzyl)-amide

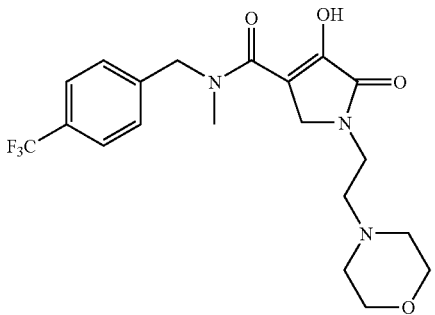

Reaction of 2-(2,2-dimethyl-5-oxo-[1,3]-dioxolan-4-ylidene)-N-methyl-N-(4-trifluoromethyl-benzyl)-acetamide (0.36 g, 1.05 mmol) with the paraformaldehyde-N-(2-aminoethyl)morpholine adduct in methanol using a procedure similar to the one described in the preparation of compound 13 gave 0.16 g (35% yield) of the title compound as a solid after chromatography on reversed phase silica gel. $^1$HNMR 400 MHz (CDCl$_3$) δ (ppm); 2.46 (4H, m, 2×NCH$_2$), 2.57 (2H, t, J=6.1 Hz, NCH$_2$), 3.04 (3H, s, NCH$_3$), 3.6 (6H, m, 2×OCH$_2$ and NCH$_2$), 4.25 (2H, s, NCH$_2$), 4.72 (2H, s, NCH$_2$), 7.41 (2H, d, J=8.0 Hz, aromatics), 7.62 (2H, d, J=8.0 Hz, aromatics). HRMS (FAB+) calculated for C$_{20}$H$_{25}$F$_3$N$_3$O$_4$: [M+H]$^+$: 428.179716. found: 428.179157.

EXAMPLE 133

Compound 859: 4-Hydroxy-1-methyl-5-oxo-2,5-dihydro-1H-pyrrole-3-carboxylic acid methoxy-(4-trifluoromethyl-benzyl)-amide

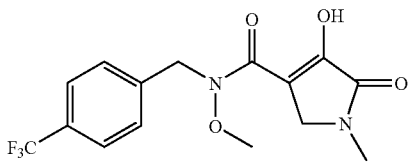

Reaction of 2-(2,2-dimethyl-5-oxo-[1,3]-dioxolan-4-ylidene)-N-methoxy-N-(4-trifluoromethylbenzyl)-acetamide (0.20 g, 0.56 mmol) with the paraformaldehyde-methylamine adduct in methanol using a procedure similar to the one described in the preparation of compound 44 (method 44B) gave 0.10 g (52% yield) of the title compound as white crystals; mp 145° C. (dec) (ethyl acetate-hexane). $^1$HNMR 400 MHz (CDCl$_3$) δ (ppm): 3.11 (3H, s, NCH$_3$), 3.75 (3H, s, OCH$_3$), 4.17 (2H, s, NCH$_2$), 4.94 (2H, s, NCH$_2$), 7.45 (2H, d, J=8.1 Hz, aromatics), 7.61 (2H, d, J=8.1 Hz, aromatics). Anal. Calcd for C$_{15}$H$_{15}$F$_3$N$_2$O$_4$: C, 52.33; H, 4.39; N, 8.13. Found: C, 52.17; H, 4.34; N, 7.98.

matics), 10.56 (1H, broad, OH). Anal. Calcd for C$_{15}$H$_{15}$F$_3$N$_2$O$_3$: C, 54.88; H, 4.61; N, 8.53. Found: C, 54.93; H, 4.57; N, 8.44.

EXAMPLE 134

Compound 860: 4-Hydroxy-1-(2-morpholin-4-yl-ethyl)-5-oxo-2,5-dihydro-1H-pyrrole-3-carboxylic acid methoxy-(4-trifluoromethyl-benzyl)-amide

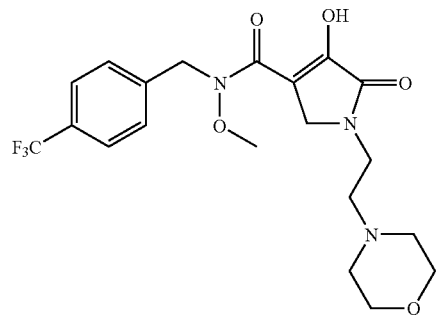

Reaction of 2-(2,2-dimethyl-5-oxo-[1,3]-dioxolan-4-ylidene)-N-methoxy-N-(4-trifluoromethyl-benzyl)-acetamide (0.41 g, 1.13 mmol) with the paraformaldehyde-N-(2-aminoethyl)morpholine adduct in methanol using a procedure similar to the one described in the preparation of compound 13 gave 0.38 g (75% yield) of the title compound as crystals after chromatography on reversed phase silica gel; mp 119° C. (dec) (ethyl acetate-hexane). $^1$HNMR 400 MHz (CDCl$_3$) δ (ppm); 2.48 (4H, m, 2×NCH$_2$), 2.58 (2H, t, J=6.3 Hz, NCH$_2$), 3.64 (2H, t, J=6.3 Hz, NCH$_2$), 3.67 (4H, m, 2×OCH$_2$), 3.75 (3H, s, OCH$_3$), 4.31 (2H, s, NCH$_2$), 4.94 (2H, s, NCH$_2$), 7.47 (2H, d, J=8.1 Hz, aromatics), 7.63 (2H, d, J=8.1 Hz, aromatics). Anal. Calcd for C$_{20}$H$_{24}$F$_3$N$_3$O$_5$: C, 54.17; H, 5.46; N, 9.48. Found: C, 54.12; H, 5.57; N, 9.52.

EXAMPLE 135

Compound 861: 4-Hydroxy-1-(2-morpholin-4-yl-ethyl)-5-oxo-2,5-dihydro-1H-pyrrole-3-carboxylic acid methoxy-(4-methylcarbamoyl-benzyl)-amide

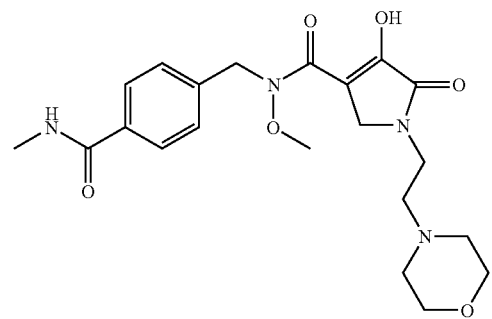

Reaction 4-({[2-(2,2-dimethyl-5-oxo-[1,3]dioxolan-4-ylidene)-acetyl]-methoxy-amino}-methyl)-N-methyl-benzamide (0.053 g, 0.15 mmol) with the paraformaldehyde-N-(2-aminoethyl)morpholine adduct in methanol using a procedure similar to the one described in the preparation of compound 13 gave 0.034 g (41% yield) of the title compound as a white solid after chromatography on reversed phase silica gel. $^1$HNMR 400 MHz (DMSO-d$_6$) δ (ppm); (TFA salt) 2.77 (3H, d, J=4.65 Hz, NCH$_3$), 3.1 (2H, broad m, NCH$_2$), 3.4–3.8 (8H, broad m, 2×NCH$_2$ and 2×OCH$_2$), 3.75 (3H, s, OCH$_2$), 3.98 (2H, broad, NCH$_2$), 4.24 (2H, s, NCH$_2$), 4.94 (2H, s, NCH$_2$), 7.39 (2H, d, J=8.4 Hz, aromatics), 7.80 (2H, d, J=8.4 Hz, aromatic), 8.41 (1H, q, J=4.5 Hz, NH). HRMS (FAB+) calculated for C$_{21}$H$_{29}$N$_4$O$_6$: [M+H]$^+$: 433.208710. found: 433.209419.

EXAMPLE 136

Compound 862: 4-Hydroxy-1-(2-morpholin-4-yl-ethyl)-5-oxo-2,5-dihydro-1H-pyrrole-3-carboxylic acid (3,4-dichlorobenzyl)-methoxy-amide

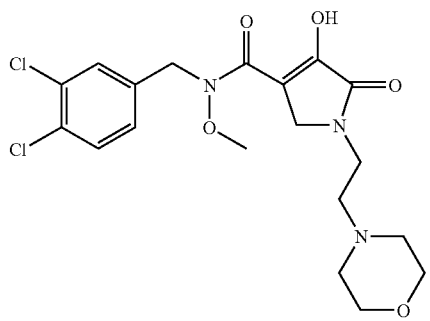

Reaction of N-(3,4-dichlorobenzyl)-2-(2,2-dimethyl-5-oxo-[1,3]-dioxolan-4-ylidene)-N-methoxy-acetamide (0.20 g, 0.56 mmol) with the paraformaldehyde-N-(2-aminoethyl)morpholine adduct in methanol using a procedure similar to the one described in the preparation of compound 13 gave 0.071 g (28% yield) of the title compound as a solid after chromatography on reversed phase silica gel. $^1$HNMR 400 MHz (DMSO-d$_6$) δ (ppm); 2.39 (4H, broad, 2×NCH$_2$), 2.47 (2H, t, J=6.3 Hz, NCH$_2$), 3.49 (2H, t, J=6.3 Hz, NCH$_2$), 3.53 (4H, broad, 2×OCH$_2$), 3.66 (3H, s, OCH$_3$), 4.16 (2H, s, NCH$_2$), 4.89 (2H, s, NCH$_2$), 7.33 (1H, dd, J=1.8 Hz and J=8.1 Hz, aromatic), 7.60 (1H, d, J=8.1 Hz, aromatic), 7.63 (1H, d, J=1.8 Hz, aromatic). HRMS (MAB/N$_2$) calculated for C$_{19}$H$_{23}$C$_2$N$_3$O$_5$: [M$^+$]: 443.101477. found: 443.103002.

EXAMPLE 137

Compound 863: 4-Hydroxy-1-methyl-5-oxo-2,5-dihydro-1H-pyrrole-3-carboxylic acid (4-fluoro-2-trifluoromethyl-benzyl)-methoxy-amide

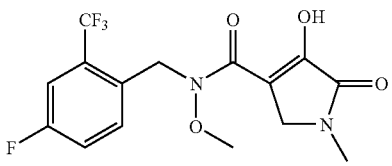

Reaction of 2-(2,2-dimethyl-5-oxo-[1,3]-dioxolan-4-ylidene)-N-(4-fluoro-2-trifluoromethylbenzyl)-N-methoxy-acetamide (0.14 g, 0.37 mmol) with the paraformaldehyde-methylamine adduct in methanol using a procedure similar to the one described in the preparation of compound 44 (method 44B) gave 0.056 g (42% yield) of the title compound as white crystals; mp 167° C. (dec) (ethyl acetate-hexane). $^1$HNMR 400 MHz (CDCl$_3$) δ (ppm); 3.13 (3H, s, NCH$_3$), 3.71 (3H, s, OCH$_3$), 4.21 (2H, s, NCH$_2$), 5.09 (2H, s, NCH$_2$), 7.22–7.27 (1H, m, aromatic), 7.39–7.46 (2H, m, aromatics). Anal. Calcd for C$_{15}$H$_{14}$F$_4$N$_2$O$_4$: C, 49.73; H, 3.89; N, 7.73. Found: C, 49.74; H, 3.92; N, 7.70.

EXAMPLE 138

Compound 864: 4-Hydroxy-1-(2-morpholin-4-yl-ethyl)-5-oxo-2,5-dihydro-1H-pyrrole-3-carboxylic acid (4-fluoro-2-trifluoromethyl-benzyl)-methoxy-amide

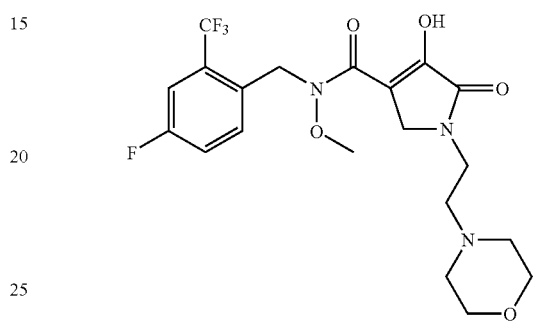

Reaction of 2-(2,2-dimethyl-5-oxo-[1,3]-dioxolan-4-ylidene)-N-(4-fluoro-2-trifluoromethyl-benzyl)-N-methoxy-acetamide (0.21 g, 0.55 mmol) with the paraformaldehyde-N-(2-aminoethyl)morpholine adduct in methanol using a procedure similar to the one described in the preparation of compound 13 gave 0.13 g (50% yield) of the title compound as a solid after chromatography on reversed phase silica gel. $^1$HNMR 400 MHz (CDCl$_3$) δ (ppm); 2.51 (4H, m, 2×NCH$_2$), 2.60 (2H, t, J=6.1 Hz, NCH$_2$), 3.65 (6H, m, 2×OCH$_2$ and NCH$_2$), 3.71 (3H, s, OCH$_3$), 4.32 (2H, s, NCH$_2$), 5.09 (2H, s, NCH$_2$), 7.23–7.27 (2H, m, aromatics), 7.39–7.48 (2H, m, aromatics). MS (ESI$^+$) calculated for C$_{20}$H$_{24}$F$_4$N$_3$O$_5$: [M+H]$^+$: 462. found: 462.

EXAMPLE 139

Compound 865: 4-Hydroxy-1-methyl-5-oxo-2,5-dihydro-1H-pyrrole-3-carboxylic acid [3-(3,4-dichlorophenyl)-propyl]-amide

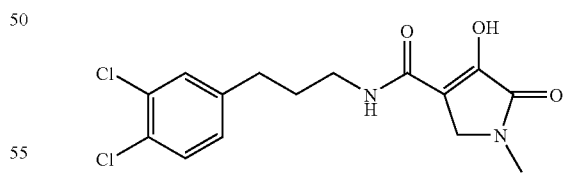

Reaction of N-[3-(3,4-dichlorophenyl)-propyl]-2-(2,2-dimethyl-5-oxo-[1,3]-dioxolan-4-ylidene)-acetamide (0.432 g, 1.20 mmol) with the paraformaldehyde-methylamine adduct in methanol using a procedure similar to the one described in the preparation of compound 44 (method 44B) gave 0.232 g (56% yield) of the title compound as white crystals; mp 157–158° C. (dec) (ethyl acetate-hexane). $^1$HNMR 400 MHz (CDCl$_3$) δ (ppm); 1.81 (2H, m, CH$_2$), 2.57 (2H, t, J=7.5 Hz, CH$_2$), 3.05 (3H, s, NCH$_3$), 3.33 (2H, m, NCH$_2$), 3.98 (2H, s, NCH$_2$), 6.95 (1H, broad t, NH), 7.05

(1H, broad dd, aromatic), 7.21 (1H, d, J=2 Hz, aromatic), 7.26 (1H, d, J=8.1 Hz, aromatic), 10.13 (1H, broad, OH). Anal. Calcd for $C_5H_{16}Cl_2N_2O_3$: C, 52.49; H, 4.70; N, 8.16. Found: C, 52.39; H, 4.80; N, 7.89.

EXAMPLE 140

Compound 866: 4-Hydroxy-1-methyl-5-oxo-2,5-dihydro-1H-pyrrole-3-carboxylic acid [3-(4-fluorophenyl)-propyl]-methyl-amide

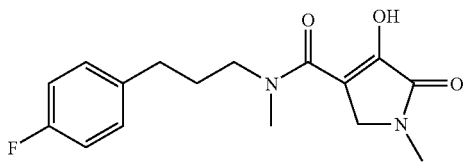

Reaction of 2-(2,2-dimethyl-5-oxo-[1,3]-dioxolan-4-ylidene)-N-[3-(4-fluorophenyl)-propyl]-N-methyl-acetamide (0.20 g, 0.62 mmol) with the paraformaldehyde-methylamine adduct in methanol using a procedure similar to the one described in the preparation of compound 44 (method 44B) gave 0.11 g (56% yield) of the title compound as white crystals; mp 129° C. (dec) (ethyl acetate-hexane). $^1$HNMR 400 MHz (CDCl$_3$) δ (ppm); 1.91 (2H, m, CH$_2$), 2.63 (2H, t, J=7.6 Hz, CH$_2$), 3.04 (3H, s, NCH$_3$), 3.05 (3H, s, NCH$_3$), 3.40 (2H, broad t, J=7.5 Hz, NCH$_2$), 3.90 (2H, broad s, NCH$_2$), 6.99 (2H, m, aromatics), 7.14 (2H, m, aromatics). Anal. Calcd for $C_{16}H_{19}FN_2O_3$: C, 62.73; H, 6.25; N, 9.14. Found: C, 62.75; H, 6.23; N, 9.11.

EXAMPLE 141

Compound 867: 4-Hydroxy-1-(2-morpholin-4-yl-ethyl)-5-oxo-2,5-dihydro-1H-pyrrole-3-carboxylic acid [3-(4-fluorophenyl)-propyl]-methyl-amide

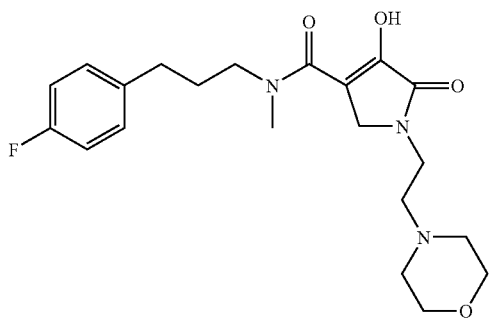

Reaction of 2-(2,2-dimethyl-5-oxo-[1,3]-dioxolan-4-ylidene)-N-[3-(4-fluorophenyl)-propyl]-N-methyl-acetamide (0.245 g, 0.76 mmol) with the paraformaldehyde—N-(2-aminoethyl)morpholine adduct in methanol using a procedure similar to the one described in the preparation of compound 13 gave 0.103 g (33% yield) of the title compound as a solid after chromatography on reversed phase silica gel. $^1$HNMR 400 MHz (CDCl$_3$) δ (ppm); 1.92 (2H, m, CH$_2$), 2.47 (4H, broad, 2×NCH$_2$), 2.54 (2H, broad t, NCH$_2$), 2.63 (2H, t, J=7.5 Hz, CH$_2$), 3.04 (3H, s, NCH$_3$), 3.42 (2H, broad t, NCH$_2$), 3.58 (2H, broad, NCH$_2$), 3.66 (4H, broad, 2×OCH$_2$), 4.12 (2H, broad s, NCH$_2$), 6.97 (2H, m, aromatics), 7.14 (2H, m, aromatics). HRMS (FAB+) calculated for $C_{21}H_{29}FN_3O_4$: [M+H]$^+$: 406.214210. found: 406.214016.

EXAMPLE 142

Compound 868: 4-Hydroxy-1-methyl-5-oxo-2,5-dihydro-1H-pyrrole-3-carboxylic acid [3-(3,4-dichlorophenyl)-propyl]-methyl-amide

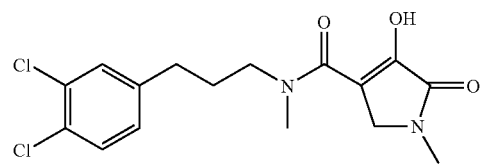

Reaction of N-[3-(3,4-dichlorophenyl)-propyl]-2-(2,2-dimethyl-5-oxo-[1,3]-dioxolan-4-ylidene)-N-methyl-acetamide (0.570 g, 1.53 mmol) with the paraformaldehyde-methylamine adduct in methanol using a procedure similar to the one described in the preparation of compound 44 (method 44B) gave 0.287 g (52% yield) of the title compound as white crystals; mp 138–140° C. (ethyl acetate-hexane). $^1$HNMR 400 MHz (CDCl$_3$) δ (ppm); 1.80 (2H, m, CH$_2$), 2.49 (2H, t, J=7.6 Hz, CH$_2$), 2.92 (3H, s, NCH$_3$), 2.95 (3H, s, NCH$_3$), 3.31 (2H, broad t, J=7.3 Hz, NCH$_2$), 3.87 (2H, broad s, NCH$_2$), 6.91 (1H, dd, J=2.0 Hz and J=8.1 Hz, aromatic), 7.16 (1H, d, J=2.0 Hz, aromatic), 7.23 (1H, d, J=8.1 Hz, aromatic), 10.94 (1H, broad s, OH). Anal. Calcd for $C_6H_{18}Cl_2N_2O_3$: C, 53.80; H, 5.08; N, 7.84. Found: C, 53.90; H, 5.17; N, 7.83.

EXAMPLE 143

Compound 869: 4-Hydroxy-1-(2-morpholin-4-yl-ethyl)-5-oxo-2,5-dihydro-1H-pyrrole-3-carboxylic acid [3-(4-fluorophenyl)-propyl]-methoxy-amide

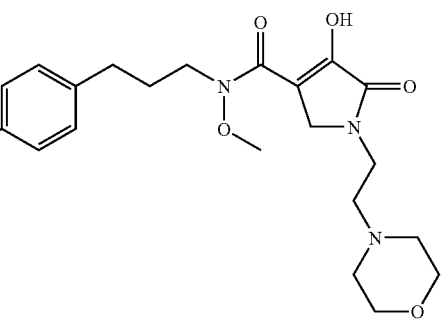

Reaction of 2-(2,2-dimethyl-5-oxo-[1,3]-dioxolan-4-ylidene)-N-[3-(4-fluorophenyl)-propyl]-N-methoxy-acetamide (0.560 g, 1.66 mmol) with the paraformaldehyde-N-(2-aminoethyl)morpholine adduct in methanol using a procedure similar to the one described in the preparation of compound 13 gave 0.446 g (63% yield) of the title compound as a solid after chromatography on reversed phase silica gel. $^1$HNMR 400 MHz (DMSO-d$_6$) δ (ppm); 1.84 (2H, m, CH$_2$), 2.40 (4H, broad, 2×NCH$_2$), 2.46 (2H, t, J=6.5 Hz, CH$_2$), 2.56 (2H, t, J=8.1 Hz, CH$_2$), 3.46 (2H, t, J=6.5 Hz, NCH$_2$), 3.52 (3H, s, OCH$_3$), 3.55 (4H, broad, 2×OCH$_2$), 3.67 (2H, t, J=7.1 Hz, NCH$_2$), 3.95 (2H, s, NCH$_2$), 7.09 (2H, m, aromatics), 7.23 (2H, m, aromatics). HRMS (FAB+) calculated for C$_{21}$H$_{29}$FN$_3$O$_5$: [M+H]$^+$: 422.209125. found: 422.208679.

EXAMPLE 144

Comppound 870: 4-Hydroxy-1-methyl-5-oxo-2,5-dihydro-1H-pyrrole-3-carboxylic acid [3-(3,4-dichlorophenyl)-propyl]-methoxy-amide

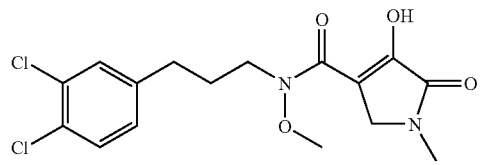

Reaction of N-[3-(3,4-dichlorophenyl)-propyl]-2-(2,2-dimethyl-5-oxo-[1,3]-dioxolan-4-ylidene)-N-methoxy-acetamide (0.480 g, 1.16 mmol) with the paraformaldehyde-methylamine adduct in methanol using a procedure similar to the one described in the preparation of compound 44 (method 44B) gave 0.250 g (58% yield) of the title compound as white crystals; mp 106–108° C. (ethyl acetate-hexane). $^1$HNMR 400 MHz (CDCl$_3$) δ (ppm); 2.01 (2H, m, CH$_2$), 2.65 (2H, t, J=7.6 Hz, CH$_2$), 3.14 (3H, s, NCH$_3$), 3.73 (3H, s, OCH$_3$), 3.77 (2H, t, J=7.0 Hz, NCH$_2$), 4.11 (2H, s, NCH$_2$), 7.04 (1H, dd, J=2.0 Hz and J=8.1 Hz, aromatic), 7.30 (1H, d, J=2.0 Hz, aromatic), 7.36 (1H, d, J=8.1 Hz, aromatic), 11.67 (1H, broad s, OH). Anal. Calcd for C$_{16}$H$_{18}$Cl$_2$N$_2$O$_4$: C, 51.49; H, 4.86; N, 7.51. Found: C, 51.65; H, 4.90; N, 7.45.

EXAMPLE 145

Compound 871: 4-Hydroxy-1-(2-morpholin-4-yl-ethyl)-5-oxo-2,5-dihydro-1H-pyrrole-3-carboxylic acid [3-(3,4-dichlorophenyl)-propyl]-methoxy-amide

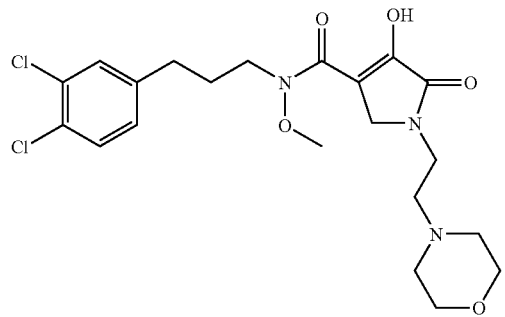

Reaction of N-[3-(3,4-dichlorophenyl)-propyl]-2-(2,2-dimethyl-5-oxo-[1,3]-dioxolan-4-ylidene)-N-methoxy-acetamide (0.378 g, 0.97 mmol) with the paraformaldehyde-N-(2-aminoethyl)morpholine adduct in methanol using a procedure similar to the one described in the preparation of compound 13 gave 0.196 g (42% yield) of the title compound as a solid after chromatography on reversed phase silica gel. $^1$HNMR 400 MHz (CDCl$_3$) δ (ppm); 1.98 (2H, m, CH$_2$), 2.49 (4H, broad, 2×NCH$_2$), 2.58 (2H, t, J=6.2 Hz, CH$_2$), 2.63 (2H, t, J=7.5 Hz, CH$_2$), 3.63 (2H, t, J=6.2 Hz, NCH$_2$), 3.68 (4H, broad, 2×OCH$_2$), 3.71 (3H, s, OCH$_3$), 3.74 (2H, t, J=7.0 Hz, NCH$_2$), 4.23 (2H, s, NCH$_2$), 7.02 (1H, dd, J=2.0 Hz and J=8.2 Hz, aromatic), 7.28 (1H, d, J=2.0 Hz, aromatic), 7.34 (1H, d, J=8.2 Hz, aromatic). HRMS (FAB+) calculated for C$_{21}$H$_{28}$Cl$_2$N$_3$O$_5$: [M+H]$^+$: 472.140602. found: 472.138651.

EXAMPLE 146

Compound 146-A: 4-Fluorobenzaldehyde O-(3-chloropropyl)-oxime

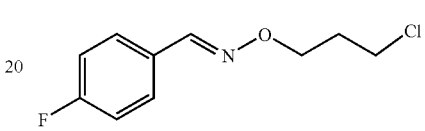

A suspension of sodium hydride (73.0 mmol, 3.0 g of a 60% suspension in mineral oil) was washed twice with hexane and then suspended in dry tetrahydrofuran (40 ml). The reaction mixture was then treated at 25° C. with 1-bromo-3-chloropropane (10 ml, 97.5 mmol) followed by a solution of 4-fluorobenzaldehyde oxime (6.78 g, 48.7 mmol) in tetrahydrofuran (30 ml) added dropwise over 10 min. The resulting mixture was then heated under reflux for 16 h. The cooled mixture was diluted with ethyl acetate, washed with brine and dried over anhydrous sodium sulfate. Evaporation of the solvent under reduced pressure and chromatography of the residue on silica gel (elution hexane-ethyl acetate, 9:1) gave 8.52 g (81%) of the title oxime as a clear oil. $^1$HNMR 400 MHz (CDCl$_3$) δ (ppm): 2.23 (2H, m, CH$_2$), 3.74 (2H, t, J=6.5 Hz, CH$_2$), 4.36 (2H, t, J=5.8 Hz, CH$_2$), 7.13 (2H, m, aromatics), 7.63 (2H, m, aromatics), 8.11 (1H, s, CH). Anal. Calcd for C$_{10}$H$_{11}$ClFNO: C, 55.69; H, 5.14; N, 6.49. Found: C, 55.44; H, 5.12; N, 6.41.

Compound 146-B: 4-Fluorobenzaldehyde O-(3-morpholin-4-yl-propyl)-oxime

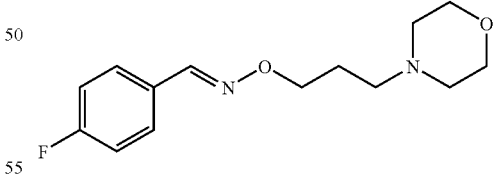

A mixture of 4-fluorobenzaldehyde O-(3-chloropropyl)-oxime (0.430 g, 2.0 mmol), morpholine (0.70 g, 8.0 mmol), sodium iodide (0.1 g) and potassium carbonate (0.55 g) in acetone (10 ml) was sealed and heated at 80° C. for 34 h. The cooled mixture was concentrated, diluted with ethyl acetate, washed with brine and dried over anhydrous sodium sulfate. Evaporation of the solvent under reduced pressure and chromatography of the residue on silica gel (elution ethyl acetate-acetone, 8:2) gave 0.376 g (70%) of the title oxime as a clear oil. $^1$HNMR 400 MHz (C$_6$D$_6$) δ (ppm): 1.94 (2H, m, CH$_2$), 2.27 (4H, m, NCH$_2$), 2.38 (2H, t, J=7.1 Hz, NCH$_2$), 3.69 (4H, m, OCH$_2$), 4.40 (2H, t, J=6.5 Hz, OCH$_2$), 6.76 (2H, m, aromatics), 7.33 (2H, m, aromatics), 8.03 (1H, s, CH).

Compound 146-C: N-(4-Fluorobenzyl)-O-(3-morpholin-4-yl-propyl)-hydroxylamine

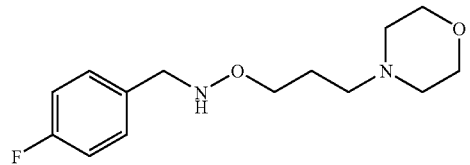

Reduction of 4-fluorobenzaldehyde O-(3-morpholin-4-yl-propyl)-oxime (0.330 g, 1.24 mmol) with sodium cyanoborohydride in acetic acid as described in the preparation of compound 44-B gave 0.330 (100% yield) of the crude title hydroxylamine as a light yellow oil which was used as such for the acylation step. $^1$HNMR 400 MHz (C$_6$D$_6$) δ (ppm): 1.69 (2H, m, CH$_2$), 2.22 (4H, m, NCH$_2$), 2.27 (2H, t, J=7.0 Hz, NCH$_2$), 3.63 (4H, m, OCH$_2$), 3.74 (2H, t, J=6.3 Hz, OCH$_2$), 3.79 (2H, s, NCH$_2$), 6.91 (2H, m, aromatics), 7.12 (2H, m, aromatics).

Compound 146-D: 2-(2,2-Dimethyl-5-oxo-[1,3]-dioxolan-4-ylidene)-N-(4-fluorobenzyl)-N-(3-morpholin-4-yl-propoxy)-acetamide

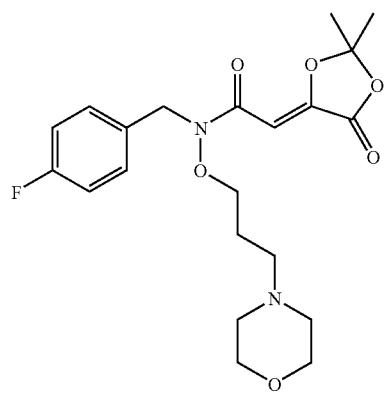

Reaction of (2,2-dimethyl-5-oxo-[1,3]dioxolan-4-ylidene)-acetyl chloride (1.0 mmol) with N-(4-fluorobenzyl)-O-(3-morpholin-4-yl-propyl)-hydroxylamine (0.268 g, mmol) as described in the preparation of compound 44-C (acid wash was skipped in this case) gave 0.200 g (47% yield) of the title amide as a clear oil after chromatography on silica gel. $^1$HNMR 400 MHz (C$_6$D$_6$) δ (ppm): 1.10 (6H, s, CH$_3$), 1.50 (2H, m, CH$_2$), 2.19 (2H, t, J=6.6 Hz, NCH$_2$), 2.20 (4H, m, NCH$_2$), 3.70 (2H, t, J=6.2 Hz, OCH$_2$), 3.71 (4H, m, OCH$_2$), 4.73 (2H, s, NCH$_2$), 6.85 (3H, m, CH and aromatics), 7.22 (2H, m, aromatics). HRMS (MAB N$_2$) calculated for C$_{21}$H$_{27}$FN$_2$O$_6$ [M$^+$]: 422.185315: found: 422.185246.

Compound 872: 4-Hydroxy-1-methyl-5-oxo-2,5-dihydro-1H-pyrrole-3-carboxylic acid (4-fluoro-benzyl)-(3-morpholin-4-yl-propoxy)-amide

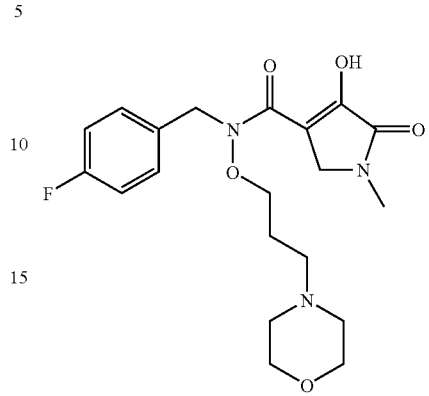

Reaction of 2-(2,2-dimethyl-5-oxo-[1,3]dioxolan-4-ylidene)-N-(4-fluoro-benzyl)-N-(3-morpholin-4-yl-propoxy)-acetamide (0.080 g, 0.18 mmol) with the paraformaldehyde-methylamine adduct in methanol using a procedure similar to the one described in the preparation of compound 44 method 44B) gave 0.027 g (35% yield) of the title compound as a white solid after chromatography on reversed phase silica gel. $^1$HNMR 400 MHz (DMSO-d$_6$) δ (ppm); 1.61 (2H, m, CH$_2$), 2.23 (2H, t, J=7.0 Hz, NCH$_2$), 2.28 (4H, broad, 2×NCH$_2$), 2.93 (3H, s, NCH$_3$), 3.54 (4H, broad, 2×OCH$_2$), 3.76 (2H, broad t, OCH$_2$), 3.97 (2H, s, NCH$_2$), 4.88 (2H, s, NCH$_2$), 7.13 (2H, m, aromatics), 7.40 (2H, m, aromatics). HRMS (MAB N$_2$) calculated for C$_{20}$H$_{26}$FN$_3$O$_5$: [M$^+$]: 407.185650. found: 407.184331.

EXAMPLE 147

Compound 873: 4-Hydroxy-1-(2-morpholin-4-yl-ethyl)-5-oxo-2,5-dihydro-1H-pyrrole-3-carboxylic acid (4-fluoro-benzyl)-(3-morpholin-4-yl-propoxy)-amide

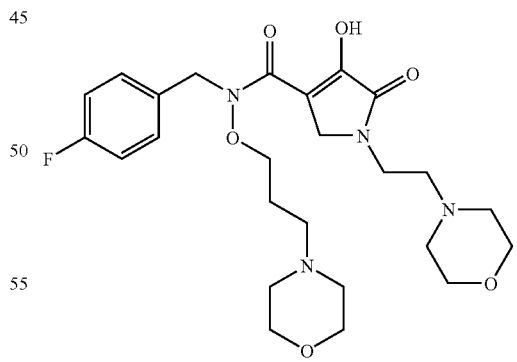

Reaction of 2-(2,2-dimethyl-5-oxo-[1,3]dioxolan-4-ylidene)-N-(4-fluoro-benzyl)-N-(3-morpholin-4-yl-propoxy)-acetamide (0.080 g, 0.19 mmol) with the paraformaldehyde-N-(2-aminoethyl)morpholine adduct in methanol using a procedure similar to the one described in the preparation of compound 13 gave 0.019 g (20% yield) of the title compound as a solid after chromatography on reversed phase silica gel. $^1$HNMR 400 MHz (CDCl$_3$) δ (ppm); 1.65

(2H, m, CH$_2$), 2.25 (2H, t, J=7.3 Hz, NCH$_2$), 2.29 (4H, broad, 2×NCH$_2$), 2.39 (4H, broad, 2×NCH$_2$), 2.46 (2H, t, J=6.6 Hz, CH$_2$), 3.50 (2H, t, J=6.6 Hz, NCH$_2$), 3.68 (8H, broad, 4×OCH$_2$), 3.84 (2H, t, J=7.0 Hz, OCH$_2$), 4.11 (2H, s, NCH$_2$), 4.87 (2H, s, NCH$_2$), 7.16 (2H, m, aromatics), 7.40 (2H, m, aromatics). HRMS (MAB N$_2$) calculated for C$_{25}$H$_{35}$FN$_4$O$_6$: [M]$^+$: 506.254064; found: 506.254892.

EXAMPLE 148

Compound 148-A: 3,4-Dichlorobenzaldehyde O-(3-chloropropyl)-oxime

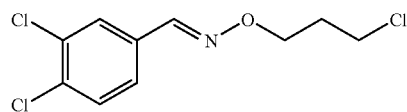

Reaction of 3,4-dichlorobenzaldehyde oxime (2.5 g, 13.15 mmol) with 1-bromo-3-chloropropane (2.6 ml, 26.3 mmol) as described in the preparation of Compound 146-A gave 2.60 g (74% yield) of the title oxime as a clear oil after chromatography on silica gel (elution hexane-ethyl acetate, 9:1). $^1$HNMR 400 MHz (CDCl$_3$) δ (ppm): 2.21 (2H, m, CH$_2$), 3.69 (2H, t, J=6.5 Hz, CH$_2$), 4.34 (2H, t, J=5.8 Hz, OCH$_2$), 7.41 (1H, dd, J=2 Hz and J=8 Hz, aromatic), 7.47 (1H, d, J=8 Hz, aromatic), 7.71 (1H, d, J=2 Hz, aromatic), 8.01 (1H, s, CH).

Compound 148-B: 3,4-Dichlorobenzaldehyde O-(3-morpholin-4-yl-propyl)-oxime

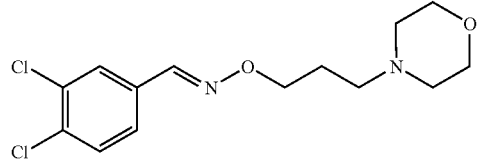

Reaction of 3,4-dichlorobenzaldehyde O-(3-chloropropyl)-oxime (2.6 g, 9.75 mmol) with morpholine (3.4 ml) as described in the preparation of compound 146-B gave 2.25 g (72% yield) the title oxime as a clear oil after chromatography on silica gel (elution ethyl acetate-acetone, 8:2). $^1$HNMR 400 MHz (C$_6$D$_6$) δ (ppm): 1.89 (2H, m, CH$_2$), 2.25 (4H, m, NCH$_2$), 2.35 (2H, t, J=7.1 Hz, NCH$_2$), 3.69 (4H, m, OCH$_2$), 4.35 (2H, t, J=6.5 Hz, OCH$_2$), 6.98 (1H, d, J=8.5 Hz, aromatic), 7.02 (1H, dd, J=1.9 Hz and J=8.5 Hz, aromatic), 7.50 (1H, d, J=1.9 Hz, aromatic), 7.77 (1H, s, CH). Anal. Calcd for C$_{14}$H$_{18}$Cl$_2$N$_2$O$_2$: C, 53.01; H, 5.71; N, 8.83. Found: C, 52.99; H, 5.69; N, 8.75.

Compound 148-C: N-(3,4-Dichlorobenzyl)-O-(3-morpholin-4-yl-propyl)-hydroxylamine

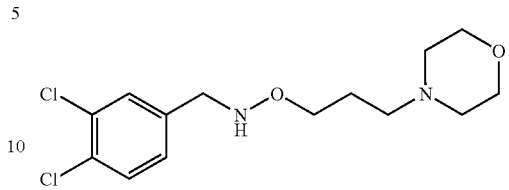

A solution of 3,4-dichlorobenzaldehyde O-(3-morpholin-4-yl-propyl)-oxime (0.160 g, 0.5 mmol) in a mixture of dichloromethane (2 ml) and acetic acid (1 ml) was treated with borane-pyridine complex (0.17 ml, 1.36 mmol) and the resulting mixture was heated under reflux (bath temperature 60° C.) for 4 h. The solvent was then evaporated under reduced pressure and the residue was treated with 10% aqueous hydrochloric acid (3 ml). The reaction mixture was then basified with solid sodium carbonate and extracted with ethyl acetate. The organic phase was then washed with brine, dried (anhydrous magnesium sulfate) and concentrated to give 0.150 g (93% yield) of the crude title hydroxylamine as a light yellow oil which was used as such for the acylation step. $^1$HNMR 400 MHz (C$_6$D$_6$) δ (ppm): 1.66 (2H, m, CH$_2$), 2.22 (2H, t, J=7.1 Hz, NCH$_2$), 2.24 (4H, m, NCH$_2$), 3.56 (2H, s, NCH$_2$), 3.69 (4H, m, OCH$_2$), 3.70 (2H, t, J=6.5 Hz, OCH$_2$), 5.2 (1H, broad, NH), 6.82 (1H, dd, J=1.9 Hz and J=8.5 Hz, aromatic), 7.13 (1H, d, J=8.5 Hz, aromatic), 7.33 (1H, d, J=1.9 Hz, aromatic).

Compound 148-D: N-(3,4-Dichlorobenzyl)-2-(2,2-dimethyl-5-oxo-[1,3]-dioxolan-4-ylidene)-N-(3-morpholin-4-yl-propoxy)-acetamide

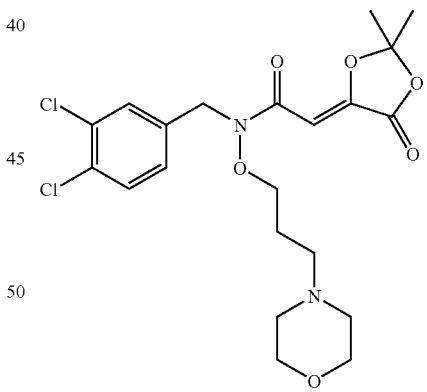

Reaction of (2,2-dimethyl-5-oxo-[1,3]dioxolan-4-ylidene)-acetyl chloride (0.49 mmol) with N-(3,4-dichlorobenzyl)-O-(3-morpholin-4-yl-propyl)-hydroxylamine (0.150 g, 0.49 mmol) as described in the preparation of compound 44-C gave 0.150 g (65% yield) of the title amide as white crystals after chromatography on silica gel: mp 77–78° C. (ether-hexane). $^1$HNMR 400 MHz (C$_6$D$_6$) δ (ppm): 1.09 (6H, s, CH$_3$), 1.47 (2H, m, CH$_2$), 2.17 (2H, t, J=6.5 Hz, NCH$_2$), 2.22 (4H, m, NCH$_2$), 3.66 (2H, t, J=6.0 Hz, OCH$_2$), 3.73 (4H, m, OCH$_2$), 4.56 (2H, s, NCH$_2$), 6.82 (1H, s, CH), 6.98 (1H, dd, J=2.0 Hz and J=8.0 Hz, aromatic), 7.06 (1H, d, J=8.0 Hz, aromatic), 7.40 (1H, d, J=2.0 Hz, aromatic). Anal. Calcd for $C_{21}H_{26}Cl_2N_2O_6$: C, 53.28; H, 5.53; N, 5.91. Found: C, 53.31; H, 5.67; N, 5.77.

Compound 874: 4-Hydroxy-1-methyl-5-oxo-2,5-dihydro-1H-pyrrole-3-carboxylic acid (3,4-dichloro-benzyl)-(3-morpholin-4-yl-propoxy)-amide

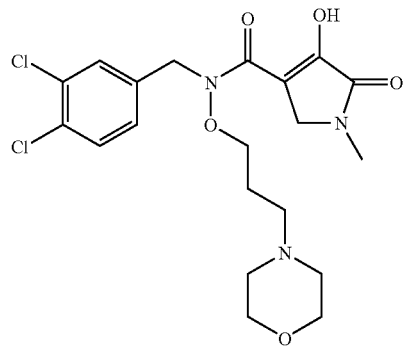

Reaction of N-(3,4-dichloro-benzyl)-2-(2,2-dimethyl-5-oxo-[1,3]dioxolan-4-ylidene)-N-(3-morpholin-4-yl-propoxy)-acetamide (0.200 g, 0.42 mmol) with the paraformaldehyde-methylamine adduct in methanol using a procedure similar to the one described in the preparation of compound 44 (method 44B) gave 0.090 g (47% yield) of the title compound as a white amorphous solid after chromatography on reversed phase silica gel. $^1$HNMR 400 MHz (DMSO-d$_6$) δ (ppm); 1.66 (2H, m, CH$_2$), 2.27 (2H, t, J=7.1 Hz, NCH$_2$), 2.32 (4H, broad, 2×NCH$_2$), 2.95 (3H, s, NCH$_3$), 3.55 (4H, broad, 2×OCH$_2$), 3.86 (2H, broad t, OCH$_2$), 4.06 (2H, s, NCH$_2$), 4.88 (2H, s, NCH$_2$), 7.35 (1H, dd, J=2 Hz and J=8.1 Hz, aromatic), 7.61 (1H, d, J=8.1 Hz, aromatic), 7.65 (1H, d, J=2 Hz, aromatic). HRMS (FAB+) calculated for $C_{20}H_{26}Cl_2N_3O_5$: [M+H]$^+$: 458.124952. found: 458.123753.

EXAMPLE 149

Compound 875: 4-Hydroxy-1-(2-morpholin-4-yl-ethyl)-5-oxo-2,5-dihydro-1H-pyrrole-3-carboxylic acid (3,4-dichloro-benzyl)-(3-morpholin-4-yl-propoxy)-amide

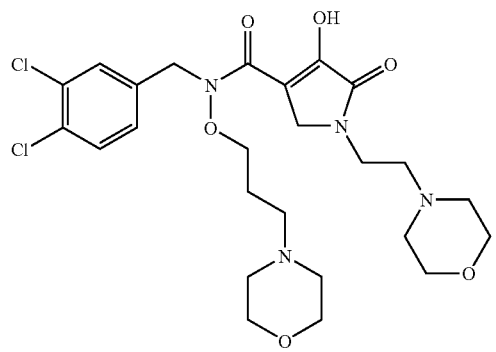

Reaction of N-(3,4-dichloro-benzyl)-2-(2,2-dimethyl-5-oxo-[1,3]dioxolan-4-ylidene)-N-(3-morpholin-4-yl-propoxy)-acetamide (0.200 g, 0.42 mmol) with the paraformaldehyde-N-(2-aminoethyl)morpholine adduct in methanol using a procedure similar to the one described in the preparation of compound 13 gave 0.160 g (68% yield) of the title compound as a solid after chromatography on reversed phase silica gel. $^1$HNMR 400 MHz (CDCl$_3$) δ (ppm); 1.56 (2H, m, CH$_2$), 2.18 (2H, t, J=7.1 Hz, NCH$_2$), 2.25 (4H, broad, 2×NCH$_2$), 2.39 (4H, broad, 2×NCH$_2$), 2.46 (2H, t, J=6.1 Hz, CH$_2$), 3.50 (2H, t, J=6.1 Hz, NCH$_2$), 3.54 (8H, broad, 4×OCH$_2$), 3.71 (2H, broad t, OCH$_2$), 3.99 (2H, s, NCH$_2$), 4.87 (2H, s, NCH$_2$), 7.40 (1H, broad d, aromatic), 7.58 (1H, d, J=8.1 Hz, aromatic), 7.73 (1H, broad s, aromatic). HRMS (FAB+) calculated for $C_{25}H_{35}Cl_2N_4O_6$: [M+H]$^+$: 557.193366. found: 557.192134.

Biological Activity

For each reaction, 5 pmole of biotin labeled substrate DNA was bound to 100 ug of Streptavidin coated PVT SPA beads (Amersham Pharmacia Biotech). 0.26 ng of recombinant integrase was incubated with the beads for 90 min at 37 C. Unbound enzyme was removed by washing the complex followed by addition of inhibitors and 0.1 fmol of P33 labeled target DNA. Reaction was stopped by adding EDTA to a final concentration of 10 mM. Samples were counted in TopCountNXT (Packard) and the CPM was used as a measure of integration. Reaction condition was as described in A. Engelman and R. Craigie, J. Virol. 69, 5908–5911 (1995). The sequences of substrate and target DNA were described in Nucleic Acid Research 22, 1121–1122 (1994). Using this assay, representative examples were found to have IC$_{50}$=0.01 to 50 μM. The table below shows the percent inhibition of HIV-integrase in the presence of 20 μM of compounds 1–79.

| Compound | % Inhibition @20 μM |
|---|---|
| 1 | 99.9 |
| 2 | 99.9 |
| 3 | 99.9 |
| 4 | 99.9 |
| 5 | 99.8 |
| 6 | 99.9 |
| 7 | 99.9 |
| 8 | 99.9 |
| 9 | 99.9 |
| 10 | 99.9 |
| 11 | 99.9 |
| 12 | 99.9 |
| 13 | 99.9 |
| 14 | 99.7 |
| 15 | 99.7 |
| 16 | 99.9 |
| 17 | 99.9 |
| 18 | 99.9 |
| 19 | 99.9 |
| 20 | 99.9 |
| 21 | 99.9 |
| 22 | 99.9 |
| 23-A | 99.9 |
| 23 | 99.9 |
| 24 | 99.9 |
| 25 | 99.9 |
| 26 | 99.9 |
| 27 | 99.9 |
| 28 | 99.9 |
| 29 | 99.9 |
| 30 | 99.9 |
| 31 | 99.9 |
| 32 | 99.9 |
| 33 | 99.9 |
| 34 | 99.9 |
| 35 | 99.9 |
| 36 | 92 |

-continued

| Compound | % Inhibition @20 µM |
|---|---|
| 37 | 99.9 |
| 38 | 99.9 |
| 39 | 99.9 |
| 40 | 99.9 |
| 41 | 99.9 |
| 42 | 99.9 |
| 43 | 99.9 |
| 45 | 99.5 |
| 46 | 99.3 |
| 47 | 99.9 |
| 49 | 98.5 |
| 50 | 92 |
| 51 | 99.9 |
| 52 | 86 |
| 53 | 99 |
| 54 | 99.9 |
| 55 | 99.9 |
| 56 | 88 |
| 57 | 99.9 |
| 58 | 99.5 |
| 59 | 99.9 |
| 60 | 99.7 |
| 61 | 99.3 |
| 62 | 97.7 |
| 63 | 12 |
| 64 | 99.7 |
| 65 | 99.9 |
| 66 | 99 |
| 67 | 96.5 |
| 68-A | 4.5 |
| 68 | 12 |
| 69 | 97 |
| 70 | 99.8 |
| 71 | 99.9 |
| 72 | 98.8 |
| 73 | 10 |
| 74 | 97.8 |
| 75 | 96.5 |
| 76 | 96 |
| 77 | 99.8 |
| 78 | 99.9 |
| 79 | 92.4 |

Inhibition of HIV Replication

Cell culture assays were performed using a single cycle, recombinant HIV virus expressing Renella luciferase. Antiviral activity was evaluated by measuring the production of luciferase in the infected cells 5 days post-infection. Susceptibility of the virus to compounds was determined by incubation in the presence of the serially-diluted compound. The 50% effective concentration ($EC_{50}$) was calculated by using the exponential form of the median effect equation where $(Fa)=1/[1+(ED_{50}/drug\ conc.)^m]$.

Representative compounds of this invention tested in this assay have $EC_{50}$'s of approximately 0.01 to 150 µM.

What is claimed:

1. A compound of Formula I, or pharmaceutically acceptable salts or solvates thereof

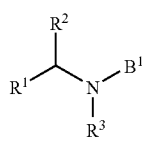

I wherein:
$R^1$ is
-phenyl substituted with 1–3 $R^4$,
-naphthyl, furanyl, thienyl, pyridyl, or imidazolyl unsubtituted or substituted with 1–3 $R^4$,
—$C_1$–$C_6$ alkyl-aryl unsubtituted or substituted with 1–3 $R^4$, or
—$C_1$–$C_5$ alkyl-O-aryl unsubtituted or substituted with 1–3 $R^4$;

$R^2$ is
—H,
—$C_1$–$C_6$ alkyl,
-aryl unsubstituted or substituted with 1–3 $R^4$, or
—$C_1$–$C_6$ alkyl aryl unsubstituted or substituted with 1–3 $R^4$;

$R^3$ is
—H,
—$C_1$–$C_6$ alkyl,
—$C_1$–$C_6$ alkyl-aryl unsubtituted or substituted with 1–3 R, or
—$OR^9$;

$R^4$ is independently selected from
-halo,
—CN,
—$C_1$–$C_6$ alkyl,
—$C_3$–$C_6$ cycloalkyl,
—$C_1$–$C_6$ haloalkyl,
—$OR^5$,
—$CO_2R^6$,
—$N(R^7)(R^8)$,
—$CON(R^7)(R^8)$,
—$SR^5$,
—$SOC_1$–$C_6$alkyl, and
—$SO_2C_1$–$C_6$alkyl;

$R^5$ and $R^6$ are independently selected from —H and —$C_1$–$C_6$ alkyl;

$R^7$ and $R^8$ are independently selected from —H and —$C_1$–$C_6$ alkyl, or $NR^7R^8$ is a heterocycle selected from pyrrolidine, piperidine, 4-hydroxypiperidine, morpholine, thiomorpholine, piperazine, and 4-methylpiperazine;

$R^9$ is
—H,
—$C_1$–$C_{10}$ alkyl,
—$C_1$–$C_6$ alkyl-aryl,
—$C_2$–$C_{10}$ alkyl-$OR^5$,
—$C_1$–$C_{10}$ alkyl-$CO_2R^6$,
—$C_1$–$C_{10}$ alkyl-$N(R^7)(R^8)$,
—$C_1$–$C_{10}$ alkyl-$CON(R^7)(R^8)$, or
—$C_1$–$C_6$ alkyl-heterocycle where the heterocycle is selected from pyrrolidine, piperidine, 4-hydroxypiperidine, morpholine, thiomorpholine, piperazine, 4-methylpiperazine, and thiazinanedioxide;

$B^1$ is selected from the group consisting of

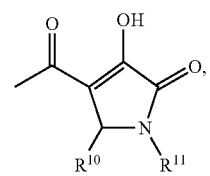

-continued

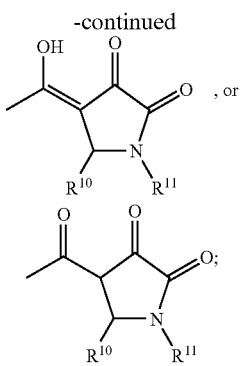

$R^{10}$ is
—H,
—$C_1$–$C_6$ alkyl,
-cycloalkyl,
—$C_1$–$C_6$ alkyl-aryl,
-phenyl unsubstituted or substituted with 1–3 $R^{12}$,
benzofuran, dihydrobenzofuran, benzodioxane, or
-heteroaryl selected from furan, thiophene, pyrrole, imidazole, oxazole, thiazole, and pyridine;

$R^{11}$ is
—$C_1$–$C_6$ alkyl,
-cycloalkyl,
-aryl unsubstituted or substituted with 1–2 $R^4$,
—$C_1$–$C_6$ alkyl-aryl unsubstituted or substituted with 1–2 $R^4$,
—$C_1$–$C_6$ alkyl-heteroaryl where the heteroaryl is selected from furan, thiophene, pyrrole, imidazole, oxazole, thiazole, and pyridine,
—$C_1$–$C_6$ alkyl-$NR^7R^8$,
—$C_1$–$C_6$ alkyl-$OR^5$,
—$C_1$–$C_6$ alkyl-$P(O)(OR^6)_2$,
—$C_1$–$C_6$ alkyl-$CO_2R^6$, or
—$C_1$–$C_6$ alkyl-$C(O)N(R^7)(R^8)$;

$R^{12}$ is
halogen,
—$C_1$–$C_6$ alkyl,
—$C_1$–$C_2$ haloalkyl,
—$C_1$–$C_3$ thioalkyl,
—$OR^{13}$,
tetrahydrofuran,
dihydropyran,
—$NR^7R^8$,
—$CO_2R^6$,
—$CONR^7R^8$, or
—$CONHCH_2Ph$ where Ph is unsubstituted or substituted with 1–2 $R^4$;

$R^{13}$ is
—H,
—$C_1$–$C_6$ alkyl,
—$C_1$–$C_6$ fluoroalkyl,
allyl,
propargyl,
phenyl,
benzyl,
—$COC_1$–$C_6$alkyl,
—$CH_2CO_2R^6$, or
—$CH_2CONR^7R^8$.

2. A compound of claim 1 where $R^1$ is phenyl substituted with 1–3 $R^4$ or $C_1$–$C_6$ alkylaryl unsubstituted or substituted with 1–3 $R^4$, $R^2$ is H, and $R^4$ is halo, CN, $C_1$–$C_6$ alkyl, $C_1$–$C_6$ haloalkyl, $OR^5$, $CO_2R^6$, or $NR^7R^8$.

3. A compound of claim 2 where $R^{10}$ is H or phenyl unsubstituted or substituted with 1–3 $R^4$.

4. A compound of claim 3 where $R^{12}$ is $OR^{13}$.

5. A compound of claim 3 where $R^{11}$ is $C_1$–$C_6$ alkyl or $C_1$–$C_6$-alkyl-heterocycle where the heterocycle is selected from pyrrolidine, piperidine, 4-hydroxypiperidine, morpholine, thiomorpholine, piperazine, 4-methylpiperazine, and thiazinanedioxide.

6. A compound of claim 1 selected from the group consisting of
4-hydroxy-5-oxo-1-(2-[4-methylpiperazin-1-yl]ethyl)-2,5-dihydro-1H-pyrrole-3-carboxylic acid (3,4-dichlorobenzyl)-methyl-amide;
4-hydroxy-5-oxo-1-(2-[morpholin-1-yl]ethyl)-2,5-dihydro-1H-pyrrole-3-carboxylic acid (3,4-dichlorobenzyl)-methyl-amide;
4-hydroxy-5-oxo-1-(2-[morpholin-1-yl]ethyl)-2,5-dihydro-1H-pyrrole-3-carboxylic acid (3,4-dimethylbenzyl)-methyoxy-amide;
4-hydroxy-5-oxo-1-(2-[morpholin-1-yl]ethyl)-2,5-dihydro-1H-pyrrole-3-carboxylic acid 3-(4-fluorophenyl)prop-1-yl-methyoxy-amide;
4-hydroxy-5-oxo-1-methyl-2,5-dihydro-1H-pyrrole-3-carboxylic acid (3,4-dichlorobenzyl)-methyl-amide;
4-hydroxy-5-oxo-1-methyl-2,5-dihydro-1H-pyrrole-3-carboxylic acid (3,4-dichlorobenzyl)-methoxy-amide;
4-hydroxy-5-oxo-1-methyl-2,5-dihydro-1H-pyrrole-3-carboxylic acid (3,4-dimethylbenzyl)-methoxy-amide;
4-hydroxy-5-oxo-1-methyl-2,5-dihydro-1H-pyrrole-3-carboxylic acid (4-fluoro-3-methylbenzyl)-methoxy-amide; and
4-hydroxy-5-oxo-1-methyl-2,5-dihydro-1H-pyrrole-3-carboxylic acid (3-fluoro-4-methylbenzyl)-methoxy-amide.

7. A pharmaceutical composition comprising a compound of claim 1, or a pharmaceutically acceptable salt or solvate thereof, and a pharmaceutically acceptable carrier.

8. The pharmaceutical composition of claim 7, further comprising a therapeutically effective amount of one or more other HIV treatment agent selected from
(a) an HIV protease inhibitor;
(b) a nucleoside reverse transcriptase inhibitor;
(c) a non-nucleoside reverse transcriptase inhibitor;
(d) an HIV-entry inhibitor;
(e) an immunomodulator;
(f) or a combination thereof.

9. A method of inhibiting HIV integrase which comprises administering a therapeutically effective amount of a compound of claim 1, or a pharmaceutically acceptable salt or solvate thereof, to a mammal in need of such treatment.

10. A method of treating an HIV infection in a patient in need thereof, comprising the administration of a therapeutically effective amount of a compound of claim 1, or a pharmaceutically acceptable salt or solvate thereof to the patient.

11. A method of therapeutically treating AIDS or ARC in a patient in need thereof, comprising the administration of a therapeutically effective amount of a compound of claim 1, or a pharmaceutically acceptable salt or solvate thereof, to the patient.

* * * * *